US011578426B2

(12) United States Patent
Luo et al.

(10) Patent No.: US 11,578,426 B2
(45) Date of Patent: Feb. 14, 2023

(54) DYNAMIC HUMAN HEAVY CHAIN ANTIBODY LIBRARIES

(71) Applicants: Adagene Inc., Grand Cayman (KY); Peter Peizhi Luo, Suzhou (CN)

(72) Inventors: Peter Peizhi Luo, Suzhou (CN); Yan Li, Suzhou (CN); Fangyong Du, Suzhou (CN)

(73) Assignee: Adagene Inc., Grand Cayman (KY)

( * ) Notice: Subject to any disclaimer, the term of this patent is extended or adjusted under 35 U.S.C. 154(b) by 232 days.

(21) Appl. No.: 16/640,679

(22) PCT Filed: Aug. 21, 2017

(86) PCT No.: PCT/CN2017/098299
§ 371 (c)(1),
(2) Date: Feb. 20, 2020

(87) PCT Pub. No.: WO2019/036842
PCT Pub. Date: Feb. 28, 2019

(65) Prior Publication Data

US 2020/0248336 A1 Aug. 6, 2020

(51) Int. Cl.
*C40B 40/08* (2006.01)
*C07K 16/00* (2006.01)
*C40B 50/04* (2006.01)

(52) U.S. Cl.
CPC .............. *C40B 40/08* (2013.01); *C07K 16/00* (2013.01); *C40B 50/04* (2013.01); *C07K 2317/51* (2013.01); *C07K 2317/56* (2013.01); *C07K 2317/565* (2013.01)

(58) Field of Classification Search
None
See application file for complete search history.

(56) References Cited

U.S. PATENT DOCUMENTS 4,816,567 A 3/1989 Cabilly et al.
5,545,806 A 8/1996 Lonberg et al.
5,545,807 A 8/1996 Surani et al.
(Continued)

FOREIGN PATENT DOCUMENTS

CN 103603057 A 2/2014
EP 440146 A2 8/1991
(Continued)

OTHER PUBLICATIONS

Better et al., (1989). "Expression of engineered antibodies and antibody fragments in microorganisms," Meth. Enzymol., 178:476-96.

(Continued)

*Primary Examiner* — Christian C Boesen
(74) *Attorney, Agent, or Firm* — Morrison & Foerster LLP

(57) ABSTRACT

Provided herein are libraries containing polynucleotides, where one of the polynucleotides encodes an antibody heavy chain with specific hypervariable regions HVR-H1 and HVR-H2. Further provided herein are libraries containing polynucleotides encoding a plurality of unique antibodies, wherein each antibody comprises a heavy chain variable region and a light chain variable region. Also provided are antibodies, polypeptide libraries, vector libraries, cells, non-human animals, antibody heavy chains, methods of making an antibody library, kits, and methods of generating a bispecific antibody related thereto.

34 Claims, 3 Drawing Sheets

Specification includes a Sequence Listing.

(56) References Cited

U.S. PATENT DOCUMENTS

| | | | |
|---|---|---|---|
| 5,569,825 A | 10/1996 | Lonberg et al. |
| 5,625,126 A | 4/1997 | Lonberg et al. |
| 5,633,425 A | 5/1997 | Lonberg et al. |
| 5,648,237 A | 7/1997 | Carter |
| 5,661,016 A | 8/1997 | Lonberg et al. |
| 5,731,168 A | 3/1998 | Carter et al. |
| 5,789,199 A | 8/1998 | Joly et al. |
| 5,807,706 A | 9/1998 | Carter et al. |
| 5,821,333 A | 10/1998 | Carter et al. |
| 5,840,523 A | 11/1998 | Simmons et al. |
| 5,959,177 A | 9/1999 | Hein et al. |
| 6,040,498 A | 3/2000 | Stomp et al. |
| 6,417,429 B1 | 7/2002 | Hein et al. |
| 6,420,548 B1 | 7/2002 | Vezina et al. |
| 7,125,978 B1 | 10/2006 | Vezina et al. |
| 7,642,228 B2 | 1/2010 | Carter et al. |
| 7,695,936 B2 | 4/2010 | Carter et al. |
| 8,216,805 B2 | 7/2012 | Carter et al. |
| 2003/0036092 A1 | 2/2003 | Iverson et al. |
| 2003/0100023 A1 | 5/2003 | Iverson et al. |
| 2004/0072740 A1 | 4/2004 | Iverson et al. |
| 2005/0266000 A1 | 12/2005 | Bond et al. |
| 2013/0089553 A1 | 4/2013 | Carter et al. |
| 2014/0179547 A1 | 6/2014 | Fischer et al. |
| 2016/0145604 A1 | 5/2016 | Du et al. |
| 2020/0362019 A1 | 11/2020 | Luo et al. |

FOREIGN PATENT DOCUMENTS

| | | | |
|---|---|---|---|
| EP | 1457559 A1 | 9/2004 |
| JP | H4-211395 A | 8/1992 |
| JP | 2013534130 A | 9/2013 |
| JP | 2013539461 A | 10/2013 |
| WO | WO-1991010741 A1 | 7/1991 |
| WO | WO-1993008829 A1 | 5/1993 |
| WO | WO-1996033735 A1 | 10/1996 |
| WO | WO-1996034096 A1 | 10/1996 |
| WO | WO-1998024893 A2 | 6/1998 |
| WO | WO-2003044198 A1 | 5/2003 |
| WO | WO-2006120230 A2 | 11/2006 |
| WO | WO-2007056441 A2 | 5/2007 |
| WO | WO-2009120922 A2 | 10/2009 |
| WO | WO-2012009568 A2 | 1/2012 |
| WO | WO-2012023053 A2 | 2/2012 |
| WO | WO-2014139130 A1 | 9/2014 |
| WO | WO-2016062989 A1 | 4/2016 |
| WO | WO-2017049296 A1 | 3/2017 |

OTHER PUBLICATIONS

Bruggemann et al., (1993). "Designer Mice: The Production of Human Antibody Repertoires in Transgenic Animals," Year in Immunol., 7:33-40.

Chen et al., (1999). "Selection and Analysis of an Optimized Anti-VEGF Antibody: Crystal Structure of an Affinity-matured Fab in Complex with Antigen", J. Mol. Biol., 293:865-881.

Clackson et al., (1991). "Making antibody fragments using phage display libraries," Nature, 352:624-628.

Ericsson et al., (2006). "Thermofluor-based High-Throughput Stability Optimization of Proteins for Structural Studies," Analytical Biochemistry, 357: 289-298.

Fellouse et al., (2004). "Synthetic Antibodies From a Four-Amino-Acid Code: A Dominant Role for Tyrosine in Antigen Recognition," Proc. Nat. Acad. Sci. USA, 101(34):12467-472.

Fischer et al., (2015). "Exploiting light chains for the scalable generation and platform purification of native human bispecific IgG," Nat. Commun., 6(6113):1-12.

Fishwild et al., (1996). "High-avidity human IgGκ monoclonal antibodies from a novel strain of minilocus transgenic mice," Nature Biotechnol., 14:845-851.

Gerngross, (2004). "Advances in the Production of Human Therapeutic Proteins in Yeasts and Filamentous Fungi," Nat. Biotech., 22:1409-1414.

Graham et al., (1977). "Characteristics of a Human Cell Line Transformed by DNA From Human Adenovirus Type 5," J. Gen Virol., 36:59-72.

Ho et al., (2006). "Isolation of anti-CD22 Fv with high affinity by Fv display on human cells," PNAS, 103:9637-9642.

Hongo et al., (1995). "Development and characterization of murine monoclonal antibodies to the latency-associated peptide of transforming growth factor beta 1," Hybridoma, 14(3):253-260.

Jakobovits et al., (1993). "Analysis of homozygous mutant chimeric mice: deletion of the immunoglobulin heavy-chain joining region blocks B-cell development and antibody production," Proc. Nat'l Acad. Sci. USA, 90:2551-5.

Jakobovits et al., (1993). "Germ-line transmission and expression of a human-derived yeast artificial chromosome," Nature, 362:255-258.

James et al., (2003). "Conformational diversity and protein evolution—a 60-year-old hypothesis revisited," Trends Biochem Sci., 28(7):361-8.

Jeong et al., (2007). "APEx 2-hybrid, a quantitative protein-protein interaction assay for antibody discovery and engineering," PNAS, 104: 8247-52.

Kohler et al., (1975). "Continuous Cultures of Fused Cells Secreting Antibody of Predefined Specificity," Nature, 256:495-97.

Lavinder et al., (2009). "High-Throughput Thermal Scanning: A General, Rapid Dye-Binding Thermal Shift Screen for Protein Engineering," J. Am. Chem. Soc., 131:3794-5.

Lee et al., (2004). "Bivalent Antibody Phage Display Mimics Natural Immunoglobulin," J. Immunol. Methods, 284(1-2):119-132.

Lee et al., (2004). "High-affinity Human Antibodies From Phage-Displayed Synthetic Fab Libraries With a Single Framework Scaffold," J. MoL Biol., 340(5):1073-1093.

Lei et al., (1987). "Characterization of the Erwinia Carotovora pelB Gene and Its Product Pectate Lyase," J. Bacteriol., 169:4379-83.

Li et al., (2006). "Optimization of Humanized IgGs in Glycoengineered Pichia Pastoris," Nat. Biotech., 24:210-215.

Lonberg et al., (1994). "Antigen-specific human antibodies from mice comprising four distinct genetic modifications," Nature, 368:856-859.

Lonberg et al., (1995). "Human Antibodies From Transgenic Mice," Intern. Rev. Immunol., 13:65-93.

Marks et al., (1991). "By-passing Immunization. Human Antibodies From V-gene Libraries Displayed on Phage," J. MoL Biol., 222:581-597.

Marks et al., (1992). "By-Passing Immunization: Building High Affinity Human Antibodies by Chain Shuffling," Bio/Technology, 10:779-783.

Mather et al., (1982). "Culture of Testicular Cells in Hormone-Supplemented Serum-Free Medium," Annals N.Y. Acad. Sci., 383:44-68.

Mather, (1980). "Establishment and Characterization of Two Distinct Mouse Testicular Epithelial Cell Lines," Biol. Reprod., 23:243-251.

Mazor et al., (2007). "Isolation of Engineered, Full-Length Antibodies From Libraries Expressed in *Escherichia coli*," Nature Biotechnology, 25:563-5.

Millstein et al., (1983). "Hybrid Hybridomas and Their Use in Immunohistochemistry," Nature, 305:537-40.

Morrison, (1994). "Success in specification," Nature, 368:812-13.

Neuberger, (1996). "Generating high-avidity human Mabs in mice," Nature Biotechnol., 14:826.

Phillips et al., (2011). "The Combined Use of the Thermofluor Assay and ThermoQ Analytical Software for the Determination of Protein Stability and Buffer Optimization as an Aid in Protein Crystallization," Current Protocols in Mol. Biol., 94: 10.28.1-10.28.15.

Sidhu et al., (2004). "Phage-displayed Antibody Libraries of Synthetic Heavy Chain Complementarity Determining Regions," J. MoL Biol., 338(2):299-310.

Skerra et al., (1991). "The Functional Expression of Antibody Fv Fragments in *Ischhuchia coli*: Improved Vectors and a Generally Applicable Purification Technique," Biotechnology, 9: 273-8.

(56) References Cited

OTHER PUBLICATIONS

Speiss et al., (2013). "Bispecific Antibodies With Natural Architecture Produced by Co-Culture of Bacteria Expressing Two Distinct Half-Antibodies," Nat Biotechnol., 31:753-8.
Traunecker et al., (1991). "Bispecific single chain molecules (Janusins) target cytotoxic lymphocytes on HIV infected cells," EMBO J., 10:3655-3659.
Urlaub et al., (1980). "Isolation of Chinese hamster cell mutants deficient in dihydrofolate reductase activity," Proc. Natl. Acad. Sci. USA, 77:4216-20.
Xu et al., (2000). "Diversity in the CDR3 Region of V(H) Is Sufficient for Most Antibody Specificities," Immunity, 13:37-45.
Yang et al., (2016). "Comparison of Biosensor Platforms in the Evaluation of High Affinity Antibody-Antigen Binding Kinetics," Anal. Biochem., 508:78-96.
Yazaki et al., (2004). "Expression of Recombinant Antibodies in Mammalian Cell Lines," Methods in Molecular Biology, 248:255-268.
Chen et al., (2008). "Construction of a Large Phage-Displayed Human Antibody Domain Library with a Scaffold Based On a Newly Identified Highly Soluble, Stable Heavy Chain Variable Domain," J. Mol. Biol., 382:779-789.
Chen et al., (2009). "Construction of a human antibody domain (VH) library," Methods Mol Biol., 525:81-99.
Extended European Search Report and Opinion for European Patent Application No. 17922355.7, dated Mar. 18, 2021, 8 pages.
International Search Report and Written Opinion for International Patent Application No. PCT/CN2017/098299, dated May 24, 2018, 10 pages.
International Search Report and Written Opinion for International Patent Application No. PCT/CN2017/098333, dated May 25, 2018, 10 pages.
Office Action received for Japanese Patent Application No. 2020-510116 dated Aug. 10, 2021, 10 pages.
Office Action received for Japanese Patent Application No. 2020-510115 dated Sep. 14, 2021, 14 pages.
Office Action received for Japanese Patent Application No. 2020-510116 dated Jan. 4, 2022, 4 pages.
Search Report and Written Opinion for Brazilian Patent Application No. 112020003622-6, completed in Aug. 3, 2021, 5 pages.

FIG. 1A

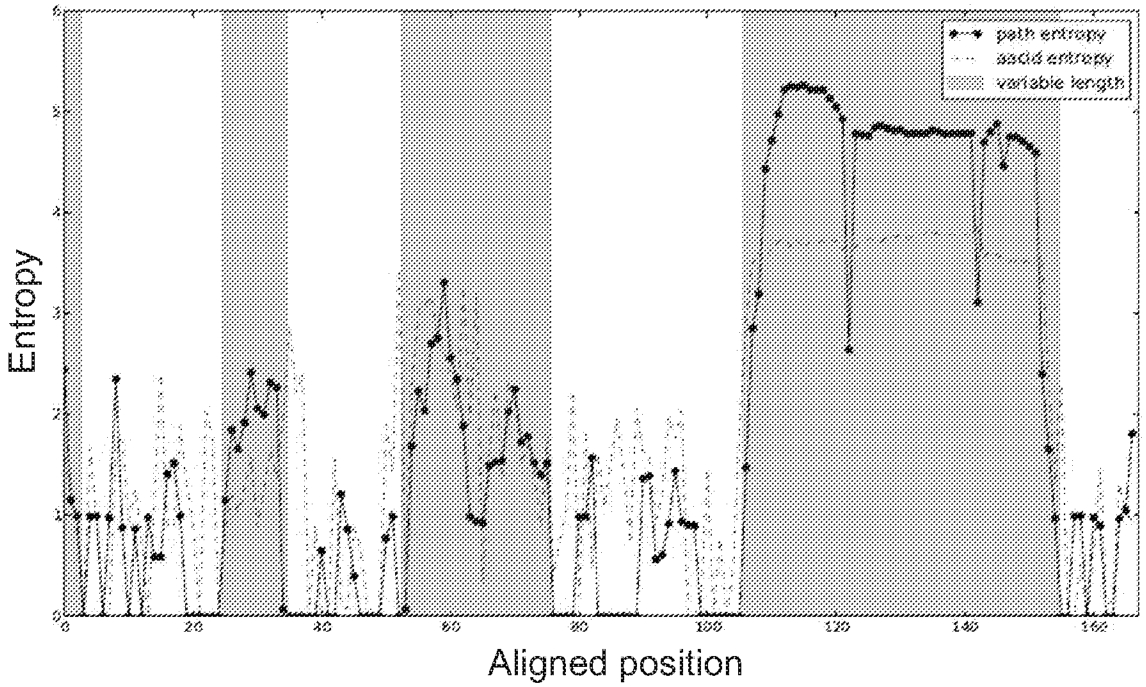

FIG. 1B

```
VH     EVQLVESGGGLVQPGGSLRLSCAASGFTFTSYGIHWVRQAPGKGLEWVSGISGAGDTTYYADSVKGRFTISRDNSKNTLYLQLNSLRAEDTAVYYCARERDYDFDYWGQGTLVTVSS
ADG    <-----------FW_H1---------><---HVR_H1-><---FW_H2-><--------HVR_H2-------><------------FW_H3-----------><-HVR_H3-><--FW_H4-->
VH     EVQLVESGGGLVQPGGSLRLSCAASGFTFTSYGIHWVRQAPGKGLEWVSGISGAGDTTYYADSVKGRFTISRDNSKNTLYLQLNSLRAEDTAVYYCARERDYDFDYWGQGTLVTVSS
Kabat  <-----------FW1-----------><---CDR1--><------FW2-----><-------CDR2------><--------------FW3-------------><-CDR3-><---FW4--->
```

DYNAMIC HUMAN HEAVY CHAIN ANTIBODY LIBRARIES

CROSS REFERENCE TO RELATED APPLICATIONS

This application is a national stage application under 35 U.S.C. § 371 of International Application No. PCT/CN2017/098299, filed internationally on Aug. 21, 2017, the contents of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 695402000200seqlisting.txt, date recorded: Feb. 18, 2020, size: 97 KB).

FIELD OF THE INVENTION

The present disclosure relates to libraries containing synthetic polynucleotides that encode antibody heavy chains (e.g., heavy chains of a dynamic human antibody), as well as antibody heavy chains, antibodies, cells, animals, methods, and kits related thereto.

BACKGROUND

Monoclonal antibodies have become extremely useful in a wide variety of fields, including biological research, medical diagnosis, and pharmaceutical products. The variability of potential binding specificities allows for antibodies with valuable specificity and potency. However, this variability makes it difficult and laborious to screen through a huge number of antibodies to identify one or more with the desired properties.

One method of identifying an antibody of interest is to screen through an antibody library, such as a library of cloned B cell sequences, a phage display library, a yeast display library, and so forth. These libraries allow one to screen through a large number of antibodies, representing a multitude of unique antibody sequences, to identify antibodies with specific properties of interest, e.g., binding to particular target, binding affinity, selectivity, and the like. However, current libraries have particular limitations. Libraries derived from a biological source, such as a human B cell repertoire, are limited to those antibody sequences that can be cloned from the source. Synthetic libraries may include non-naturally occurring sequences as compared to biologically derived libraries, but they too are limited by the amount of antibodies that can be synthesized in a particular timeframe. Further, extremely large libraries require more time-consuming and exhaustive screening approaches; otherwise, only a fraction of the library can practically be screened for an antibody of interest.

Therefore, a need exists for the development of dynamic antibody libraries containing a robust set of dynamic units with well-defined developable sequence profiles for designing and constructing dynamic antibodies that are potentially more relevant functionally. Such libraries would greatly improve not only the diversity of the antibody binding sites on antibodies within the library, but also the efficiency of screening for antibodies harboring novel and/or conformational epitopes on a given antigen. Moreover, such libraries would increase the likelihood with which a particular antibody of interest might be identified with a high affinity and developability profile.

All references cited herein, including patent applications, patent publications, and UniProtKB/Swiss-Prot Accession numbers are herein incorporated by reference in their entirety, as if each individual reference were specifically and individually indicated to be incorporated by reference.

BRIEF SUMMARY

To meet the above and other needs, disclosed herein are antibody sequences, such as heavy chain hypervariable regions (HVRs) and heavy chain variable regions (e.g., $V_H$ regions), that allow for dynamic human antibodies. These sequences were designed to allow for antibodies with highly flexible HVR sequence loops that are able to bind their targets with high potency and/or recognize multiple useful epitopes, and/or cross-react with epitopes shared among different species at low sequence identity (around 60% sequence identity or less). Advantageously, these antibody sequences allow the creation of much smaller libraries that nonetheless contain a multitude of useful antibodies, and/or a much larger diversity at a given library size. Such libraries can be used to identify new antibodies of interest that are specific for a wide range of targets or, in some cases, cross-reactive against multiple targets of interest. Furthermore, a novel concept and methodology is introduced and implemented herein for designing and constructing dynamic antibody libraries using newly identified dynamic units to capture a broad range of conformational flexibility of antibody binding sites in compact physical libraries. Moreover, the results using such antibodies (as described below) highlight the ability to identify antibodies from these libraries which target conformational epitopes and/or evolutionally conserved sites on a given antigen from different species with low sequence identity (e.g., below 60% to 70%).

Accordingly, in one aspect, provided herein are one or more HVR-H1 amino acid sequences, and/or one or more polynucleotides (e.g., synthetic polynucleotides) encoding the same, wherein the HVR-H1 comprises an amino acid sequence according to a formula selected from the group consisting of: Formula (I): X1TFX2X3YX4IHWV (SEQ ID NO:198), wherein X1 is F or Y, X2 is S or T, X3 is D, G, N, or S, and X4 is A, G, or W; Formula (II): YSIX1SGX2X3WX4WI (SEQ ID NO:199), wherein X1 is S or T, X2 is H or Y, X3 is H or Y, and X4 is A, D, G, N, S, or T; and Formula (III): FSLSTX1GVX2VX3WI (SEQ ID NO:200), wherein X1 is G or S, X2 is A or G, and X3 is A, G, S, or T. In some embodiments, the HVR-H1 comprises an amino acid sequence selected from the group consisting of SEQ ID NOS:1-52 and 137-158. In some embodiments, the HVR-H1 comprises an amino acid sequence selected from the group consisting of SEQ ID NOS:1-52.

In another aspect, provided herein are one or more HVR-H2 amino acid sequences, and/or one or more polynucleotides (e.g., synthetic polynucleotides) encoding the same, wherein the HVR-H2 comprises an amino acid sequence according to a formula selected from the group consisting of: Formula (IV): LAX1IX2WX3X4DKX5YSX6SLKSRL (SEQ ID NO:201), wherein X1 is L or R, X2 is D or Y, X3 is A, D, S, or Y, X4 is D or G, X5 is R, S, or Y, and X6 is P or T; Formula (V): IGX1IX2X3SGSTYYSPSLKSRV (SEQ ID NO:202), wherein X1 is A, D, E, S, or Y, X2 is S or Y, and X3 is H or Y; Formula (VI): IGX1IYX2SGX3TX4YNPSLKSRV (SEQ ID NO:203), wherein X1 is D, E, R, S, or Y, X2 is H or Y, X3 is N or S, and X4 is N or Y; Formula (VII): VSX1ISGX2GX3X4TYYADSVKGRF (SEQ ID NO: 204), wherein X1 is A, G, S, V, or Y, X2 is A, D, S, or Y, X3 is D, G, or S, and X4 is S or T; Formula (VIII): IGX1INPNX2GX3TX4YAQKFQGRV (SEQ ID NO:205), wherein X1 is I, R, or W, X2 is F or R, X3 is D, G, or S, and X4 is K or N; Formula (IX): IGX1IX2PSX3GX4TX5YAQKFQGRV (SEQ ID NO:206), wherein X1 is I, R, or W, X2 is S or Y, X3 is G or S, X4 is D, G, or S, and X5 is K or N; and Formula (X): VGRIX1SKX2X3GX4TTX5YAAX6VKGRF (SEQ ID NO: 207), wherein X1 is K or R, X2 is A or T, X3 is D or Y, X4 is G or Y, X5 is D or E, and X6 is P or S. In some embodiments, the HVR-H2 comprises an amino acid sequence according to a formula selected from the group consisting of: Formula (IV); Formula (VII); Formula (VIII); Formula (IX); Formula (XI): IGX1IX2X3SGSTYYSPSLKSRV (SEQ ID NO:208), wherein X1 is A, D, or E, X2 is S or Y, and X3 is H or Y; Formula (XII): IGX1IYX2SGX3TX4YNPSLKSRV (SEQ ID NO:209), wherein X1 is D, E, or S, X2 is H or Y, X3 is N or S, and X4 is N or Y; and Formula (XIII): VGRIX1SKX2X3GX4TTEYAAX5VKGRF (SEQ ID NO:210), wherein X1 is K or R, X2 is A or T, X3 is D or Y, X4 is G or Y, X5 is P or S. In some embodiments, the HVR-H2 comprises an amino acid sequence selected from the group consisting of SEQ ID NOS: 53-136 and 159-164. In some embodiments, the HVR-H2 comprises an amino acid sequence selected from the group consisting of SEQ ID NOS: 53-136.

In another aspect, provided herein are one or more HVR-H3 amino acid sequences, and/or one or more polynucleotides (e.g., synthetic polynucleotides) encoding the same, wherein the HVR-H3 comprises an amino acid sequence selected from the group consisting of SEQ ID NOS:223-256.

In another aspect, provided herein are one or more HVR-L1 amino acid sequences, and/or one or more polynucleotides (e.g., synthetic polynucleotides) encoding the same, wherein the HVR-L1 comprises an amino acid sequence selected from the group consisting of SEQ ID NOS:257-264.

In another aspect, provided herein are one or more HVR-L3 amino acid sequences, and/or one or more polynucleotides (e.g., synthetic polynucleotides) encoding the same, wherein the HVR-L3 comprises an amino acid sequence selected from the group consisting of SEQ ID NOS:265-274.

In another aspect, provided herein is a polynucleotide (e.g., a synthetic polynucleotide) encoding an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III). In some embodiments, provided herein is a library comprising polynucleotides (e.g., synthetic polynucleotides), wherein at least one (e.g., at least one, at least two, at least three, at least four, at least five, at least ten etc.) of the polynucleotides in the library encodes an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III). In some embodiments, provided herein is a library comprising polynucleotides (e.g., synthetic polynucleotides), wherein each of the polynucleotides in the library encodes an antibody heavy chain variable region comprising a HVR-H1, HVR-H2, and a HVR-H3, wherein the HVR-H1 comprises an amino acid sequence according to a formula selected from the group consisting of Formula (I), Formula (II), and Formula (III).

In some embodiments, the HVR-H1 comprises an amino acid sequence selected from the group consisting of SEQ ID NOS: 1-52 and 137-158. In some embodiments, the HVR-H1 comprises an amino acid sequence selected from the group consisting of SEQ ID NOS: 1-52. In some embodiments, the HVR-H1 comprises an amino acid sequence selected from the group consisting of SEQ ID NOs: 1, 4, 5, 7, 8, 9, 11, 13, 16, 18, 19, 20, 21, 22, 23, 24, 25, 26, 27, 28, 31, 33, 34, 38, 40, 42, 43, 45, 47, 49, 50, and 51. In some embodiments, the HVR-H1 comprises an amino acid sequence selected from the group consisting of SEQ ID NOS: 2, 3, 14, 15, 30, 32, 35, 37, 39, 41, 44, 46, and 48. In some embodiments, the HVR-H1 comprises an amino acid sequence selected from the group consisting of SEQ ID NOS: 6, 10, 17, 29, 36, and 52.

In some embodiments that may be combined with any of the preceding embodiments, the heavy chain variable region comprises an HVR-H1, a HVR-H2, and a HVR-H3, wherein the HVR-H3 comprises an amino acid sequence selected from the group consisting of SEQ ID NOS: 223-256.

In some embodiments, the heavy chain variable region further comprises a FW-H1 comprising the amino acid sequence of SEQ ID NO:165. In some embodiments, the heavy chain variable region further comprises a FW-H2 comprising the amino acid sequence of SEQ ID NO:166. In some embodiments, the heavy chain variable region further comprises a FW-H3 comprising the amino acid sequence of SEQ ID NO:167. In some embodiments, the heavy chain variable region further comprises a FW-H4 comprising the amino acid sequence of SEQ ID NO:168. In some embodiments, the heavy chain variable region comprises at least two (e.g., at least two, at least three, or all four) of a FW-H1 comprising the amino acid sequence of SEQ ID NO:165, a FW-H2 comprising the amino acid sequence of SEQ ID NO:166, a FW-H3 comprising the amino acid sequence of SEQ ID NO:167, and a FW-H14 comprising the amino acid sequence of SEQ ID NO:168, in any combination. In some embodiments, the FW-H3 sequence comprises an arginine to lysine mutation at R19 of SEQ ID NO:167.

In another aspect, provided herein is a polynucleotide (e.g., a synthetic polynucleotide) encoding an antibody heavy chain variable region comprising a HVR-H1, a HVR-H2, and a HVR-H3, wherein the HVR-H2 comprises an amino acid sequence according to a formula selected from the group consisting of Formula (IV), Formula (V), Formula (VI), Formula (VII), Formula (VIII), Formula (IX), and Formula (X). In some embodiments, provided herein is a library comprising polynucleotides (e.g., synthetic polynucleotides), wherein at least one (e.g., at least one, at least two, at least three, at least four, at least five, at least ten etc.) of the polynucleotides in the library encodes an antibody heavy chain variable region comprising a HVR-H1, a HVR-H2, and a HVR-H3, wherein the HVR-H2 comprises an amino acid sequence according to a formula selected from the group consisting of Formula (IV), Formula (V), Formula (VI), Formula (VII), Formula (VIII), Formula (IX), and Formula (X). In some embodiments, provided herein is a library comprising polynucleotides (e.g., synthetic polynucleotides), wherein each of the polynucleotides in the library encodes an antibody heavy chain variable region comprising a HVR-H1, HVR-H2, and a HVR-H3, wherein the HVR-H2 comprises an amino acid sequence according to a formula selected from the group consisting of Formula (IV), Formula (V), Formula (VI), Formula (VII), Formula (VIII), Formula (IX), and Formula (X).

In some embodiments, provided herein is a polynucleotide (e.g., a synthetic polynucleotide) encoding an antibody heavy chain variable region comprising a HVR-H1, a HVR-H2, and a HVR-H3, wherein the HVR-H2 comprises an amino acid sequence according to a formula selected from the group consisting of Formula (IV), Formula (VII), Formula (VIII), Formula (IX), Formula (XI), Formula (XII), and Formula (XIII). In some embodiments, provided herein is a library comprising polynucleotides (e.g., synthetic polynucleotides), wherein at least one (e.g., at least one, at least two, at least three, at least four, at least five, at least ten etc.) of the polynucleotides in the library encodes an antibody heavy chain variable region comprising a HVR-H1, a HVR-H2, and a HVR-H3, wherein the HVR-H2 comprises an amino acid sequence according to a formula selected from the group consisting of Formula (IV), Formula (VII), Formula (VIII), Formula (IX), Formula (XI), Formula (XII), and Formula (XIII). In some embodiments, provided herein is a library comprising polynucleotides (e.g., synthetic polynucleotides), wherein each of the polynucleotides in the library encodes an antibody heavy chain variable region comprising a HVR-H1, HVR-H2, and a HVR-H3, wherein the HVR-H2 comprises an amino acid sequence according to a formula selected from the group consisting of Formula (IV), Formula (VII), Formula (VIII), Formula (IX), Formula (XI), Formula (XII), and Formula (XIII).

In some embodiments, the HVR-H2 comprises an amino acid sequence selected from the group consisting of SEQ ID NOS: 53-136 and 159-164. In some embodiments, the HVR-H2 comprises an amino acid sequence selected from the group consisting of SEQ ID NOS: 53-136. In some embodiments, the HVR-H2 comprises an amino acid sequence selected from the group consisting of SEQ ID NOs: 53, 60, 63, 65, 66, 67, 70, 82, 89, 93, 95, 105, 109, 110, 117, 121, 122, 123, 124, 128, 129, 130, 131, 132, and 134. In some embodiments, the HVR-H2 comprises an amino acid sequence selected from the group consisting of SEQ ID NOS: 55, 56, 59, 61, 62, 64, 68, 69, 71, 73, 74, 75, 76, 77, 78, 79, 72, 81, 83, 86, 90, 91, 99, 100, 103, 106, 107, 108, 112, 113, 116, 118, 126, 135, and 136. In some embodiments, the HVR-H2 comprises an amino acid sequence selected from the group consisting of SEQ ID NOS: 54, 57, 58, 80, 84, 85, 87, 88, 92, 94, 96, 97, 98, 101, 102, 104, 111, 114, 115, 119, 120, 125, 127 and 133.

In some embodiments that may be combined with any of the preceding embodiments, the heavy chain variable region comprises an HVR-H1, a HVR-H2, and a HVR-H3, wherein the HVR-H3 comprises an amino acid sequence selected from the group consisting of SEQ ID NOS: 223-256.

In some embodiments, the heavy chain variable region further comprises a FW-H1 comprising the amino acid sequence of SEQ ID NO:165. In some embodiments, the heavy chain variable region further comprises a FW-H2 comprising the amino acid sequence of SEQ ID NO:166. In some embodiments, the heavy chain variable region further comprises a FW-H3 comprising the amino acid sequence of SEQ ID NO:167. In some embodiments, the heavy chain variable region further comprises a FW-H4 comprising the amino acid sequence of SEQ ID NO:168. In some embodiments, the heavy chain variable region comprises at least two (e.g., at least two, at least three, or all four) of a FW-H1 comprising the amino acid sequence of SEQ ID NO:165, a FW-H12 comprising the amino acid sequence of SEQ ID NO:166, a FW-H13 comprising the amino acid sequence of SEQ ID NO:167, and a FW-H14 comprising the amino acid sequence of SEQ ID NO:168, in any combination. In some embodiments, the FW-H13 sequence comprises an arginine to lysine mutation at R19 of SEQ ID NO:167.

In another aspect, provided herein is a polynucleotide (e.g., a synthetic polynucleotide) encoding an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (V), Formula (VI), Formula (VII), Formula (VIII), Formula (IX), and Formula (X). In some embodiments, provided herein is a library comprising polynucleotides (e.g., synthetic polynucleotides), wherein at least one (e.g., at least one, at least two, at least three, at least four, at least five, at least ten etc.) of the polynucleotides in the library encodes an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (V), Formula (VI), Formula (VII), Formula (VIII), Formula (IX), and Formula (X). In some embodiments, provided herein is a library comprising polynucleotides (e.g., synthetic polynucleotides), wherein each of the polynucleotides in the library encodes an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (V), Formula (VI), Formula (VII), Formula (VIII), Formula (IX), and Formula (X).

In some embodiments, provided herein is a polynucleotide (e.g., a synthetic polynucleotide) encoding an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (VII), Formula (VIII), Formula (IX), Formula (XI), Formula (XII), and Formula (XIII). In some embodiments, provided herein is a library comprising polynucleotides (e.g., synthetic polynucleotides), wherein at least one (e.g., at least one, at least two, at least three, at least four, at least five, at least ten etc.) of the polynucleotides in the library encodes an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (VII), Formula (VIII), Formula (IX), Formula (XI), Formula (XII), and Formula (XIII). In some embodiments, provided herein is a library comprising polynucleotides (e.g., synthetic polynucleotides), wherein each of the polynucleotides in the library encodes an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (VII), Formula (VIII), Formula (IX), Formula (XI), Formula (XII), and Formula (XIII).

In some embodiments, the HVR-H1 comprises an amino acid sequence selected from the group consisting of SEQ ID NOS: 1-52 and 137-158. In some embodiments, the HVR-H2 comprises an amino acid sequence selected from the group consisting of SEQ ID NOS: 53-136 and 159-164. In some embodiments, the HVR-H1 comprises an amino acid sequence selected from the group consisting of SEQ ID NOS: 1-52 and 137-158, and the HVR-H2 comprises an amino acid sequence selected from the group consisting of SEQ ID NOS: 53-136 and 159-164. In some embodiments, the HVR-H1 comprises an amino acid sequence selected from the group consisting of SEQ ID NOS: 1-52. In some embodiments, the HVR-H2 comprises an amino acid sequence selected from the group consisting of SEQ ID NOS: 53-136. In some embodiments, the HVR-H1 comprises an amino acid sequence selected from the group consisting of SEQ ID NOS: 1-52, and the HVR-H2 comprises an amino acid sequence selected from the group consisting of SEQ ID NOS: 53-136. In some embodiments, the HVR-H1 comprises an amino acid sequence selected from the group consisting of SEQ ID NOs: 1, 4, 5, 7, 8, 9, 11, 13, 16, 18, 19, 20, 21, 22, 23, 24, 25, 26, 27, 28, 31, 33, 34, 38, 40, 42, 43, 45, 47, 49, 50, and 51, and the HVR-H2 comprises an amino acid sequence selected from the group consisting of SEQ ID NOs: 53, 60, 63, 65, 66, 67, 70, 82, 89, 93, 95, 105, 109, 110, 117, 121, 122, 123, 124, 128, 129, 130, 131, 132, and 134. In some embodiments, the HVR-H1 comprises an amino acid sequence selected from the group consisting of SEQ ID NOs: 2, 3, 14, 15, 30, 32, 35, 37, 39, 41, 44, 46, and 48, and the HVR-H2 comprises an amino acid sequence selected from the group consisting of SEQ ID NOs: 55, 56, 59, 61, 62, 64, 68, 69, 71, 73, 74, 75, 76, 77, 78, 79, 72, 81, 83, 86, 90, 91, 99, 100, 103, 106, 107, 108, 112, 113, 116, 118, 126, 135, and 136. In some embodiments, the HVR-H1 comprises an amino acid sequence selected from the group consisting of SEQ ID NOs: 6, 10, 17, 29, 36, and 52, and the HVR-H2 comprises an amino acid sequence selected from the group consisting of SEQ ID NOs: 54, 57, 58, 80, 84, 85, 87, 88, 92, 94, 96, 97, 98, 101, 102, 104, 111, 114, 115, 119, 120, 125, 127 and 133.

In some embodiments, the heavy chain variable region comprises a HVR-H1, a HVR-H2, and a HVR-H3, wherein the HVR-H1 and HVR-H2 are selected from the group consisting of: a HVR-H1 comprising the amino acid sequence of Formula (II) and a HVR-H2 comprising the amino acid sequence of Formula (IX); a HVR-H1 comprising the amino acid sequence of Formula (II) and a HVR-H2 comprising the amino acid sequence of Formula (VII); a HVR-H1 comprising the amino acid sequence of Formula (I) and a HVR-H2 comprising the amino acid sequence of Formula (VII); a HVR-H1 comprising the amino acid sequence of Formula (I) and a HVR-H2 comprising the amino acid sequence of Formula (IX); a HVR-H1 comprising the amino acid sequence of Formula (II) and a HVR-H2 comprising the amino acid sequence of Formula (W); a HVR-H1 comprising the amino acid sequence of Formula (II) and a HVR-H2 comprising the amino acid sequence of Formula (V); a HVR-H1 comprising the amino acid sequence of Formula (II) and a HVR-H2 comprising the amino acid sequence of Formula (VI); a HVR-H1 comprising the amino acid sequence of Formula (I) and a HVR-H2 comprising the amino acid sequence of Formula (VI); a HVR-H1 comprising the amino acid sequence of Formula (III) and a HVR-H2 comprising the amino acid sequence of Formula (VI); a HVR-H1 comprising the amino acid sequence of Formula (III) and a HVR-H2 comprising the amino acid sequence of Formula (VII); a HVR-H1 comprising the amino acid sequence of Formula (II) and a HVR-H2 comprising the amino acid sequence of Formula (VIII); a HVR-H1 comprising the amino acid sequence of Formula (I) and a HVR-H2 comprising the amino acid sequence of Formula (V); a HVR-H1 comprising the amino acid sequence of Formula (III) and a HVR-H2 comprising the amino acid sequence of Formula (V); and a HVR-H1 comprising the amino acid sequence of Formula (I) and a HVR-H2 comprising the amino acid sequence of Formula (VIII). In some embodiments, the HVR-H1 and HVR-H2 are selected from the group consisting of: a HVR-H1 comprising the amino acid sequence of Formula (II) and a HVR-H2 comprising the amino acid sequence of Formula (XI); a HVR-H1 comprising the amino acid sequence of Formula (II) and a HVR-H2 comprising the amino acid sequence of Formula (XII); a HVR-H1 comprising the amino acid sequence of Formula (I) and a HVR-H2 comprising the amino acid sequence of Formula (XII); a HVR-H1 comprising the amino acid sequence of Formula (III) and a HVR-H2 comprising the amino acid sequence of Formula (XII); a HVR-H1 comprising the amino acid sequence of Formula (I) and a HVR-H2 comprising the amino acid sequence of Formula (XI); and a HVR-H1 comprising the amino acid sequence of Formula (III) and a HVR-H2 comprising the amino acid sequence of Formula (XI). In some embodiments, the HVR-H1 and HVR-H2 are selected from the group consisting of: a HVR-H1 comprising the amino acid sequence of Formula (I) and a HVR-H2 comprising the amino acid sequence of Formula (IV); a HVR-H1 comprising the amino acid sequence of Formula (III) and a HVR-H2 comprising the amino acid sequence of Formula (IV); a HVR-H1 comprising the amino acid sequence of Formula (II) and a HVR-H2 comprising the amino acid sequence of Formula (X); a HVR-H1 comprising the amino acid sequence of Formula (III) and a HVR-H2 comprising the amino acid sequence of Formula (IX); a HVR-H1 comprising the amino acid sequence of Formula (I) and a HVR-H2 comprising the amino acid sequence of Formula (X); a HVR-H1 comprising the amino acid sequence of Formula (III) and a HVR-H2 comprising the amino acid sequence of Formula (VIII); and a HVR-H1 comprising the amino acid sequence of Formula (III) and a HVR-H2 comprising the amino acid sequence of Formula (X). In some embodiments, the HVR-H1 and HVR-H2 are selected from the group consisting of: a HVR-H1 comprising the amino acid sequence of Formula (II) and a HVR-H2 comprising the amino acid sequence of Formula (XIII); a HVR-H1 comprising the amino acid sequence of Formula (I) and a HVR-H2 comprising the amino acid sequence of Formula (XIII); and a HVR-H1 comprising the amino acid sequence of Formula (III) and a HVR-H2 comprising the amino acid sequence of Formula (XIII).

In some embodiments, the heavy chain variable region comprises a HVR-H1, a HVR-H2, and a HVR-H3, wherein the HVR-H1 and HVR-H2 are selected from the group consisting of: a HVR-H1 comprising the amino acid sequence of SEQ ID NO:157, and a HVR-H2 comprising the amino acid sequence of SEQ ID NO:63; a HVR-H1 comprising the amino acid sequence of SEQ ID NO:1, and a HVR-H2 comprising the amino acid sequence of SEQ ID NO:122; a HVR-H1 comprising the amino acid sequence of SEQ ID NO:138, and a HVR-H2 comprising the amino acid sequence of SEQ ID NO:63; a HVR-H1 comprising the amino acid sequence of SEQ ID NO:154, and a HVR-H2 comprising the amino acid sequence of SEQ ID NO:63; a HVR-H1 comprising the amino acid sequence of SEQ ID NO:158, and a HVR-H2 comprising the amino acid sequence of SEQ ID NO:161; a HVR-H1 comprising the amino acid sequence of SEQ ID NO:158, and a HVR-H2 comprising the amino acid sequence of SEQ ID NO:63; a HVR-H1 comprising the amino acid sequence of SEQ ID NO:145, and a HVR-H2 comprising the amino acid sequence of SEQ ID NO:128; a HVR-H1 comprising the amino acid sequence of SEQ ID NO:22, and a HVR-H2 comprising the amino acid sequence of SEQ ID NO:61; a HVR-H1 comprising the amino acid sequence of SEQ ID NO:31, and a HVR-H2 comprising the amino acid sequence of SEQ ID NO:63; a HVR-H1 comprising the amino acid sequence of SEQ ID NO:153, and a HVR-H2 comprising the amino acid sequence of SEQ ID NO:63; a HVR-H1 comprising the amino acid sequence of SEQ ID NO:155, and a HVR-H2 comprising the amino acid sequence of SEQ ID NO:67; a HVR-H1 comprising the amino acid sequence of SEQ ID NO:156, and a HVR-H2 comprising the amino acid sequence of SEQ ID NO:100; a HVR-H1 comprising the amino acid sequence of SEQ ID NO:51, and a HVR-H2 comprising the amino acid sequence of SEQ ID NO:162; a HVR-H1 comprising the amino acid sequence of SEQ ID NO:138, and a HVR-H2 comprising the amino acid sequence of SEQ ID NO:123; a HVR-H1 comprising the amino acid sequence of SEQ ID NO:139, and a HVR-H2 comprising the amino acid sequence of SEQ ID NO:110; a HVR-H1 comprising the amino acid sequence of SEQ ID NO:8, and a HVR-H2 comprising the amino acid sequence of SEQ ID NO:126; a HVR-H1 comprising the amino acid sequence of SEQ ID NO:13, and a HVR-H2 comprising the amino acid sequence of SEQ ID NO:129; a HVR-H1 comprising the amino acid sequence of SEQ ID NO:31, and a HVR-H2 comprising the amino acid sequence of SEQ ID NO:124; a HVR-H1 comprising the amino acid sequence of SEQ ID NO:25, and a HVR-H2 comprising the amino acid sequence of SEQ ID NO:130; a HVR-H1 comprising the amino acid sequence of SEQ ID NO:150, and a HVR-H2 comprising the amino acid sequence of SEQ ID NO:132; a HVR-H1 comprising the amino acid sequence of SEQ ID NO:158, and a HVR-H2 comprising the amino acid sequence of SEQ ID NO:162; a HVR-H1 comprising the amino acid sequence of SEQ ID NO:12, and a HVR-H2 comprising the amino acid sequence of SEQ ID NO:82; a HVR-H1 comprising the amino acid sequence of SEQ ID NO:149, and a HVR-H2 comprising the amino acid sequence of SEQ ID NO:117; and a HVR-H1 comprising the amino acid sequence of SEQ ID NO:7, and a HVR-H2 comprising the amino acid sequence of SEQ ID NO:134. In some embodiments, the HVR-H1 and HVR-H2 are selected from the group consisting of: a HVR-H1 comprising the amino acid sequence of SEQ ID NO:26, and a HVR-H2 comprising the amino acid sequence of SEQ ID NO:53; a HVR-H1 comprising the amino acid sequence of SEQ ID NO:151, and a HVR-H2 comprising the amino acid sequence of SEQ ID NO:53; a HVR-H1 comprising the amino acid sequence of SEQ ID NO:34, and a HVR-H2 comprising the amino acid sequence of SEQ ID NO:63; a HVR-H1 comprising the amino acid sequence of SEQ ID NO:50, and a HVR-H2 comprising the amino acid sequence of SEQ ID NO:162; a HVR-H1 comprising the amino acid sequence of SEQ ID NO:158, and a HVR-H2 comprising the amino acid sequence of SEQ ID NO:104; a HVR-H1 comprising the amino acid sequence of SEQ ID NO:5, and a HVR-H2 comprising the amino acid sequence of SEQ ID NO:121; a HVR-H1 comprising the amino acid sequence of SEQ ID NO:6, and a HVR-H2 comprising the amino acid sequence of SEQ ID NO:116; a HVR-H1 comprising the amino acid sequence of SEQ ID NO:7, and a HVR-H2 comprising the amino acid sequence of SEQ ID NO:121; a HVR-H1 comprising the amino acid sequence of SEQ ID NO:17, and a HVR-H2 comprising the amino acid sequence of SEQ ID NO:63; a HVR-H1 comprising the amino acid sequence of SEQ ID NO:25, and a HVR-H2 comprising the amino acid sequence of SEQ ID NO:101; a HVR-H1 comprising the amino acid sequence of SEQ ID NO:25, and a HVR-H2 comprising the amino acid sequence of SEQ ID NO:114; a HVR-H1 comprising the amino acid sequence of SEQ ID NO:29, and a HVR-H2 comprising the amino acid sequence of SEQ ID NO:112; a HVR-H1 comprising the amino acid sequence of SEQ ID NO:152, and a HVR-H2 comprising the amino acid sequence of SEQ ID NO:63; a HVR-H1 comprising the amino acid sequence of SEQ ID NO:156, and a HVR-H2 comprising the amino acid sequence of SEQ ID NO:89; a HVR-H1 comprising the amino acid sequence of SEQ ID NO:157, and a HVR-H2 comprising the amino acid sequence of SEQ ID NO:94; a HVR-H1 comprising the amino acid sequence of SEQ ID NO:48, and a HVR-H2 comprising the amino acid sequence of SEQ ID NO:58; a HVR-H1 comprising the amino acid sequence of SEQ ID NO:50, and a HVR-H2 comprising the amino acid sequence of SEQ ID NO:89; a HVR-H1 comprising the amino acid sequence of SEQ ID NO:50, and a HVR-H2 comprising the amino acid sequence of SEQ ID NO:163; a HVR-H1 comprising the amino acid sequence of SEQ ID NO:158, and a HVR-H2 comprising the amino acid sequence of SEQ ID NO:160; a HVR-H1 comprising the amino acid sequence of SEQ ID NO:158, and a HVR-H2 comprising the amino acid sequence of SEQ ID NO:87; a HVR-H1 comprising the amino acid sequence of SEQ ID NO:158, and a HVR-H2 comprising the amino acid sequence of SEQ ID NO:92; a HVR-H1 comprising the amino acid sequence of SEQ ID NO:158, and a HVR-H2 comprising the amino acid sequence of SEQ ID NO:93; a HVR-H1 comprising the amino acid sequence of SEQ ID NO:158, and a HVR-H2 comprising the amino acid sequence of SEQ ID NO:97; a HVR-H1 comprising the amino acid sequence of SEQ ID NO:158, and a HVR-H2 comprising the amino acid sequence of SEQ ID NO:103; a HVR-H1 comprising the amino acid sequence of SEQ ID NO:158, and a HVR-H2 comprising the amino acid sequence of SEQ ID NO:164; a HVR-H1 comprising the amino acid sequence of SEQ ID NO:137, and a HVR-H2 comprising the amino acid sequence of SEQ ID NO:54; a HVR-H1 comprising the amino acid sequence of SEQ ID NO:3, and a HVR-H2 comprising the amino acid sequence of SEQ ID NO:127; a HVR-H1 comprising the amino acid sequence of SEQ ID NO:4, and a HVR-H2 comprising the amino acid sequence of SEQ ID NO:85; a HVR-H1 comprising the amino acid sequence of SEQ ID NO:4, and a HVR-H2 comprising the amino acid sequence of SEQ ID NO:110; a HVR-H1 comprising the amino acid sequence of SEQ ID NO:139, and a HVR-H2 comprising the amino acid sequence of SEQ ID NO:109; a HVR-H1 comprising the amino acid sequence of SEQ ID NO:139, and a HVR-H2 comprising the amino acid sequence of SEQ ID NO:121; a HVR-H1 comprising the amino acid sequence of SEQ ID NO:8, and a HVR-H2 comprising the amino acid sequence of SEQ ID NO:120; a HVR-H1 comprising the amino acid sequence of SEQ ID NO:140, and a HVR-H2 comprising the amino acid sequence of SEQ ID NO:131; a HVR-H1 comprising the amino acid sequence of SEQ ID NO:141, and a HVR-H2 comprising the amino acid sequence of SEQ ID NO:116; a HVR-H1 comprising the amino acid sequence of SEQ ID NO:142, and a HVR-H2 comprising the amino acid sequence of SEQ ID NO:159; a HVR-H1 comprising the amino acid sequence of SEQ ID NO:143, and a HVR-H2 comprising the amino acid sequence of SEQ ID NO:116; a HVR-H1 comprising the amino acid sequence of SEQ ID NO:144, and a HVR-H2 comprising the amino acid sequence of SEQ ID NO:121; a HVR-H1 comprising the amino acid sequence of SEQ ID NO:146, and a HVR-H2 comprising the amino acid sequence of SEQ ID NO:110; a HVR-H1 comprising the amino acid sequence of SEQ ID NO:147, and a HVR-H2 comprising the amino acid sequence of SEQ ID NO:133; a HVR-H1 comprising the amino acid sequence of SEQ ID NO:148, and a HVR-H2 comprising the amino acid sequence of SEQ ID NO:63; and a HVR-H1 comprising the amino acid sequence of SEQ ID NO:13, and a HVR-H2 comprising the amino acid sequence of SEQ ID NO:118.

In some embodiments that may be combined with any of the preceding embodiments, the polynucleotides in the library contain less than about $6.5*10^4$ (e.g., less than about $6.5*10^4$, less than about $5.5*10^4$, less than about $2.5*10^4$, less than about $1*10^4$, less than about 6700, less than about 6660, less than about 5000, less than about 2500, less than about 1000, less than about 690, less than about 500, less than about 100, less than about 50, etc.) unique combinations of HVR-H1 and HVR-H2 sequences. In some embodiments, the polynucleotides in the library (e.g., synthetic polynucleotides) contain about 62272 or less unique combinations of HVR-H1 and HVR-H2 sequences. In some embodiments, the polynucleotides in the library (e.g., synthetic polynucleotides) contain about 60928 or less unique combinations of HVR-H1 and HVR-H2 sequences. In some embodiments, the polynucleotides in the library (e.g., synthetic polynucleotides) contain about 54656 or less unique combinations of HVR-H1 and HVR-H2 sequences. In some embodiments, the polynucleotides in the library (e.g., synthetic polynucleotides) contain about 6660 or less unique combinations of HVR-H1 and HVR-H2 sequences. In some embodiments, the polynucleotides in the library (e.g., synthetic polynucleotides) contain about 690 or less unique combinations of HVR-H1 and HVR-H2 sequences. In some embodiments, at least one of the HVR-H1 and HVR-H2 of the antibody heavy chain variable region adopts multiple conformations, as assayed by structural determination and/or computational modeling.

In some embodiments that may be combined with any of the preceding embodiments, the heavy chain variable region comprises an HVR-H1, a HVR-H2, and a HVR-H3, wherein the HVR-H3 comprises an amino acid sequence selected from the group consisting of SEQ ID NOS: 223-256.

In some embodiments, the heavy chain variable region further comprises a FW-H1 comprising the amino acid sequence of SEQ ID NO:165. In some embodiments, the heavy chain variable region further comprises a FW-H2 comprising the amino acid sequence of SEQ ID NO:166. In some embodiments, the heavy chain variable region further comprises a FW-H3 comprising the amino acid sequence of SEQ ID NO:167. In some embodiments, the heavy chain variable region further comprises a FW-H4 comprising the amino acid sequence of SEQ ID NO:168. In some embodiments, the heavy chain variable region comprises at least two (e.g., at least two, at least three, or all four) of a FW-H1 comprising the amino acid sequence of SEQ ID NO:165, a FW-H12 comprising the amino acid sequence of SEQ ID NO:166, a FW-H13 comprising the amino acid sequence of SEQ ID NO:167, and a FW-H14 comprising the amino acid sequence of SEQ ID NO:168, in any combination. In some embodiments, the FW-H13 sequence comprises an arginine to lysine mutation at R19 of SEQ ID NO:167. In some embodiments, the heavy chain variable region comprises a sequence selected from the group consisting of SEQ ID NOs: 169, 171, 173, 175, 177, 179, 181, 183, 185, 187, 189, 191, 193, and 195.

In some embodiments, the polynucleotides in the library encode full-length antibody heavy chains. In some embodiments, the libraries further comprise one or more polynucleotides (e.g., synthetic polynucleotides) that encode antibody light chain variable regions. In some embodiments, the antibody light chain variable regions comprise a HVR-L1, a HVR-L2 and a HVR-L3, wherein the HVR-L1 comprises an amino acid sequence selected from the group consisting of SEQ ID NOs: 257-264 and/or the HVR-L3 comprises an amino acid sequence selected from the group consisting of SEQ ID NOs: 265-274. In some embodiments, the polynucleotides that encode antibody light chain variable regions include at least one unique sequence, at least 100 unique sequences, at least 280 unique sequences, at least $10^3$ unique sequences, at least $10^4$ unique sequences, at least $10^5$ unique sequences, at least $10^6$ unique sequences, at least $10^7$ unique sequences, at least $10^8$ unique sequences, or least about $10^9$ unique sequences. In some embodiments, the one or more polynucleotides in the library that encodes antibody light chain variable regions encode full-length antibody light chains.

In another aspect, provided herein are polynucleotides (e.g., synthetic polynucleotides) encoding a plurality of unique antibodies, wherein each antibody comprises a heavy chain variable region and a light chain variable region, wherein the heavy chain variable region of each antibody of the plurality comprises an identical sequence and is encoded by any of the polynucleotides encoding a heavy chain variable region as described above. In some embodiments, provided herein are libraries comprising polynucleotides (e.g., synthetic polynucleotides) encoding a plurality of unique antibodies, wherein each antibody comprises a heavy chain variable region and a light chain variable region, wherein the heavy chain variable region of each antibody of the plurality comprises an identical sequence and is encoded by any of the polynucleotides encoding a heavy chain variable region as described above In some embodiments, the light chain variable regions comprise a HVR-L1, a HVR-L2 and a HVR-L3, wherein the HVR-L1 comprises an amino acid sequence selected from the group consisting of SEQ ID NOs: 257-264 and/or the HVR-L3 comprises an amino acid sequence selected from the group consisting of SEQ ID NOs: 265-274. In some embodiments, the light chain variable regions of the antibodies in the library include at least one unique sequence, at least 100 unique sequences, at least 280 unique sequences, at least $10^3$ unique sequences, at least $10^4$ unique sequences, at least $10^5$ unique sequences, at least $10^6$ unique sequences, at least $10^7$ unique sequences, at least $10^8$ unique sequences, or least about $10^9$ unique sequences.

In another aspect, provided herein is a vector comprising any of the polynucleotides as described above. In some embodiments, provided herein is a library comprising vectors, wherein at least one (e.g., at least one, at least two, at least five, at least 10, at least 25, at least 50, at least 100, at least 250, at least 500, at least 690, at least 750, at least 1000, at least 2500, at least 5000, at least 6000, at least 6500, etc.)

of the vectors in the library comprises any of the polynucleotides as described above. In some embodiments, at least two of the vectors in the library comprise a polynucleotide as described above. In some embodiments, at least 100 of the vectors in the library comprise a polynucleotide as described above. In some embodiments, at least 500 of the vectors in the library comprise a polynucleotide as described above. In some embodiments, at least 1000 of the vectors in the library comprise a polynucleotide as described above. In some embodiments, at least 5000 of the vectors in the library comprise a polynucleotide as described above. In some embodiments, at least 6500 of the vectors in the library comprise a polynucleotide as described above. In some embodiments, provided herein is a library comprising vectors, wherein each of the vectors in the library comprises any of the polynucleotides as described above. In some embodiments, the vector is an expression vector. In some embodiments, the vector is a display vector. In some embodiments, the library comprising vectors further comprises at least one (e.g., at least one, at least two, at least five, at least 10, at least 25, at least 50, at least 100, at least 250, at least 500, at least 690, at least 750, at least 1000, at least 2500, at least 5000, at least 6000, at least 6500, etc.) vector that encodes a light chain variable region polypeptide. In some embodiments, the light chain variable regions comprise a HVR-L1, a HVR-L2 and a HVR-L3, wherein the HVR-L1 comprises an amino acid sequence selected from the group consisting of SEQ ID NOs: 257-264 and/or the HVR-L3 comprises an amino acid sequence selected from the group consisting of SEQ ID NOs: 265-274. In some embodiments, the at least one vector in the library encodes light chain variable regions which include at least one unique sequence, at least 100 unique sequences, at least 280 unique sequences, at least $10^3$ unique sequences, at least $10^4$ unique sequences, at least $10^5$ unique sequences, at least $10^6$ unique sequences, at least $10^7$ unique sequences, at least $10^8$ unique sequences, or least about $10^9$ unique sequences.

In another aspect, provided herein is a cell comprising any of the polynucleotides and/or vectors as described above. In some embodiments, provided herein is a library comprising a population of cells, wherein at least one (e.g., at least one, at least two, at least five, at least 10, at least 100, at least $10^3$, at least $10^4$, at least $10^5$, at least $10^6$, at least $10^7$, at least $10^8$, at least $10^9$, etc.) of the cells in the library comprises any of the polynucleotides and/or vectors as described above. In some embodiments, at least two of the cells in the library comprise a polynucleotide and/or vector as described above. In some embodiments, at least 100 of the cells in the library comprise a polynucleotide and/vector as described above. In some embodiments, provided herein is a library comprising a population of cells, wherein each of the cells in the library comprises any of the polynucleotides and/or vectors as described above. In some embodiments, the cell is a bacterial, yeast, or mammalian cell (e.g., non-human animal cells or isolated human cells).

In another aspect, provided herein is an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III). In some embodiments, provided herein is a library comprising antibody heavy chain variable regions, wherein at least one (e.g., at least one, at least two, at least three, at least four, at least five, at least ten etc.) of the heavy chain variable regions in the library comprises a HVR-H1, a HVR-H2, and a HVR-H3, wherein the HVR-H1 comprises an amino acid sequence according to a formula selected from the group consisting of Formula (I), Formula (II), and Formula (III). In some embodiments, provided herein is a library comprising antibody heavy chain variable regions, wherein each of the heavy chain variable regions in the library comprises a HVR-H1, HVR-H2, and a HVR-H3, wherein the HVR-H1 comprises an amino acid sequence according to a formula selected from the group consisting of Formula (I), Formula (II), and Formula (III).

In some embodiments, the HVR-H1 comprises an amino acid sequence selected from the group consisting of SEQ ID NOS: 1-52 and 137-158. In some embodiments, the HVR-H1 comprises an amino acid sequence selected from the group consisting of SEQ ID NOS: 1-52. In some embodiments, the HVR-H1 comprises an amino acid sequence selected from the group consisting of SEQ ID NOs: 1, 4, 5, 7, 8, 9, 11, 13, 16, 18, 19, 20, 21, 22, 23, 24, 25, 26, 27, 28, 31, 33, 34, 38, 40, 42, 43, 45, 47, 49, 50, and 51. In some embodiments, the HVR-H1 comprises an amino acid sequence selected from the group consisting of SEQ ID NOS: 2, 3, 14, 15, 30, 32, 35, 37, 39, 41, 44, 46, and 48. In some embodiments, the HVR-H1 comprises an amino acid sequence selected from the group consisting of SEQ ID NOS: 6, 10, 17, 29, 36, and 52.

In some embodiments that may be combined with any of the preceding embodiments, the heavy chain variable region comprises an HVR-H1, a HVR-H2, and a HVR-H3, wherein the HVR-H3 comprises an amino acid sequence selected from the group consisting of SEQ ID NOS: 223-256.

In some embodiments, the heavy chain variable region further comprises a FW-H1 comprising the amino acid sequence of SEQ ID NO:165. In some embodiments, the heavy chain variable region further comprises a FW-112 comprising the amino acid sequence of SEQ ID NO:166. In some embodiments, the heavy chain variable region further comprises a FW-113 comprising the amino acid sequence of SEQ ID NO:167. In some embodiments, the heavy chain variable region further comprises a FW-114 comprising the amino acid sequence of SEQ ID NO:168. In some embodiments, the heavy chain variable region comprises at least two (e.g., at least two, at least three, or all four) of a FW-H1 comprising the amino acid sequence of SEQ ID NO:165, a FW-H12 comprising the amino acid sequence of SEQ ID NO:166, a FW-H13 comprising the amino acid sequence of SEQ ID NO:167, and a FW-H14 comprising the amino acid sequence of SEQ ID NO:168, in any combination. In some embodiments, the FW-H13 sequence comprises an arginine to lysine mutation at R19 of SEQ ID NO:167.

In another aspect, provided herein is an antibody heavy chain variable region comprising a HVR-H1, a HVR-H2, and a HVR-H3, wherein the HVR-H2 comprises an amino acid sequence according to a formula selected from the group consisting of Formula (IV), Formula (V), Formula (VI), Formula (VII), Formula (VIII), Formula (IX), and Formula (X). In some embodiments, provided herein is a library comprising antibody heavy chain variable regions, wherein at least one (e.g., at least one, at least two, at least three, at least four, at least five, at least ten etc.) of the heavy chain variable regions in the library comprises a HVR-H1, a HVR-H2, and a HVR-H3, wherein the HVR-H2 comprises an amino acid sequence according to a formula selected from the group consisting of Formula (IV), Formula (V), Formula (VI), Formula (VII), Formula (VIII), Formula (IX), and Formula (X). In some embodiments, provided herein is a library comprising antibody heavy chain variable regions, wherein each of the heavy chain variable regions in the library comprises a HVR-H1, HVR-H2, and a HVR-H3, wherein the HVR-H2 comprises an amino acid sequence according to a formula selected from the group consisting of Formula (IV), Formula (V), Formula (VI), Formula (VII), Formula (VIII), Formula (IX), and Formula (X).

In some embodiments, provided herein is an antibody heavy chain variable region comprising a HVR-H1, a HVR-H2, and a HVR-H3, wherein the HVR-H2 comprises an amino acid sequence according to a formula selected from the group consisting of Formula (IV), Formula (VII), Formula (VIII), Formula (IX), Formula (XI), Formula (XII), and Formula (XIII). In some embodiments, provided herein is a library comprising antibody heavy chain variable regions, wherein at least one (e.g., at least one, at least two, at least three, at least four, at least five, at least ten etc.) of the heavy chain variable regions in the library comprises a HVR-H1, a HVR-H2, and a HVR-H3, wherein the HVR-H2 comprises an amino acid sequence according to a formula selected from the group consisting of Formula (IV), Formula (VII), Formula (VIII), Formula (IX), Formula (XI), Formula (XII), and Formula (XIII). In some embodiments, provided herein is a library comprising antibody heavy chain variable regions, wherein each of the heavy chain variable regions in the library comprises a HVR-H1, HVR-H2, and a HVR-H3, wherein the HVR-H2 comprises an amino acid sequence according to a formula selected from the group consisting of Formula (IV), Formula (VII), Formula (VIII), Formula (IX), Formula (XI), Formula (XII), and Formula (XIII).

In some embodiments, the HVR-H2 comprises an amino acid sequence selected from the group consisting of SEQ ID NOS: 53-136 and 159-164. In some embodiments, the HVR-H2 comprises an amino acid sequence selected from the group consisting of SEQ ID NOS: 53-136. In some embodiments, the HVR-H2 comprises an amino acid sequence selected from the group consisting of SEQ ID NOs: 53, 60, 63, 65, 66, 67, 70, 82, 89, 93, 95, 105, 109, 110, 117, 121, 122, 123, 124, 128, 129, 130, 131, 132, and 134. In some embodiments, the HVR-H2 comprises an amino acid sequence selected from the group consisting of SEQ ID NOS: 55, 56, 59, 61, 62, 64, 68, 69, 71, 73, 74, 75, 76, 77, 78, 79, 72, 81, 83, 86, 90, 91, 99, 100, 103, 106, 107, 108, 112, 113, 116, 118, 126, 135, and 136. In some embodiments, the HVR-H2 comprises an amino acid sequence selected from the group consisting of SEQ ID NOS: 54, 57, 58, 80, 84, 85, 87, 88, 92, 94, 96, 97, 98, 101, 102, 104, 111, 114, 115, 119, 120, 125, 127 and 133.

In some embodiments that may be combined with any of the preceding embodiments, the heavy chain variable region comprises an HVR-H1, a HVR-H2, and a HVR-H3, wherein the HVR-H3 comprises an amino acid sequence selected from the group consisting of SEQ ID NOS: 223-256.

In some embodiments, the heavy chain variable region further comprises a FW-H1 comprising the amino acid sequence of SEQ ID NO:165. In some embodiments, the heavy chain variable region further comprises a FW-112 comprising the amino acid sequence of SEQ ID NO:166. In some embodiments, the heavy chain variable region further comprises a FW-H3 comprising the amino acid sequence of SEQ ID NO:167. In some embodiments, the heavy chain variable region further comprises a FW-H4 comprising the amino acid sequence of SEQ ID NO:168. In some embodiments, the heavy chain variable region comprises at least two (e.g., at least two, at least three, or all four) of a FW-H1 comprising the amino acid sequence of SEQ ID NO:165, a FW-H12 comprising the amino acid sequence of SEQ ID NO:166, a FW-H13 comprising the amino acid sequence of SEQ ID NO:167, and a FW-H14 comprising the amino acid sequence of SEQ ID NO:168, in any combination. In some embodiments, the FW-H13 sequence comprises an arginine to lysine mutation at R19 of SEQ ID NO:167.

In another aspect, provided herein is an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (V), Formula (VI), Formula (VII), Formula (VIII), Formula (IX), and Formula (X). In some embodiments, provided herein is a library comprising antibody heavy chain variable regions, wherein at least one (e.g., at least one, at least two, at least three, at least four, at least five, at least ten etc.) of the heavy chain variable regions in the library comprises a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (V), Formula (VI), Formula (VII), Formula (VIII), Formula (IX), and Formula (X). In some embodiments, provided herein is a library comprising antibody heavy chain variable regions, wherein each of the heavy chain variable regions in the library comprises a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (V), Formula (VI), Formula (VII), Formula (VIII), Formula (IX), and Formula (X).

In some embodiments, provided herein is an antibody heavy chain variable region comprising a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (VII), Formula (VIII), Formula (IX), Formula (XI), Formula (XII), and Formula (XIII). In some embodiments, provided herein is a library comprising antibody heavy chain variable regions, wherein at least one (e.g., at least one, at least two, at least three, at least four, at least five, at least ten etc.) of the heavy chain variable regions in the library comprises a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (VII), Formula (VIII), Formula (IX), Formula (XI), Formula (XII), and Formula (XIII). In some embodiments, provided herein is a library comprising antibody heavy chain variable regions, wherein each of the heavy chain variable regions in the library comprises a HVR-H1, a HVR-H2, and a HVR-H3, wherein the HVR-H1 comprises an amino acid sequence according to a formula selected from the group consisting of Formula (I), Formula (II), and Formula (III), and wherein the HVR-H2 comprises an amino acid sequence according to a formula selected from the group consisting of Formula (IV), Formula (VII), Formula (VIII), Formula (IX), Formula (XI), Formula (XII), and Formula (XIII).

In some embodiments, the HVR-H1 comprises an amino acid sequence selected from the group consisting of SEQ ID NOS: 1-52 and 137-158. In some embodiments, the HVR-H2 comprises an amino acid sequence selected from the group consisting of SEQ ID NOS: 53-136 and 159-164. In some embodiments, the HVR-H1 comprises an amino acid sequence selected from the group consisting of SEQ ID NOS: 1-52 and 137-158, and the HVR-H2 comprises an amino acid sequence selected from the group consisting of SEQ ID NOS: 53-136 and 159-164. In some embodiments, the HVR-H1 comprises an amino acid sequence selected from the group consisting of SEQ ID NOS: 1-52. In some embodiments, the HVR-H2 comprises an amino acid sequence selected from the group consisting of SEQ ID NOS: 53-136. In some embodiments, the HVR-H1 comprises an amino acid sequence selected from the group consisting of SEQ ID NOS: 1-52, and the HVR-H2 comprises an amino acid sequence selected from the group consisting of SEQ ID NOS: 53-136. In some embodiments, the HVR-H1 comprises an amino acid sequence selected from the group consisting of SEQ ID NOs: 1, 4, 5, 7, 8, 9, 11, 13, 16, 18, 19, 20, 21, 22, 23, 24, 25, 26, 27, 28, 31, 33, 34, 38, 40, 42, 43, 45, 47, 49, 50, and 51, and the HVR-H2 comprises an amino acid sequence selected from the group consisting of SEQ ID NOs: 53, 60, 63, 65, 66, 67, 70, 82, 89, 93, 95, 105, 109, 110, 117, 121, 122, 123, 124, 128, 129, 130, 131, 132, and 134. In some embodiments, the HVR-H1 comprises an amino acid sequence selected from the group consisting of SEQ ID NOs: 2, 3, 14, 15, 30, 32, 35, 37, 39, 41, 44, 46, and 48, and the HVR-H2 comprises an amino acid sequence selected from the group consisting of SEQ ID NOs: 55, 56, 59, 61, 62, 64, 68, 69, 71, 73, 74, 75, 76, 77, 78, 79, 72, 81, 83, 86, 90, 91, 99, 100, 103, 106, 107, 108, 112, 113, 116, 118, 126, 135, and 136. In some embodiments, the HVR-H1 comprises an amino acid sequence selected from the group consisting of SEQ ID NOs: 6, 10, 17, 29, 36, and 52, and the HVR-H2 comprises an amino acid sequence selected from the group consisting of SEQ ID NOs: 54, 57, 58, 80, 84, 85, 87, 88, 92, 94, 96, 97, 98, 101, 102, 104, 111, 114, 115, 119, 120, 125, 127 and 133.

In some embodiments, the heavy chain variable region comprises a HVR-H1, a HVR-H2, and a HVR-H3, wherein the HVR-H1 and HVR-H2 are selected from the group consisting of: a HVR-H1 comprising the amino acid sequence of Formula (II) and a HVR-H2 comprising the amino acid sequence of Formula (IX); a HVR-H1 comprising the amino acid sequence of Formula (II) and a HVR-H2 comprising the amino acid sequence of Formula (VII); a HVR-H1 comprising the amino acid sequence of Formula (I) and a HVR-H2 comprising the amino acid sequence of Formula (VII); a HVR-H1 comprising the amino acid sequence of Formula (I) and a HVR-H2 comprising the amino acid sequence of Formula (IX); a HVR-H1 comprising the amino acid sequence of Formula (II) and a HVR-H2 comprising the amino acid sequence of Formula (W); a HVR-H1 comprising the amino acid sequence of Formula (II) and a HVR-H2 comprising the amino acid sequence of Formula (V); a HVR-H1 comprising the amino acid sequence of Formula (II) and a HVR-H2 comprising the amino acid sequence of Formula (VI); a HVR-H1 comprising the amino acid sequence of Formula (I) and a HVR-H2 comprising the amino acid sequence of Formula (VI); a HVR-H1 comprising the amino acid sequence of Formula (III) and a HVR-H2 comprising the amino acid sequence of Formula (VI); a HVR-H1 comprising the amino acid sequence of Formula (III) and a HVR-H2 comprising the amino acid sequence of Formula (VII); a HVR-H1 comprising the amino acid sequence of Formula (II) and a HVR-H2 comprising the amino acid sequence of Formula (VIII); a HVR-H1 comprising the amino acid sequence of Formula (I) and a HVR-H2 comprising the amino acid sequence of Formula (V); a HVR-H1 comprising the amino acid sequence of Formula (III) and a HVR-H2 comprising the amino acid sequence of Formula (V); and a HVR-H1 comprising the amino acid sequence of Formula (I) and a HVR-H2 comprising the amino acid sequence of Formula (VIII). In some embodiments, the HVR-H1 and HVR-H2 are selected from the group consisting of: a HVR-H1 comprising the amino acid sequence of Formula (II) and a HVR-H2 comprising the amino acid sequence of Formula (XI); a HVR-H1 comprising the amino acid sequence of Formula (II) and a HVR-H2 comprising the amino acid sequence of Formula (XII); a HVR-H1 comprising the amino acid sequence of Formula (I) and a HVR-H2 comprising the amino acid sequence of Formula (XII); a HVR-H1 comprising the amino acid sequence of Formula (III) and a HVR-H2 comprising the amino acid sequence of Formula (XII); a HVR-H1 comprising the amino acid sequence of Formula (I) and a HVR-H2 comprising the amino acid sequence of Formula (XI); and a HVR-H1 comprising the amino acid sequence of Formula (III) and a HVR-H2 comprising the amino acid sequence of Formula (XI). In some embodiments, the HVR-H1 and HVR-H2 are selected from the group consisting of: a HVR-H1 comprising the amino acid sequence of Formula (I) and a HVR-H2 comprising the amino acid sequence of Formula (IV); a HVR-H1 comprising the amino acid sequence of Formula (III) and a HVR-H2 comprising the amino acid sequence of Formula (IV); a HVR-H1 comprising the amino acid sequence of Formula (II) and a HVR-H2 comprising the amino acid sequence of Formula (X); a HVR-H1 comprising the amino acid sequence of Formula (III) and a HVR-H2 comprising the amino acid sequence of Formula (IX); a HVR-H1 comprising the amino acid sequence of Formula (I) and a HVR-H2 comprising the amino acid sequence of Formula (X); a HVR-H1 comprising the amino acid sequence of Formula (III) and a HVR-H2 comprising the amino acid sequence of Formula (VIII); and a HVR-H1 comprising the amino acid sequence of Formula (III) and a HVR-H2 comprising the amino acid sequence of Formula (X). In some embodiments, the HVR-H1 and HVR-H2 are selected from the group consisting of: a HVR-H1 comprising the amino acid sequence of Formula (II) and a HVR-H2 comprising the amino acid sequence of Formula (XIII); a HVR-H1 comprising the amino acid sequence of Formula (I) and a HVR-H2 comprising the amino acid sequence of Formula (XIII); and a HVR-H1 comprising the amino acid sequence of Formula (III) and a HVR-H2 comprising the amino acid sequence of Formula (XIII).

In some embodiments, the heavy chain variable region comprises a HVR-H1, a HVR-H2, and a HVR-H3, wherein the HVR-H1 and HVR-H2 are selected from the group consisting of: a HVR-H1 comprising the amino acid sequence of SEQ ID NO:157, and a HVR-H2 comprising the amino acid sequence of SEQ ID NO:63; a HVR-H1 comprising the amino acid sequence of SEQ ID NO:1, and a HVR-H2 comprising the amino acid sequence of SEQ ID NO:122; a HVR-H1 comprising the amino acid sequence of SEQ ID NO:138, and a HVR-H2 comprising the amino acid sequence of SEQ ID NO:63; a HVR-H1 comprising the amino acid sequence of SEQ ID NO:154, and a HVR-H2 comprising the amino acid sequence of SEQ ID NO:63; a HVR-H1 comprising the amino acid sequence of SEQ ID NO:158, and a HVR-H2 comprising the amino acid sequence of SEQ ID NO:161; a HVR-H1 comprising the amino acid sequence of SEQ ID NO:158, and a HVR-H2 comprising the amino acid sequence of SEQ ID NO:63; a HVR-H1 comprising the amino acid sequence of SEQ ID NO:145, and a HVR-H2 comprising the amino acid sequence of SEQ ID NO:128; a HVR-H1 comprising the amino acid sequence of SEQ ID NO:22, and a HVR-H2 comprising the amino acid sequence of SEQ ID NO:61; a HVR-H1 comprising the amino acid sequence of SEQ ID NO:31, and a HVR-H2 comprising the amino acid sequence of SEQ ID NO:63; a HVR-H1 comprising the amino acid sequence of SEQ ID NO:153, and a HVR-H2 comprising the amino acid sequence of SEQ ID NO:63; a HVR-H1 comprising the amino acid sequence of SEQ ID NO:155, and a HVR-H2 comprising the amino acid sequence of SEQ ID NO:67; a HVR-H1 comprising the amino acid sequence of SEQ ID NO:156, and a HVR-H2 comprising the amino acid sequence of SEQ ID NO:100; a HVR-H1 comprising the amino acid sequence of SEQ ID NO:51, and a HVR-H2 comprising the amino acid sequence of SEQ ID NO:162; a HVR-H1 comprising the amino acid sequence of SEQ ID NO:138, and a HVR-H2 comprising the amino acid sequence of SEQ ID NO:123; a HVR-H1 comprising the amino acid sequence of SEQ ID NO:139, and a HVR-H2 comprising the amino acid sequence of SEQ ID NO:110; a HVR-H1 comprising the amino acid sequence of SEQ ID NO:8, and a HVR-H2 comprising the amino acid sequence of SEQ ID NO:126; a HVR-H1 comprising the amino acid sequence of SEQ ID NO:13, and a HVR-H2 comprising the amino acid sequence of SEQ ID NO:129; a HVR-H1 comprising the amino acid sequence of SEQ ID NO:31, and a HVR-H2 comprising the amino acid sequence of SEQ ID NO:124; a HVR-H1 comprising the amino acid sequence of SEQ ID NO:25, and a HVR-H2 comprising the amino acid sequence of SEQ ID NO:130; a HVR-H1 comprising the amino acid sequence of SEQ ID NO:150, and a HVR-H2 comprising the amino acid sequence of SEQ ID NO:132; a HVR-H1 comprising the amino acid sequence of SEQ ID NO:158, and a HVR-H2 comprising the amino acid sequence of SEQ ID NO:162; a HVR-H1 comprising the amino acid sequence of SEQ ID NO:12, and a HVR-H2 comprising the amino acid sequence of SEQ ID NO:82; a HVR-H1 comprising the amino acid sequence of SEQ ID NO:149, and a HVR-H2 comprising the amino acid sequence of SEQ ID NO:117; and a HVR-H1 comprising the amino acid sequence of SEQ ID NO:7, and a HVR-H2 comprising the amino acid sequence of SEQ ID NO:134. In some embodiments, the HVR-H1 and HVR-H2 are selected from the group consisting of: a HVR-H1 comprising the amino acid sequence of SEQ ID NO:26, and a HVR-H2 comprising the amino acid sequence of SEQ ID NO:53; a HVR-H1 comprising the amino acid sequence of SEQ ID NO:151, and a HVR-H2 comprising the amino acid sequence of SEQ ID NO:53; a HVR-H1 comprising the amino acid sequence of SEQ ID NO:34, and a HVR-H2 comprising the amino acid sequence of SEQ ID NO:63; a HVR-H1 comprising the amino acid sequence of SEQ ID NO:50, and a HVR-H2 comprising the amino acid sequence of SEQ ID NO:162; a HVR-H1 comprising the amino acid sequence of SEQ ID NO:158, and a HVR-H2 comprising the amino acid sequence of SEQ ID NO:104; a HVR-H1 comprising the amino acid sequence of SEQ ID NO:5, and a HVR-H2 comprising the amino acid sequence of SEQ ID NO:121; a HVR-H1 comprising the amino acid sequence of SEQ ID NO:6, and a HVR-H2 comprising the amino acid sequence of SEQ ID NO:116; a HVR-H1 comprising the amino acid sequence of SEQ ID NO:7, and a HVR-H2 comprising the amino acid sequence of SEQ ID NO:121; a HVR-H1 comprising the amino acid sequence of SEQ ID NO:17, and a HVR-H2 comprising the amino acid sequence of SEQ ID NO:63; a HVR-H1 comprising the amino acid sequence of SEQ ID NO:25, and a HVR-H2 comprising the amino acid sequence of SEQ ID NO:101; a HVR-H1 comprising the amino acid sequence of SEQ ID NO:25, and a HVR-H2 comprising the amino acid sequence of SEQ ID NO:114; a HVR-H1 comprising the amino acid sequence of SEQ ID NO:29, and a HVR-H2 comprising the amino acid sequence of SEQ ID NO:112; a HVR-H1 comprising the amino acid sequence of SEQ ID NO:152, and a HVR-H2 comprising the amino acid sequence of SEQ ID NO:63; a HVR-H1 comprising the amino acid sequence of SEQ ID NO:156, and a HVR-H2 comprising the amino acid sequence of SEQ ID NO:89; a HVR-H1 comprising the amino acid sequence of SEQ ID NO:157, and a HVR-H2 comprising the amino acid sequence of SEQ ID NO:94; a HVR-H1 comprising the amino acid sequence of SEQ ID NO:48, and a HVR-H2 comprising the amino acid sequence of SEQ ID NO:58; a HVR-H1 comprising the amino acid sequence of SEQ ID NO:50, and a HVR-H2 comprising the amino acid sequence of SEQ ID NO:89; a HVR-H1 comprising the amino acid sequence of SEQ ID NO:50, and a HVR-H2 comprising the amino acid sequence of SEQ ID NO:163; a HVR-H1 comprising the amino acid sequence of SEQ ID NO:158, and a HVR-H2 comprising the amino acid sequence of SEQ ID NO:160; a HVR-H1 comprising the amino acid sequence of SEQ ID NO:158, and a HVR-H2 comprising the amino acid sequence of SEQ ID NO:87; a HVR-H1 comprising the amino acid sequence of SEQ ID NO:158, and a HVR-H2 comprising the amino acid sequence of SEQ ID NO:92; a HVR-H1 comprising the amino acid sequence of SEQ ID NO:158, and a HVR-H2 comprising the amino acid sequence of SEQ ID NO:93; a HVR-H1 comprising the amino acid sequence of SEQ ID NO:158, and a HVR-H2 comprising the amino acid sequence of SEQ ID NO:97; a HVR-H1 comprising the amino acid sequence of SEQ ID NO:158, and a HVR-H2 comprising the amino acid sequence of SEQ ID NO:103; a HVR-H1 comprising the amino acid sequence of SEQ ID NO:158, and a HVR-H2 comprising the amino acid sequence of SEQ ID NO:164; a HVR-H1 comprising the amino acid sequence of SEQ ID NO:137, and a HVR-H2 comprising the amino acid sequence of SEQ ID NO:54; a HVR-H1 comprising the amino acid sequence of SEQ ID NO:3, and a HVR-H2 comprising the amino acid sequence of SEQ ID NO:127; a HVR-H1 comprising the amino acid sequence of SEQ ID NO:4, and a HVR-H2 comprising the amino acid sequence of SEQ ID NO:85; a HVR-H1 comprising the amino acid sequence of SEQ ID NO:4, and a HVR-H2 comprising the amino acid sequence of SEQ ID NO:110; a HVR-H1 comprising the amino acid sequence of SEQ ID NO:139, and a HVR-H2 comprising the amino acid sequence of SEQ ID NO:109; a HVR-H1 comprising the amino acid sequence of SEQ ID NO:139, and a HVR-H2 comprising the amino acid sequence of SEQ ID NO:121; a HVR-H1 comprising the amino acid sequence of SEQ ID NO:8, and a HVR-H2 comprising the amino acid sequence of SEQ ID NO:120; a HVR-H1 comprising the amino acid sequence of SEQ ID NO:140, and a HVR-H2 comprising the amino acid sequence of SEQ ID NO:131; a HVR-H1 comprising the amino acid sequence of SEQ ID NO:141, and a HVR-H2 comprising the amino acid sequence of SEQ ID NO:116; a HVR-H1 comprising the amino acid sequence of SEQ ID NO:142, and a HVR-H2 comprising the amino acid sequence of SEQ ID NO:159; a HVR-H1 comprising the amino acid sequence of SEQ ID NO:143, and a HVR-H2 comprising the amino acid sequence of SEQ ID NO:116; a HVR-H1 comprising the amino acid sequence of SEQ ID NO:144, and a HVR-H2 comprising the amino acid sequence of SEQ ID NO:121; a HVR-H1 comprising the amino acid sequence of SEQ ID NO:146, and a HVR-H2 comprising the amino acid sequence of SEQ ID NO:110; a HVR-H1 comprising the amino acid sequence of SEQ ID NO:147, and a HVR-H2 comprising the amino acid sequence of SEQ ID NO:133; a HVR-H1 comprising the amino acid sequence of SEQ ID NO:148, and a HVR-H2 comprising the amino acid sequence of SEQ ID NO:63; and a HVR-H1 comprising the amino acid sequence of SEQ ID NO:13, and a HVR-H2 comprising the amino acid sequence of SEQ ID NO:118.

In some embodiments that may be combined with any of the preceding embodiments, the heavy chain variable region comprises an HVR-H1, a HVR-H2, and a HVR-H3, wherein the HVR-H3 comprises an amino acid sequence selected from the group consisting of SEQ ID NOS: 223-256.

In some embodiments, the heavy chain variable region further comprises a FW-H1 comprising the amino acid sequence of SEQ ID NO:165. In some embodiments, the heavy chain variable region further comprises a FW-H2 comprising the amino acid sequence of SEQ ID NO:166. In some embodiments, the heavy chain variable region further comprises a FW-H3 comprising the amino acid sequence of SEQ ID NO:167. In some embodiments, the heavy chain variable region further comprises a FW-H4 comprising the amino acid sequence of SEQ ID NO:168. In some embodiments, the heavy chain variable region comprises at least two (e.g., at least two, at least three, or all four) of a FW-H1 comprising the amino acid sequence of SEQ ID NO:165, a FW-H12 comprising the amino acid sequence of SEQ ID NO:166, a FW-H13 comprising the amino acid sequence of SEQ ID NO:167, and a FW-H14 comprising the amino acid sequence of SEQ ID NO:168, in any combination. In some embodiments, the FW-H13 sequence comprises an arginine to lysine mutation at R19 of SEQ ID NO:167. In some embodiments, the heavy chain variable region comprises a sequence selected from the group consisting of SEQ ID NOs: 169, 171, 173, 175, 177, 179, 181, 183, 185, 187, 189, 191, 193, and 195.

In some embodiments that may be combined with any of the preceding embodiments, the heavy chain variable regions in the library contain less than about $6.5*10^4$ (e.g., less than about $6.5*10^4$, less than about $5.5*10^4$, less than about $2.5*10^4$, less than about $1*10^4$, less than about 6700, less than about 6660, less than about 5000, less than about 2500, less than about 1000, less than about 690, less than about 500, less than about 100, less than about 50, etc.) unique combinations ofHVR-H1 and HVR-H2 sequences. In some embodiments, the heavy chain variable regions in the library contain about 62272 or less unique combinations of HVR-H1 and HVR-H2 sequences. In some embodiments, the heavy chain variable regions in the library contain about 60928 or less unique combinations of HVR-H1 and HVR-H2 sequences. In some embodiments, the heavy chain variable regions in the library contain about 54656 or less unique combinations of HVR-H1 and HVR-H2 sequences. In some embodiments, the heavy chain variable regions in the library contain about 6660 or less unique combinations of HVR-H1 and HVR-H2 sequences. In some embodiments, the heavy chains variable regions in the library contain about 690 or less unique combinations of HVR-H1 and HVR-H2 sequences. In some embodiments, at least one of the HVR-H1 and HVR-H2 of the antibody heavy chain variable regions adopts multiple conformations, as assayed by structural determination and/or computational modeling.

In another aspect, provided herein is an antibody heavy chain variable region and an antibody light chain variable region, wherein the antibody heavy chain variable region is any of the heavy chain variable regions as described herein. In some embodiments, provided herein is a library comprising antibody heavy chain variable regions and antibody light chain variable regions, wherein at least one (e.g., at least one, at least two, at least five, at least 10, at least 100, etc.) of the antibody heavy chain variable regions in the library is any of the heavy chain variable regions as described herein. In some embodiments, provided herein is a library comprising antibody heavy chain variable regions and antibody light chain variable regions, wherein each of the antibody heavy chain variable regions in the library is any of the heavy chain variable regions as described herein. In some embodiments, the antibody light chain variable region comprises a HVR-L1, a HVR-L2 and a HVR-L3, wherein the HVR-L1 comprises an amino acid sequence selected from the group consisting of SEQ ID NOs: 257-264 and/or the HVR-L3 comprises an amino acid sequence selected from the group consisting of SEQ ID NOs: 265-274. In some embodiments, the light chain variable regions in the library include at least one unique sequence, at least 100 unique sequences, at least 280 unique sequences, at least $10^3$ unique sequences, at least $10^4$ unique sequences, at least $10^5$ unique sequences, at least $10^6$ unique sequences, at least $10^7$ unique sequences, at least $10^8$ unique sequences, or least about $10^9$ unique sequences.

In another aspect, provided herein is an antigen binding domain comprising an antibody heavy chain variable region, wherein the antigen binding domain comprises any of the antibody heavy chain variable regions as described herein. In some embodiments, provided herein is a library comprising antigen binding domains comprising antibody heavy chain variable regions, wherein at least one (e.g., at least one, at least two, at least five, at least 10, at least 100, etc.) of the antigen binding domains in the library comprises any of the heavy chain variable regions as described herein. In some embodiments, provided herein is a library comprising antigen binding domains comprising antibody heavy chain variable regions, wherein each of the antigen binding domains in the library comprises any of the heavy chain variable regions as described herein. In some embodiments, the antigen binding domain further comprises an antibody light chain variable region comprising a HVR-L1, a HVR-L2 and a HVR-L3, wherein the HVR-L1 comprises an amino acid sequence selected from the group consisting of SEQ ID NOs: 257-264 and/or the HVR-L3 comprises an amino acid sequence selected from the group consisting of SEQ ID NOs: 265-274. In some embodiments, antigen binding domains comprising the light chain variable regions in the library include light chain variable regions comprising at least one unique sequence, at least 100 unique sequences, at least 280 unique sequences, at least $10^3$ unique sequences, at least $10^4$ unique sequences, at least $10^5$ unique sequences, at least $10^6$ unique sequences, at least $10^7$ unique sequences, at least $10^8$ unique sequences, or least about $10^9$ unique sequences.

In another aspect, provided herein is an antibody comprising an antibody heavy chain variable region, wherein the antibody comprises any of the antibody heavy chain variable regions as described herein. In some embodiments, provided herein is a library comprising antibodies, wherein at least one (e.g., at least one, at least two, at least five, at least 10, at least 100, etc.) of the antibodies in the library comprises any of the antibody heavy chain variable regions as described herein. In some embodiments, provided herein is a library comprising antibodies, wherein each of the antibodies in the library comprises any of the heavy chain variable regions as described herein. In some embodiments, the antibody further comprises an antibody light chain variable region comprising a HVR-L1, a HVR-L2 and a HVR-L3, wherein the HVR-L1 comprises an amino acid sequence selected from the group consisting of SEQ ID NOs: 257-264 and/or the HVR-L3 comprises an amino acid sequence selected from the group consisting of SEQ ID NOs: 265-274. In some embodiments, antibodies comprising the light chain variable regions in the library include light chain variable regions comprising at least one unique sequence, at least 100 unique sequences, at least 280 unique sequences, at least $10^3$ unique sequences, at least $10^4$ unique sequences, at least $10^5$ unique sequences, at least $10^6$ unique sequences, at least $10^7$ unique sequences, at least $10^8$ unique sequences, or least about $10^9$ unique sequences.

In some embodiments that may be combined with any of the preceding embodiments, the antibodies contain less than about $6.5*10^4$ unique combinations of HVR-H1 and HVR-H2 sequences. In some embodiments that may be combined with any of the preceding embodiments, the antibodies contain less than about $5.5*10^4$ unique combinations of HVR-H1 and HVR-H2 sequences. In some embodiments, the antibodies contain about 62272 or less unique combinations of HVR-H1 and HVR-H2 sequences. In some embodiments, the antibodies contain about 60928 or less unique combinations of HVR-H1 and HVR-H2 sequences. In some embodiments, the antibodies contain about 54656 or less unique combinations of HVR-H1 and HVR-H2 sequences. In some embodiments, the antibodies contain about 6660 or less unique combinations of HVR-H1 and HVR-H2 sequences. In some embodiments, the antibodies contain about 690 or less unique combinations of HVR-H1 and HVR-H2 sequences. In some embodiments, at least one of the HVR-H1 and HVR-H2 of the antibody heavy chain variable region adopts multiple conformations, as assayed by structural determination and/or computational modeling.

In some embodiments that may be combined with any of the preceding embodiments, the antibody binds at least 1 target with an equilibrium dissociation constant (Kd) of between about $10^{-7}$ and about $10^{-11}$M. In some embodiments, the antibody has a melting temperature (Tm) of between about 60° C. and about 90° C.

In another aspect, provided herein is a polypeptide (e.g., scaffold polypeptides) comprising one or more (e.g., one or more, two or more, three or more, four or more, five or more etc.) HVRs of the present disclosure. In some embodiments, provided herein are libraries comprising polypeptides, wherein at least one (e.g., at least one, at least two, at least five, at least 10, at least 25, at least 50, at least 100, at least 250, at least 500, at least 750, at least 1000, at least 2500, at least 5000, at least 6000, at least 6500, etc.) of the polypeptides in the library comprises one or more HVRs of the present disclosure. In some embodiments, provided herein are libraries comprising polypeptides, wherein each of the polypeptides in the library comprises one or more HVRs of the present disclosure. In some embodiments, the polypeptide comprises an HVR-H1 comprising an amino acid sequence selected from any HVR-H1 sequence as described herein (e.g., a HVR-H1 according to a formula selected from the group consisting of Formula (I), Formula (II), and Formula (III); and SEQ ID NOS:1-52 and 137-158). In some embodiments, the polypeptide comprises an HVR-H2 comprising an amino acid sequence selected from any HVR-H2 as described herein (e.g., a HVR-H2 according to formula selected from the group consisting of Formula (IV), Formula (V), Formula (VI), Formula (VII), Formula (VIII), Formula (IX), Formula (X), Formula (XI), Formula (XII) and Formula (XIII); and SEQ ID NOS:53-136 and 159-164). In some embodiments, the polypeptide comprises an HVR-H3 comprising an amino acid sequence selected from any HVR-H3 sequence as described herein (e.g., SEQ ID NOs: 223-256). In some embodiments, the polypeptide comprises an HVR-L1 comprising an amino acid sequence selected from any HVR-L1 sequence as described herein (e.g., SEQ ID NOs: 257-264). In some embodiments, the polypeptide comprises an HVR-L3 comprising an amino acid sequence selected from any HVR-L3 sequence as described herein (e.g., SEQ ID NOs: 265-274). In some embodiments, the polypeptide comprises two or more (e.g., two or more, three or more, four or more, or all five) of the HVR-H1, HVR-H2, HVR-H3, HVR-L1, and/or HVR-L3 sequences described herein. In some embodiments, provided herein are polynucleotides and libraries comprising polynucleotides encoding any of the polypeptides as described above.

In another aspect, provided herein is a phage comprising at least one polypeptide on its surface wherein the at least one polypeptide comprises any of the antibody heavy chain variable regions described herein. In some embodiments, the at least one polypeptide is any of the antigen binding domains as described herein. In some embodiments, provided herein is a library of phages, wherein at least one (e.g., at least one, at least two, at least five, at least 10, at least 25, at least 50, at least 100, at least 250, at least 500, at least 750, at least 1000, at least 2500, at least 5000, at least 6000, at least 6500, etc.) phage in the library comprises at least one polypeptide on its surface comprising any of the antibody heavy chain variable regions described herein. In some embodiments, the at least one phage in the library comprises at least one polypeptide on its surface comprising any of the antigen binding domains as described herein. In some embodiments, provided herein is a library comprising phages, wherein each of the phages in the library comprises at least one polypeptide on its surface comprising any of the antibody heavy chain variable regions described herein. In some embodiments, the at least one polypeptide is any of the antigen binding domains as described herein.

In another aspect, provided herein is a non-human animal comprising at least one polynucleotide encoding any of the antibody heavy chain variable regions described herein (e.g., any of the polynucleotides or polynucleotide libraries described herein). In some embodiments, the non-human animal comprises at least one polynucleotide encoding any of the antibodies described herein. In some embodiments, the non-human animal is a mammal (e.g., a mouse, rat, rabbit, camel, or non-human primate).

In another aspect, provided herein are methods of preparing a library comprising providing and assembling any of the polynucleotide sequences of the libraries as described herein.

In another aspect, provided herein are methods of screening for a polypeptide that binds to a target, comprising incubating any of the libraries comprising polyeptpdies described herein (e.g., a library of antigen binding domains, a library of antibodies, a library of phages, etc.) with a target, and selecting one or more polypeptides from the library that binds to the target.

In another aspect, provided herein are methods of making an antibody library comprising the steps: (a) selecting one, two or three heavy chain HVRs comprising a sequence having multiple conformations; and (b) assembling polynucleotide sequences to produce a library of synthetic polynucleotides encoding a plurality of antibody heavy chain variable region sequences. In some embodiments, at least one of the plurality of antibody heavy chain variable region sequences is any of the heavy chain variable region sequences described herein. In some embodiments, each of the plurality of antibody heavy chain variable region sequences are any of the heavy chain variable region sequences described herein.

In another aspect, provided herein are methods of preparing polypeptides (e.g., heavy chain variable regions, antibody heavy chains, antibodies, scaffold polypeptides, etc.) comprising culturing a cell comprising any of the polynucleotides, polynucleotide libraries, vectors, and/or vector libraries as described above to produce the polypeptide. In some embodiments, the polypeptide is collected from the cultured cell, and is further purified.

In another aspect, provided herein are methods of generating a bispecific antibody comprising two antibody heavy chain variable regions and two identical light chain variable regions, comprising: (a) screening for a first antigen binding domain that binds to a first antigen, wherein the first antigen binding domain comprises a first antibody heavy chain variable region and a first antibody light chain variable region, wherein the first antibody heavy chain variable region comprises any of the heavy chain variable regions described herein; (b) screening for a second antigen binding domain that binds to a second antigen, wherein the second antigen binding domain comprises a second antibody heavy chain variable region and a second antibody light chain variable region, wherein the second antibody heavy chain variable region has the same sequence as the first antibody heavy chain variable region; and (c) producing a bispecific antibody comprising the first antigen binding domain and the second antigen binding domain.

In another aspect, provided herein are bispecific antibodies comprising: (a) a first binding domain comprising a first heavy chain variable region and a first light chain variable region, wherein the first binding domain binds to a first target; (b) a second binding domain comprising a second heavy chain variable region and a second light chain variable region, wherein the second binding domain binds to a second target, wherein the second heavy chain variable region has a sequence identical to the first heavy chain variable region sequence; wherein each of the first and second heavy chain variable regions comprises any of the heavy chain variable regions described herein. In some embodiments, the bispecific antibodies comprise a first light chain and a second light chain, wherein the first light chain comprises the first light chain variable region and the second light chain comprises the second light chain variable region, and both the first and second light chains each comprise a kappa $C_L$ domain (e.g., a human kappa $C_L$ domain). In some embodiments, the bispecific antibodies comprise a first light chain and a second light chain, wherein the first light chain comprises the first light chain variable region and the second light chain comprises the second light chain variable region, and both the first and second light chains each comprise a lambda $C_L$ domain (e.g., a human lambda $C_L$ domain). In some embodiments, the bispecific antibodies comprise a first light chain and a second light chain, wherein the first light chain comprises the first light chain variable region and a kappa $C_L$ domain (e.g., a human kappa $C_L$ domain), and the second light chain comprises the second light chain variable region and a lambda $C_L$ domain (e.g., a human lambda $C_L$ domain). In some embodiments, the bispecific antibodies comprise a first light chain and a second light chain, wherein the first light chain comprises the first light chain variable region and a lambda $C_L$ domain (e.g., a human lambda $C_L$ domain), and the second light chain comprises the second light chain variable region and a kappa $C_L$ domain (e.g., a human kappa $C_L$ domain).

In another aspect, provided herein are kits comprising any of the polynucleotides, polynucleotide libraries, vectors, and/or vector libraries (or any cells or population of cells comprising them) as described herein. In some embodiments, provided herein are kits comprising any of the heavy chain variable regions, heavy chain variable region libraries, antigen binding domains, antigen binding domain libraries, antibodies, antibody libraries, polypeptides (e.g., scaffold polypeptides), polypeptide libraries, phages, and/or phage libraries as described herein.

It is to be understood that one, some, or all of the properties of the various embodiments described above and herein may be combined to form other embodiments of the present disclosure. These and other aspects of the present disclosure will become apparent to one of skill in the art. These and other embodiments of the present disclosure are further described by the detailed description that follows.

BRIEF DESCRIPTION OF THE DRAWINGS

FIG. 1A shows an entropy plot by residue number for the amino acids of a $V_H$ domain. 113 $V_H$ structures of human antibodies were used to calculate the entropy.

FIG. 1B shows the definition of the hyper-variable regions (HVRs) used herein for an exemplary antibody heavy chain variable domain (VH) sequence (SEQ ID NO:197) in comparison to the Kabat definition of the complementarity-determining regions (CDRs) for the same VII sequence.

DETAILED DESCRIPTION

Figure 2A:
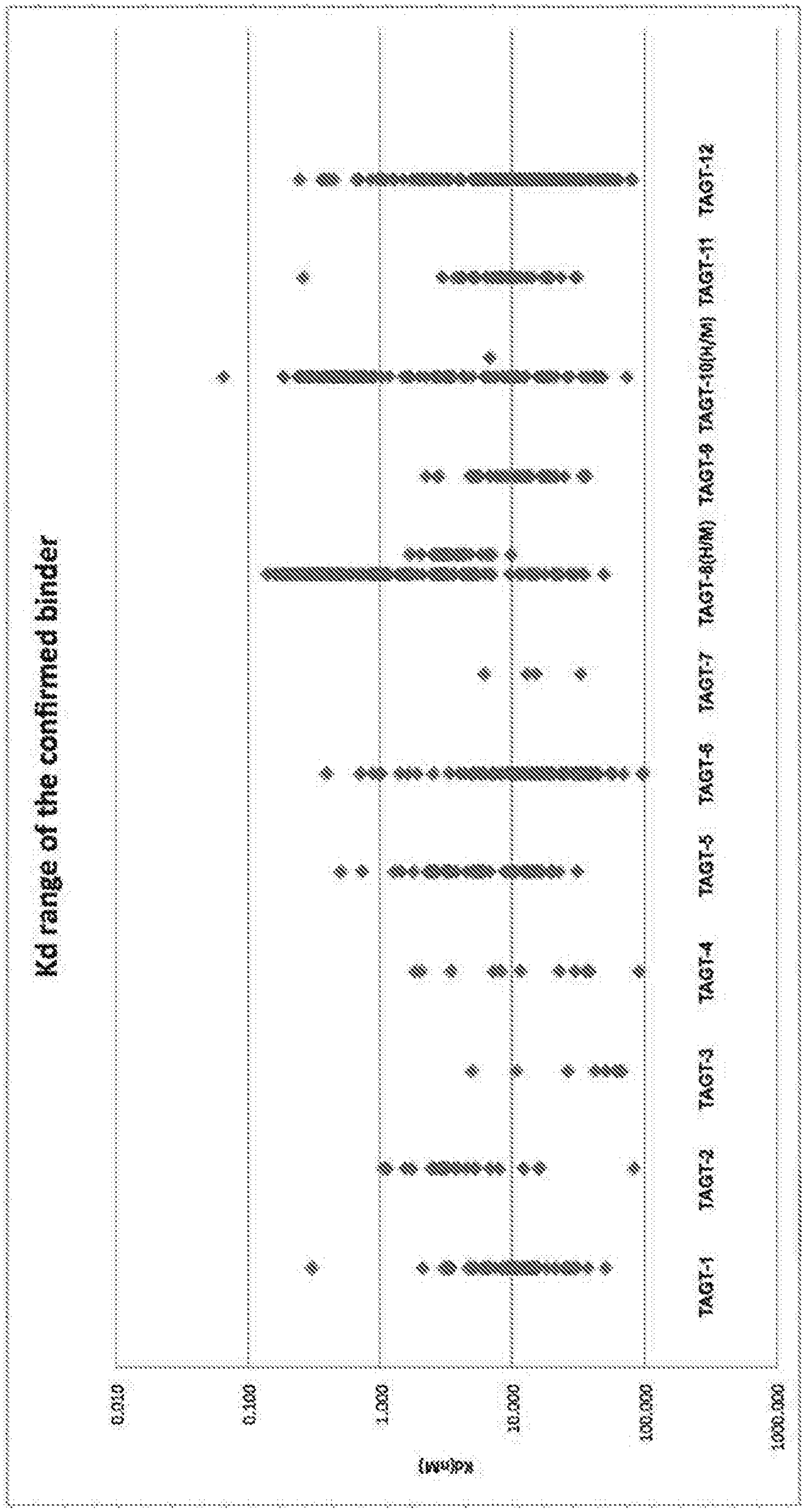
FIG. 2A shows the affinity measurements for fabs with confirmed binding to the antigens TAGT-1 to TAGT-12.

The present disclosure provides libraries containing synthetic (e.g., non-naturally occurring) polynucleotides that encode antibody heavy chains (e.g., heavy chains of a dynamic human antibody). Advantageously, the antibody heavy chains disclosed herein include HVR sequences designed to generate highly flexible loops for more effective substrate binding and/or specificity against multiple substrates of interest. These HVR sequences allow the creation of smaller antibody libraries with broader epitope coverage than existing techniques.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR* 2: *A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press;

*Animal Cell Culture* (R. I. Freshney), ed., 1987); Introduction *to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

Before describing the present disclosure in detail, it is to be understood that this present disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the present disclosure described herein include "comprising," "consisting," and "consisting essentially of" aspects and embodiments.

The term "antibody" is used herein in the broadest sense and specifically covers monoclonal antibodies (including full length monoclonal antibodies), polyclonal antibodies, multispecific antibodies (e.g., bispecific antibodies), and antibody fragments (e.g., a single-chain variable fragment or scFv) so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology,* 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The term "full-length antibody" (the terms "intact" antibody or "whole" antibody may be used interchangeably herein) may refer to an antibody in its substantially intact form, as opposed to an antibody fragment. Similarly, the term "full-length antibody heavy chain" (the terms "intact" antibody heavy chain or "whole" antibody heavy chain may be used interchangeably herein) may refer to an antibody heavy chain in its substantially intact form, as opposed to an antibody heavy chain fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler and Milstein., *Nature,* 256:495-97 (1975); Hongo et al., *Hybridoma,* 14 (3):253-260 (1995), Harlow et al., *Antibodies: A Laboratory Manual*, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

As used herein, "hypervariable region (HVR)" refers to the regions of an antibody domain which are hypervariable in sequence and/or form structurally defined loops. Generally, antibodies comprise six HVRs; three in the VH (H1, H2, H3), and three in the VL (L1, L2, L3). See, e.g., Xu et al., *Immunity* 13:37-45 (2000); Johnson and Wu, in *Methods in Molecular Biology* 248:1-25 (Lo, ed., Human Press, Totowa, N.J., 2003). Each VH and VL is composed of three HVRs and four framework (FW) regions arranged from amino terminus to carboxy terminus in the following order: FW1-HVR1-FW2-HVR2-FW3-HVR3-FW4. Throughout the present disclosure, the three HVRs of the heavy chain are referred to as HVR-H1, HVR-H2, and HVR-H3. Throughout the present disclosure, the four framework regions of the heavy chain are referred to as FW-H1, FW-H2, FW-H3 and FW-H4. For comparison, the definition of the HVRs (as used herein) is contrasted with the Kabat definition of the complementarity-determining regions (CDRs) (Yvonne Chen et al. (1999) "Selection and Analysis of an Optimized Anti-VEGF Antibody: Crystal Structure of an Affinity-matured Fab in Complex with Antigen", *J. Mol. Biol.* 293, 865-881) for the exemplary antibody heavy chain variable domain shown in FIG. 1B.

As used herein, "library" refers to a set of two or more entities having a shared class. For example, a library containing polynucleotides may refer to a set of two or more polynucleotides. The term "library" is used herein in the broadest sense and specifically covers sub-libraries that may or may not be combined.

As used herein, "unique" refers to a member of a set that is different from other members of the set. For example, a unique antibody from a library encoding a plurality of polynucleotides encoding antibodies may refer to an antibody having a particular sequence not shared by other antibodies encoded by the library. As a practical matter, it is to be understood that a "unique" member of a physical realization of a library may be present in more than one copy. For example, a library may contain a plurality of "unique" antibodies, with one or more of the "unique" antibody molecules occurring in more than one copy.

As used herein, "diversity" refers to a variety and/or heterogeneity. For example, a diversity of antibodies in a library may refer to a variety of antibodies with unique sequences present in the library.

The terms "polypeptide," "protein," and "peptide" are used interchangeably herein and may refer to polymers of two or more amino acids.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A cell (e.g., a cell or population of cells comprising a synthetic polynucleotide or library of synthetic polynucleotides) includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) (e.g., a synthetic polynucleotide that encodes an antibody heavy chain variable region of the present disclosure).

A "non-human animal" refers to any animal not classified as a human, such as domestic, farm, or zoo animals, sports, pet animals (such as dogs, horses, cats, cows, etc.), as well as animals used in research. Research animals may refer without limitation to nematodes, arthropods, vertebrates, mammals, frogs, rodents (e.g., mice or rats), fish (e.g., zebrafish or pufferfish), birds (e.g., chickens), dogs, cats, and non-human primates (e.g., rhesus monkeys, cynomolgus monkeys, chimpanzees, etc.). In preferred embodiments, the animal is one that produces antibodies.

III. Antibody Libraries and Generation of Libraries

Certain aspects of the present disclosure relate to libraries of polynucleotides, e.g., that encode an antibody heavy chain variable region ($V_H$) or light chain variable region ($V_L$). A library of the present disclosure can contain one or more polynucleotides encoding a heavy chain variable region comprising a HVR-H1, a HVR-H2, and a HVR-H3, wherein the HVR-H1 and HVR-H2 are any of the HVR-H1s and/or HVR-H2s described herein.

In some embodiments, a library of the present disclosure contains a smaller number of unique heavy chain HVR sequences and/or unique $V_H$ sequences than typical antibody libraries. Advantageously, such libraries can provide sufficient diversity for the identification of antibodies binding one or more of a number of antigens of interest while also allowing for more efficient screening due to the reduced library size. In some embodiments, a library of the present disclosure includes or consists of polynucleotides containing less than about 10000, less than about 9000, less than about 8000, or less than about 7000 unique combinations of HVR-H1 and HVR-H2 sequences. In certain embodiments, a library of the present disclosure includes or consists of polynucleotides containing about 6600 or less unique combinations of HVR-H1 and HVR-H2 sequences.

In some embodiments, a library contains a plurality of polynucleotides, with at least one of the polynucleotides encoding an antibody heavy chain variable region of the present disclosure (e.g., comprising a HVR-H1 and HVR-H2 of the present disclosure).

In some embodiments, one or more of the polynucleotides encode an antibody heavy chain variable region comprising a HVR-H1, a HVR-H2, and a HVR-H3, wherein the HVR-H1 comprises an amino acid sequence according to a formula selected from the group consisting of (Formula I) X1TFX2X3YX4IHWV, wherein X1 is F or Y, X2 is S or T, X3 is D, G, N, or S, and X4 is A, G, or W(SEQ ID NO:198); (Formula II) YSIX1SGX2X3WX4WI, wherein X1 is S or T, X2 is H or Y, X3 is H or Y, and X4 is A, D, G, N, S, or T (SEQ ID NO:199); and (Formula III) FSLSTX1GVX2VX3WI, wherein X1 is G or S, X2 is A or G, and X3 is A, G, S, or T(SEQ ID NO:200). In some embodiments, one or more of the polynucleotides encode an antibody heavy chain variable region comprising a HVR-H1, a HVR-H2, and a HVR-H3, wherein the HVR-H2 comprises an amino acid sequence according to a formula selected from the group consisting of (Formula IV) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T(SEQ ID NO:201); (Formula V) IGX1IX2X3SGSTYYSPSLKSRV, wherein X1 is A, D, E, S, or Y, X2 is S or Y, and X3 is H or Y(SEQ ID NO:202); (Formula VI) IGX1IYX2SGX3TX4YNPSLKSRV, wherein X1 is D, E, R, S, or Y, X2 is H or Y, X3 is N or S, and X4 is N or Y(SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T(SEQ ID NO:204); (Formula VIII) IGX1INPNX2GX3TX4YAQKFQGRV, wherein X1 is I, R, or W, X2 is F or R, X3 is D, G, or S, and X4 is K or N(SEQ ID NO:205); (Formula IX) IGX1IX2PSX3GX4TX5YAQKFQGRV, wherein X1 is I, R, or W, X2 is S or Y, X3 is G or S, X4 is D, G, or S, and X5 is K or N(SEQ ID NO:206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S(SEQ ID NO:207). In some embodiments, the HVR-H2 comprises an amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XI) IGX1IYX2SGX3TX4YNPSLKSRV, wherein X1 is D, E, or S, X2 is H or Y, X3 is N or S, and X4 is N or Y(SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S(SEQ ID NO:210). In some embodiments, one or more of the polynucleotides encode an antibody heavy chain variable region comprising a HVR-H1, a HVR-H2, and a HVR-H3, wherein the HVR-H1 comprises an amino acid sequence according to a formula selected from the group consisting of (Formula I) X1TFX2X3YX4IHWV, wherein X1 is F or Y, X2 is S or T, X3 is D, G, N, or S, and X4 is A, G, or W(SEQ ID NO:198); (Formula II) YSIX1SGX2X3WX4WI, wherein X1 is S or T, X2 is H or Y, X3 is H or Y, and X4 is A, D, G, N, S, or T (SEQ ID NO:199); and (Formula FSLSTX1GVX2VX3WI, wherein X1 is G or S, X2 is A or G, and X3 is A, G, S, or T(SEQ ID NO:200); and an HVR-H2 comprises an amino acid sequence according to a formula selected from the group consisting of (Formula W) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T(SEQ ID NO:201); (Formula V) IGX1IX2X3SGSTYYSPSLKSRV, wherein X1 is A, D, E, S, or Y, X2 is S or Y, and X3 is H or Y(SEQ ID NO:202); (Formula VI) IGX1IYX2SGX3TX4YNPSLKSRV, wherein X1 is D, E, R, S, or Y, X2 is H or Y, X3 is N or S, and X4 is N or Y(SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T(SEQ ID NO:204); (Formula VIII) IGX1INPNX2GX3TX4YAQKFQGRV, wherein X1 is I, R, or W, X2 is F or R, X3 is D, G, or S, and X4 is K or N(SEQ ID NO:205); (Formula IX) IGX1IX2PSX3GX4TX5YAQKFQGRV, wherein X1 is I, R, or W, X2 is S or Y, X3 is G or S, X4 is D, G, or S, and X5 is K or N(SEQ ID NO:206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S(SEQ ID NO:207). In some embodiments, one or more of the polynucleotides encode an antibody heavy chain variable region comprising a HVR-H1, a HVR-H2, and a HVR-H3, wherein the HVR-H1 comprises an amino acid sequence according to a formula selected from the group consisting of (Formula I) X1TFX2X3YX4IHW, wherein X1 is F or Y, X2 is S or T, X3 is D, G, N, or S, and X4 is A, G, or W(SEQ ID NO:198); (Formula II) YSIX1SGX2X3WX4WI, wherein X1 is S or T, X2 is H or Y, X3 is H or Y, and X4 is A, D, G, N, S, or T (SEQ ID NO:199); and (Formula III) FSLSTX1GVX2VX3WI, wherein X1 is G or S, X2 is A or G, and X3 is A, G, S, or T(SEQ ID NO:200); and an HVR-H2 comprises an amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XI) IGX1IYX2SGX3TX4YNPSLKSRV, wherein X1 is D, E, or S, X2 is H or Y, X3 is N or S, and X4 is N or Y(SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S(SEQ ID NO:210). In some embodiments, one or more polynucleotides of the library are in a vector (e.g., an expression vector or display vector).

In some embodiments, at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 225, at least 250, at least 500, at least 1000, at least 1250, at least 1500, at least 1750, at least 2000, at least 2250, at least 2500, at least 2750, at least 3000, at least 3250, at least 3500, at least 3750, at least 4000, at least 4250, at least 4500, at least 4750, at least 5000, at least 5250, at least 5500, at least 5750, at least 6000, at least 6250, or at least 6500 of the polynucleotides encodes an antibody heavy chain variable region comprising a HVR-H1, a HVR-H2 and a HVR-H3, wherein the HVR-H1 comprises an amino acid sequence according to a formula selected from the group consisting of (Formula I) X1TFX2X3YX4IHWV, wherein X1 is F or Y, X2 is S or T, X3 is D, G, N, or S, and X4 is A, G, or W(SEQ ID NO:198); (Formula II) YSIX1SGX2X3WX4WI, wherein X1 is S or T, X2 is H or Y, X3 is H or Y, and X4 is A, D, G, N, S, or T (SEQ ID NO:199); and (Formula III) FSLSTX1GVX2VX3WI, wherein X1 is G or S, X2 is A or G, and X3 is A, G, S, or T(SEQ ID NO:200); and/or an HVR-H2 comprising the amino acid sequence according to a formula selected from the group consisting of (Formula W) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T(SEQ ID NO:201); (Formula V) IGX1IX2X3SGSTYYSPSLKSRV, wherein X1 is A, D, E, S, or Y, X2 is S or Y, and X3 is H or Y(SEQ ID NO:202); (Formula VI) IGX1IYX2SGX3TX4YNPSLKSRV, wherein X1 is D, E, R, S, or Y, X2 is H or Y, X3 is N or S, and X4 is N or Y(SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T(SEQ ID NO:204); (Formula VIII) IGX1INPNX2GX3TX4YAQKFQGRV, wherein X1 is I, R, or W, X2 is F or R, X3 is D, G, or S, and X4 is K or N(SEQ ID NO:205); (Formula IX) IGX1IX2PSX3GX4TX5YAQKFQGRV, wherein X1 is I, R, or W, X2 is S or Y, X3 is G or S, X4 is D, G, or S, and X5 is K or N(SEQ ID NO:206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S(SEQ ID NO:207); and/or less than about $6.5*10^4$ (e.g., less than about $6.5*10^4$, less than about $5.5*10^4$, less than about $2.5*10^4$, less than about $1*10^4$, less than about 6700, less than about 6660, less than about 5000, less than about 2500, less than about 1000, less than about 690, less than about 500, less than about 100, less than about 50, etc.), less than or equal to 62272, less than or equal to 60928, less than or equal to 54656, or less than or equal to 6660 of the polynucleotides encodes an antibody heavy chain variable region comprising and HVR-H1, HVR-H2, and HVR-H3, wherein the HVR-H1 comprises an amino acid sequence according to a formula selected from the group consisting of (Formula I) X1TFX2X3YX4IHWV, wherein X1 is F or Y, X2 is S or T, X3 is D, G, N, or S, and X4 is A, G, or W(SEQ ID NO:198); (Formula II) YSIX1SGX2X3WX4WI, wherein X1 is S or T, X2 is H or Y, X3 is H or Y, and X4 is A, D, G, N, S, or T (SEQ ID NO:199); and (Formula III) FSLSTX1GVX2VX3WI, wherein X1 is G or S, X2 is A or G, and X3 is A, G, S, or T(SEQ ID NO:200); and an HVR-H2 comprising the amino acid sequence according to a formula selected from the group consisting of (Formula IV) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T(SEQ ID NO:201); (Formula V) IGX1IX2X3SGSTYYSPSLKSRV, wherein X1 is A, D, E, S, or Y, X2 is S or Y, and X3 is H or Y(SEQ ID NO:202); (Formula VI) IGX1IYX2SGX3TX4YNPSLKSRV, wherein X1 is D, E, R, S, or Y, X2 is H or Y, X3 is N or S, and X4 is N or Y(SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T(SEQ ID NO:204); (Formula VIII) IGX1INPNX2GX3TX4YAQKFQGRV, wherein X1 is I, R, or W, X2 is F or R, X3 is D, G, or S, and X4 is K or N(SEQ ID NO:205); (Formula IX) IGX1IX2PSX3GX4TX5YAQKFQGRV, wherein X1 is I, R, or W, X2 is S or Y, X3 is G or S, X4 is D, G, or S, and X5 is K or N(SEQ ID NO:206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S(SEQ ID NO:207). In some embodiments, one or more polynucleotides of the library are in a vector (e.g., an expression vector or display vector).

In some embodiments, at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 225, at least 250, at least 500, at least 1000, at least 1250, at least 1500, at least 1750, at least 2000, at least 2250, at least 2500, at least 2750, at least 3000, at least 3250, at least 3500, at least 3750, at least 4000, at least 4250, at least 4500, at least 4750, at least 5000, at least 5250, at least 5500, at least 5750, at least 6000, at least 6250, or at least 6500 of the polynucleotides encodes an antibody heavy chain variable region comprising a HVR-H1, a HVR-H2 and a HVR-H3, wherein the HVR-H1 comprises an amino acid sequence according to a formula selected from the group consisting of (Formula I) X1TFX2X3YX4IHWV, wherein X1 is F or Y, X2 is S or T, X3 is D, G, N, or S, and X4 is A, G, or W(SEQ ID NO:198); (Formula II) YSIX1SGX2X3WX4WI, wherein X1 is S or T, X2 is H or Y, X3 is H or Y, and X4 is A, D, G, N, S, or T (SEQ ID NO:199); and (Formula FSLSTX1GVX2VX3WI, wherein X1 is G or S, X2 is A or G, and X3 is A, G, S, or T(SEQ ID NO:200); and/or an HVR-H2 comprising the amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XI) IGX1IYX2SGX3TX4YNPSLKSRV, wherein X1 is D, E, or S, X2 is H or Y, X3 is N or S, and X4 is N or Y(SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S(SEQ ID NO:210); and/or less than about $6.5*10^4$ (e.g., less than about $6.5*10^4$, less than about $5.5*10^4$, less than about $2.5*10^4$, less than about $1*10^4$, less than about 6700, less than about 6660, less than about 5000, less than about 2500, less than about 1000, less than about 690, less than about 500, less than about 100, less than about 50, etc.), less than or equal to 62272, less than or equal to 60928, less than or equal to 54656, or less than or equal to 6660 of the polynucleotides encodes an antibody heavy chain variable region comprising and HVR-H1, HVR-H2, and HVR-H3, wherein the HVR-H1 comprises an amino acid sequence according to a formula selected from the group consisting of (Formula I) X1TFX2X3YX4IHWV, wherein X1 is F or Y, X2 is S or T, X3 is D, G, N, or S, and X4 is A, G, or W(SEQ ID NO:198); (Formula II) YSIX1SGX2X3WX4WI, wherein X1 is S or T, X2 is H or Y, X3 is H or Y, and X4 is A, D, G, N, S, or T (SEQ ID NO:199); and (Formula FSLSTX1GVX2VX3WI, wherein X1 is G or S, X2 is A or G, and X3 is A, G, S, or T(SEQ ID NO:200); and an HVR-H2 comprising the amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XI) IGX1IYX2SGX3TX4YNPSLKSRV, wherein X1 is D, E, or S, X2 is H or Y, X3 is N or S, and X4 is N or Y(SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S(SEQ ID NO:210). In some embodiments, one or more polynucleotides of the library are in a vector (e.g., an expression vector or display vector).

In some embodiments, the polynucleotides in the library encodes an antibody heavy chain variable region comprising an HVR-H1 comprising the amino acid sequence according to the formula X1TFX2X3YX4IHWV, wherein X1 is F or Y, X2 is S or T, X3 is D, G, N, or S, and X4 is A, G, or W (SEQ ID NO:198); and an HVR-H2 comprising the amino acid sequence according to a formula selected from the group consisting of (Formula IV) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T(SEQ ID NO:201); (Formula V) IGX1IX2X3SGSTYYSPSLKSRV, wherein X1 is A, D, E, S, or Y, X2 is S or Y, and X3 is H or Y(SEQ ID NO:202); (Formula VI) IGX1IYX2SGX3TX4YNPSLKSRV, wherein X1 is D, E, R, S, or Y, X2 is H or Y, X3 is N or S, and X4 is N or Y(SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T(SEQ ID NO:204); (Formula VIII) IGX1INPNX2GX3TX4YAQKFQGRV, wherein X1 is I, R, or W, X2 is F or R, X3 is D, G, or S, and X4 is K or N(SEQ ID NO:205); (Formula IX) IGX1IX2PSX3GX4TX5YAQKFQGRV, wherein X1 is I, R, or W, X2 is S or Y, X3 is G or S, X4 is D, G, or S, and X5 is K or N(SEQ ID NO:206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S(SEQ ID NO:207).

In some embodiments, the polynucleotides in the library encodes an antibody heavy chain variable region comprising an HVR-H1 comprising the amino acid sequence according to the formula X1TFX2X3YX4IHWV, wherein X1 is F or Y, X2 is S or T, X3 is D, G, N, or S, and X4 is A, G, or W (SEQ ID NO:198); and an HVR-H2 comprising the amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XI) IGX1IYX2SGX3TX4YNPSLKSRV, wherein X1 is D, E, or S, X2 is H or Y, X3 is N or S, and X4 is N or Y(SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S(SEQ ID NO:210).

In some embodiments, the polynucleotides in the library encodes an antibody heavy chain variable region comprising an HVR-H1 comprising the amino acid sequence according to the formula YSIX1SGX2X3WX4WI, wherein X1 is S or T, X2 is H or Y, X3 is H or Y, and X4 is A, D, G, N, S, or T (SEQ ID NO:19); and an HVR-H2 comprising the amino acid sequence according to a formula selected from the group consisting of (Formula IV) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T(SEQ ID NO:201); (Formula V) IGX1IX2X3SGSTYYSPSLKSRV, wherein X1 is A, D, E, S, or Y, X2 is S or Y, and X3 is H or Y(SEQ ID NO:202); (Formula VI) IGX1IYX2SGX3TX4YNPSLKSRV, wherein X1 is D, E, R, S, or Y, X2 is H or Y, X3 is N or S, and X4 is N or Y(SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T(SEQ ID NO:204); (Formula VIII) IGX1INPNX2GX3TX4YAQKFQGRV, wherein X1 is I, R, or W, X2 is F or R, X3 is D, G, or S, and X4 is K or N(SEQ ID NO:205); (Formula IX) IGX1IX2PSX3GX4TX5YAQKFQGRV, wherein X1 is I, R, or W, X2 is S or Y, X3 is G or S, X4 is D, G, or S, and X5 is K or N(SEQ ID NO:206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S(SEQ ID NO:207).

In some embodiments, the polynucleotides in the library encodes an antibody heavy chain variable region comprising an HVR-H1 comprising the amino acid sequence according to the formula YSIX1SGX2X3WX4WI, wherein X1 is S or T, X2 is H or Y, X3 is H or Y, and X4 is A, D, G, N, S, or T (SEQ ID NO:199); and an HVR-H2 comprising the amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XI) IGX1IYX2SGX3TX4YNPSLKSRV, wherein X1 is D, E, or S, X2 is H or Y, X3 is N or S, and X4 is N or Y(SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S(SEQ ID NO:210).

In some embodiments, the polynucleotides in the library encodes an antibody heavy chain variable region comprising an HVR-H1 comprising the amino acid sequence according to the formula FSLSTX1GVX2VX3WI, wherein X1 is G or S, X2 is A or G, and X3 is A, G, S, or T (SEQ ID NO:200); and an HVR-H2 comprising the amino acid sequence according to a formula selected from the group consisting of (Formula W) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T(SEQ ID NO:201); (Formula V) IGX1IX2X3SGSTYYSPSLKSRV, wherein X1 is A, D, E, S, or Y, X2 is S or Y, and X3 is H or Y(SEQ ID NO:202); (Formula VI) IGX1IYX2SGX3TX4YNPSLKSRV, wherein X1 is D, E, R, S, or Y, X2 is H or Y, X3 is N or S, and X4 is N or Y(SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T(SEQ ID NO:204); (Formula VIII) IGX1INPNX2GX3TX4YAQKFQGRV, wherein X1 is I, R, or W, X2 is F or R, X3 is D, G, or S, and X4 is K or N(SEQ ID NO:205); (Formula IX) IGX1IX2PSX3GX4TX5YAQKFQGRV, wherein X1 is I, R, or W, X2 is S or Y, X3 is G or S, X4 is D, G, or S, and X5 is K or N(SEQ ID NO:206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S(SEQ ID NO:207).

In some embodiments, the polynucleotides in the library encodes an antibody heavy chain variable region comprising an HVR-H1 comprising the amino acid sequence according to the formula FSLSTX1GVX2VX3WI, wherein X1 is G or S, X2 is A or G, and X3 is A, G, S, or T (SEQ ID NO:200); and an HVR-H2 comprising the amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XI) IGX1IYX2SGX3TX4YNPSLKSRV, wherein X1 is D, E, or S, X2 is H or Y, X3 is N or S, and X4 is N or Y(SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S(SEQ ID NO:210).

In some embodiments, the polynucleotide library encodes an antibody heavy chain variable region comprising a HVR-H1, HVR-H2, and HVR-H3, wherein the HVR-H1 comprises an amino acid sequence selected from the group consisting of SEQ ID NOS:1-52 and 137-158. In some embodiments, the polynucleotide library encodes an antibody heavy chain variable region comprising a HVR-H1, HVR-H2, and HVR-H3, wherein the HVR-H1 comprises an amino acid sequence selected from the group consisting of SEQ ID NOS:1-52.

In some embodiments, the polynucleotide library encodes an antibody heavy chain variable region comprising a HVR-H1, HVR-H2, and HVR-H3, wherein the HVR-H2 comprises an amino acid sequence selected from the group consisting of SEQ ID NOS:53-136 and 159-164. In some embodiments, the polynucleotide library encodes an antibody heavy chain variable region comprising a HVR-H1, HVR-H2, and HVR-H3, wherein the HVR-H2 comprises an amino acid sequence selected from the group consisting of SEQ ID NOS:53-136.

In some embodiments, the polynucleotide library encodes an antibody heavy chain variable region comprising a HVR-H1, HVR-H2, and HVR-H3, wherein the HVR-H1 comprises an amino acid sequence selected from the group consisting of Formula (I), Formula (II), and Formula (III), or the HVR-2 comprises an amino acid sequence selected from the group consisting of Formula (IV), Formula (V), Formula (VI), Formula (VII), Formula (VIII), Formula (IX), Formula (X), Formula (XI), Formula (XII), and Formula (XIII). In some embodiments, the polynucleotide library encodes an antibody heavy chain variable region comprising a HVR-H1, a HVR-H2 and a HVR-H3, wherein the HVR-H1 comprises an amino acid sequence selected from the group consisting of SEQ ID NOs: 1-52, or wherein the HVR-H2 comprises an amino acid sequence selected from the group consisting of SEQ ID NOs: 53-136. In some embodiments, the HVR-H1 comprises an amino acid sequence selected from the group consisting of SEQ ID NOs: 1, 4, 5, 7, 8, 9, 11, 13, 16, 18, 19, 20, 21, 22, 23, 24, 25, 26, 27, 28, 31, 33, 34, 38, 40, 42, 43, 45, 47, 49, 50, and 51, or wherein the HVR-H2 comprises an amino acid sequence selected from the group consisting of SEQ ID NOs: 53, 60, 63, 65, 66, 67, 70, 82, 89, 93, 95, 105, 109, 110, 117, 121, 122, 123, 124, 128, 129, 130, 131, 132, and 134. In some embodiments, the HVR-H1 comprises an amino acid sequence selected from the group consisting of SEQ ID NOs: 2, 3, 14, 15, 30, 32, 35, 37, 39, 41, 44, 46, and 48, or wherein the HVR-H2 comprises an amino acid sequence selected from the group consisting of SEQ ID NOs: 55, 56, 59, 61, 62, 64, 68, 69, 71, 73, 74, 75, 76, 77, 78, 79, 72, 81, 83, 86, 90, 91, 99, 100, 103, 106, 107, 108, 112, 113, 116, 118, 126, 135, and 136. In some embodiments, the HVR-H1 comprises an amino acid sequence selected from the group consisting of SEQ ID NOs: 6, 10, 17, 29, 36, and 52, or wherein the HVR-H2 comprises an amino acid sequence selected from the group consisting of SEQ ID NOs: 54, 57, 58, 80, 84, 85, 87, 88, 92, 94, 96, 97, 98, 101, 102, 104, 111, 114, 115, 119, 120, 125, 127 and 133.

In some embodiments, the polynucleotide library encodes an antibody heavy chain variable region comprising a HVR-H1, HVR-H2, and HVR-H3, wherein the HVR-H3 is any HVR-H3 known in the art. In some embodiments, the HVR-H3 comprises an amino acid sequence selected from the group consisting of SEQ ID NOs: 223-256.

The heavy chain HVR sequences described herein may be included in any combination in a library of the present disclosure. In some embodiments, a heavy chain variable region comprises an HVR-H1 comprising an amino acid sequence selected from the group consisting of SEQ ID NOS:1-52 and 137-158, and an HVR-H2 comprising an amino acid sequence selected from the group consisting of SEQ ID NOS:53-136 and 159-164. In some embodiments, a heavy chain variable region comprises an HVR-H1 comprising an amino acid sequence selected from the group consisting of SEQ ID NOS:1-52, and an HVR-H2 comprising an amino acid sequence selected from the group consisting of SEQ ID NOS:53-136. In some embodiments, a heavy chain variable region comprises an HVR-H1 comprising an amino acid sequence selected from the group consisting of SEQ ID NOS:1-52 and 137-158, and an HVR-H3 comprising an amino acid sequence selected from the group consisting of SEQ ID NOS:223-256. In some embodiments, a heavy chain variable region comprises an HVR-H1 comprising an amino acid sequence selected from the group consisting of SEQ ID NOS:1-52, and an HVR-H3 comprising an amino acid sequence selected from the group consisting of SEQ ID NOS:223-256. In some embodiments, a heavy chain variable region comprises an HVR-H2 comprising an amino acid sequence selected from the group consisting of SEQ ID NOS:53-136 and 159-164 and a HVR-H3 comprising an amino acid sequence selected from the group consisting of SEQ ID NOs: 223-256. In some embodiments, a heavy chain variable region comprises an HVR-H2 comprising an amino acid sequence selected from the group consisting of SEQ ID NOS:53-136 and a HVR-H3 comprising an amino acid sequence selected from the group consisting of SEQ ID NOs: 223-256. In some embodiments, a heavy chain variable region comprises an HVR-H1 comprising an amino acid sequence selected from the group consisting of SEQ ID NOS:1-52 and 137-158, an HVR-H2 comprising an amino acid sequence selected from the group consisting of SEQ ID NOS:53-136 and 159-164, and a HVR-H3 comprising an amino acid sequence selected from the group consisting of SEQ ID NOs: 223-256. In some embodiments, a heavy chain variable region comprises an HVR-H1 comprising an amino acid sequence selected from the group consisting of SEQ ID NOS:1-52, an HVR-H2 comprising an amino acid sequence selected from the group consisting of SEQ ID NOS:53-136, and a HVR-H3 comprising an amino acid sequence selected from the group consisting of SEQ ID NOs: 223-256.

In certain embodiments, a heavy chain variable region comprises three of a HVR-H1, a HVR-H2, and a HVR-H3, wherein the HVR-H1 and HVR-H2 are selected from the group consisting of: a HVR-H1 comprising the amino acid sequence of Formula (II) and a HVR-H2 comprising the amino acid sequence of Formula (IX); a HVR-H1 comprising the amino acid sequence of Formula (II) and a HVR-H2 comprising the amino acid sequence of Formula (VII); a HVR-H1 comprising the amino acid sequence of Formula (I) and a HVR-H2 comprising the amino acid sequence of Formula (VII); a HVR-H1 comprising the amino acid sequence of Formula (I) and a HVR-H2 comprising the amino acid sequence of Formula (IX); a HVR-H1 comprising the amino acid sequence of Formula (II) and a HVR-H2 comprising the amino acid sequence of Formula (IV); a HVR-H1 comprising the amino acid sequence of Formula (II) and a HVR-H2 comprising the amino acid sequence of Formula (V); a HVR-H1 comprising the amino acid sequence of Formula (II) and a HVR-H2 comprising the amino acid sequence of Formula (VI); a HVR-H1 comprising the amino acid sequence of Formula (I) and a HVR-H2 comprising the amino acid sequence of Formula (VI); a HVR-H1 comprising the amino acid sequence of Formula (III) and a HVR-H2 comprising the amino acid sequence of Formula (VI); a HVR-H1 comprising the amino acid sequence of Formula (III) and a HVR-H2 comprising the amino acid sequence of Formula (VII); a HVR-H1 comprising the amino acid sequence of Formula (II) and a HVR-H2 comprising the amino acid sequence of Formula (VIII); a HVR-H1 comprising the amino acid sequence of Formula (I) and a HVR-H2 comprising the amino acid sequence of Formula (V); a HVR-H1 comprising the amino acid sequence of Formula (III) and a HVR-H2 comprising the amino acid sequence of Formula (V); and a HVR-H1 comprising the amino acid sequence of Formula (I) and a HVR-H2 comprising the amino acid sequence of Formula (VIII). In some embodiments, the HVR-H1 and HVR-H2 are selected from the group consisting of: a HVR-H1 comprising the amino acid sequence of Formula (II) and a HVR-H2 comprising the amino acid sequence of Formula (XI); a HVR-H1 comprising the amino acid sequence of Formula (II) and a HVR-H2 comprising the amino acid sequence of Formula (XII); a HVR-H1 comprising the amino acid sequence of Formula (I) and a HVR-H2 comprising the amino acid sequence of Formula (XII); a HVR-H1 comprising the amino acid sequence of Formula (III) and a HVR-H2 comprising the amino acid sequence of Formula (XII); a HVR-H1 comprising the amino acid sequence of Formula (I) and a HVR-H2 comprising the amino acid sequence of Formula (XI); and a HVR-H1 comprising the amino acid sequence of Formula (III) and a HVR-H2 comprising the amino acid sequence of Formula (XI). In some embodiments, the HVR-H1 and HVR-H2 are selected from the group consisting of: a HVR-H1 comprising the amino acid sequence of Formula (I) and a HVR-H2 comprising the amino acid sequence of Formula (IV); a HVR-H1 comprising the amino acid sequence of Formula (III) and a HVR-H2 comprising the amino acid sequence of Formula (IV); a HVR-H1 comprising the amino acid sequence of Formula (II) and a HVR-H2 comprising the amino acid sequence of Formula (X); a HVR-H1 comprising the amino acid sequence of Formula (III) and a HVR-H2 comprising the amino acid sequence of Formula (IX); a HVR-H1 comprising the amino acid sequence of Formula (I) and a HVR-H2 comprising the amino acid sequence of Formula (X); a HVR-H1 comprising the amino acid sequence of Formula (III) and a HVR-H2 comprising the amino acid sequence of Formula (VIII); and a HVR-H1 comprising the amino acid sequence of Formula (III) and a HVR-H2 comprising the amino acid sequence of Formula (X). In some embodiments, the HVR-H1 and HVR-H2 are selected from the group consisting of: a HVR-H1 comprising the amino acid sequence of Formula (II) and a HVR-H2 comprising the amino acid sequence of Formula (XIII); a HVR-H1 comprising the amino acid sequence of Formula (I) and a HVR-H2 comprising the amino acid sequence of Formula (XIII); and a HVR-H1 comprising the amino acid sequence of Formula (III) and a HVR-H2 comprising the amino acid sequence of Formula (XIII).

In certain embodiments, a heavy chain variable region comprises three of a HVR-H1, a HVR-H2, and a HVR-H3, wherein the HVR-H1 and HVR-H2 are selected from the group consisting of: a HVR-H1 comprising the amino acid sequence of SEQ ID NO:157, and a HVR-H2 comprising the amino acid sequence of SEQ ID NO:63; a HVR-H1 comprising the amino acid sequence of SEQ ID NO:1, and a HVR-H2 comprising the amino acid sequence of SEQ ID NO:122; a HVR-H1 comprising the amino acid sequence of SEQ ID NO:138, and a HVR-H2 comprising the amino acid sequence of SEQ ID NO:63; a HVR-H1 comprising the amino acid sequence of SEQ ID NO:154, and a HVR-H2 comprising the amino acid sequence of SEQ ID NO:63; a HVR-H1 comprising the amino acid sequence of SEQ ID NO:158, and a HVR-H2 comprising the amino acid sequence of SEQ ID NO:161; a HVR-H1 comprising the amino acid sequence of SEQ ID NO:158, and a HVR-H2 comprising the amino acid sequence of SEQ ID NO:63; a HVR-H1 comprising the amino acid sequence of SEQ ID NO:145, and a HVR-H2 comprising the amino acid sequence of SEQ ID NO:128; a HVR-H1 comprising the amino acid sequence of SEQ ID NO:22, and a HVR-H2 comprising the amino acid sequence of SEQ ID NO:61; a HVR-H1 comprising the amino acid sequence of SEQ ID NO:31, and a HVR-H2 comprising the amino acid sequence of SEQ ID NO:63; a HVR-H1 comprising the amino acid sequence of SEQ ID NO:153, and a HVR-H2 comprising the amino acid sequence of SEQ ID NO:63; a HVR-H1 comprising the amino acid sequence of SEQ ID NO:155, and a HVR-H2 comprising the amino acid sequence of SEQ ID NO:67; a HVR-H1 comprising the amino acid sequence of SEQ ID NO:156, and a HVR-H2 comprising the amino acid sequence of SEQ ID NO:100; a HVR-H1 comprising the amino acid sequence of SEQ ID NO:51, and a HVR-H2 comprising the amino acid sequence of SEQ ID NO:162; a HVR-H1 comprising the amino acid sequence of SEQ ID NO:138, and a HVR-H2 comprising the amino acid sequence of SEQ ID NO:123; a HVR-H1 comprising the amino acid sequence of SEQ ID NO:139, and a HVR-H2 comprising the amino acid sequence of SEQ ID NO:110; a HVR-H1 comprising the amino acid sequence of SEQ ID NO:8, and a HVR-H2 comprising the amino acid sequence of SEQ ID NO:126; a HVR-H1 comprising the amino acid sequence of SEQ ID NO:13, and a HVR-H2 comprising the amino acid sequence of SEQ ID NO:129; a HVR-H1 comprising the amino acid sequence of SEQ ID NO:31, and a HVR-H2 comprising the amino acid sequence of SEQ ID NO:124; a HVR-H1 comprising the amino acid sequence of SEQ ID NO:25, and a HVR-H2 comprising the amino acid sequence of SEQ ID NO:130; a HVR-H1 comprising the amino acid sequence of SEQ ID NO:150, and a HVR-H2 comprising the amino acid sequence of SEQ ID NO:132; a HVR-H1 comprising the amino acid sequence of SEQ ID NO:158, and a HVR-H2 comprising the amino acid sequence of SEQ ID NO:162; a HVR-H1 comprising the amino acid sequence of SEQ ID NO:12, and a HVR-H2 comprising the amino acid sequence of SEQ ID NO:82; a HVR-H1 comprising the amino acid sequence of SEQ ID NO:149, and a HVR-H2 comprising the amino acid sequence of SEQ ID NO:117; and a HVR-H1 comprising the amino acid sequence of SEQ ID NO:7, and a HVR-H2 comprising the amino acid sequence of SEQ ID NO:134. In some embodiments, the HVR-H1 and HVR-H2 are selected from the group consisting of: a HVR-H1 comprising the amino acid sequence of SEQ ID NO:26, and a HVR-H2 comprising the amino acid sequence of SEQ ID NO:53; a HVR-H1 comprising the amino acid sequence of SEQ ID NO:151, and a HVR-H2 comprising the amino acid sequence of SEQ ID NO:53; a HVR-H1 comprising the amino acid sequence of SEQ ID NO:34, and a HVR-H2 comprising the amino acid sequence of SEQ ID NO:63; a HVR-H1 comprising the amino acid sequence of SEQ ID NO:50, and a HVR-H2 comprising the amino acid sequence of SEQ ID NO:162; a HVR-H1 comprising the amino acid sequence of SEQ ID NO:158, and a HVR-H2 comprising the amino acid sequence of SEQ ID NO:104; a HVR-H1 comprising the amino acid sequence of SEQ ID NO:5, and a HVR-H2 comprising the amino acid sequence of SEQ ID NO:121; a HVR-H1 comprising the amino acid sequence of SEQ ID NO:6, and a HVR-H2 comprising the amino acid sequence of SEQ ID NO:116; a HVR-H1 comprising the amino acid sequence of SEQ ID NO:7, and a HVR-H2 comprising the amino acid sequence of SEQ ID NO:121; a HVR-H1 comprising the amino acid sequence of SEQ ID NO:17, and a HVR-H2 comprising the amino acid sequence of SEQ ID NO:63; a HVR-H1 comprising the amino acid sequence of SEQ ID NO:25, and a HVR-H2 comprising the amino acid sequence of SEQ ID NO:101; a HVR-H1 comprising the amino acid sequence of SEQ ID NO:25, and a HVR-H2 comprising the amino acid sequence of SEQ ID NO:114; a HVR-H1 comprising the amino acid sequence of SEQ ID NO:29, and a HVR-H2 comprising the amino acid sequence of SEQ ID NO:112; a HVR-H1 comprising the amino acid sequence of SEQ ID NO:152, and a HVR-H2 comprising the amino acid sequence of SEQ ID NO:63; a HVR-H1 comprising the amino acid sequence of SEQ ID NO:156, and a HVR-H2 comprising the amino acid sequence of SEQ ID NO:89; a HVR-H1 comprising the amino acid sequence of SEQ ID NO:157, and a HVR-2 comprising the amino acid sequence of SEQ ID NO:94; a HVR-H1 comprising the amino acid sequence of SEQ ID NO:48, and a HVR-H2 comprising the amino acid sequence of SEQ ID NO:58; a HVR-H1 comprising the amino acid sequence of SEQ ID NO:50, and a HVR-H2 comprising the amino acid sequence of SEQ ID NO:89; a HVR-H1 comprising the amino acid sequence of SEQ ID NO:50, and a HVR-H2 comprising the amino acid sequence of SEQ ID NO:163; a HVR-H1 comprising the amino acid sequence of SEQ ID NO:158, and a HVR-H2 comprising the amino acid sequence of SEQ ID NO:160; a HVR-H1 comprising the amino acid sequence of SEQ ID NO:158, and a HVR-H2 comprising the amino acid sequence of SEQ ID NO:87; a HVR-H1 comprising the amino acid sequence of SEQ ID NO:158, and a HVR-2 comprising the amino acid sequence of SEQ ID NO:92; a HVR-H1 comprising the amino acid sequence of SEQ ID NO:158, and a HVR-H2 comprising the amino acid sequence of SEQ ID NO:93; a HVR-H1 comprising the amino acid sequence of SEQ ID NO:158, and a HVR-2 comprising the amino acid sequence of SEQ ID NO:97; a HVR-H1 comprising the amino acid sequence of SEQ ID NO:158, and a HVR-H2 comprising the amino acid sequence of SEQ ID NO:103; a HVR-H1 comprising the amino acid sequence of SEQ ID NO:158, and a HVR-H2 comprising the amino acid sequence of SEQ ID NO:164; a HVR-H1 comprising the amino acid sequence of SEQ ID NO:137, and a HVR-H2 comprising the amino acid sequence of SEQ ID NO:54; a HVR-H1 comprising the amino acid sequence of SEQ ID NO:3, and a HVR-H2 comprising the amino acid sequence of SEQ ID NO:127; a HVR-H1 comprising the amino acid sequence of SEQ ID NO:4, and a HVR-H2 comprising the amino acid sequence of SEQ ID NO:85; a HVR-H1 comprising the amino acid sequence of SEQ ID NO:4, and a HVR-H2 comprising the amino acid sequence of SEQ ID NO:110; a HVR-H1 comprising the amino acid sequence of SEQ ID NO:139, and a HVR-H2 comprising the amino acid sequence of SEQ ID NO:109; a HVR-H1 comprising the amino acid sequence of SEQ ID NO:139, and a HVR-H2 comprising the amino acid sequence of SEQ ID NO:121; a HVR-H1 comprising the amino acid sequence of SEQ ID NO:8, and a HVR-H2 comprising the amino acid sequence of SEQ ID NO:120; a HVR-H1 comprising the amino acid sequence of SEQ ID NO:140, and a HVR-H2 comprising the amino acid sequence of SEQ ID NO:131; a HVR-H1 comprising the amino acid sequence of SEQ ID NO:141, and a HVR-H2 comprising the amino acid sequence of SEQ ID NO:116; a HVR-H1 comprising the amino acid sequence of SEQ ID NO:142, and a HVR-H2 comprising the amino acid sequence of SEQ ID NO:159; a HVR-H1 comprising the amino acid sequence of SEQ ID NO:143, and a HVR-H2 comprising the amino acid sequence of SEQ ID NO:116; a HVR-H1 comprising the amino acid sequence of SEQ ID NO:144, and a HVR-H2 comprising the amino acid sequence of SEQ ID NO:121; a HVR-H1 comprising the amino acid sequence of SEQ ID NO:146, and a HVR-H2 comprising the amino acid sequence of SEQ ID NO:110; a HVR-H1 comprising the amino acid sequence of SEQ ID NO:147, and a HVR-H2 comprising the amino acid sequence of SEQ ID NO:133; a HVR-H1 comprising the amino acid sequence of SEQ ID NO:148, and a HVR-H2 comprising the amino acid sequence of SEQ ID NO:63; and a HVR-H1 comprising the amino acid sequence of SEQ ID NO:13, and a HVR-H2 comprising the amino acid sequence of SEQ ID NO:118.

In some embodiments, a heavy chain variable region comprises three of a HVR-H1, a HVR-H2, and a HVR-H3, wherein the HVR-H1 and HVR-H2 are listed in Table 1. In some embodiments, the HVR-H3 comprises an amino acid sequence selected from the group consisting of SEQ ID NOs: 223-256. In some embodiments, a heavy chain variable region comprises a sequence selected from the group consisting of SEQ ID NOS: 169, 171, 173, 175, 177, 179, 181, 183, 185, 187, 189, 191, 193, and 195, or a sequence having at least 80%, at least 85%, at least 90%, at least 91%, at least 92%, at least 93%, at least 94%, at least 95%, at least 96%, at least 97%, at least 98%, or at least 99% sequence identity to a sequence selected from SEQ ID NOS: 169, 171, 173, 175, 177, 179, 181, 183, 185, 187, 189, 191, 193, and 195.

In some embodiments, a heavy chain variable region further comprises variable region heavy chain framework sequences juxtaposed between the HVRs according to the formula: (FW-H1)-(HVR-H1)-(FW-H2)-(HVR-H2)-(FW-H3)-(HVR-H3)-(FW-H4). In some embodiments, one, two, three, or four of the framework sequences is/are the following:

```
                                    (SEQ ID NO: 165)
FW-H1 is EVQLVESGGGLVQPGGSLRLSCAASG

                                    (SEQ ID NO: 166)
FW-H2 is RQAPGKGLEW

                                    (SEQ ID NO: 167)
FW-H3 is TISRDNSKNTLYLQLNSLRAEDTAVYYC

                                    (SEQ ID NO: 168)
FW-H4 is WGQGTLVTVSS.
```

In some embodiments, the heavy chain variable region comprises an alternate FW-H3 sequence with an arginine to lysine mutation at R19 of SEQ ID NO:167. In some embodiments, one, two, three, or four of the framework sequences is/are an FW-H1 of SEQ ID NO:165, an FW-H12 of SEQ ID NO:166, an FW-H13 or SEQ ID NO:167 with an arginine to lysine mutation at R19, and an FW-H14 of SEQ ID NO:168.

In some embodiments, a library contains a plurality of polynucleotides, with at least one of the polynucleotides encoding an antibody light chain variable region (e.g., comprising a HVR-L1, HVR-L2, and HVR-L3). In some embodiments, the antibody light chain variable region comprises an HVR-L1 comprising an amino acid sequence selected from the group consisting of SEQ ID NOs: 257-264. In some embodiments, the antibody light chain variable region comprises an HVR-L3 comprising an amino acid sequence selected from the group consisting of SEQ ID NOs: 265-274. In some embodiments, the antibody light chain variable region comprises an HVR-L1 comprising an amino acid sequence selected from the group consisting of SEQ ID NOs: 257-264, and an HVR-L3 comprising an amino acid sequence selected from the group consisting of SEQ ID NOs: 265-274 In some embodiments, a library contains a plurality of polynucleotides that encodes at least one, at least 50, at least 100, at least 250, at least 500, at least $10^3$, at least $10^4$, at least $10^5$, at least $10^6$, at least $10^7$, at least $10^8$, at least $10^9$, at least $10^{10}$, at least $10^{11}$, or at least $10^{12}$ unique sequences of antibody light chain variable regions. In some embodiments, a library contains a plurality of polynucleotides that encodes at least $10^3$ unique sequences of antibody light chain variable regions. In some embodiments, a library contains a plurality of polynucleotides that encodes at least $10^5$ unique sequences of antibody light chain variable regions. In some embodiments, a library contains a plurality of polynucleotides that encodes at least $10^9$ unique sequences of antibody light chain variable regions. In other embodiments, a library contains a polynucleotide that encodes one antibody light chain variable region. In some embodiments, a library contains a plurality of polynucleotides that encodes from 1 to about $10^3$ unique sequences of antibody light chain variable regions. In some embodiments, the antibody light chain variable region is any of the antibody light chain variable regions found in the patent application(s) (the disclosures of which are each incorporated herein by reference in their entireties). In some embodiments, the antibody light chain variable region comprises any of the HVR-L1, HVR-L2, and/or HVR-L3 sequences found in the patent application(s) (the disclosures of which are each incorporated herein by reference in their entireties).

In some embodiments, one or more of the polynucleotides of a library encode(s) full-length antibody heavy chain(s). In other embodiments, one or more of the polynucleotides of a library encode(s) heavy chain Fab fragment(s). In some embodiments, one or more of the polynucleotides of a library encode(s) single-chain variable fragment(s).

In some embodiments, a library contains a plurality of polynucleotides that encodes a plurality of unique antibodies. In some embodiments, each antibody comprises a heavy chain variable region and a light chain variable region. In some embodiments, the heavy chain variable region of each antibody of the plurality comprises an identical sequence and comprises a HVR-H1, a HVR-H2 and a HVR-H3. In some embodiments, at least one or at least two of the HVR-H1 and HVR-H2 comprise an amino acid sequence selected from a HVR-H1 sequence of the present disclosure (e.g., X1TFX2X3YX4IHWV, wherein X1 is F or Y, X2 is S or T, X3 is D, G, N, or S, and X4 is A, G, or W (SEQ ID NO:198); YSIX1SGX2X3WX4WI, wherein X1 is S or T, X2 is H or Y, X3 is H or Y, and X4 is A, D, G, N, S, or T (SEQ ID NO:199); and FSLSTX1GVX2VX3WI, wherein X1 is G or S, X2 is A or G, and X3 is A, G, S, or T (SEQ ID NO:200); and SEQ ID NOS:1-52 and 137-158), and a HVR-H2 sequence of the present disclosure (e.g., LAX1IX2WX3X4DKX5YSX6SLKSRL, wherein X1 is L or R, X2 is D or Y, X3 is A, D, S, or Y, X4 is D or G, X5 is R, S, or Y, and X6 is P or T (SEQ ID NO:201); IGX1IX2X3SGSTYYSPSLKSRV, wherein X1 is A, D, E, S, or Y, X2 is S or Y, and X3 is H or Y(SEQ ID NO:202); IGX1IYX2SGX3TX4YNPSLKSRV, wherein X1 is D, E, R, S, or Y, X2 is H or Y, X3 is N or S, and X4 is N or Y (SEQ ID NO:203); VSX1ISGX2GX3X4TYYADSVKGRF, wherein X1 is A, G, S, V, or Y, X2 is A, D, S, or Y, X3 is D, G, or S, and X4 is S or T (SEQ ID NO:204); IGX1INPNX2GX3TX4YAQKFQGRV, wherein X1 is I, R, or W, X2 is F or R, X3 is D, G, or S, and X4 is K or N (SEQ ID NO:205); IGX1IX2PSX3GX4TX5YAQKFQGRV, wherein X1 is I, R, or W, X2 is S or Y, X3 is G or S, X4 is D, G, or S, and X5 is K or N (SEQ ID NO:206); VGRIX1SKX2X3GX4TTX5YAAX6VKGRF, wherein X1 is K or R, X2 is A or T, X3 is D or Y, X4 is G or Y, X5 is D or E, and X6 is P or S (SEQ ID NO:207); IGX1IX2X3SGSTYYSPSLKSRV, wherein X1 is A, D, or E, X2 is S or Y, and X3 is H or Y (SEQ ID NO:208);

IGX1IYX2SGX3TX4YNPSLKSRV, wherein X1 is D, E, or S, X2 is H or Y, X3 is N or S, and X4 is N or Y (SEQ ID NO:209); and VGRIX1SKX2X3GX4TTEYAAX5VKGRF, wherein X1 is K or R, X2 is A or T, X3 is D or Y, X4 is G or Y, and X5 is P or S (SEQ ID NO:210); and SEQ ID NOS:53-136 and 159-164). The heavy chain HVR sequences described herein may be included in any combination in a library of the present disclosure that also includes polynucleotides encoding one or more light chain variable region(s).

In some embodiments, a library of the present disclosure includes one or more vectors encoding one or more polynucleotides (e.g., synthetic polynucleotides) of the present disclosure.

Further provided herein is a method of preparing a library, e.g., by providing and assembling the polynucleotide sequences (e.g., synthetic polynucleotide(s)) of a library of the present disclosure. Further provided herein is a method of making a library, e.g., by selecting one, two, or three heavy chain HVRs (e.g., one or two heavy chain HVRs of the present disclosure) comprising a sequence having multiple conformations and assembling polynucleotide sequences to produce a library of polynucleotides (e.g., synthetic polynucleotides) encoding a plurality of antibody heavy chain variable region sequences. In some embodiments, the antibody heavy chain variable region sequences are human antibody sequences. In some embodiments, the antibody heavy chain variable region comprises a HVR-H1, a HVR-H2 and a HVR-H3, and the HVR-H1 and/or HVR-H2 comprise an amino acid sequence selected from a HVR-H1 sequence of the present disclosure (e.g., X1TFX2X3YX4IHWV, wherein X1 is F or Y, X2 is S or T, X3 is D, G, N, or S, and X4 is A, G, or W (SEQ ID NO:198); YSIX1SGX2X3WX4WI, wherein X1 is S or T, X2 is H or Y, X3 is H or Y, and X4 is A, D, G, N, S, or T (SEQ ID NO:199); and FSLSTX1GVX2VX3WI, wherein X1 is G or S, X2 is A or G, and X3 is A, G, S, or T (SEQ ID NO:200); and SEQ ID NOS:1-52 and 137-158), and a HVR-H2 sequence of the present disclosure (e.g., LAX1IX2WX3X4DKX5YSX6SLKSRL, wherein X1 is L or R, X2 is D or Y, X3 is A, D, S, or Y, X4 is D or G, X5 is R, S, or Y, and X6 is P or T (SEQ ID NO:201); IGX1IX2X3SGSTYYSPSLKSRV, wherein X1 is A, D, E, S, or Y, X2 is S or Y, and X3 is H or Y (SEQ ID NO:202); IGX1IYX2SGX3TX4YNPSLKSRV, wherein X1 is D, E, R, S, or Y, X2 is H or Y, X3 is N or S, and X4 is N or Y (SEQ ID NO:203); VSX1ISGX2GX3X4TYYADSVKGRF, wherein X1 is A, G, S, V, or Y, X2 is A, D, S, or Y, X3 is D, G, or S, and X4 is S or T (SEQ ID NO:204); IGX1INPNX2GX3TX4YAQKFQGRV, wherein X1 is I, R, or W, X2 is F or R, X3 is D, G, or S, and X4 is K or N (SEQ ID NO:205); IGX1IX2PSX3GX4TX5YAQKFQGRV, wherein X1 is I, R, or W, X2 is S or Y, X3 is G or S, X4 is D, G, or S, and X5 is K or N (SEQ ID NO:206); VGRIX1SKX2X3GX4TTX5YAAX6VKGRF, wherein X1 is K or R, X2 is A or T, X3 is D or Y, X4 is G or Y, X5 is D or E, and X6 is P or S (SEQ ID NO:207); IGX1IX2X3SGSTYYSPSLKSRV, wherein X1 is A, D, or E, X2 is S or Y, and X3 is H or Y (SEQ ID NO:208); IGX1IYX2SGX3TX4YNPSLKSRV, wherein X1 is D, E, or S, X2 is H or Y, X3 is N or S, and X4 is N or Y (SEQ ID NO:209); and VGRIX1SKX2X3GX4TTEYAAX5VKGRF, wherein X1 is K or R, X2 is A or T, X3 is D or Y, X4 is G or Y, and X5 is P or S (SEQ ID NO:210); and SEQ ID NOS:53-136 and 159-164).

In some embodiments, at least one of the HVR-H1, HVR-H2, and HVR-H3 of the antibody heavy chain variable region adopts multiple conformations. In some embodiments, the multiple conformations can be assayed or detected using techniques known in the art, including, without limitation, structural determination (e.g., X-ray crystallography or NMR) and/or computational modeling.

Polynucleotides encoding a set of antibody light and/or heavy chain variable regions can be cloned into any suitable vector for expression of a portion or the entire light or heavy chain sequences. In some embodiments, the polynucleotide cloned into a vector allows production of a portion or the entire light or heavy chain sequence fused to all or a portion of a viral coat protein (i.e., creating a fusion protein) and displayed on the surface of a particle or cell. Several types of vectors are available and may be used to practice the present disclosure, for example, phagemid vectors. Phagemid vectors generally contain a variety of components including promoters, signal sequences, phenotypic selection genes, origin of replication sites, and other necessary components as are known to those of ordinary skill in the art. In some embodiments, the polynucleotides encoding a set of antibody light and/or heavy chain variable regions can be cloned into vectors for expression in bacterial cells for bacterial display or in yeast cells for yeast display. Exemplary vectors are described in US PG Pub. No. US20160145604. In some embodiments, the vector is a display vector comprising, from 5' to 3', a polynucleotide encoding an amino acid sequence to be displayed on a surface (e.g., a surface of phage, bacteria, yeast, or mammalian cells), a restriction site, a second polynucleotide encoding a surface peptide capable of being displayed on the surface, and a second restriction site. In some embodiments, the second polynucleotide encodes a phage coat protein, a yeast outer wall protein, a bacterial outer membrane protein, a cell surface tether domain, or an adapter, or a truncation or derivative thereof. In certain embodiments, the second polynucleotide is gene III of filamentous phage M13, or a truncation or derivative thereof. In some embodiments, the surface peptide is for phage display, yeast display, bacterial display or mammalian display, or shuttling display there between. In some embodiments, when expressed, the amino acid sequence and the surface peptide are displayed as a fusion protein on the surface. In some embodiments, the vector further comprises a fusion tag 5' to the first restriction site or 3' to the second restriction site.

Certain aspects of the present disclosure relate to a population of cells containing vector(s) described herein. Antibody light and/or heavy chains encoded by polynucleotides generated by any of the techniques described herein, or other suitable techniques, can be expressed and screened to identify antibodies having desired structure and/or activity. Expression of the antibodies can be carried out, for example, using cell-free extracts (e.g., ribosome display), phage display, prokaryotic cells (e.g., bacterial display), or eukaryotic cells (e.g., yeast display). In some embodiments, the cells are bacterial cells, yeast cells, or mammalian cells. Methods for transfecting bacterial cells, yeast cells, or mammalian cells are known in the art and described in the references cited herein. Expression (e.g., from a library of the present disclosure) of polypeptides (e.g., antibody chains) in these cell types, as well as screening for antibodies of interest, are described in more detail below.

Alternatively, the polynucleotides can be expressed in an *E. coli* expression system, such as that described by Pluckthun and Skerra. (Meth. Enzymol., 1989, 178: 476; Biotechnology, 1991, 9: 273). The mutant proteins can be expressed for secretion in the medium and/or in the cytoplasm of the bacteria, as described by Better and Horwitz, Meth. Enzymol., 1989, 178: 476. In some embodiments, the single domains encoding $V_H$ and $V_L$, are each attached to the 3' end of a sequence encoding a signal sequence, such as the ompA, phoA or pelB signal sequence (Lei et al., J. Bacteriol., 1987, 169: 4379). These gene fusions are assembled in a dicistronic construct, so that they can be expressed from a single vector and secreted into the periplasmic space of *E. coli* where they will refold and can be recovered in active form. (Skerra et al., Biotechnology, 1991, 9: 273). For example, antibody heavy chain genes can be concurrently expressed with antibody light chain genes to produce antibodies or antibody fragments.

In other embodiments, the antibody sequences are expressed on the membrane surface of a prokaryote, e.g., *E. coli*, using a secretion signal and lipidation moiety as described, e.g., in US20040072740; US20030100023; and US20030036092.

Alternatively, antibodies can be expressed and screened by anchored periplasmic expression (APEx 2-hybrid surface display), as described, for example, in Jeong et al., PNAS, 2007, 104: 8247 or by other anchoring methods as described, for example, in Mazor et al., Nature Biotechnology, 2007, 25: 563.

Higher eukaryotic cells, such as mammalian cells, for example myeloma cells (e.g., NS/0 cells), hybridoma cells, Chinese hamster ovary (CHO), and human embryonic kidney (HEK) cells, can also be used for expression of the antibodies of the present disclosure. Typically, antibodies expressed in mammalian cells are designed to be secreted into the culture medium, or expressed on the surface of the cell. The antibody or antibody fragments can be produced, for example, as intact antibody molecules or as individual $V_H$ and $V_L$, fragments, Fab fragments, single domains, or as single chains (scFv).

In other embodiments, antibodies can be selected using mammalian cell display (Ho et al., PNAS, 2006, 103: 9637). In some embodiments, as described above and exemplified below, antibodies can be selected after production of a portion or the entire light or heavy chain sequence fused to all or a portion of a viral coat protein (i.e., creating a fusion protein) and displayed on the surface of a particle or cell, e.g., using phage display.

Certain aspects of the present disclosure relate to a non-human animal comprising a polynucleotide library of the present disclosure. For example, a non-human animal of the present disclosure may be modified such that its genome includes a polynucleotide encoding a heavy chain variable region of the present disclosure. In a non-limiting example, a transgenic mouse is generated that includes a heavy chain immunoglobulin locus modified to express one or more of the heavy chain variable regions of the present disclosure. In some embodiments, the transgenic animal (e.g., mouse) expresses antibodies or heavy chains encoded by the polynucleotides. Techniques for modifying one or more immunoglobulin loci of a non-human animal are known in the art (e.g., methods used to generate Xenomouse™).

The screening of the antibodies derived from the libraries of the present disclosure can be carried out by any appropriate means known in the art. For example, binding activity can be evaluated by standard immunoassay and/or affinity chromatography. Screening of the antibodies of the present disclosure for catalytic function, e.g., proteolytic function can be accomplished using a standard assays, e.g., a hemoglobin plaque assay. Determining binding affinity of an antibody to a target can be assayed in vitro using a variety of well-known techniques, e.g., a BIACORE™ instrument, which measures binding rates of an antibody to a given target or antigen based on surface plasmon resonance, or Bio-Layer Interferometry (BLI), as exemplified below using the ForteBio Octet® RED96 platform (Pall Life Sciences). In vivo assays can be conducted using any of a number of animal models and then subsequently tested, as appropriate, in humans. Cell-based biological assays are also contemplated. The antibodies or antigen binding fragments can be further selected for functional activity, for example, antagonist or agonist activity. Exemplary screening methods are described herein. For example, in some embodiments, affinity of binding between fab fragment(s) and one or more target(s) is measured using BLI by tagging antigens with human IgG1-Fc tag and capture by Anti-hIgG-Fc Capture (AHC) Biosensor. Fabs can be tagged at their C-terminus of the CH1 domain with a His6 tag, over-expressed in a host cell such as *E. coli*, and purified, e.g., using a Ni-NTA resin. Affinity can then be measured using AHC sensors (anti-human IgG-Fc capture dip and read biosensors) dipped into wells containing the purified fabs diluted, e.g., to 5-10 μg/mL with kinetic buffer.

After binders are identified by binding to the target or antigen, and/or functional assays the nucleic acid can be extracted. Extracted DNA can then be used directly to transform *E. coli* host cells or alternatively, the encoding sequences can be amplified, for example using PCR with suitable primers, and sequenced by any typical sequencing method. Variable domain DNA of the binders can be restriction enzyme digested and then inserted into a vector for protein expression.

IV. Antibodies and Antibody Production

Provided herein are antibodies identified and selected from the libraries described herein. Certain aspects of the present disclosure relate to antibody light chain or heavy chain HVRs, variable regions comprising the HVRs, and/or polynucleotide(s) encoding the same. In some embodiments, the HVRs and/or variable regions are part of an antibody fragment, full-length antibody, or single-chain variable fragment (scFv).

In some embodiments, a heavy chain variable region comprises an HVR-H1, HVR-H2, and HVR-H3, wherein the HVR-H1 comprises an amino acid sequence according to a formula selected from the group consisting of (Formula I) X1 TFX2X3YX4IHWV, wherein X1 is F or Y, X2 is S or T, X3 is D, G, N, or S, and X4 is A, G, or W (SEQ ID NO:198); (Formula II) YSIX1SGX2X3WX4WI, wherein X1 is S or T, X2 is H or Y, X3 is H or Y, and X4 is A, D, G, N, S, or T (SEQ ID NO: 199); and (Formula III) FSLSTX1GVX2VX3WI, wherein X1 is G or S, X2 is A or G, and X3 is A, G, S, or T (SEQ ID NO:200). In some embodiments, a heavy chain variable region comprises an HVR-H1, HVR-H2, and HVR-H3, wherein the HVR-H2 comprises an amino acid sequence according to a formula selected from the group consisting of (Formula IV) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T (SEQ ID NO:201); (Formula V) IGX1IX2X3SGSTYYSPSLKSRV, wherein X1 is A, D, E, S, or Y, X2 is S or Y, and X3 is H or Y (SEQ ID NO:202); (Formula VI) IGX11YX2SGX3TX4YNPSLKSRV, wherein X1 is D, E, R, S, or Y, X2 is H or Y, X3 is N or S, and X4 is N or Y (SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T (SEQ ID NO:204); (Formula VIII) IGX1INPNX2GX3TX4YAQKFQGRV, wherein X1 is I, R, or W, X2 is F or R, X3 is D, G, or S, and X4 is K or N (SEQ ID NO:205); (Formula IX)

IGX1IX2PSX3GX4TX5YAQKFQGRV, wherein X1 is I, R, or W, X2 is S or Y, X3 is G or S, X4 is D, G, or S, and X5 is K or N (SEQ ID NO: 206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S (SEQ ID NO:207). In some embodiments, the HVR-H2 comprises an amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XII) IGX1IYX2SGX3TX4YNPSLKSRV, wherein X1 is D, E, or S, X2 is H or Y, X3 is N or S, and X4 is N or Y (SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S (SEQ ID NO:210). In some embodiments, a heavy chain variable region comprises an HVR-H1, HVR-H2, and HVR-H3, wherein the HVR-H1 comprises the amino acid sequence according to a formula selected from the group consisting of (Formula I) X1TFX2X3YX4IHWV, wherein X1 is F or Y, X2 is S or T, X3 is D, G, N, or S, and X4 is A, G, or W (SEQ ID NO:198); (Formula II) YSIX1SGX2X3WX4WI, wherein X1 is S or T, X2 is H or Y, X3 is H or Y, and X4 is A, D, G, N, S, or T (SEQ ID NO: 199); and (Formula III) FSLSTX1GVX2VX3WI, wherein X1 is G or S, X2 is A or G, and X3 is A, G, S, or T (SEQ ID NO:200); and an HVR-H2 comprising the amino acid sequence according to a formula selected from the group consisting of (Formula W) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T (SEQ ID NO:201); (Formula V) IGX1IX2X3SGSTYYSPSLKSRV, wherein X1 is A, D, E, S, or Y, X2 is S or Y, and X3 is H or Y (SEQ ID NO:202); (Formula VI) IGX11YX2SGX3TX4YNPSLKSRV, wherein X1 is D, E, R, S, or Y, X2 is H or Y, X3 is N or S, and X4 is N or Y (SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T (SEQ ID NO:204); (Formula VIII) IGX1INPNX2GX3TX4YAQKFQGRV, wherein X1 is I, R, or W, X2 is F or R, X3 is D, G, or S, and X4 is K or N (SEQ ID NO:205); (Formula IX) IGX1IX2PSX3GX4TX5YAQKFQGRV, wherein X1 is I, R, or W, X2 is S or Y, X3 is G or S, X4 is D, G, or S, and X5 is K or N (SEQ ID NO: 206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S (SEQ ID NO:207). In some embodiments, a heavy chain variable region comprises an HVR-H1, HVR-H2, and HVR-H3, wherein the HVR-H1 comprises the amino acid sequence according to a formula selected from the group consisting of (Formula I) X1TFX2X3YX4IHWV, wherein X1 is F or Y, X2 is S or T, X3 is D, G, N, or S, and X4 is A, G, or W (SEQ ID NO:198); (Formula II) YSIX1SGX2X3WX4WI, wherein X1 is S or T, X2 is H or Y, X3 is H or Y, and X4 is A, D, G, N, S, or T (SEQ ID NO: 199); and (Formula III) FSLSTX1GVX2VX3WI, wherein X1 is G or S, X2 is A or G, and X3 is A, G, S, or T (SEQ ID NO:200); and an HVR-H2 comprising the amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XII) IGX1IYX2SGX3TX4YNPSLKSRV, wherein X1 is D, E, or S, X2 is H or Y, X3 is N or S, and X4 is N or Y (SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S (SEQ ID NO:210).

In some embodiments, the heavy chain variable region comprises an HVR-H1 comprising the amino acid sequence according to the formula X1TFX2X3YX4IHWV, wherein X1 is F or Y, X2 is S or T, X3 is D, G, N, or S, and X4 is A, G, or W (SEQ ID NO:198); and an HVR-H2 comprising an amino acid sequence according to a formula selected from the group consisting of (Formula IV) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T (SEQ ID NO:201); (Formula V) IGX1IX2X3SGSTYYSPSLKSRV, wherein X1 is A, D, E, S, or Y, X2 is S or Y, and X3 is H or Y (SEQ ID NO:202); (Formula VI) IGX1IYX2SGX3TX4YNPSLKSRV, wherein X1 is D, E, R, S, or Y, X2 is H or Y, X3 is N or S, and X4 is N or Y (SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T (SEQ ID NO:204); (Formula VIII) IGX1INPNX2GX3TX4YAQKFQGRV, wherein X1 is I, R, or W, X2 is F or R, X3 is D, G, or S, and X4 is K or N (SEQ ID NO:205); (Formula IX) IGX1IX2PSX3GX4TX5YAQKFQGRV, wherein X1 is I, R, or W, X2 is S or Y, X3 is G or S, X4 is D, G, or S, and X5 is K or N (SEQ ID NO: 206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S (SEQ ID NO:207).

In some embodiments, the heavy chain variable region comprises an HVR-H1 comprising the amino acid sequence according to the formula X1TFX2X3YX4IHWV, wherein X1 is F or Y, X2 is S or T, X3 is D, G, N, or S, and X4 is A, G, or W (SEQ ID NO:198); and an HVR-H2 comprising an amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XII) IGX1IYX2SGX3TX4YNPSLKSRV, wherein X1 is D, E, or S, X2 is H or Y, X3 is N or S, and X4 is N or Y (SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S (SEQ ID NO:210).

In some embodiments, the heavy chain variable region comprises an HVR-H1 comprising the amino acid sequence according to the formula YSIX1SGX2X3WX4WI, wherein X1 is S or T, X2 is H or Y, X3 is H or Y, and X4 is A, D, G, N, S, or T (SEQ ID NO:199); and an HVR-H2 comprising an amino acid sequence according to a formula selected from the group consisting of (Formula IV) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T (SEQ ID NO:201); (Formula V) IGX1IX2X3SGSTYYSPSLKSRV, wherein X1 is A, D, E, S, or Y, X2 is S or Y, and X3 is H or Y (SEQ ID NO:202); (Formula VI) IGX1IYX2SGX3TX4YNPSLKSRV, wherein X1 is D, E, R, S, or Y, X2 is H or Y, X3 is N or S, and X4 is N or Y (SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T (SEQ ID NO:204); (Formula VIII) IGX1INPNX2GX3TX4YAQKFQGRV, wherein X1 is I, R, or W, X2 is F or R, X3 is D, G, or S, and X4 is K or N (SEQ ID NO:205); (Formula IX)

IGX1IX2PSX3GX4TX5YAQKFQGRV, wherein X1 is I, R, or W, X2 is S or Y, X3 is G or S, X4 is D, G, or S, and X5 is K or N (SEQ ID NO: 206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S (SEQ ID NO:207).

In some embodiments, the heavy chain variable region comprises an HVR-H1 comprising the amino acid sequence according to the formula YSIX1SGX2X3WX4WI, wherein X1 is S or T, X2 is H or Y, X3 is H or Y, and X4 is A, D, G, N, S, or T (SEQ ID NO:199); and an HVR-H2 comprising an amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XII) IGX1IYX2SGX3TX4YNPSLKSRV, wherein X1 is D, E, or S, X2 is H or Y, X3 is N or S, and X4 is N or Y (SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S (SEQ ID NO:210).

In some embodiments, the heavy chain variable region comprises an HVR-H1 comprising the amino acid sequence according to the formula FSLSTX1GVX2VX3WI, wherein X1 is G or S, X2 is A or G, and X3 is A, G, S, or T (SEQ ID NO:200); and an HVR-H2 comprising an amino acid sequence according to a formula selected from the group consisting of (Formula IV) LAX1IX2WX3X4DKX5YSX6SLKSRL, wherein X1 is L or R, X2 is D or Y, X3 is A, D, S, or Y, X4 is D or G, X5 is R, S, or Y, and X6 is P or T (SEQ ID NO:201); (Formula V) IGX1IX2X3SGSTYYSPSLKSRV, wherein X1 is A, D, E, S, or Y, X2 is S or Y, and X3 is H or Y (SEQ ID NO:202); (Formula VI) IGX1IYX2SGX3TX4YNPSLKSRV, wherein X1 is D, E, R, S, or Y, X2 is H or Y, X3 is N or S, and X4 is N or Y (SEQ ID NO:203); (Formula VII) VSX1ISGX2GX3X4TYYADSVKGRF, wherein X1 is A, G, S, V, or Y, X2 is A, D, S, or Y, X3 is D, G, or S, and X4 is S or T (SEQ ID NO:204); (Formula VIII) IGX1INPNX2GX3TX4YAQKFQGRV, wherein X1 is I, R, or W, X2 is F or R, X3 is D, G, or S, and X4 is K or N (SEQ ID NO:205); (Formula IX) IGX1IX2PSX3GX4TX5YAQKFQGRV, wherein X1 is I, R, or W, X2 is S or Y, X3 is G or S, X4 is D, G, or S, and X5 is K or N (SEQ ID NO: 206); and (Formula X) VGRIX1SKX2X3GX4TTX5YAAX6VKGRF, wherein X1 is K or R, X2 is A or T, X3 is D or Y, X4 is G or Y, X5 is D or E, and X6 is P or S (SEQ ID NO:207).

In some embodiments, the heavy chain variable region comprises an HVR-H1 comprising the amino acid sequence according to the formula FSLSTX1GVX2VX3WI, wherein X1 is G or S, X2 is A or G, and X3 is A, G, S, or T (SEQ ID NO:200); and an HVR-H2 comprising an amino acid sequence according to a formula selected from the group consisting of (Formula XI) IGX1IX2X3SGSTYYSPSLKSRV, wherein X1 is A, D, or E, X2 is S or Y, and X3 is H or Y (SEQ ID NO:208); (Formula XII) IGX1IYX2SGX3TX4YNPSLKSRV, wherein X1 is D, E, or S, X2 is H or Y, X3 is N or S, and X4 is N or Y (SEQ ID NO:209); and (Formula XII) VGRIX1SKX2X3GX4TTEYAAX5VKGRF, wherein X1 is K or R, X2 is A or T, X3 is D or Y, X4 is G or Y, and X5 is P or S (SEQ ID NO:210).

In some embodiments, the heavy chain variable region comprises HVR-H1, HVR-H2, and HVR-H3, wherein the HVR-H1 and/or HVR-H2 comprise an amino acid sequence listed in Table 1 below.

TABLE 1

| Heavy chain HVR sequences | |
|---|---|
| SEQ ID NO. | Designed Sequence |
| HVR-H1 | |
| 1 | FTFTDYGIHWV |
| 2 | FTFTGYAIHWV |
| 3 | FTFTNYGIHWV |
| 4 | YTFSDYAIHWV |
| 5 | YTFSDYGIHWV |
| 6 | YTFSGYAIHWV |
| 7 | YTFSGYGIHWV |
| 8 | YTFSNYGIHWV |
| 9 | YTFSSYGIHWV |
| 10 | YTFSGYWIHWV |
| 11 | YTFSNYWIHWV |
| 12 | FTFSGYWIHWV |
| 13 | FTFSNYWIHWV |
| 14 | YTFSDYWIHWV |
| 15 | YSISSGHHWAWI |
| 16 | YSISSGHYWNWI |
| 17 | YSISSGHYWSWI |
| 18 | YSISSGHYWTWI |
| 19 | YSISSGYHWAWI |
| 20 | YSISSGYHWDWI |
| 21 | YSISSGYHWGWI |
| 22 | YSISSGYHWNWI |
| 23 | YSISSGYHWSWI |
| 24 | YSISSGHHWDWI |
| 25 | YSISSGYYWDWI |
| 26 | YSISSGYYWNWI |
| 27 | YSISSGYYWTWI |
| 28 | YSITSGHHWAWI |
| 29 | YSITSGHHWDWI |
| 30 | YSITSGHHWGWI |
| 31 | YSITSGHHWNWI |
| 32 | YSITSGHHWSWI |
| 33 | YSISSGHHWGWI |
| 34 | YSITSGHYWAWI |
| 35 | YSITSGHYWDWI |
| 36 | YSITSGHYWGWI |
| 37 | YSITSGHYWNWI |

TABLE 1-continued

| Heavy chain HVR sequences | |
|---|---|
| SEQ ID NO. | Designed Sequence |
| 38 | YSITSGHYWSWI |
| 39 | YSITSGYHWAWI |
| 40 | YSITSGYHWGWI |
| 41 | YSISSGHHWNWI |
| 42 | YSITSGYHWNWI |
| 43 | YSITSGYHWSWI |
| 44 | YSITSGYYWDWI |
| 45 | YSISSGHHWTWI |
| 46 | YSISSGHYWDWI |
| 47 | FSLSTSGVAVSWI |
| 48 | FSLSTGGVAVGWI |
| 49 | FSLSTGGVAVSWI |
| 50 | FSLSTGGVGVAWI |
| 51 | FSLSTGGVGVSWI |
| 52 | FSLSTSGVAVAWI |
| 137 | FTFSDYAIHWV |
| 138 | FTFSDYGIHWV |
| 139 | YTFSNYAIHWV |
| 140 | YTFSSYAIHWV |
| 141 | YTFTDYAIHWV |
| 142 | YTFTDYGIHWV |
| 143 | YTFTNYAIHWV |
| 144 | YTFTNYGIHWV |
| 145 | FTFSGYGIHWV |
| 146 | FTFSNYAIHWV |
| 147 | FTFSSYGIHWV |
| 148 | FTFSDYWIHWV |
| 149 | FTFTSYWIHWV |
| 150 | YSISSGYYWGWI |
| 151 | YSITSGYYWNWI |
| 152 | YSITSGYYWSWI |
| 153 | YSISSGHYWAWI |
| 154 | YSISSGHYWGWI |
| 155 | FSLSTSGVAVGWI |
| 156 | FSLSTSGVGVAWI |
| 157 | FSLSTSGVGVGWI |
| 158 | FSLSTGGVGVGWI |

TABLE 1-continued

| Heavy chain HVR sequences | |
|---|---|
| SEQ ID NO. | Designed Sequence |
| | HVR-H2 |
| 53 | LARIDWDDDKRYSPSLKSRL |
| 54 | LALIDWDDDKRYSPSLKSRL |
| 55 | LALIDWDDDKRYSTSLKSRL |
| 56 | LALIDWDDDKYYSPSLKSRL |
| 57 | LALIDWADDKYYSPSLKSRL |
| 58 | LALIDWAGDKSYSTSLKSRL |
| 59 | LARIDWDDDKYYSPSLKSRL |
| 60 | LARIDWDDDKYYSTSLKSRL |
| 61 | LARIDWDGDKYYSTSLKSRL |
| 62 | IGDIYHSGSTYYSPSLKSRV |
| 63 | IGEIYHSGSTYYSPSLKSRV |
| 64 | IGEIYYSGSTYYSPSLKSRV |
| 65 | IGSIYHSGNTNYNPSLKSRV |
| 66 | IGEIYHSGNTYYNPSLKSRV |
| 67 | IGEIYHSGSTYYNPSLKSRV |
| 68 | IGEIYYSGSTYYNPSLKSRV |
| 69 | IGDIYHSGNTYYNPSLKSRV |
| 70 | IGDIYHSGSTYYNPSLKSRV |
| 71 | VSAISGYGDTTYYADSVKGRF |
| 72 | VSAISGYGGSTYYADSVKGRF |
| 73 | VSAISGYGGTTYYADSVKGRF |
| 74 | VSGISGAGDTTYYADSVKGRF |
| 75 | VSGISGDGDTTYYADSVKGRF |
| 76 | VSGISGDGGSTYYADSVKGRF |
| 77 | VSGISGYGDTTYYADSVKGRF |
| 78 | VSGISGYGGTTYYADSVKGRF |
| 79 | VSVISGDGDTTYYADSVKGRF |
| 80 | VSVISGYGGSTYYADSVKGRF |
| 81 | VSGISGDGSTTYYADSVKGRF |
| 82 | VSGISGYGSTTYYADSVKGRF |
| 83 | VSVISGSGSTTYYADSVKGRF |
| 84 | VSVISGYGSSTYYADSVKGRF |
| 85 | VSVISGYGSTTYYADSVKGRF |
| 86 | VSAISGYGSTTYYADSVKGRF |
| 87 | VSSISGYGDTTYYADSVKGRF |
| 88 | VSSISGYGGSTYYADSVKGRF |
| 89 | VSSISGYGGTTYYADSVKGRF |

TABLE 1-continued

| Heavy chain HVR sequences | |
|---|---|
| SEQ ID NO. | Designed Sequence |
| 90 | VSYISGAGDTTYYADSVKGRF |
| 91 | VSSISGAGDTTYYADSVKGRF |
| 92 | VSYISGAGGTTYYADSVKGRF |
| 93 | VSYISGDGDTTYYADSVKGRF |
| 94 | VSYISGDGGSTYYADSVKGRF |
| 95 | VSYISGDGGTTYYADSVKGRF |
| 96 | VSYISGSGDTTYYADSVKGRF |
| 97 | VSSISGAGGSTYYADSVKGRF |
| 98 | VSYISGYGDTTYYADSVKGRF |
| 99 | VSYISGYGGTTYYADSVKGRF |
| 100 | VSSISGAGGTTYYADSVKGRF |
| 101 | VSSISGDGDTTYYADSVKGRF |
| 102 | VSSISGDGGTTYYADSVKGRF |
| 103 | VSSISGAGSSTYYADSVKGRF |
| 104 | VSSISGAGSTTYYADSVKGRF |
| 105 | VSSISGDGSSTYYADSVKGRF |
| 106 | VSSISGDGSTTYYADSVKGRF |
| 107 | VSSISGYGSSTYYADSVKGRF |
| 108 | VSSISGYGSTTYYADSVKGRF |
| 109 | IGWINPNRGDTKYAQKFQGRV |
| 110 | IGWINPNRGDTNYAQKFQGRV |
| 111 | IGWINPNRGGTKYAQKFQGRV |
| 112 | IGWINPNRGGTNYAQKFQGRV |
| 113 | IGWINPNRGSTKYAQKFQGRV |
| 114 | IGWINPNRGSTNYAQKFQGRV |
| 115 | IGRINPNFGDTNYAQKFQGRV |
| 116 | IGWINPNFGDTNYAQKFQGRV |
| 117 | IGWINPNFGSTKYAQKFQGRV |
| 118 | IGWINPNFGSTNYAQKFQGRV |
| 119 | IGIINPNRGDTKYAQKFQGRV |
| 120 | IGIINPNRGDTNYAQKFQGRV |
| 121 | IGIINPNFGDTNYAQKFQGRV |
| 122 | IGWISPSGGGTKYAQKFQGRV |
| 123 | IGWISPSGGGTNYAQKFQGRV |
| 124 | IGWISPSSGGTKYAQKFQGRV |
| 125 | IGWISPSSGGTNYAQKFQGRV |
| 126 | IGWIYPSGGGTKYAQKFQGRV |
| 127 | IGWIYPSGGGTNYAQKFQGRV |

TABLE 1-continued

| Heavy chain HVR sequences | |
|---|---|
| SEQ ID NO. | Designed Sequence |
| 128 | IGWISPSGGSTNYAQKFQGRV |
| 129 | IGWISPSSGSTKYAQKFQGRV |
| 130 | IGWISPSSGSTNYAQKFQGRV |
| 131 | IGWISPSGGSTKYAQKFQGRV |
| 132 | IGIIYPSGGGTNYAQKFQGRV |
| 133 | IGIISPSGGGTKYAQKFQGRV |
| 134 | IGIISPSGGGTNYAQKFQGRV |
| 135 | IGIIYPSGGSTNYAQKFQGRV |
| 136 | VGRIKSKTDGYTTEYAAPVKGRF |
| 159 | VSAISGSGSTTYYADSVKGRF |
| 160 | VSSISGSGDTTYYADSVKGRF |
| 161 | VSSISGSGGSTYYADSVKGRF |
| 162 | VSSISGSGGTTYYADSVKGRF |
| 163 | VSSISGDGGSTYYADSVKGRF |
| 164 | VSSISGSGSTTYYADSVKGRF |

In some embodiments, the heavy chain variable region comprises HVR-H1, HVR-H2, and HVR-H3, wherein the HVR-H3 is any HVR-H3 known in the art. In some embodiments, the HVR-H3 comprises an amino acid sequence selected from the group consisting of SEQ ID NOs: 223-256.

In some embodiments, provided herein is an antibody heavy chain with a heavy chain variable region comprising an HVR-H1, HVR-H2, and HVR-H3, wherein the HVR-H1 and/or HVR-H2 are any of the HVR-H1s and/or HVR-H2s described herein. In some embodiments, the HVR-H1 comprises an amino acid sequence selected from any HVR-H1 sequence of the present disclosure (e.g., X1TFX2X3YX4IHWV, wherein X1 is F or Y, X2 is S or T, X3 is D, G, N, or S, and X4 is A, G, or W (SEQ ID NO:198); YSIX1SGX2X3WX4WI, wherein X1 is S or T, X2 is H or Y, X3 is H or Y, and X4 is A, D, G, N, S, or T (SEQ ID NO:199); and FSLSTX1GVX2VX3WI, wherein X1 is G or S, X2 is A or G, and X3 is A, G, S, or T (SEQ ID NO:200); and SEQ ID NOS:1-52 and 137-158). In some embodiments, the HVR-H2 comprises an amino acid sequence selected from any HVR-H2 of the present disclosure (e.g., LAX1IX2WX3X4DKX5YSX6SLKSRL, wherein X1 is L or R, X2 is D or Y, X3 is A, D, S, or Y, X4 is D or G, X5 is R, S, or Y, and X6 is P or T (SEQ ID NO:201); IGX1IX2X3SGSTYYSPSLKSRV, wherein X1 is A, D, E, S, or Y, X2 is S or Y, and X3 is H or Y (SEQ ID NO:202); IGX1IYX2SGX3TX4YNPSLKSRV, wherein X1 is D, E, R, S, or Y, X2 is H or Y, X3 is N or S, and X4 is N or Y (SEQ ID NO:203); VSX1ISGX2GX3X4TYYADSVKGRF, wherein X1 is A, G, S, V, or Y, X2 is A, D, S, or Y, X3 is D, G, or S, and X4 is S or T (SEQ ID NO:204); IGX1INPNX2GX3TX4YAQKFQGRV, wherein X1 is I, R, or W, X2 is F or R, X3 is D, G, or S, and X4 is K or N (SEQ ID NO:205); IGX1IX2PSX3GX4TX5YAQKFQGRV, wherein X1 is I, R, or W, X2 is S or Y, X3 is G or S, X4 is D, G, or S, and X5 is K or N (SEQ ID NO:206); VGRIX1SKX2X3GX4TTX5YAAX6VKGRF, wherein X1 is K or R, X2 is A or T, X3 is D or Y, X4 is G or Y, X5 is D or E, and X6 is P or S (SEQ ID NO:207); IGX1IX2X3SGSTYYSPSLKSRV, wherein X1 is A, D, or E, X2 is S or Y, and X3 is H or Y (SEQ ID NO:208); IGX1IYX2SGX3TX4YNPSLKSRV, wherein X1 is D, E, or S, X2 is H or Y, X3 is N or S, and X4 is N or Y (SEQ ID NO:209); and VGRIX1SKX2X3GX4TTEYAAX5VKGRF, wherein X1 is K or R, X2 is A or T, X3 is D or Y, X4 is G or Y, and X5 is P or S (SEQ ID NO:210); and SEQ ID NOS:53-136 and 159-164).

In some embodiments, provided herein is an antibody heavy chain with a heavy chain variable region comprising an HVR-H1, HVR-H2, and HVR-H3, wherein the HVR-H1 comprises an amino acid sequence selected from the group consisting of SEQ ID NOS:1-52 and 137-158. In some embodiments, the HVR-H1 comprises an amino acid sequence selected from the group consisting of SEQ ID NOS:1-52.

In some embodiments, provided herein is an antibody heavy chain with a heavy chain variable region comprising an HVR-H1, HVR-H2, and HVR-H3, wherein the HVR-H2 comprises an amino acid sequence selected from the group consisting of SEQ ID NOS:53-136 and 159-164. In some embodiments, the HVR-H2 comprises an amino acid sequence selected from the group consisting of SEQ ID NOS:53-136.

In some embodiments, provided herein is an antibody heavy chain with a heavy chain variable region comprising a HVR-H1, HVR-H2, and HVR-H3, wherein the HVR-H1 comprises an amino acid sequence selected from the group consisting of Formula (I), Formula (II), and Formula (III), or the HVR-H2 comprises an amino acid sequence selected from the group consisting of Formula (IV), Formula (V), Formula (VI), Formula (VII), Formula (VIII), Formula (IX), Formula (X), Formula (XI), Formula (XII), and Formula (XIII). In some embodiments, provided herein is an antibody heavy chain with a heavy chain variable region comprising a HVR-H1, a HVR-H2 and a HVR-H3, wherein the HVR-H1 comprises an amino acid sequence selected from the group consisting of SEQ ID NOs: 1-52, or wherein the HVR-H2 comprises an amino acid sequence selected from the group consisting of SEQ ID NOs: 53-136. In some embodiments, the HVR-H1 comprises an amino acid sequence selected from the group consisting of SEQ ID NOs: 1, 4, 5, 7, 8, 9, 11, 13, 16, 18, 19, 20, 21, 22, 23, 24, 25, 26, 27, 28, 31, 33, 34, 38, 40, 42, 43, 45, 47, 49, 50, and 51, or wherein the HVR-H2 comprises an amino acid sequence selected from the group consisting of SEQ ID NOs: 53, 60, 63, 65, 66, 67, 70, 82, 89, 93, 95, 105, 109, 110, 117, 121, 122, 123, 124, 128, 129, 130, 131, 132, and 134. In some embodiments, the HVR-H1 comprises an amino acid sequence selected from the group consisting of SEQ ID NOs: 2, 3, 14, 15, 30, 32, 35, 37, 39, 41, 44, 46, and 48, or wherein the HVR-H2 comprises an amino acid sequence selected from the group consisting of SEQ ID NOs: 55, 56, 59, 61, 62, 64, 68, 69, 71, 73, 74, 75, 76, 77, 78, 79, 72, 81, 83, 86, 90, 91, 99, 100, 103, 106, 107, 108, 112, 113, 116, 118, 126, 135, and 136. In some embodiments, the HVR-H1 comprises an amino acid sequence selected from the group consisting of SEQ ID NOs: 6, 10, 17, 29, 36, and 52, or wherein the HVR-H2 comprises an amino acid sequence selected from the group consisting of SEQ ID NOs: 54, 57, 58, 80, 84, 85, 87, 88, 92, 94, 96, 97, 98, 101, 102, 104, 111, 114, 115, 119, 120, 125, 127 and 133.

In some embodiments, provided herein is an antibody heavy chain with a heavy chain variable region comprising an HVR-H1, HVR-H2, and HVR-H3, wherein the HVR-H1 comprises an amino acid sequence selected from SEQ ID NOS:1-52 and 137-158, and the HVR-H2 comprises an amino acid sequence selected from SEQ ID NOS:53-136 and 159-164. In some embodiments, the HVR-H1 comprises an amino acid sequence selected from SEQ ID NOS:1-52, and the HVR-H2 comprises an amino acid sequence selected from SEQ ID NOS:53-136.

In certain embodiments, a heavy chain variable region comprises three of a HVR-H1, a HVR-H2, and a HVR-H3, wherein the HVR-H1 and HVR-H2 are selected from the group consisting of: a HVR-H1 comprising the amino acid sequence of Formula (II) and a HVR-H2 comprising the amino acid sequence of Formula (IX); a HVR-H1 comprising the amino acid sequence of Formula (II) and a HVR-H2 comprising the amino acid sequence of Formula (VII); a HVR-H1 comprising the amino acid sequence of Formula (I) and a HVR-H2 comprising the amino acid sequence of Formula (VII); a HVR-H1 comprising the amino acid sequence of Formula (I) and a HVR-H2 comprising the amino acid sequence of Formula (IX); a HVR-H1 comprising the amino acid sequence of Formula (II) and a HVR-H2 comprising the amino acid sequence of Formula (IV); a HVR-H1 comprising the amino acid sequence of Formula (II) and a HVR-H2 comprising the amino acid sequence of Formula (V); a HVR-H1 comprising the amino acid sequence of Formula (II) and a HVR-H2 comprising the amino acid sequence of Formula (VI); a HVR-H1 comprising the amino acid sequence of Formula (I) and a HVR-H2 comprising the amino acid sequence of Formula (VI); a HVR-H1 comprising the amino acid sequence of Formula (III) and a HVR-H2 comprising the amino acid sequence of Formula (VI); a HVR-H1 comprising the amino acid sequence of Formula (III) and a HVR-H2 comprising the amino acid sequence of Formula (VII); a HVR-H1 comprising the amino acid sequence of Formula (II) and a HVR-H2 comprising the amino acid sequence of Formula (VIII); a HVR-H1 comprising the amino acid sequence of Formula (I) and a HVR-H2 comprising the amino acid sequence of Formula (V); a HVR-H1 comprising the amino acid sequence of Formula (III) and a HVR-H2 comprising the amino acid sequence of Formula (V); and a HVR-H1 comprising the amino acid sequence of Formula (I) and a HVR-H2 comprising the amino acid sequence of Formula (VIII). In some embodiments, the HVR-H1 and HVR-H2 are selected from the group consisting of: a HVR-H1 comprising the amino acid sequence of Formula (II) and a HVR-H2 comprising the amino acid sequence of Formula (XI); a HVR-H1 comprising the amino acid sequence of Formula (II) and a HVR-H2 comprising the amino acid sequence of Formula (XII); a HVR-H1 comprising the amino acid sequence of Formula (I) and a HVR-H2 comprising the amino acid sequence of Formula (XII); a HVR-H1 comprising the amino acid sequence of Formula (III) and a HVR-H2 comprising the amino acid sequence of Formula (XII); a HVR-H1 comprising the amino acid sequence of Formula (I) and a HVR-H2 comprising the amino acid sequence of Formula (XI); and a HVR-H1 comprising the amino acid sequence of Formula (III) and a HVR-H2 comprising the amino acid sequence of Formula (XI). In some embodiments, the HVR-H1 and HVR-H2 are selected from the group consisting of: a HVR-H1 comprising the amino acid sequence of Formula (I) and a HVR-H2 comprising the amino acid sequence of Formula (IV); a HVR-H1 comprising the amino acid sequence of Formula (III) and a HVR-H2 comprising the amino acid sequence of Formula (IV); a HVR-H1 comprising the amino acid sequence of Formula (II) and a HVR-H2 comprising the amino acid sequence of Formula (X); a HVR-H1 comprising the amino acid sequence of Formula (III) and a HVR-H2 comprising the amino acid sequence of Formula (IX); a HVR-H1 comprising the amino acid sequence of Formula (I) and a HVR-H2 comprising the amino acid sequence of Formula (X); a HVR-H1 comprising the amino acid sequence of Formula (III) and a HVR-H2 comprising the amino acid sequence of Formula (VIII); and a HVR-H1 comprising the amino acid sequence of Formula (III) and a HVR-H2 comprising the amino acid sequence of Formula (X). In some embodiments, the HVR-H1 and HVR-H2 are selected from the group consisting of: a HVR-H1 comprising the amino acid sequence of Formula (II) and a HVR-H2 comprising the amino acid sequence of Formula (XIII); a HVR-H1 comprising the amino acid sequence of Formula (I) and a HVR-H2 comprising the amino acid sequence of Formula (XIII); and a HVR-H1 comprising the amino acid sequence of Formula (III) and a HVR-H2 comprising the amino acid sequence of Formula (XIII).

The heavy chain HVR sequences described herein may be included in any combination in an antibody heavy chain or heavy chain variable region of the present disclosure. In some embodiments, a heavy chain variable region comprises an HVR-H1 comprising an amino acid sequence selected from the group consisting of SEQ ID NOS: 1-52 and 137-158, and a HVR-H2 comprising an amino acid sequence selected from the group consisting of SEQ ID NOS:53-136 and 159-164. In some embodiments, a heavy chain variable region comprises an HVR-H1 comprising an amino acid sequence selected from the group consisting of SEQ ID NOS: 1-52, and a HVR-H2 comprising an amino acid sequence selected from the group consisting of SEQ ID NOS:53-136. In some embodiments, a heavy chain variable region comprises an HVR-H1 comprising an amino acid sequence selected from the group consisting of SEQ ID NOS:1-52 and 137-158, and an HVR-H3 comprising an amino acid sequence selected from the group consisting of SEQ ID NOS:223-256. In some embodiments, a heavy chain variable region comprises an HVR-H1 comprising an amino acid sequence selected from the group consisting of SEQ ID NOS:1-52, and an HVR-H3 comprising an amino acid sequence selected from the group consisting of SEQ ID NOS:223-256. In some embodiments, a heavy chain variable region comprises an HVR-H2 comprising an amino acid sequence selected from the group consisting of SEQ ID NOS:53-136 and 159-164 and a HVR-H3 comprising an amino acid sequence selected from the group consisting of SEQ ID NOs: 223-256. In some embodiments, a heavy chain variable region comprises an HVR-H2 comprising an amino acid sequence selected from the group consisting of SEQ ID NOS:53-136 and a HVR-H3 comprising an amino acid sequence selected from the group consisting of SEQ ID NOs: 223-256. In some embodiments, a heavy chain variable region comprises an HVR-H1 comprising an amino acid sequence selected from the group consisting of SEQ ID NOS:1-52 and 137-158, an HVR-H2 comprising an amino acid sequence selected from the group consisting of SEQ ID NOS:53-136 and 159-164, and a HVR-H3 comprising an amino acid sequence selected from the group consisting of SEQ ID NOs: 223-256. In some embodiments, a heavy chain variable region comprises an HVR-H1 comprising an amino acid sequence selected from the group consisting of SEQ ID NOS:1-52, an HVR-H2 comprising an amino acid sequence selected from the group consisting of SEQ ID NOS:53-136, and a HVR-H3 comprising an amino acid sequence selected from the group consisting of SEQ ID NOs: 223-256.

In certain embodiments, a heavy chain variable region comprises three of a HVR-H1, a HVR-H2, and a HVR-H3, wherein the HVR-H1 and HVR-H2 are selected from the group consisting of: a HVR-H1 comprising the amino acid sequence of SEQ ID NO:157, and a HVR-H2 comprising the amino acid sequence of SEQ ID NO:63; a HVR-H1 comprising the amino acid sequence of SEQ ID NO:1, and a HVR-H2 comprising the amino acid sequence of SEQ ID NO:122; a HVR-H1 comprising the amino acid sequence of SEQ ID NO:138, and a HVR-H2 comprising the amino acid sequence of SEQ ID NO:63; a HVR-H1 comprising the amino acid sequence of SEQ ID NO:154, and a HVR-H2 comprising the amino acid sequence of SEQ ID NO:63; a HVR-H1 comprising the amino acid sequence of SEQ ID NO:158, and a HVR-H2 comprising the amino acid sequence of SEQ ID NO:161; a HVR-H1 comprising the amino acid sequence of SEQ ID NO:158, and a HVR-H2 comprising the amino acid sequence of SEQ ID NO:63; a HVR-H1 comprising the amino acid sequence of SEQ ID NO:145, and a HVR-H2 comprising the amino acid sequence of SEQ ID NO:128; a HVR-H1 comprising the amino acid sequence of SEQ ID NO:22, and a HVR-H2 comprising the amino acid sequence of SEQ ID NO:61; a HVR-H1 comprising the amino acid sequence of SEQ ID NO:31, and a HVR-H2 comprising the amino acid sequence of SEQ ID NO:63; a HVR-H1 comprising the amino acid sequence of SEQ ID NO:153, and a HVR-H2 comprising the amino acid sequence of SEQ ID NO:63; a HVR-H1 comprising the amino acid sequence of SEQ ID NO:155, and a HVR-H2 comprising the amino acid sequence of SEQ ID NO:67; a HVR-H1 comprising the amino acid sequence of SEQ ID NO:156, and a HVR-H2 comprising the amino acid sequence of SEQ ID NO:100; a HVR-H1 comprising the amino acid sequence of SEQ ID NO:51, and a HVR-H2 comprising the amino acid sequence of SEQ ID NO:162; a HVR-H1 comprising the amino acid sequence of SEQ ID NO:138, and a HVR-H2 comprising the amino acid sequence of SEQ ID NO:123; a HVR-H1 comprising the amino acid sequence of SEQ ID NO:139, and a HVR-H2 comprising the amino acid sequence of SEQ ID NO:110; a HVR-H1 comprising the amino acid sequence of SEQ ID NO:8, and a HVR-H2 comprising the amino acid sequence of SEQ ID NO:126; a HVR-H1 comprising the amino acid sequence of SEQ ID NO:13, and a HVR-H2 comprising the amino acid sequence of SEQ ID NO:129; a HVR-H1 comprising the amino acid sequence of SEQ ID NO:31, and a HVR-H2 comprising the amino acid sequence of SEQ ID NO:124; a HVR-H1 comprising the amino acid sequence of SEQ ID NO:25, and a HVR-H2 comprising the amino acid sequence of SEQ ID NO:130; a HVR-H1 comprising the amino acid sequence of SEQ ID NO:150, and a HVR-H2 comprising the amino acid sequence of SEQ ID NO:132; a HVR-H1 comprising the amino acid sequence of SEQ ID NO:158, and a HVR-H2 comprising the amino acid sequence of SEQ ID NO:162; a HVR-H1 comprising the amino acid sequence of SEQ ID NO:12, and a HVR-H2 comprising the amino acid sequence of SEQ ID NO:82; a HVR-H1 comprising the amino acid sequence of SEQ ID NO:149, and a HVR-H2 comprising the amino acid sequence of SEQ ID NO:117; and a HVR-H1 comprising the amino acid sequence of SEQ ID NO:7, and a HVR-H2 comprising the amino acid sequence of SEQ ID NO:134. In some embodiments, the HVR-H1 and HVR-H2 are selected from the group consisting of: a HVR-H1 comprising the amino acid sequence of SEQ ID NO:26, and a HVR-H2 comprising the amino acid sequence of SEQ ID NO:53; a HVR-H1 comprising the amino acid sequence of SEQ ID NO:151, and a HVR-H2 comprising the amino acid sequence of SEQ ID NO:53; a HVR-H1 comprising the amino acid sequence of SEQ ID NO:34, and a HVR-H2 comprising the amino acid sequence of SEQ ID NO:63; a HVR-H1 comprising the amino acid sequence of SEQ ID NO:50, and a HVR-H2 comprising the amino acid sequence of SEQ ID NO:162; a HVR-H1 comprising the amino acid sequence of SEQ ID NO:158, and a HVR-H2 comprising the amino acid sequence of SEQ ID NO:104; a HVR-H1 comprising the amino acid sequence of SEQ ID NO:5, and a HVR-H2 comprising the amino acid sequence of SEQ ID NO:121; a HVR-H1 comprising the amino acid sequence of SEQ ID NO:6, and a HVR-H2 comprising the amino acid sequence of SEQ ID NO:116; a HVR-H1 comprising the amino acid sequence of SEQ ID NO:7, and a HVR-H2 comprising the amino acid sequence of SEQ ID NO:121; a HVR-H1 comprising the amino acid sequence of SEQ ID NO:17, and a HVR-H2 comprising the amino acid sequence of SEQ ID NO:63; a HVR-H1 comprising the amino acid sequence of SEQ ID NO:25, and a HVR-H2 comprising the amino acid sequence of SEQ ID NO:101; a HVR-H1 comprising the amino acid sequence of SEQ ID NO:25, and a HVR-H2 comprising the amino acid sequence of SEQ ID NO:114; a HVR-H1 comprising the amino acid sequence of SEQ ID NO:29, and a HVR-H2 comprising the amino acid sequence of SEQ ID NO:112; a HVR-H1 comprising the amino acid sequence of SEQ ID NO:152, and a HVR-H2 comprising the amino acid sequence of SEQ ID NO:63; a HVR-H1 comprising the amino acid sequence of SEQ ID NO:156, and a HVR-H2 comprising the amino acid sequence of SEQ ID NO:89; a HVR-H1 comprising the amino acid sequence of SEQ ID NO:157, and a HVR-2 comprising the amino acid sequence of SEQ ID NO:94; a HVR-H1 comprising the amino acid sequence of SEQ ID NO:48, and a HVR-H2 comprising the amino acid sequence of SEQ ID NO:58; a HVR-H1 comprising the amino acid sequence of SEQ ID NO:50, and a HVR-H2 comprising the amino acid sequence of SEQ ID NO:89; a HVR-H1 comprising the amino acid sequence of SEQ ID NO:50, and a HVR-H2 comprising the amino acid sequence of SEQ ID NO:163; a HVR-H1 comprising the amino acid sequence of SEQ ID NO:158, and a HVR-H2 comprising the amino acid sequence of SEQ ID NO:160; a HVR-H1 comprising the amino acid sequence of SEQ ID NO:158, and a HVR-H2 comprising the amino acid sequence of SEQ ID NO:87; a HVR-H1 comprising the amino acid sequence of SEQ ID NO:158, and a HVR-2 comprising the amino acid sequence of SEQ ID NO:92; a HVR-H1 comprising the amino acid sequence of SEQ ID NO:158, and a HVR-H2 comprising the amino acid sequence of SEQ ID NO:93; a HVR-H1 comprising the amino acid sequence of SEQ ID NO:158, and a HVR-2 comprising the amino acid sequence of SEQ ID NO:97; a HVR-H1 comprising the amino acid sequence of SEQ ID NO:158, and a HVR-H2 comprising the amino acid sequence of SEQ ID NO:103; a HVR-H1 comprising the amino acid sequence of SEQ ID NO:158, and a HVR-H2 comprising the amino acid sequence of SEQ ID NO:164; a HVR-H1 comprising the amino acid sequence of SEQ ID NO:137, and a HVR-H2 comprising the amino acid sequence of SEQ ID NO:54; a HVR-H1 comprising the amino acid sequence of SEQ ID NO:3, and a HVR-H2 comprising the amino acid sequence of SEQ ID NO:127; a HVR-H1 comprising the amino acid sequence of SEQ ID NO:4, and a HVR-H2 comprising the amino acid sequence of SEQ ID NO:85; a HVR-H1 comprising the amino acid sequence of SEQ ID NO:4, and a HVR-H2 comprising the amino acid sequence of SEQ ID NO:110; a HVR-H1 comprising the amino acid sequence of SEQ ID NO:139, and a HVR-H2 comprising the amino acid sequence of SEQ ID NO:109; a HVR-H1 comprising the amino acid sequence of SEQ ID NO:139, and a HVR-H2 comprising the amino acid sequence of SEQ ID NO:121; a HVR-H1 comprising the amino acid sequence of SEQ ID NO:8, and a HVR-H2 comprising the amino acid sequence of SEQ ID NO:120; a HVR-H1 comprising the amino acid sequence of SEQ ID NO:140, and a HVR-H2 comprising the amino acid sequence of SEQ ID NO:131; a HVR-H1 comprising the amino acid sequence of SEQ ID NO:141, and a HVR-H2 comprising the amino acid sequence of SEQ ID NO:116; a HVR-H1 comprising the amino acid sequence of SEQ ID NO:142, and a HVR-H2 comprising the amino acid sequence of SEQ ID NO:159; a HVR-H1 comprising the amino acid sequence of SEQ ID NO:143, and a HVR-H2 comprising the amino acid sequence of SEQ ID NO:116; a HVR-H1 comprising the amino acid sequence of SEQ ID NO:144, and a HVR-H2 comprising the amino acid sequence of SEQ ID NO:121; a HVR-H1 comprising the amino acid sequence of SEQ ID NO:146, and a HVR-H2 comprising the amino acid sequence of SEQ ID NO:110; a HVR-H1 comprising the amino acid sequence of SEQ ID NO:147, and a HVR-H2 comprising the amino acid sequence of SEQ ID NO:133; a HVR-H1 comprising the amino acid sequence of SEQ ID NO:148, and a HVR-H2 comprising the amino acid sequence of SEQ ID NO:63; and a HVR-H1 comprising the amino acid sequence of SEQ ID NO:13, and a HVR-H2 comprising the amino acid sequence of SEQ ID NO:118.

In some embodiments, a heavy chain variable region comprises three of a HVR-H1, a HVR-H2, and a HVR-H3, wherein the HVR-H1 and HVR-H2 are listed in Table 1. In some embodiments, the HVR-H3 comprises an amino acid sequence selected from the group consisting of SEQ ID NOs:223-256. In some embodiments, a heavy chain variable region comprises a sequence selected from SEQ ID NOS: 169, 171, 173, 175, 177, 179, 181, 183, 185, 187, 189, 191, 193, and 195, or a sequence having at least 80%, at least 85%, at least 90%, at least 91%, at least 92%, at least 93%, at least 94%, at least 95%, at least 96%, at least 97%, at least 98%, or at least 99% sequence identity to a sequence selected from SEQ ID NOS: 169, 171, 173, 175, 177, 179, 181, 183, 185, 187, 189, 191, 193, and 195.

In some embodiments, a heavy chain variable region further comprises variable region heavy chain framework sequences juxtaposed between the HVRs according to the formula: (FW-H1)-(HVR-H1)-(FW-H2)-(HVR-H2)-(FW-H3)-(HVR-H3)-(FW-H4). In some embodiments, one, two, three, or four of the framework sequences is/are the following:

```
                                    (SEQ ID NO: 165)
FW-H1 is EVQLVESGGGLVQPGGSLRLSCAASG

                                    (SEQ ID NO: 166)
FW-H2 is RQAPGKGLEW

                                    (SEQ ID NO: 167)
FW-H3 is TISRDNSKNTLYLQLNSLRAEDTAVYYC

                                    (SEQ ID NO: 168)
FW-H4 is WGQGTLVTVSS.
```

In some embodiments, the heavy chain variable region comprises an alternate FW-H3 sequence with an arginine to lysine mutation at R19 of SEQ ID NO:167. In some embodiments, one, two, three, or four of the framework sequences is/are an FW-H1 of SEQ ID NO:165, an FW-H12 of SEQ ID NO:166, an FW-H13 or SEQ ID NO:167 with an arginine to lysine mutation at R19, and an FW-H14 of SEQ ID NO:168.

In some embodiments, further provided herein is an antibody comprising a heavy chain and a light chain, where the heavy chain includes a heavy chain variable region of the present disclosure, and where the light chain includes any light chain variable region (e.g., comprising a HVR-L1, HVR-L2, and HVR-L3) known in the art. In some embodiments, the antibody light chain variable region comprises an HVR-L1 comprising an amino acid sequence selected from the group consisting of SEQ ID NOs: 257-264. In some embodiments, the antibody light chain variable region comprises an HVR-L3 comprising an amino acid sequence selected from the group consisting of SEQ ID NOs: 265-274. In some embodiments, the antibody light chain variable region comprises an HVR-L1 comprising an amino acid sequence selected from the group consisting of SEQ ID NOs: 257-264, and an HVR-L3 comprising an amino acid sequence selected from the group consisting of SEQ ID NOs: 265-274. In some embodiments, the antibody light chain comprises any of the antibody light chain variable regions found in the patent application(s) (the disclosures of which are each incorporated herein by reference in their entireties). In some embodiments, the antibody light chain comprises a light chain variable region comprising any of the HVR-L1, HVR-L2, and/or HVR-L3 sequences found in the patent application(s) (the disclosures of which are each incorporated herein by reference in their entireties).

IgG-derived scaffolds such as Fab and single chain Fv (scFv), as well as stabilized Fv or scFv, have been designed and prepared with the ability to specifically recognize and tightly bind antigens. Alternative protein scaffolds, or non-IgG like scaffolds, have been explored for analogous applications. Several protein families with non-Ig architecture such as the protein A, fibronectin, the ankyrin repeat, Adnectins, Affibodies, Anticalins, DARPins, engineered Kunitz inhibitors or the lipocalins, cyclic and polycyclic peptides can be empowered with novel binding sites by employing methods of combinatorial engineering, such as site-directed random mutagenesis in combination with phage display, yeast display, or other molecular selection techniques. These novel alternative binding reagents are collectively called engineered protein scaffolds, illustrating the fact that a rigid natural protein structure is used to modify an existing—or to implement a new—binding site for a prescribed target using the dynamic binding motifs or units introduced here. Compared with antibodies or their recombinant fragments, these protein scaffolds often provide practical advantages including elevated stability and high production yield in microbial expression systems. As these novel binding proteins are obtained by means of a biomolecular engineering process in order to achieve tight target-binding activity, they may also be subjected to further selection schemes focused at other desired properties (such as solubility, thermal stability, protease resistance etc.). Consequently, engineered protein scaffolds have become attractive for many applications in biotechnology and biomedical research, especially for multi-specific binding motifs. The effort to generate such an alternative binding protein with beneficial properties are directed toward therapeutic use with special emphasis on biomolecular structure and function as well as on approaches toward clinical application.

In some embodiments, further provided herein is one or more polypeptides (e.g., a scaffold polypeptide, including IgG-derived scaffold polypeptides (such as Fabs, single chain Fvs, and stabilized Fvs) or non-IgG-derived scaffold polypeptides (such as protein A, fibronectin, ankyrin repeat, Adnectins, Affibodies, Anticalins, DARPins, engineered Kunitz inhibitors or the lipocalins, cyclic and polycyclic peptides)) comprising one or more HVRs described herein. In some embodiments, the polypeptide comprises an HVR-H1 comprising an amino acid sequence selected from any HVR-H1 sequence of the present disclosure (e.g., X1TFX2X3YX4IHWV, wherein X1 is F or Y, X2 is S or T, X3 is D, G, N, or S, and X4 is A, G, or W (SEQ ID NO:198); YSIX1SGX2X3WX4WI, wherein X1 is S or T, X2 is H or Y, X3 is H or Y, and X4 is A, D, G, N, S, or T (SEQ ID NO:199); and FSLSTX1GVX2VX3WI, wherein X1 is G or S, X2 is A or G, and X3 is A, G, S, or T (SEQ ID NO:200); and SEQ ID NOS:1-52 and 137-158). In some embodiments, the polypeptide comprises an HVR-H2 comprising an amino acid sequence selected from any HVR-H2 of the present disclosure (e.g., LAX1IX2WX3X4DKX5YSX6SLKSRL, wherein X1 is L or R, X2 is D or Y, X3 is A, D, S, or Y, X4 is D or G, X5 is R, S, or Y, and X6 is P or T (SEQ ID NO:201); IGX1IX2X3SGSTYYSPSLKSRV, wherein X1 is A, D, E, S, or Y, X2 is S or Y, and X3 is H or Y (SEQ ID NO:202); IGX1IYX2SGX3TX4YNPSLKSRV, wherein X1 is D, E, R, S, or Y, X2 is H or Y, X3 is N or S, and X4 is N or Y (SEQ ID NO:203); VSX1ISGX2GX3X4TYYADSVKGRF, wherein X1 is A, G, S, V, or Y, X2 is A, D, S, or Y, X3 is D, G, or S, and X4 is S or T (SEQ ID NO:204); IGX1INPNX2GX3TX4YAQKFQGRV, wherein X1 is I, R, or W, X2 is F or R, X3 is D, G, or S, and X4 is K or N (SEQ ID NO:205); IGX1IX2PSX3GX4TX5YAQKFQGRV, wherein X1 is I, R, or W, X2 is S or Y, X3 is G or S, X4 is D, G, or S, and X5 is K or N (SEQ ID NO:206); VGRIX1SKX2X3GX4TTX5YAAX6VKGRF, wherein X1 is K or R, X2 is A or T, X3 is D or Y, X4 is G or Y, X5 is D or E, and X6 is P or S (SEQ ID NO:207); IGX1IX2X3SGSTYYSPSLKSRV, wherein X1 is A, D, or E, X2 is S or Y, and X3 is H or Y (SEQ ID NO:208); IGX1IYX2SGX3TX4YNPSLKSRV, wherein X1 is D, E, or S, X2 is H or Y, X3 is N or S, and X4 is N or Y (SEQ ID NO:209); and VGRIX1SKX2X3GX4TTEYAAX5VKGRF, wherein X1 is K or R, X2 is A or T, X3 is D or Y, X4 is G or Y, and X5 is P or S (SEQ ID NO:210); and SEQ ID NOS:53-136 and 159-164). In some embodiments, the polypeptide comprises an HVR-H3 comprising an amino acid sequence selected from any HVR-H3 sequence of the present disclosure (e.g., SEQ ID NOs: 223-256). In some embodiments, the polypeptide comprises an HVR-L1 comprising an amino acid sequence selected from any HVR-L1 sequence of the present disclosure (e.g., SEQ ID NOs: 257-264). In some embodiments, the polypeptide comprises an HVR-L3 comprising an amino acid sequence selected from any HVR-L3 sequence of the present disclosure (e.g., SEQ ID NOs: 265-274).

In some embodiments, the polypeptide comprises two or more (e.g., two or more, three or more, four or more, or all five) of the HVR-H1, HVR-H2, HVR-H3, HVR-L1, and/or HVR-L3 sequences described herein. In some embodiments, the polypeptide comprises two of the HVR-H1, HVR-H2, HVR-H3, HVR-L1, and/or HVR-L3 sequences described herein, wherein the two are a HVR-H1 and a HVR-H2; a HVR-H1 and a HVR-H3; a HVR-H1 and a HVR-L1; a HVR-H1 and a HVR-L3; a HVR-H2 and a HVR-H3; a HVR-H2 and a HVR-L1; a HVR-H2 and a HVR-L3; a HVR-H3 and a HVR-L1; a HVR-H3 and a HVR-L3; or a HVR-L1 and a HVR-L3. In some embodiments, the polypeptide comprises three of the HVR-H1, HVR-H2, HVR-H3, HVR-L1, and/or HVR-L3 sequences described herein, wherein the three are a HVR-H1, a HVR-H2, and a HVR-H3; a HVR-H1, a HVR-H2, and a HVR-L1; a HVR-H1, a HVR-H2, and a HVR-L3; a HVR-H1, a HVR-H3, and a HVR-L1; a HVR-H1, a HVR-H3, and a HVR-L3; a HVR-H1, a HVR-L1 and a HVR-L3; a HVR-H2, a HVR-H3, and a HVR-L1; a HVR-H2, a HVR-H3, and a HVR-L3; a HVR-H2, a HVR-L1, and a HVR-L3; or a HVR-H3, a HVR-L1, and a HVR-L3. In some embodiments, the polypeptide comprises four of the HVR-H1, HVR-H2, HVR-H3, HVR-L1, and/or HVR-L3 sequences described herein, wherein the four are a HVR-H1, a HVR-H2, a HVR-H3, and a HVR-L1; a HVR-H1, a HVR-H2, a HVR-H3, and a HVR-L3; a HVR-H1, a HVR-H2, a HVR-L1, and a HVR-L3; a HVR-H1, a HVR-H3, a HVR-L1, and a HVR-L3; or a HVR-H2, a HVR-H3, a HVR-L1, and a HVR-L3. In some embodiments, the polypeptide comprises five of the HVR-H1, HVR-H2, HVR-H3, HVR-L1, and/or HVR-L3 sequences described herein, wherein the five are a HVR-H1, a HVR-H2, a HVR-H3, a HVR-L1, and a HVR-L3.

In some embodiments, further provided herein is an antibody fragment or scFv comprising a light chain variable region and a heavy chain variable region of the present disclosure.

In some embodiments, an antibody or antibody fragment of the present disclosure binds at least 1 target (e.g., a target protein or an epitope) or at least two targets with particular binding affinities. For example, in some embodiments, an antibody or antibody fragment of the present disclosure binds at least 1 target or at least two targets with an equilibrium dissociation constant (Kd) of about $10^{-7}$M or less, $10^{-8}$ M or less, $10^{-9}$ M or less, $10^{-10}$ M or less, or $10^{-11}$ M or less. In some embodiments, an antibody or antibody fragment of the present disclosure binds at least 1 target or at least two targets with an equilibrium dissociation constant (Kd) of between about $10^{-7}$ and about $10^{-11}$M. Exemplary assays for determining binding affinity are described and exemplified infra (See e.g., the ForteBio assay of Example 4 below).

In some embodiments, an antibody or antibody fragment of the present disclosure has a melting temperature (Tm) of at least 60° C. For example, in some embodiments, an antibody or antibody fragment of the present disclosure has a Tm of between about 60° C. and about 90° C., between about 65° C. and about 90° C., between about 70° C. and about 90° C., between about 75° C. and about 90° C., between about 80° C. and about 90° C., between about 85° C. and about 90° C., or at least about 65° C., at least about 70° C., at least about 72° C., at least about 75° C., at least about 80° C., or at least about 85° C. In some embodiments, an antibody or antibody fragment of the present disclosure has a Tm of between about 60° C. and about 90° C. Various methods of measuring Tm for an antibody or antibody fragment are known in the art. Exemplary assays for determining antibody Tm are described and exemplified infra (See e.g., the DSF assay of Example 4 below).

Antibodies of the present disclosure may be produced using recombinant methods and compositions, e.g., as described in U.S. Pat. No. 4,816,567. In some embodiments, isolated nucleic acids encoding any antibody described herein are provided. Such nucleic acids may encode an amino acid sequence comprising the $V_L$ and/or an amino acid sequence comprising the $V_H$ of the antibodies (e.g., the light and/or heavy chains of the antibodies). In some embodiments, one or more vectors (e.g., expression vectors) comprising such nucleic acids are provided herein. In some embodiments, a host cell comprising such nucleic acids is provided. In one such embodiment, a host cell comprises (e.g., has been transformed with): (1) a vector comprising a nucleic acid that encodes an amino acid sequence comprising the $V_L$, of the antibody and an amino acid sequence comprising the $V_H$ of the antibody, or (2) a first vector comprising a nucleic acid that encodes an amino acid sequence comprising the $V_L$, of the antibody and a second vector comprising a nucleic acid that encodes an amino acid sequence comprising the $V_H$ of the antibody. In some embodiments, the host cell is eukaryotic, e.g. a Chinese Hamster Ovary (CHO) cell or lymphoid cell (e.g., YO, NSO, Sp20 cell). In some embodiments, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of antibodies of the present disclosure, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B.K.C. Lo, ed., Humana Press, Totowa, N.J., 2003), pp. 245-254, describing expression of antibody fragments in *E. coli.*) After expression, the antibody may be isolated from the bacterial cell paste in a soluble fraction and may be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, Nat. Biotech. 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BEM); mouse sertoli cells (TM4 cells as described, e.g., in Mather, *Biol. Reprod.* 23:243-251

(1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as YO, NSO and Sp2/0. For a review of certain mammalian host cell lines suitable for antibody production, see, e.g., Yazaki and Wu, *Methods in Molecular Biology, Vol.* 248 (B.K.C. Lo, ed., Humana Press, Totowa, N.J.), pp. 255-268 (2003).

Bispecific Antibodies with Identical/Common/Single Heavy Chains

Further provided herein is a bispecific antibody having an identical heavy chain variable region of the present disclosure (e.g., having two light chain variable regions with different binding specificities and two identical heavy chain variable regions). In some embodiments, the bispecific antibody comprises two different light chains, wherein the first light chain comprises a kappa $C_L$ domain (e.g., a human kappa $C_L$ domain), and the second light chain comprises a lambda $C_L$ domain (e.g., a human lambda $C_L$ domain). Methods of making and/or purifying bispecific antibodies comprising a kappa $C_L$ domain and a lambda $C_L$ domain are known in the art (See e.g., Fischer et al. (2015), *Nat. Commun.* 6:6113; US20140179547). For example, a bispecific antibody comprising: a) two identical heavy chain variable regions (e.g., any one of the heavy chain variable regions described herein), b) a first light chain comprising a first light chain variable region and a kappa $C_L$ domain, and c) a second light chain comprising a second light chain variable region and a lambda $C_L$ domain (e.g., the constant region of a second light chain comprising a kappa $C_L$ domain is switched with a lambda $C_L$ domain) may be constructed and expressed (e.g., cloned into one or more expression vectors and expressed in one or more suitable host cells). The resulting bispecific IgG constructed in this way (e.g., comprising both a kappa and a lambda $C_L$ domain) may be purified using the following steps: first, total IgGs are recovered from the culture supernatant using protein A or IgG-CH1 Capture Select affinity chromatography, resulting in the elimination of free light chains and other contaminants; next, IgGs containing a kappa $C_L$ domain are captured using KappaSelect affinity resin, and monospecific IgGs with light chains containing only lambda $C_L$ domains are eliminated in the column flow through; finally, pure bispecific kappa-lambda-bodies are recovered using LambdaFabSelect affinity resin, and separated from the monospecific IgGs with light chains containing only kappa $C_L$ domains that do not bind to the resin. Alternatively, the bispecific common heavy chain IgG (e.g., as described above) can be purified by protein A and resolved using resins specific to each light chain $C_L$ domain based on differences in one or more biophysical properties of the differing light chains (such as different molecular weights, different isoelectric points (pI), etc.).

In some embodiments, the bispecific antibody comprises two antibody light chain variable regions and two identical heavy chain variable regions, where the bispecific antibody includes: a first binding domain that binds to a first target or antigen and comprises a first antibody light chain variable region and a first heavy chain variable region; and a second binding domain that binds to a second target or antigen and comprises a second antibody light chain variable region and a second antibody heavy chain variable region; where the second antibody heavy chain variable region has a sequence identical to the first antibody heavy chain variable region sequence. In some embodiments, the first and second binding domains bind to different target biomolecules. In some embodiment, the first and second binding domains bind to different epitopes on a same biomolecule. In some embodiments, the first antibody heavy chain variable region is part of a first antibody heavy chain comprising the first heavy chain variable region and a first heavy chain constant region (e.g., comprising CH1, hinge, CH2 and CH3). In some embodiments, the second antibody heavy chain variable region is part of a second antibody heavy chain comprising the second heavy chain variable region and a second heavy chain constant region (e.g., comprising CH1, hinge, CH2 and CH3). In some embodiments, the first antibody light chain variable region is part of a first antibody light chain comprising the first light chain variable region and a first light chain constant region. In some embodiments, the second antibody light chain variable region is part of a second antibody light chain comprising the second light chain variable region and a second light chain constant region. In some embodiments, the first and the second antibody heavy chains have sequences identical to a heavy chain of the present disclosure.

Further provided herein is a method of generating a bispecific antibody having an identical heavy chain variable region of the present disclosure (e.g., having two light chain variable regions with different binding specificities and two identical heavy chain variable regions). In some embodiments, the method includes (a) selecting a first antigen binding domain that binds to a first antigen and comprises a first antibody light chain variable region and a first heavy chain variable region of the present disclosure; (b) selecting a second antigen binding domain that binds to a second antigen and comprises a second antibody light chain variable region and a second heavy chain variable region of the present disclosure, where the second antibody heavy chain variable region has a sequence identical to the first antibody heavy chain variable region sequence; and (c) producing the bispecific antibody comprising a light chain variable region comprising the amino acid sequence of the first antibody light chain variable region, a light chain variable region comprising the amino acid sequence of the second antibody light chain variable region, a heavy chain variable region comprising the amino acid sequence of the first antibody heavy chain variable region sequence, and a heavy chain variable region comprising the amino acid sequence of the second antibody heavy chain variable region sequence. In some embodiments, the first heavy chain variable region is encoded by a polynucleotide from a library of the present disclosure.

In some embodiments, bispecific antibodies described herein may have additional specificities. For example, one of the antigen or target binding sites of the bispecific antibody may bind to more than one target specifically.

Methods for making/generating bispecific antibodies are known in the art. Production of full length bispecific antibodies can be based on the co-expression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

V. Kits

In another aspect, provided herein is a kit comprising a library of polynucleotides of the present disclosure. In some embodiments, the kit further comprises a package insert comprising instructions for expressing, modifying, screening, or otherwise using the library, e.g., to identify an antibody HVR or variable region of interest. In some embodiments, the kit further comprises one or more buffers, e.g., for storing, transferring, transfecting, or otherwise using one or more of the polynucleotides (e.g., synthetic polynucleotides). In some embodiments, the kit further comprises one or more containers for storing one or more of the polynucleotides. In some embodiments, the kit further comprises one or more vectors, e.g., for transfection of a host cell with one or more of the polynucleotides.

EXAMPLES

The present disclosure will be more fully understood by reference to the following examples. The examples should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1

Identification of the Minimal Set of Dynamic Motifs on Hypervariable Regions To understand variability of antibody variable domains at a structural level, an algorithm was developed to map the geometric alignment for antibody variable domains, and further, to calculate the structural and sequence entropy based upon the geometric alignment. Taking such an approach combines the classical theory of antibody diversity being determined by the well-established process of V(D)J recombination coupled with conformational diversity from dynamic units (template-directed conformational selection by Linus Pauling; See e.g., James, L. and Tawfik, D. “Conformational diversity and protein evolution—a 60-year-old hypothesis revisited”, Trends Biochem Sci. 2003 July; 28(7):361-8) to allow sampling of an almost infinite epitope space by selection and adaptation of antibody binding sites. As an example, this algorithm was used to analyze the structural and sequence variability of 113 high-resolution crystal structures of human antibody variable heavy chain domains. Entropy was calculated and plotted for every position of the variable heavy chain domain, (FIG. 1A; structural entropy in bold line, sequence entropy in dotted line). The results obtained by calculating the structural and sequence entropy based upon geometric alignment were used to locate the hyper-variable (HVR) regions, and to identify the critical positions on these variable regions. For comparison, the HVRs (as defined by the methodology described above) and CDRs (as defined by Kabat) were identified for an exemplary antibody heavy chain variable domain sequence (FIG. 1B).

Interestingly, variability as assessed by structural alignments was generally lower than the variability observed with sequence alignments. While variability was generally lower as assessed by structural alignments, there were a number of sites/regions with dramatic structural variation, suggesting these variable sites may play critical roles in antibody function. Furthermore, some of those hyper-variable regions showed high flexibility with multiple conformations. The identification of regions of highly variable residues gave a more comprehensive picture of the conservation and variability of antibody variable domains that could be exploited in new antibody designs. The identification of the dynamic motif made it possible to cover a wide range of structural diversity with a reduced number of amino acid sequences. The surprising advantage of this approach to antibody design was that a more limited number of dynamic motifs could be employed in the variable regions to cover a wide range of antibody structural diversity and provide broad flexibility in these antibodies which may allow binding to multiple antigens of interest. As such, dynamic heavy chain libraries were constructed using single human germline or germline-derived sequences for the invariant residues, while a limited number of dynamic motifs (as compared to $10^6$, $10^{10}$ or more) were used in the hyper-variable regions HVR H1 and HVR H2 to capture the wide range of structural variability identified in these two regions.

Example 2

Construction of the Common Heavy Chain Libraries

Construction of the Heavy Chain Libraries

To begin construction of the heavy chain libraries, 3 groups of degenerate oligos were designed for the variable region HVR-H1 based on the formulas shown in Table 2, resulting in 112 unique HVR-H1 sequences. 7 groups of degenerate oligos were designed for the variable region HVR-H2 based on the formulas shown in Table 2, resulting in 565 unique HVR-H2 sequences. The synthesized degenerate oligos were converted into double stranded DNA through the following protocol: 0.75 μL of 0.2 μM template oligos were mixed with 10 μL 5× PrimeSTAR buffer, 4 μL dNTP mixture, 1 μL of 100 μM forward primer, 1 μL of 100 μM reverse primer, 0.5 μL of PrimeSTAR HS DNA Polymerase (2.5 U/μL), and 33 μL of water. The PCR solutions were preheated at 96° C. for 5 minutes, then 14 cycles (96° C. for 15 seconds, 60° C. for 15 seconds, 72° C. for six seconds) were performed, followed by extension at 72° C. for three minutes. The VH_vr1s were amplified using the primer pair F_1999 (CGTTTGTCCTGTGCAGCTTCCGG) (SEQ ID NO:211) and R_1999 (CGAGGCCCTTACCCGGGGCCTGACG) (SEQ ID NO:212), while VH_vr2s were amplified using the primer pair F_2003 (CCGGGTAAGGGCCTCGAGTGG) (SEQ ID NO:213) and R_2003 (GAGCACGTCCGTTCGAATTGTCGCGACTTATAG) (SEQ ID NO:214).

The double stranded VII_vr1s and VII_vr2s were joined together through overlapping sequences at their 5' or 3' ends. The protocol used was as follows: 20 ng of VH_vr1 and 20 ng of VII_vr2 templates were mixed with 10 μL 5× PrimeSTAR buffer, 4 μL dNTP mixture, 1 μL of 100 μM F_1999 primer, 1 μL of 100 μM R_2003 primer, 0.5 μL of PrimeSTAR HS DNA Polymerase (2.5 U/μL), and water (up to 50 μL), and the mixtures were preheated at 96° C. for 5 minutes, then 14 cycles (96° C. for 15 seconds, 60° C. for 15 seconds, 72° C. for 10 seconds) were performed, followed by extension at 72° C. for three minutes. These PCR fragments were then purified through gel electrophoresis (GENEray Gel Extraction kit), digested with BspEI and BstBI (Thermo Scientific), and subsequently cloned into a filter vector FTV014 digested with the same two enzymes. The ligation mixture was transformed into DH10B cells by electroporation, and the number of colonies exceeding 10 fold of calculated diversity was collected for plasmid preparation. The purified plasmids constituted library VH-vr12

SpeI (NEB), and the vr3-encoding fragments were purified through gel electrophoresis (GENEray Gel Extraction kit), and cloned into the VH-vr12 library plasmid mixture digested with the same two restriction enzymes. The ligation products were desalted (QIAquick® PCR Purification Kit (QIAGEN)) before rolling circle amplification (RCA) was performed. RCA was carried out as follows: 40 ng ligation

TABLE 2 formulas for HVR-H1 and HVR-H2 designed variant sequences

| Variant Group | Amino Acid Sequence Formula | $X_1$ Residue Identity | $X_2$ Residue Identity | $X_3$ Residue Identity | $X_4$ Residue Identity | $X_5$ Residue Identity | $X_6$ Residue Identity |
|---|---|---|---|---|---|---|---|
| HVR-H1_A (SEQ ID NO: 198) | X1TFX2X3YX4IHWV | F, Y | S, T | D, G, N, S | A, G, W | n/a | n/a |
| HVR-H1_B (SEQ ID NO: 199) | YSIX1SGX2X3WX4WI | S, T | H, Y | H, Y | A, D, G, N, S, T | n/a | n/a |
| HVR-H1_C (SEQ ID NO: 200) | FSLSTX1GVX2VX3WI | G, S | A, G | A, G, S, T | n/a | n/a | n/a |
| HVR-H2_A (SEQ ID NO: 201) | LAX1IX2WX3X4DKX5Y SX6SLKSRL | L, R | D, Y | A, D, S, Y | D, G | R, S, Y | P, T |
| HVR-H2_B (SEQ ID NO: 202) | IGX1IX2X3SGSTYYSPS LKSRV | A, D, E, S, Y | S, Y | H, Y | n/a | n/a | n/a |
| HVR-H2_C (SEQ ID NO: 203) | IGX1IYX2SGX3TX4YNP SLKSRV | D, E, R, S, Y | H, Y | N, S | N, Y | n/a | n/a |
| HVR-H2_D (SEQ ID NO: 204) | VSX1ISGX2GX3X4TYY ADSVKGRF | A, G, S, V, Y | A, D, S, Y | D, G, S | S, T | n/a | n/a |
| HVR-H2_E (SEQ ID NO: 205) | IGX1INPNX2GX3TX4YA QKFQGRV | I, R, W | F, R | D, G, S | K, N | n/a | n/a |
| HVR-H2_F (SEQ ID NO: 206) | IGX1IX2PSX3GX4TX5Y AQKFQGRV | I, R, W | S, Y | G, S | D, G, S | K, N | n/a |
| HVR-H2_G (SEQ ID NO: 207) | VGRIX1SKX2X3GX4TT X5YAAX6VKGRF | K, R | A, T | D, Y | G, Y | D, E | P, S |

n/a, not applicable.

Hundreds of degenerate oligos encoding the VII_vr3 with sequence diversity approaching $10^5$ were designed and synthesized, and converted into double strand DNA through the following protocol: 0.75 μL of 0.2 μM template oligos were mixed with 10 μL 5× PrimeSTAR buffer, 4 μL dNTP mixture, 1 μL of 100 μM forward primer, 1 μL of 100 μM reverse primer, 0.5 μL of PrimeSTAR HS DNA Polymerase (2.5 U/μL), and 33 μL of water. The PCR solutions were preheated at 96° C. for 5 minutes, then 14 cycles (96° C. for 15 seconds, 60° C. for 15 seconds, 72° C. for six seconds) were performed, followed by extension at 72° C. for three minutes. The forward primer was S1089 (ACAACT-GAACAGCTTAAGAGCTGAGGACACTGCCGTCTATT-ATTG) (SEQ ID NO:215) and the reverse primer was S1090 (GAGGAGACGGTGACTAGTGTTCCTTGACCCCA) (SEQ ID NO:216). The resulting synthesized DNAs were then purified through gel electrophoresis (GENEray Gel Extraction kit), digested with AflII and SpeI (Thermo Scientific), and subsequently cloned into the filter vector FTV012 digested with the same two restriction enzymes. The ligation mixture was transformed into DH10B cells by electroporation, and the number of colonies exceeding 10 fold of calculated diversity was collected for plasmid preparation. The purified plasmids constituted library VH-vr3.

To assemble the full length VH library, the purified VH-vr3 library plasmid mixture was digested with AflII and products were mixed with 10 μL 10× NEBuffer 4, 50 μL of 100 μM pd(N)8, and water (up to 88.5 μL), heated to 95° C. for three minutes, and annealed for 65 cycles (30 second each cycle) with each cycle decreasing by 1° C. The annealed reactions were incubated overnight at 30° C. after the addition of 10 μL of 10 mM dNTP mix, 1 μL of 100×BSA, and 0.5 μL of Phi29 DNA polymerase. The RCA products were first digested with NotI, DNA fragments were purified (QIAquick® PCR Purification Kit), and further digested with XhoI. The digested products were then ligated with T4 DNA ligase (Thermo Scientific). After purification through ethanol precipitation, the ligation products were transformed into DH10B cells by electroporation. The purified plasmids constituted library VH-vr123. These constructs each shared the same framework regions, namely FW-H1 (SEQ ID NO:165), FW-H12 (SEQ ID NO:166), FW-H13 (SEQ ID NO:167), and FW-H4 (SEQ ID NO:168).

The above-mentioned mixtures of plasmids for the two heavy chain libraries were digested with PvuI and Acc65I, and ligated into the phagemid vector Fad40 that was also digested with the same two restriction enzymes. The ligation mixtures were transformed into DH10B cells, the resulting libraries were purified, quantified, and stored for the assembly of the complete phagemid library.

Construction of the VL Library

To begin construction of the light chain libraries, 18 groups of degenerate oligos and 5 defined oligos were designed for the variable region VL_vr1 and VL_vr2 respectively. They were converted into double stranded DNA through the following protocol: 0.75 μL of 0.2 μM template oligos were mixed with 10 μL 5x PrimeSTAR buffer, 4 μL dNTP mixture, 1 μL of 100 μM forward primer, 1 μL of 100 μM reverse primer, 0.5 μL of PrimeSTAR HS DNA Polymerase (2.5 U/μL), and 33 μL of water. The PCR solutions were preheated at 96° C. for 5 minutes, then 14 cycles (96° C. for 15 seconds, 60° C. for 15 seconds, 72° C. for six seconds) were performed, followed by extension at 72° C. for three minutes. The VL_vr1s were amplified using the primer pair F_2898 (TACTTATGTAGGCGATCGGGTCACCATCACCTGC) (SEQ ID NO:217) and R_2898 (CGGAGCTTTTCCTGGTTTCTGTTGATAC) (SEQ ID NO:218), while VL_vr2s were amplified using the primer pair F_2013 (GAAACCAGGAAAAGCTCCGAAG) (SEQ ID NO:219) and R_2013 (CGTCCCGGAACCGGATCCAGAGAAGCGAG) (SEQ ID NO:220).

The double stranded VL_vr1s and VL_vr2s were joined together through overlapping sequences at their 5' or 3' ends. The protocol used was as follows: 20 ng of VL_vr1 and 20 ng of VL_vr2 templates were mixed with 10 μL 5× PrimeSTAR buffer, 4 μL dNTP mixture, 1 μL of 100 μM F_2898 primer, 1 μL of 100 μM R_2013 primer, 0.5 μL of PrimeSTAR HS DNA Polymerase (2.5 U/μL), and water (up to 50 μL), and the mixtures were preheated at 96° C. for 5 minutes, then 14 cycles (96° C. for 15 seconds, 60° C. for 15 seconds, 72° C. for 10 seconds) were performed, followed by extension at 72° C. for three minutes. These PCR fragments were then purified through gel electrophoresis (GENEray Gel Extraction kit), digested with PvuI and BamHI (Thermo Scientific), and subsequently cloned into a filter vector FTV015 digested with the same two enzymes. The ligation mixture was transformed into DH10B cells by electroporation, and the number of colonies exceeding 10 fold of calculated diversity was collected for plasmid preparation. The purified plasmids constituted library VL-vr12.

22 groups of degenerate oligos encoding VL_vr3 were designed, synthesized, and converted into double stranded DNA through the following protocol: 0.75 μL of 0.2 μM template oligos were mixed with 10 μL 5× PrimeSTAR buffer, 4 μL dNTP mixture, 1 μL of 100 μM forward primer F2929 (ACCATCAGCAGTCTGCAGCCGGAAGACTTCGCAAC) (SEQ ID NO:221), 1 μL of 100 μM reverse primer R2929 (GATCTCCACCTTGGTACCCTGTCCGAA) (SEQ ID NO:222), 0.5 μL of PrimeSTAR HS DNA Polymerase (2.5 U/μL), and 33 μL of water. The PCR solutions were preheated at 96° C. for 5 minutes, then 14 cycles (96° C. for 15 seconds, 60° C. for 15 seconds, 72° C. for six seconds) were performed, followed by extension at 72° C. for three minutes. The double stranded DNAs encoding the VL_vr3 were then purified through gel electrophoresis (GENEray Gel Extraction kit), digested with PstI and Acc65I (Thermo Scientific), and subsequently cloned into the filter vector FTV013 digested with the same two restriction enzymes. The ligation mixture was transformed into DH10B cells by electroporation, and the number of colonies exceeding 10 fold of calculated diversity was collected for plasmid preparation. The purified plasmids constituted library VL-vr3.

To assemble the full length VL library, the purified VL-vr3 library plasmid mixture was digested with PstI and Acc65I (NEB), and the vr3-encoding fragments were purified through gel electrophoresis (GENEray Gel Extraction kit), and subsequently cloned into VL-vr12 library plasmid mixture that had been digested with the same two restriction enzymes. The ligation products were transformed into DH10B cells by electroporation, and the number of colonies exceeding 10 fold of calculated diversity was collected for plasmid preparation. The purified plasmids constituted library VL-vr123. The vr123 inserts from the library plasmids VL-vr123 were then moved into the phagemid vector Fad40, using the restriction enzymes PvuI and Acc65I. The size of the library containing Fad40-vr123 reached $4*10^7$.

Construction of the Complete Dynamic Library

The dynamic library was composed of the heavy chain library derived from the VH-vr123 library and the light chain library derived from the Fad40-vr123 library. Both the VH-vr123 library plasmids and the Fad40-vr123 library plasmids were digested with BspEI and SpeI (Thermo Scientific). The DNA fragments encoding the heavy chain derived from the VH-vr123 library were cloned into the vector backbones derived from Fad40-vr123 library. The ligation products were desalted (QIAquick® PCR Purification Kit (QIAGEN)) before rolling circle amplification (RCA). RCA was carried out as follows: 40 ng ligation products were mixed with 10 μL 10× NEBuffer 4, 50 μL of 100 μM pd(N)8, and water (up to 88.5 μL), heated to 95° C. for three minutes, and annealed for 65 cycles (30 second each cycle) with each cycle decreasing by 1° C. The annealed reactions were incubated overnight at 30° C. after the addition of 10 μL of 10 mM dNTP mix, 1 μL of 100×BSA, and 0.5 μL of Phi29 DNA polymerase. The RCA products were first digested with NotI, DNA fragments were purified (QIAquick® PCR Purification Kit), and further digested with Acc65I. The digested products were then ligated with T4 DNA ligase (Thermo Scientific). After purification through ethanol precipitation, the ligation products were transformed into ER2738 cells by electroporation. A total number of $1.4*10^{10}$ colonies were collected from plates (2xYT, 1% glucose, 100 μg/mL ampicillin) to make the DPL6 library.

Example 3

Screening the Common Heavy Chain Libraries to Isolate Antibodies of Interest Preparation of Dynamic Library Phagemid Particles To prepare the dynamic library phagemid particles for antigen panning, 5.0 liters of ER2738 cells harboring the dynamic library (described in Example 2 above) were inoculated in media containing 2xYT, 2% glucose, 100 μg/mL ampicillin and 12.5 μg/mL tetracycline at a starting $OD_{600}$ of 0.1. The cultures were grown at 37° C., shaking at 250 rpm, until they reached $OD_{600}$ of 0.6-0.8. The cells were then infected with M13K07 helper phages at a multiplicity of infection (MOI) of 10 for 30 minutes at 37° C. The infected ER2738 cells were grown overnight at 22° C. in 3.2 liters of media containing 2xYT, 100 μg/mL ampicillin and 50 μg/mL kanamycin. Culture supernatants were then harvested by centrifugation at 10,000 rpm for 15 minutes, and filtered through a 0.45 μm low-binding membrane filter (Corning). The phagemid particles were then precipitated from the filtered supernatant using PEG/NaCl, and resuspended in PBS. An additional round of PEG/NaCl precipitation, followed by resuspension in PBS, was conducted. Phage titers were determined by $OD_{268}$ measurement (assuming 1 unit at $OD_{268}$ is approximately $1*10^{13}$ phage particles/mL) and confirmed by plaque assay. Library phagemid particles were stocked in 20% glycerol at −80° C.

Phage Library Panning

Antigen proteins at a concentration of 1-30 μg/ml were coated on Maxisorp strips (Thermo Scientific, Cat. No.

446469) overnight at 4° C. Multiple wells of antigens were prepared for each library. The coated wells were first blocked with 5% milk in PBS for 1-2 hours at room temperature and washed with PBS. Then 1,100 μL/well of phagemid particle solution (typically 1-5*$10^{12}$ phages in 2% milk-PBS) was added into 4 parallel wells and incubated for 1-2 hours. Wells were then washed several times with PBS with increasing concentrations of Tween 20 (from 0.1% to 0.3%), and finally with PBS alone. The bound phagemid particles were eluted from the wells with 100 μL of 0.2 M glycine-HCl for 10 minutes at room temperature. The eluted phages were immediately neutralized with 18 μL of 1M Tris-HCl (pH 9.1)

Alternatively, phagemid library panning was performed using Dynabeads (M280, Streptavidin, Invitrogen, Cat. No. 60210) through KingFisher (Thermo Scientific) according to the manufacturer's instructions. 300 μL of Dynabeads were washed with PBS and incubated with biotinylated anti-human Fc for 20 minutes at room temperature. The beads were then blocked with 5% BSA in PBS for one hour at room temperature. Fc-fusion antigens (70-100 pmols) were captured by one hour incubation at room temperature. The beads were then washed once with PBS, and incubated with 1 mL of phage library solution (typically 5*$10^{12}$ to 1*$10^{13}$ phage particles in 5% BSA-PBS) for 1-2 hours. The beads were then washed several times with PBS/Tween (0.1% to 0.3%) and PBS, and the bound phages were eluted from the beads with 100 μL of 0.2 M glycine-HC1 for 10 minutes at room temperature. The eluted phages were immediately neutralized with 18 μL of 1 M Tris-HCl (pH 9.1). A total of three or four rounds of panning were conducted against each of the antigens, and more than 10 fold excess of purified human Fc was included to reduce background binding.

For some of the antigens tested, 2 mL of antigens (10-30 μg/mL) were used to coat immune-tubes overnight at 4° C. The volume of blocking, washing, and elution solutions were increased accordingly.

Amplification of Enriched Phage

The eluted, enriched phage pool was further amplified as follows: ER2738 cells were infected with the eluted phagemid particles at 37° C. for 30 minutes. The infected cells were then plated out on 2xYT agar plates with 2% glucose, 100 μg/mL ampicillin and 12.5 μg/mL tetracycline. The colonies were harvested from plates, grown in 100 ml of 2% glucose, 100 μg/mL ampicillin and 12.5 μg/mL tetracycline, and infected with M13K07 helper phage. The amplified phages were purified and quantified by the processes described above. Usually, the eluted phages after the final round of panning were used to infect ER2738 cells, and the resulting ER2738 colonies were picked for supernatant ELISA screening assays.

Supernatant Sandwich Elisa Assay

A sensitive sandwich Elisa assay was developed to measure the Fabs present in bacterial supernatant. Microplates were coated with polyclonal anti-human IgG (Fab specific) (Sigma 15260) to capture Fabs present in the bacterial supernatant, and then HRP labeled goat anti-human Fc was used to detect the amount of Fabs captured. The $A_{450}$ of each well was measured to determine the Fab binding activity. The primary hits were defined as those whose ELISA signals were at least twice that of background, and were further characterized in the following example (Example 4).

Twelve human targets (TAGT-1, TAGT-2, TAGT-3, TAGT-4, TAGT-5, TAGT-6, TAGT-7, TAGT-8H, TAGT-9, TAGT-10H, TAGT-11, and TAGT-12), as well as two corresponding mouse targets (TAGT-8M and TAGT-10M), were screened with the constructed libraries. With these 14 antigens, a total of 690 unique positive hits with high affinity were identified. Most of the variant groups (Table 2) could form antibodies that bound to different target antigens, or were cross reactive between two species (e.g., bound TAGT-8H and TAGT-8M). The variant groups from confirmed binders were subsets of the designed variant groups shown in Table 2. A majority of the designed variants were also found in the confirmed binders (Table 3). (See the designed formulas of Table 2 vs. the formulas from the positive hits of Table 3).

TABLE 3 formulas for HVR-H1 and HVR-H2 designed variant sequences from positive hits

| Variant Group | Amino Acid Sequence Formula | $X_1$ Residue Identity | $X_2$ Residue Identity | $X_3$ Residue Identity | $X_4$ Residue Identity | $X_5$ Residue Identity | $X_6$ Residue Identity |
|---|---|---|---|---|---|---|---|
| HVR-H1_1 (SEQ ID NO: 198) | X1TFX2X3YX4IHWV | F, Y | S, T | D, G, N, S | A, G, W | n/a | n/a |
| HVR-H1_2 (SEQ ID NO: 199) | YSIX1SGX2X3WX4WI | S, T | H, Y | H, Y | A, D, G, N, S, T | n/a | n/a |
| HVR-H1_3 (SEQ ID NO: 200) | FSLSTX1GVX2VX3WI | G, S | A, G | A, G, S, T | n/a | n/a | n/a |
| HVR-H2_1 (SEQ ID NO: 201) | LAX1IX2WX3X4DKX5YSX6SLKSRL | L, R | D, Y | A, D, S, Y | D, G | R, S, Y | P, T |
| HVR-H2_2 (SEQ ID NO: 208) | IGX1IX2X3SGSTYYSPSLKSRV | A, D, E | S, Y | H, Y | n/a | n/a | n/a |
| HVR-H2_3 (SEQ ID NO: 209) | IGX1IYX2SGX3TX4YNPSLKSRV | D, E, S | H, Y | N, S | N, Y | n/a | n/a |
| HVR-H2_4 (SEQ ID NO: 204) | VSX1ISGX2GX3X4TYYADSVKGRF | A, G, S, V, Y | A, D, S, Y | D, G, S | S, T | n/a | n/a |
| HVR-H2_5 (SEQ ID NO: 205) | IGX1INPNX2GX3TX4YAQKFQGRV | I, R, W | F, R | D, G, S | K, N | n/a | n/a |

TABLE 3-continued formulas for HVR-H1 and HVR-H2 designed variant sequences from positive hits

| Variant Group | Amino Acid Sequence Formula | $X_1$ Residue Identity | $X_2$ Residue Identity | $X_3$ Residue Identity | $X_4$ Residue Identity | $X_5$ Residue Identity | $X_6$ Residue Identity |
|---|---|---|---|---|---|---|---|
| HVR-H2_6 (SEQ ID NO: 206) | IGX1IX2PSX3GX4TX5Y AQKFQGRV | I, R, W | S, Y | G, S | D, G, S | K, N | n/a |
| HVR-H2_7 (SEQ ID NO: 210) | VGRIX1SKX2X3GX4TT EYAAX5VKGRF | K, R | A, T | D, Y | G, Y | P, S | n/a |

n/a, not applicable.

Example 4

Characterization of Antibodies In Vitro

The Fabs corresponding to the primary hits identified in Example 3 above, which were tagged at their C-terminus of the CH1 domain with a His6 tag, were over-expressed in *E. coli*, and were purified through Ni-NTA resin (Thermo Fisher Scientific) according to the manufacturer's instructions. Their affinities were measured by the ForteBio Octet RED96 System. Briefly, the AHC sensors (anti-human IgG-Fc capture dip and read biosensors) were used to capture antigen Fc-His fusion protein (Sino Biological #10039-H03H) were used, and dipped into wells containing the purified Fabs that were diluted to 5-10 μg/mL with kinetic buffer (See also, ForteBio, *Anti-human IgG Capture* (*AHC*) *Biosensors, Product Insert* 41-0072-PD (2008); Yang et al. (2016), Anal. Biochem. 508:78-96). The acquired ForteBio data were processed with Data Acquisition software 7.1, and kinetic data were fitted to a 1:1 Langmuir binding model. Fab melting temperatures were measured by Differential Scanning Fluorimetry (DSF) assay. Briefly, the temperature and fluorescence monitoring was done using a qPCR machine (real time PCR). SYPRO® Orange was diluted from a 5000× stock 50 fold to 100× with PBS buffers; 16 μl of each Fab (~0.5 mg/ml) was added to each well in a 96-well microplate and mixed with 4 μl of 100× SYPRO® Orange. A LightCycler®480 System was used to measure fluorescence intensity. The excitation wavelength was set at 483 nm, and the emission wavelength was set at 568 nm. The temperature was increased from 25° C. to 90° C. at an increment of 1.2 to 1.3° C. per minute, and an equilibration time of 15 seconds at each measurement temperature was applied. The data were analyzed using the LightCycler®480 Software. The midpoint of hydrophobic exposure, Tm, was defined as the temperature corresponding to the maximum value of the first derivative of the first fluorescence transition. (See also, Lavinder et al. (2009), J. Am. Chem. Soc.131: 3794-3795; Ericsson et al. (2006), Analytical Biochemistry 357: 289-298; Phillips and Hernandez de la Pena (2011), Current Protocols in Mol. Biol. 94: 10.28.1-10.28.15).

Figure 2B:
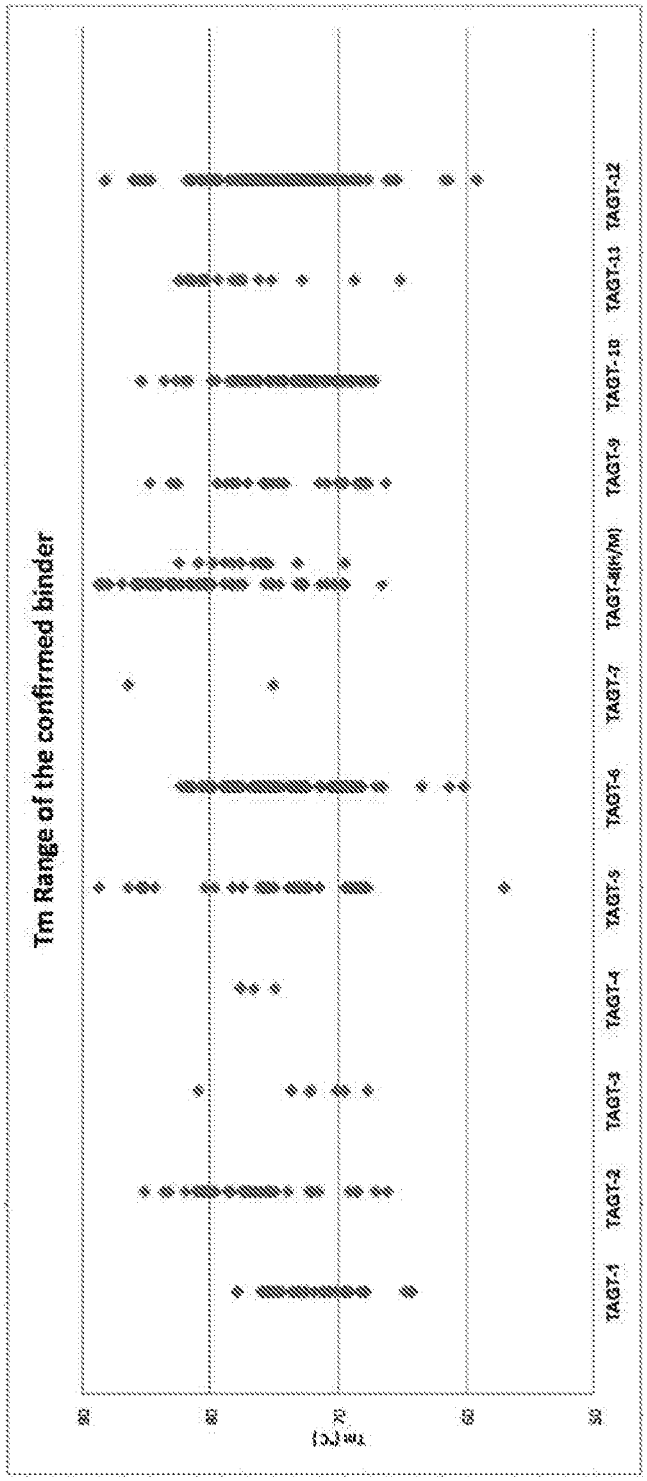
FIG. 2B shows the melting temperature (Tm) measurements for fabs with confirmed binding to the antigens TAGT-1 to TAGT-12.

The 12 human target antigens (TAGT-1, TAGT-2, TAGT-3, TAGT-4, TAGT-5, TAGT-6, TAGT-7, TAGT-8H, TAGT-9, TAGT-10H, TAGT-11 and TAGT-12) were unrelated proteins sharing sequence identity lower than 26%. The sequence identity between human antigen TAGT-8H and mouse antigen TAGT-8M was 70%, while the sequence identity between human antigen TAGT-1011 and mouse antigen TAGT-10M was 60%. Multiple antibodies targeting 14 different antigens with high affinity could be successfully identified and selected from the dynamic libraries. The affinities of most binders were in the nanomolar range, and some even reached the sub-nanomolar range (FIG. 2A). In addition, the confirmed binders demonstrated good stability, with Tm ranges shown in FIG. 2B.

Example 5

Application of the Dynamic Heavy Chain Libraries

To further examine the robustness and flexibility of the heavy chain libraries, the libraries were screened against the 14 target antigens described in Example 4 above by pairing the heavy chains with different light chain libraries having a diversity varying from $10^7$ to 280, and all the way to a single light chain (i.e., a common light chain). The limit of the diversity design in both the heavy and light chain libraries was explored by trimming the physical size of their respective pairing partners (e.g., light chain libraries with a diversity ranging from $10^7$ to 280, 20, and to a single light chain) while exploring the flexibility and/or the dynamic diversity of the light chain itself. The capacity of these dynamic light chain libraries in pairing with the dynamic heavy chain libraries provided a strong rational for the library design when generating and engineering the diverse antibody hits/leads against known and challenging target antigens. Positive hits having high affinity were identified from each of the libraries tested, and a total of 690 unique positive hits were measured and confirmed with affinity data (Table 4). Their ability for binding different targets, as well as their epitope variation (including, but not limited to, the fine differences in epitope recognition between two species, as shown by the cross-species reactivity with human and murine targets with sequence identity around 60%) were examined. Positive hits using each combination of HVR-H1_1, HVR-H1_2, or HVRH-1_3, and HVR-H2_1, HVR-H2_2, or HVRH-2_3, HVR-H2_4, HVR-H_5, HVRH-2_6, or HVR-H2_7 were observed. These results indicate the power and potential of using these dynamic hypervariable region units for making antibody and protein libraries that recognize a wide range of targets for therapeutic, diagnostic and/or research reagents when they are grafted on or designed into antibody (and/or alternative protein) scaffolds. The dynamic nature of these heavy chain hypervariable region units in designing and constructing antibody (and/or non-antibody) scaffolds, when paired with light chain libraries having a wide diversity (e.g., ranging from $10^7$ to 280, down to a single unique sequence), is a strong validation of the dynamic antibody design concept for creating novel binding reagents useful in therapeutic, diagnostic and/or research settings.

TABLE 4

| Affinity data for confirmed hits | | | |
|---|---|---|---|
| HVR-H1 and H2 Usage | Hit ID | Target ID | Kd (M) |
| HVR-H1_1 and HVR-H2_6 | 3757 | TAGT-6 | 1.84E−08 |
| | 3762 | TAGT-6 | 3.04E−08 |
| | 3780 | TAGT-8 | 1.47E−09 |
| | 3865 | TAGT-11 | 9.48E−09 |
| | 3869 | TAGT-11 | 2.35E−08 |
| | 3898 | TAGT-11 | 1.83E−08 |
| | 4030 | TAGT-8 | 4.90E−09 |
| | 4033 | TAGT-8 | 8.75E−10 |
| | 4043 | TAGT-8 | 2.69E−09 |
| | 4050 | TAGT-10 | 1.65E−08 |
| | 4084 | TAGT-8 | 2.94E−09 |
| | 4101 | TAGT-8 | 2.12E−09 |
| | 4103 | TAGT-8 | 3.59E−10 |
| | 4163 | TAGT-8 | 1.37E−08 |
| | 4614 | TAGT-8 | 3.53E−10 |
| | 4615 | TAGT-8 | 2.28E−10 |
| | 4617 | TAGT-8 | 2.88E−10 |
| | 4618 | TAGT-8 | 1.08E−09 |
| | 4620 | TAGT-8 | 3.48E−10 |
| | 4622 | TAGT-8 | 2.74E−10 |
| | 4623 | TAGT-8 | 4.85E−10 |
| | 4624 | TAGT-8 | 1.00E−12 |
| | 4625 | TAGT-8 | 4.02E−10 |
| | 4627 | TAGT-8 | 1.82E−10 |
| | 4630 | TAGT-8 | 2.67E−10 |
| | 4631 | TAGT-8 | 1.83E−10 |
| | 4633 | TAGT-8 | 3.22E−10 |
| | 4634 | TAGT-8 | 2.07E−10 |
| | 4638 | TAGT-8 | 3.14E−10 |
| | 4642 | TAGT-8 | 1.89E−10 |
| | 4644 | TAGT-8 | 2.48E−10 |
| | 4645 | TAGT-8 | 2.96E−10 |
| | 4650 | TAGT-8 | 3.57E−10 |
| | 4651 | TAGT-8 | 3.01E−10 |
| | 4652 | TAGT-8 | 2.94E−10 |
| | 4653 | TAGT-8 | 3.27E−10 |
| | 4654 | TAGT-8 | 2.32E−10 |
| | 4658 | TAGT-8 | 1.42E−10 |
| | 4659 | TAGT-8 | 2.12E−10 |
| | 4661 | TAGT-8 | 1.62E−09 |
| | 4662 | TAGT-8 | 8.98E−10 |
| | 4665 | TAGT-8 | 3.69E−10 |
| | 4666 | TAGT-8 | 1.17E−09 |
| | 4668 | TAGT-8 | 5.79E−10 |
| | 4670 | TAGT-8 | 8.21E−10 |
| | 4673 | TAGT-8 | 3.23E−10 |
| | 4674 | TAGT-8 | 5.02E−10 |
| | 4675 | TAGT-8 | 1.00E−12 |
| | 4676 | TAGT-8 | 1.62E−10 |
| | 4678 | TAGT-8 | 5.98E−10 |
| | 4681 | TAGT-8 | 5.43E−10 |
| | 4683 | TAGT-8 | 8.97E−10 |
| | 4684 | TAGT-8 | 6.69E−10 |
| | 4685 | TAGT-8 | 4.78E−10 |
| | 4686 | TAGT-8 | 4.78E−10 |
| | 4687 | TAGT-8 | 4.08E−10 |
| | 4689 | TAGT-8 | 1.63E−10 |
| | 4690 | TAGT-8 | 4.67E−10 |
| | 4792 | TAGT-10 | 7.39E−09 |
| | 5103 | TAGT-10 | 2.67E−09 |
| | 5149 | TAGT-11 | 2.91E−09 |
| | 5159 | TAGT-11 | 4.09E−09 |
| | 5160 | TAGT-11 | 8.07E−09 |
| | 5162 | TAGT-11 | 9.87E−09 |
| | 5163 | TAGT-11 | 1.71E−08 |
| | 5165 | TAGT-11 | 4.06E−09 |
| | 5709 | TAGT-11 | 1.93E−08 |
| | 5740 | TAGT-11 | 7.26E−09 |
| | 5752 | TAGT-11 | 6.33E−09 |
| | 5935 | TAGT-12 | 8.78E−09 |
| | 5970 | TAGT-12 | 1.35E−08 |
| | 5994 | TAGT-12 | 1.58E−08 |
| | 5997 | TAGT-12 | 8.51E−09 |
| | 6008 | TAGT-12 | 5.10E−08 |
| | 6032 | TAGT-2 | 1.63E−08 |

TABLE 4-continued

| Affinity data for confirmed hits | | | |
|---|---|---|---|
| HVR-H1 and H2 Usage | Hit ID | Target ID | Kd (M) |
| | 6531 | TAGT-3 | 1.08E−08 |
| | 7030 | TAGT-8 | 3.47E−08 |
| | 7035 | TAGT-8 | 3.04E−09 |
| | 7038 | TAGT-8 | 2.33E−08 |
| | 7043 | TAGT-8 | 1.34E−08 |
| | 7044 | TAGT-8 | 1.12E−09 |
| | 7045 | TAGT-8 | 1.11E−09 |
| | 7055 | TAGT-8 | 7.57E−10 |
| | 7213 | TAGT-12 | 8.87E−09 |
| | 7215 | TAGT-12 | 1.61E−08 |
| | 7222 | TAGT-12 | 1.26E−09 |
| | 7231 | TAGT-12 | 3.38E−09 |
| | 7232 | TAGT-12 | 8.06E−09 |
| | 7243 | TAGT-12 | 4.95E−09 |
| | 7357 | TAGT-3 | 6.14E−08 |
| | BH3002 | TAGT-8 | 2.51E−10 |
| | BH3004 | TAGT-8 | 3.00E−10 |
| | BH3005 | TAGT-8 | 3.46E−10 |
| | BH3006 | TAGT-8 | 1.94E−10 |
| HVR-H1_1 and HVR-H2_5 | 4025 | TAGT-8 | 2.89E−09 |
| | 4031 | TAGT-8 | 1.06E−09 |
| | 4054 | TAGT-10 | 1.58E−08 |
| | 4055 | TAGT-10 | 1.07E−08 |
| | 4060 | TAGT-10 | 1.10E−08 |
| | 4061 | TAGT-10 | 3.42E−08 |
| | 4065 | TAGT-10 | 4.31E−08 |
| | 4066 | TAGT-10 | 4.76E−08 |
| | 4181 | TAGT-10 | 4.27E−08 |
| | 4182 | TAGT-10 | 4.24E−09 |
| | 4693 | TAGT-10 | 4.87E−10 |
| | 4696 | TAGT-10 | 4.58E−10 |
| | 4697 | TAGT-10 | 6.21E−10 |
| | 4698 | TAGT-10 | 5.70E−10 |
| | 4700 | TAGT-10 | 2.62E−10 |
| | 4701 | TAGT-10 | 5.60E−10 |
| | 4702 | TAGT-10 | 5.02E−10 |
| | 4703 | TAGT-10 | 2.85E−10 |
| | 4704 | TAGT-10 | 6.65E−10 |
| | 4705 | TAGT-10 | 3.02E−10 |
| | 4706 | TAGT-10 | 2.50E−10 |
| | 4707 | TAGT-10 | 4.29E−10 |
| | 4708 | TAGT-10 | 5.29E−10 |
| | 4710 | TAGT-10 | 6.26E−10 |
| | 4714 | TAGT-10 | 4.46E−10 |
| | 4717 | TAGT-10 | 4.61E−10 |
| | 4718 | TAGT-10 | 5.32E−10 |
| | 4722 | TAGT-10 | 7.46E−10 |
| | 4725 | TAGT-10 | 4.84E−10 |
| | 4729 | TAGT-10 | 8.80E−10 |
| | 4731 | TAGT-10 | 4.67E−10 |
| | 4732 | TAGT-10 | 3.33E−10 |
| | 4738 | TAGT-10 | 5.34E−10 |
| | 4741 | TAGT-10 | 1.66E−09 |
| | 4743 | TAGT-10 | 7.40E−09 |
| | 4744 | TAGT-10 | 3.73E−10 |
| | 4748 | TAGT-10 | 3.92E−10 |
| | 4749 | TAGT-10 | 2.55E−10 |
| | 4750 | TAGT-10 | 7.86E−10 |
| | 4752 | TAGT-10 | 3.34E−09 |
| | 4753 | TAGT-10 | 3.43E−10 |
| | 4759 | TAGT-10 | 6.59E−10 |
| | 4766 | TAGT-10 | 4.09E−10 |
| | 4788 | TAGT-10 | 2.88E−10 |
| | 4794 | TAGT-10 | 5.56E−10 |
| | 4798 | TAGT-10 | 4.35E−09 |
| | 4803 | TAGT-10 | 1.88E−10 |
| | 4805 | TAGT-10 | 4.26E−10 |
| | 4808 | TAGT-10 | 8.28E−10 |
| | 4909 | TAGT-10 | 2.90E−10 |
| | 5126 | TAGT-8 | 9.54E−09 |
| | 5129 | TAGT-8 | 1.12E−09 |
| | 5132 | TAGT-8 | 3.06E−09 |
| | 5145 | TAGT-8 | 7.00E−09 |
| | 5295 | TAGT-9 | 2.21E−09 |
| | 6179 | TAGT-10 | 1.99E−09 |

TABLE 4-continued

Affinity data for confirmed hits

| HVR-H1 and H2 Usage | Hit ID | Target ID | Kd (M) |
|---|---|---|---|
| | 6180 | TAGT-10 | 6.11E−09 |
| | 6183 | TAGT-10 | 2.70E−09 |
| | 6184 | TAGT-10 | <1.0E−12 |
| | 6185 | TAGT-10 | 1.57E−09 |
| | 6187 | TAGT-10 | 2.74E−08 |
| | 6188 | TAGT-10 | 8.76E−09 |
| | 6189 | TAGT-10 | 2.38E−10 |
| | 6190 | TAGT-10 | 2.55E−09 |
| | 6191 | TAGT-10 | 6.58E−11 |
| | 6193 | TAGT-10 | 3.18E−09 |
| | 6194 | TAGT-10 | 2.49E−10 |
| | 6195 | TAGT-10 | 4.30E−09 |
| | 6196 | TAGT-10 | <1.0E−12 |
| | 6197 | TAGT-10 | 8.56E−09 |
| | 6198 | TAGT-10 | 2.85E−09 |
| | 6202 | TAGT-10 | 1.03E−09 |
| | 6203 | TAGT-10 | 1.05E−08 |
| | 6204 | TAGT-10 | 6.46E−09 |
| | 6206 | TAGT-10 | 3.44E−09 |
| | 6208 | TAGT-10 | 3.50E−09 |
| | 6209 | TAGT-10 | 3.35E−09 |
| | 6210 | TAGT-10 | 5.17E−10 |
| | 6212 | TAGT-10 | 2.25E−09 |
| | 6214 | TAGT-10 | 1.51E−09 |
| | 6216 | TAGT-10 | 6.58E−10 |
| | 6217 | TAGT-10 | 4.99E−09 |
| | 6219 | TAGT-10 | 3.15E−09 |
| | 6220 | TAGT-10 | 3.45E−09 |
| | 6539 | TAGT-4 | 3.45E−09 |
| | 7025 | TAGT-8 | 4.87E−08 |
| | 7036 | TAGT-8 | 1.59E−08 |
| | 7037 | TAGT-8 | 2.10E−08 |
| | 7047 | TAGT-8 | 2.15E−08 |
| | 7066 | TAGT-8 | 1.80E−08 |
| | 7067 | TAGT-8 | 3.41E−08 |
| | 7068 | TAGT-8 | 1.11E−08 |
| | 7073 | TAGT-8 | 3.19E−09 |
| HVR-H1_3 and HVR-H2_4 | 4074 | TAGT-6 | 1.95E−08 |
| | 4131 | TAGT-6 | <1.0E−12 |
| | 4132 | TAGT-6 | <1.0E−12 |
| | 4200 | TAGT-6 | 5.68E−08 |
| | 4216 | TAGT-6 | 2.59E−08 |
| | 4878 | TAGT-12 | 4.07E−09 |
| | 5291 | TAGT-1 | 6.57E−09 |
| | 5312 | TAGT-6 | 4.50E−07 |
| | 5326 | TAGT-6 | 7.84E−07 |
| | 5345 | TAGT-6 | 1.02E−08 |
| | 5346 | TAGT-6 | 1.61E−08 |
| | 5347 | TAGT-6 | 1.21E−08 |
| | 5348 | TAGT-6 | 1.02E−08 |
| | 5355 | TAGT-6 | 8.71E−10 |
| | 5364 | TAGT-6 | 7.26E−09 |
| | 5367 | TAGT-6 | 1.49E−08 |
| | 5371 | TAGT-6 | 3.97E−09 |
| | 5405 | TAGT-6 | 1.01E−08 |
| | 5415 | TAGT-6 | 1.64E−08 |
| | 5417 | TAGT-6 | 4.04E−08 |
| | 5418 | TAGT-6 | 2.02E−08 |
| | 5905 | TAGT-12 | 3.83E−08 |
| | 5910 | TAGT-12 | 3.30E−08 |
| | 5911 | TAGT-12 | 3.35E−08 |
| | 5912 | TAGT-12 | 1.68E−08 |
| | 5914 | TAGT-12 | 3.30E−08 |
| | 5915 | TAGT-12 | 1.82E−08 |
| | 5918 | TAGT-12 | 3.46E−08 |
| | 5919 | TAGT-12 | 2.38E−08 |
| | 5920 | TAGT-12 | 1.88E−08 |
| | 5922 | TAGT-12 | 1.95E−08 |
| | 5923 | TAGT-12 | 1.60E−08 |
| | 5927 | TAGT-12 | 4.35E−08 |
| | 5929 | TAGT-12 | 3.20E−08 |
| | 5961 | TAGT-12 | 2.41E−08 |
| | 5962 | TAGT-12 | 8.06E−08 |
| | 5963 | TAGT-12 | 2.07E−08 |
| | 5964 | TAGT-12 | 1.40E−08 |

TABLE 4-continued

Affinity data for confirmed hits

| HVR-H1 and H2 Usage | Hit ID | Target ID | Kd (M) |
|---|---|---|---|
| | 5974 | TAGT-12 | 5.02E−08 |
| | 5976 | TAGT-12 | 2.88E−08 |
| | 5977 | TAGT-12 | 2.70E−08 |
| | 5978 | TAGT-12 | 3.25E−08 |
| | 5996 | TAGT-12 | 2.21E−08 |
| | 5999 | TAGT-12 | 6.29E−08 |
| | 6000 | TAGT-12 | 7.86E−08 |
| | 6004 | TAGT-12 | 5.50E−08 |
| | 6543 | TAGT-3 | 6.78E−08 |
| | 7077 | TAGT-6 | 1.88E−08 |
| | 7078 | TAGT-6 | 2.52E−08 |
| | 7079 | TAGT-6 | 2.99E−08 |
| | 7080 | TAGT-6 | 2.44E−08 |
| | 7081 | TAGT-6 | 4.31E−08 |
| | 7087 | TAGT-6 | 6.96E−08 |
| | 7088 | TAGT-6 | 4.36E−08 |
| | 7090 | TAGT-6 | 5.55E−08 |
| | 7100 | TAGT-6 | 3.50E−08 |
| | 7105 | TAGT-6 | 3.33E−08 |
| | 7107 | TAGT-6 | 1.22E−07 |
| | 7109 | TAGT-6 | 3.20E−08 |
| | 7120 | TAGT-6 | 3.45E−08 |
| | 7128 | TAGT-6 | 3.97E−08 |
| | 7131 | TAGT-6 | 3.04E−08 |
| | 7133 | TAGT-6 | 4.03E−08 |
| | 7135 | TAGT-6 | 3.17E−08 |
| | 7190 | TAGT-6 | 1.03E−08 |
| | 7201 | TAGT-6 | 3.26E−08 |
| | 7209 | TAGT-12 | 9.36E−09 |
| | 7210 | TAGT-12 | 9.85E−09 |
| | 7211 | TAGT-12 | 1.26E−08 |
| | 7216 | TAGT-12 | 1.88E−08 |
| | 7218 | TAGT-12 | 1.49E−08 |
| | 7219 | TAGT-12 | 1.44E−08 |
| | 7220 | TAGT-12 | 9.12E−09 |
| | 7225 | TAGT-12 | 9.53E−09 |
| | 7226 | TAGT-12 | 7.57E−09 |
| | 7235 | TAGT-12 | 2.18E−08 |
| | 7237 | TAGT-12 | 2.13E−08 |
| | 7240 | TAGT-12 | 1.17E−08 |
| | 7241 | TAGT-12 | 6.43E−09 |
| | 7242 | TAGT-12 | 1.71E−08 |
| | 7245 | TAGT-12 | 1.38E−08 |
| | 7246 | TAGT-12 | 6.22E−09 |
| | 7247 | TAGT-12 | 8.93E−09 |
| | 7251 | TAGT-12 | 2.69E−08 |
| | 7252 | TAGT-12 | 9.56E−09 |
| | 7253 | TAGT-12 | 1.62E−08 |
| | 7255 | TAGT-12 | 1.20E−08 |
| | 7256 | TAGT-12 | 7.08E−09 |
| | 7257 | TAGT-12 | 1.11E−08 |
| | 7420 | TAGT-9 | 1.38E−08 |
| | 7425 | TAGT-9 | 1.77E−08 |
| HVR-H1_2 and HVR-H2_4 | 3761 | TAGT-6 | 9.65E−08 |
| | 3763 | TAGT-6 | 9.30E−09 |
| | 4029 | TAGT-8 | 1.89E−09 |
| | 4034 | TAGT-8 | 4.27E−09 |
| | 4045 | TAGT-8 | 1.10E−09 |
| | 4073 | TAGT-6 | <1.0E−12 |
| | 4075 | TAGT-6 | <1.0E−12 |
| | 4076 | TAGT-6 | 7.44E−09 |
| | 4077 | TAGT-6 | <1.0E−12 |
| | 4123 | TAGT-6 | 5.98E−09 |
| | 4124 | TAGT-6 | 4.43E−09 |
| | 4125 | TAGT-6 | <1.0E−12 |
| | 4126 | TAGT-6 | 7.27E−09 |
| | 4127 | TAGT-6 | <1.0E−12 |
| | 4129 | TAGT-6 | <1.0E−12 |
| | 4133 | TAGT-6 | 3.90E−10 |
| | 4135 | TAGT-6 | <1.0E−12 |
| | 4137 | TAGT-6 | <1.0E−12 |
| | 4140 | TAGT-6 | <1.0E−12 |
| | 4141 | TAGT-6 | <1.0E−12 |
| | 4201 | TAGT-6 | 1.41E−08 |
| | 4217 | TAGT-6 | 9.67E−08 |

TABLE 4-continued

Affinity data for confirmed hits

| HVR-H1 and H2 Usage | Hit ID | Target ID | Kd (M) |
|---|---|---|---|
| | 4218 | TAGT-6 | 2.85E−08 |
| | 4222 | TAGT-6 | 5.55E−08 |
| | 4816 | TAGT-12 | 5.32E−09 |
| | 4842 | TAGT-12 | 4.01E−10 |
| | 4895 | TAGT-7 | 6.20E−09 |
| | 4903 | TAGT-12 | 1.91E−09 |
| | 5212 | TAGT-1 | 9.19E−09 |
| | 5218 | TAGT-1 | 6.04E−09 |
| | 5225 | TAGT-1 | 3.10E−10 |
| | 5235 | TAGT-1 | 1.41E−08 |
| | 5236 | TAGT-1 | 1.49E−08 |
| | 5272 | TAGT-1 | 2.49E−08 |
| | 5275 | TAGT-1 | 9.65E−09 |
| | 5282 | TAGT-1 | 1.07E−08 |
| | 5298 | TAGT-6 | 3.41E−07 |
| | 5301 | TAGT-6 | 2.61E−07 |
| | 5316 | TAGT-6 | 1.14E−08 |
| | 5317 | TAGT-6 | 3.34E−07 |
| | 5320 | TAGT-6 | 6.13E−07 |
| | 5321 | TAGT-6 | 7.16E−07 |
| | 5328 | TAGT-6 | 3.42E−07 |
| | 5329 | TAGT-6 | 2.84E−06 |
| | 5336 | TAGT-6 | 6.04E−07 |
| | 5341 | TAGT-6 | 2.93E−08 |
| | 5349 | TAGT-6 | 6.20E−09 |
| | 5351 | TAGT-6 | 7.29E−09 |
| | 5357 | TAGT-6 | 7.14E−09 |
| | 5360 | TAGT-6 | 2.41E−08 |
| | 5363 | TAGT-6 | 9.87E−09 |
| | 5369 | TAGT-6 | 2.05E−08 |
| | 5399 | TAGT-9 | 3.62E−08 |
| | 5403 | TAGT-6 | 8.26E−09 |
| | 5408 | TAGT-6 | 2.36E−08 |
| | 5409 | TAGT-6 | 1.70E−08 |
| | 5411 | TAGT-6 | 1.25E−08 |
| | 5416 | TAGT-6 | 1.09E−08 |
| | 5420 | TAGT-6 | 1.41E−08 |
| | 5431 | TAGT-9 | 1.19E−08 |
| | 5437 | TAGT-9 | 1.92E−08 |
| | 5694 | TAGT-11 | 9.45E−09 |
| | 5716 | TAGT-11 | 8.14E−09 |
| | 5732 | TAGT-11 | 5.24E−09 |
| | 5906 | TAGT-12 | 1.50E−08 |
| | 5926 | TAGT-12 | 3.23E−08 |
| | 5933 | TAGT-12 | 3.13E−08 |
| | 5983 | TAGT-12 | 2.09E−08 |
| | 5992 | TAGT-12 | 1.70E−08 |
| | 5993 | TAGT-12 | 1.13E−08 |
| | 5995 | TAGT-12 | 1.42E−08 |
| | 6473 | TAGT-4 | 2.30E−08 |
| | 6555 | TAGT-3 | 4.18E−08 |
| | 7097 | TAGT-6 | 2.43E−08 |
| | 7183 | TAGT-6 | 1.48E−08 |
| | 7262 | TAGT-5 | 2.63E−09 |
| | 7264 | TAGT-5 | 3.17E−09 |
| | 7312 | TAGT-5 | 3.11E−09 |
| | 7315 | TAGT-5 | 5.15E−09 |
| | 7426 | TAGT-9 | 1.12E−08 |
| | 7427 | TAGT-9 | 5.58E−09 |
| HVR-H1_1 and HVR-H2_4 | 3760 | TAGT-6 | 1.26E−08 |
| | 4048 | TAGT-10 | 3.24E−09 |
| | 4049 | TAGT-10 | 9.37E−09 |
| | 4051 | TAGT-10 | 1.80E−08 |
| | 4056 | TAGT-10 | 1.09E−08 |
| | 4058 | TAGT-10 | 1.13E−08 |
| | 4062 | TAGT-10 | 2.11E−08 |
| | 4063 | TAGT-10 | 1.90E−08 |
| | 4067 | TAGT-10 | 1.97E−08 |
| | 4080 | TAGT-6 | <1.0E−12 |
| | 4130 | TAGT-6 | 1.00E−09 |
| | 4138 | TAGT-6 | 1.60E−08 |
| | 4139 | TAGT-6 | 1.65E−09 |
| | 4723 | TAGT-10 | 9.11E−10 |
| | 4733 | TAGT-10 | 3.05E−10 |
| | 4734 | TAGT-10 | 5.72E−10 |
| | 4767 | TAGT-10 | 2.77E−10 |
| | 4771 | TAGT-10 | 7.23E−10 |
| | 4797 | TAGT-10 | 5.63E−10 |
| | 4807 | TAGT-10 | 1.17E−09 |
| | 4829 | TAGT-12 | 3.36E−09 |
| | 5194 | TAGT-1 | 1.29E−08 |
| | 5200 | TAGT-1 | 1.53E−08 |
| | 5210 | TAGT-1 | 3.41E−09 |
| | 5297 | TAGT-6 | 1.77E−06 |
| | 5300 | TAGT-6 | 1.53E−08 |
| | 5315 | TAGT-6 | 2.10E−06 |
| | 5353 | TAGT-6 | 1.61E−08 |
| | 5354 | TAGT-6 | 4.96E−09 |
| | 5438 | TAGT-9 | 9.30E−09 |
| | 5510 | TAGT-2 | 2.62E−09 |
| | 5513 | TAGT-2 | 1.07E−09 |
| | 5526 | TAGT-2 | 1.54E−09 |
| | 5528 | TAGT-2 | 4.55E−09 |
| | 5532 | TAGT-2 | 3.65E−09 |
| | 5553 | TAGT-2 | 6.83E−09 |
| | 5554 | TAGT-2 | 2.88E−09 |
| | 5557 | TAGT-2 | 3.24E−09 |
| | 5558 | TAGT-2 | 2.43E−09 |
| | 5561 | TAGT-2 | 1.64E−08 |
| | 5565 | TAGT-2 | 3.02E−09 |
| | 5568 | TAGT-2 | 1.14E−09 |
| | 5600 | TAGT-2 | 5.33E−09 |
| | 5612 | TAGT-2 | 7.85E−09 |
| | 5614 | TAGT-2 | 5.29E−09 |
| | 5622 | TAGT-2 | 3.06E−09 |
| | 5642 | TAGT-2 | 3.84E−09 |
| | 5710 | TAGT-11 | 1.01E−08 |
| | 5739 | TAGT-11 | 1.29E−08 |
| | 5745 | TAGT-11 | 1.06E−08 |
| | 5746 | TAGT-11 | 5.00E−09 |
| | 5754 | TAGT-11 | 9.52E−09 |
| | 6221 | TAGT-10 | 6.92E−10 |
| | 6471 | TAGT-4 | 3.05E−08 |
| | 6536 | TAGT-4 | 2.03E−09 |
| | 6537 | TAGT-4 | 1.85E−09 |
| | 6540 | TAGT-4 | 8.08E−09 |
| | 7204 | TAGT-5 | 2.33E−09 |
| | 7212 | TAGT-12 | 1.70E−08 |
| | 7260 | TAGT-5 | 2.30E−09 |
| | 7271 | TAGT-5 | 3.13E−08 |
| | 7276 | TAGT-5 | 1.02E−08 |
| | 7311 | TAGT-5 | 9.20E−09 |
| | 7317 | TAGT-5 | 2.02E−08 |
| | 7323 | TAGT-5 | 3.23E−09 |
| | 7365 | TAGT-5 | 1.82E−09 |
| | 7366 | TAGT-5 | 3.76E−09 |
| | 7369 | TAGT-5 | 2.46E−09 |
| | 7371 | TAGT-5 | 2.31E−08 |
| | 7373 | TAGT-5 | 5.13E−09 |
| | 7374 | TAGT-5 | 1.97E−08 |
| | 7378 | TAGT-5 | 5.66E−09 |
| | 7411 | TAGT-4 | 3.82E−08 |
| | 7415 | TAGT-4 | 9.33E−08 |
| | 7418 | TAGT-9 | 3.41E−08 |
| | 7419 | TAGT-9 | 1.72E−08 |
| | 7429 | TAGT-9 | 2.12E−08 |
| | 7431 | TAGT-9 | 3.53E−08 |
| HVR-H1_2 and HVR-H2_6 | 4027 | TAGT-8 | 1.55E−09 |
| | 4027 | TAGT-8M | 3.81E−09 |
| | 4032 | TAGT-8 | 5.11E−09 |
| | 4032 | TAGT-8M | 4.84E−09 |
| | 4038 | TAGT-8 | 2.98E−09 |
| | 4204 | TAGT-10 | 6.83E−09 |
| | 4204 | TAGT-10M | 6.89E−09 |
| | 4813 | TAGT-12 | 2.45E−10 |
| | 4828 | TAGT-12 | 1.10E−09 |
| | 4849 | TAGT-12 | 8.40E−10 |
| | 4850 | TAGT-12 | 1.23E−09 |
| | 4874 | TAGT-12 | 4.19E−09 |
| | 4925 | TAGT-7 | 1.32E−08 |

TABLE 4-continued

Affinity data for confirmed hits

| HVR-H1 and H2 Usage | Hit ID | Target ID | Kd (M) |
|---|---|---|---|
| | 4928 | TAGT-7 | 3.26E−08 |
| | 5012 | TAGT-8 | 1.76E−09 |
| | 5012 | TAGT-8M | 2.03E−09 |
| | 5014 | TAGT-8 | 2.43E−09 |
| | 5014 | TAGT-8M | 3.87E−09 |
| | 5016 | TAGT-8 | 3.56E−09 |
| | 5016 | TAGT-8M | 2.84E−09 |
| | 5020 | TAGT-8 | 8.78E−10 |
| | 5020 | TAGT-8M | 7.00E−09 |
| | 5022 | TAGT-8 | 3.68E−09 |
| | 5022 | TAGT-8M | 3.03E−09 |
| | 5023 | TAGT-8 | 9.46E−10 |
| | 5023 | TAGT-8M | 5.77E−09 |
| | 5024 | TAGT-8 | 4.52E−09 |
| | 5024 | TAGT-8M | 3.48E−09 |
| | 5030 | TAGT-8 | 7.03E−10 |
| | 5030 | TAGT-8M | 4.27E−09 |
| | 5037 | TAGT-8 | 1.06E−09 |
| | 5037 | TAGT-8M | 4.36E−09 |
| | 5039 | TAGT-8 | 4.30E−10 |
| | 5039 | TAGT-8M | 2.69E−09 |
| | 5040 | TAGT-8 | 4.37E−10 |
| | 5040 | TAGT-8M | 3.13E−09 |
| | 5041 | TAGT-8 | 1.68E−09 |
| | 5041 | TAGT-8M | 1.67E−09 |
| | 5045 | TAGT-8 | 1.00E−09 |
| | 5045 | TAGT-8M | 3.91E−09 |
| | 5048 | TAGT-8 | 5.10E−10 |
| | 5048 | TAGT-8M | 2.52E−09 |
| | 5066 | TAGT-8 | 5.23E−09 |
| | 5066 | TAGT-8M | 9.99E−09 |
| | 5070 | TAGT-8 | 1.34E−09 |
| | 5070 | TAGT-8M | 6.63E−09 |
| | 5074 | TAGT-8 | 4.31E−09 |
| | 5074 | TAGT-8M | 2.98E−09 |
| | 5082 | TAGT-8 | 4.79E−09 |
| | 5082 | TAGT-8M | 3.23E−09 |
| | 5113 | TAGT-12 | 6.80E−09 |
| | 5114 | TAGT-12 | 3.42E−08 |
| | 5116 | TAGT-12 | 1.46E−08 |
| | 5119 | TAGT-12 | 7.54E−09 |
| | 5121 | TAGT-12 | 9.29E−09 |
| | 5123 | TAGT-12 | 5.67E−09 |
| | 5125 | TAGT-12 | 2.42E−08 |
| | 5128 | TAGT-12 | 7.12E−09 |
| | 5138 | TAGT-12 | 8.55E−09 |
| | 5273 | TAGT-1 | 1.34E−08 |
| | 5423 | TAGT-9 | 4.90E−09 |
| | 5720 | TAGT-11 | 1.93E−08 |
| | 5924 | TAGT-12 | 5.95E−08 |
| | 5934 | TAGT-12 | 1.66E−08 |
| | 6026 | TAGT-2 | 2.95E−09 |
| | 6526 | TAGT-4 | 1.16E−08 |
| | 7040 | TAGT-8 | 2.72E−08 |
| | 7228 | TAGT-12 | 7.62E−09 |
| | 7244 | TAGT-12 | 1.05E−08 |
| | 7254 | TAGT-12 | 1.07E−08 |
| | 7258 | TAGT-12 | 9.72E−09 |
| | 7358 | TAGT-3 | 5.15E−08 |
| | 7442 | TAGT-9 | 6.83E−09 |
| | 7443 | TAGT-9 | 1.27E−08 |
| HVR-H1_2 and HVR-H2_1 | 4052 | TAGT-10 | 9.73E−09 |
| | 4059 | TAGT-10 | 3.30E−07 |
| | 5094 | TAGT-10 | 4.34E−08 |
| | 5095 | TAGT-10 | 1.27E−08 |
| | 5097 | TAGT-10 | 1.27E−08 |
| | 5099 | TAGT-10 | 4.20E−08 |
| | 5109 | TAGT-10 | 2.59E−08 |
| | 5215 | TAGT-1 | 6.64E−09 |
| | 5271 | TAGT-1 | 1.24E−08 |
| | 5274 | TAGT-1 | 2.52E−08 |
| | 5299 | TAGT-6 | 1.37E−08 |
| | 5432 | TAGT-9 | 4.83E−09 |
| | 5491 | TAGT-11 | 1.43E−08 |
| | 5744 | TAGT-11 | 1.14E−08 |

TABLE 4-continued

Affinity data for confirmed hits

| HVR-H1 and H2 Usage | Hit ID | Target ID | Kd (M) |
|---|---|---|---|
| | 5936 | TAGT-10 | 1.75E−08 |
| | 6475 | TAGT-4 | 7.22E−09 |
| | 7207 | TAGT-5 | 4.99E−10 |
| | 7272 | TAGT-5 | 3.49E−09 |
| | 7313 | TAGT-5 | 5.69E−09 |
| | 7388 | TAGT-5 | 2.72E−09 |
| | 7389 | TAGT-5 | 4.50E−09 |
| | 7395 | TAGT-5 | 1.65E−08 |
| | 7421 | TAGT-9 | 2.47E−08 |
| | 7440 | TAGT-9 | 6.79E−09 |
| | 7513 | TAGT-9 | 8.43E−09 |
| HVR-H1_2 and HVR-H2_2 | 4812 | TAGT-12 | 2.89E−09 |
| | 4815 | TAGT-12 | 5.91E−09 |
| | 4817 | TAGT-12 | 2.06E−09 |
| | 4818 | TAGT-12 | 1.02E−09 |
| | 4836 | TAGT-12 | 2.49E−09 |
| | 4841 | TAGT-12 | 4.50E−10 |
| | 4846 | TAGT-12 | 3.19E−09 |
| | 4852 | TAGT-12 | 2.26E−09 |
| | 4860 | TAGT-12 | 2.44E−09 |
| | 4876 | TAGT-12 | 7.75E−09 |
| | 4880 | TAGT-12 | 2.77E−09 |
| | 4897 | TAGT-12 | 6.83E−10 |
| | 4901 | TAGT-12 | 3.19E−09 |
| | 4904 | TAGT-12 | 5.39E−09 |
| | 5115 | TAGT-12 | 1.16E−08 |
| | 5220 | TAGT-1 | 5.03E−09 |
| | 5404 | TAGT-6 | 3.30E−09 |
| | 5421 | TAGT-9 | 1.05E−08 |
| | 5422 | TAGT-9 | 5.12E−09 |
| | 5584 | TAGT-2 | 1.76E−09 |
| | 5658 | TAGT-11 | 2.61E−10 |
| | 7273 | TAGT-5 | 6.01E−09 |
| | 7316 | TAGT-5 | 2.04E−08 |
| | 7394 | TAGT-5 | 8.75E−09 |
| HVR-H1_2 and HVR-H2_3 | 4037 | TAGT-8 | 5.53E−09 |
| | 4041 | TAGT-8 | 1.54E−09 |
| | 4180 | TAGT-10 | 7.39E−08 |
| | 4809 | TAGT-12 | 3.69E−10 |
| | 4820 | TAGT-12 | 3.96E−09 |
| | 4825 | TAGT-12 | 6.05E−09 |
| | 4837 | TAGT-12 | 5.36E−09 |
| | 4838 | TAGT-12 | 2.52E−09 |
| | 4839 | TAGT-12 | 6.16E−09 |
| | 4844 | TAGT-12 | 6.95E−10 |
| | 4847 | TAGT-12 | 3.64E−10 |
| | 4879 | TAGT-12 | 3.13E−09 |
| | 4911 | TAGT-7 | 1.50E−08 |
| | 5228 | TAGT-1 | 3.06E−08 |
| | 5292 | TAGT-1 | 1.57E−08 |
| | 5398 | TAGT-9 | 1.97E−08 |
| | 7248 | TAGT-12 | 1.28E−08 |
| | 7249 | TAGT-12 | 5.36E−09 |
| | 7380 | TAGT-5 | 1.24E−08 |
| | 7386 | TAGT-5 | 1.32E−08 |
| | 7444 | TAGT-9 | 5.53E−09 |
| | 7508 | TAGT-9 | 1.36E−08 |
| HVR-H1_1 and HVR-H2_1 | 4097 | TAGT-8 | 6.24E−09 |
| | 5202 | TAGT-1 | 1.50E−08 |
| | 5203 | TAGT-1 | 1.31E−08 |
| | 5207 | TAGT-1 | 7.44E−09 |
| | 5221 | TAGT-1 | 1.18E−08 |
| | 5226 | TAGT-1 | 8.36E−09 |
| | 5230 | TAGT-1 | 9.21E−09 |
| | 5238 | TAGT-1 | 5.04E−08 |
| | 5280 | TAGT-1 | 8.43E−09 |
| | 5281 | TAGT-1 | 4.70E−09 |
| | 5285 | TAGT-1 | 1.42E−08 |
| | 5288 | TAGT-1 | 1.08E−08 |
| | 5425 | TAGT-9 | 2.15E−08 |
| | 7032 | TAGT-8 | 2.08E−08 |
| | 7268 | TAGT-5 | 3.76E−09 |
| | 7277 | TAGT-5 | 2.56E−09 |
| | 7278 | TAGT-5 | 1.53E−08 |
| | 7390 | TAGT-5 | 1.44E−09 |

TABLE 4-continued

| Affinity data for confirmed hits | | | |
|---|---|---|---|
| HVR-H1 and H2 Usage | Hit ID | Target ID | Kd (M) |
| HVR-H1_2 and HVR-H2_5 | 4102 | TAGT-8 | 2.54E−09 |
| | 4116 | TAGT-10 | <1.0E−12 |
| | 4827 | TAGT-12 | 1.51E−09 |
| | 4834 | TAGT-12 | 9.68E−10 |
| | 4851 | TAGT-12 | 3.84E−10 |
| | 4863 | TAGT-12 | 6.63E−10 |
| | 4875 | TAGT-12 | 1.03E−09 |
| | 5217 | TAGT-1 | 1.08E−08 |
| | 5921 | TAGT-12 | 8.01E−09 |
| | 5930 | TAGT-12 | 5.66E−09 |
| | 5932 | TAGT-12 | 1.12E−08 |
| | 5968 | TAGT-12 | 1.27E−08 |
| | 5980 | TAGT-12 | 1.14E−08 |
| | 5990 | TAGT-12 | 1.15E−08 |
| | 6010 | TAGT-12 | 2.83E−08 |
| | 7310 | TAGT-5 | 1.41E−08 |
| | 7379 | TAGT-5 | 5.43E−09 |
| HVR-H1_1 and HVR-H2_3 | 4161 | TAGT-8 | 2.98E−08 |
| | 4177 | TAGT-8 | 1.48E−08 |
| | 4823 | TAGT-12 | 2.62E−09 |
| | 5192 | TAGT-1 | 2.16E−08 |
| | 5193 | TAGT-1 | 3.69E−08 |
| | 5204 | TAGT-1 | 1.48E−08 |
| | 5234 | TAGT-1 | 1.28E−08 |
| | 5237 | TAGT-1 | 3.28E−09 |
| | 5615 | TAGT-2 | 1.22E−08 |
| | 5733 | TAGT-11 | 7.15E−09 |
| | 5741 | TAGT-11 | 1.91E−08 |
| | 7324 | TAGT-5 | 5.68E−09 |
| | 7367 | TAGT-5 | 2.04E−08 |
| | 7372 | TAGT-5 | 7.27E−10 |
| | 7506 | TAGT-9 | 7.73E−09 |
| HVR-H1_3 and HVR-H2_1 | 5208 | TAGT-1 | 3.36E−09 |
| | 5283 | TAGT-1 | 2.88E−08 |
| | 5303 | TAGT-6 | 5.12E−09 |
| | 5310 | TAGT-6 | 5.72E−09 |
| | 5314 | TAGT-6 | 8.39E−09 |
| | 5318 | TAGT-6 | 1.90E−08 |
| | 5342 | TAGT-6 | 3.89E−08 |
| | 5359 | TAGT-6 | 7.10E−10 |
| | 5365 | TAGT-6 | 2.56E−09 |
| | 5370 | TAGT-6 | 1.91E−09 |
| | 5413 | TAGT-6 | 9.93E−10 |
| | 7275 | TAGT-5 | 6.85E−09 |
| HVR-H1_1 and HVR-H2_2 | 4840 | TAGT-12 | 2.08E−09 |
| | 5195 | TAGT-1 | 2.62E−08 |
| | 5201 | TAGT-1 | 5.33E−09 |
| | 5211 | TAGT-1 | 2.11E−09 |
| | 5216 | TAGT-1 | 3.08E−09 |
| | 5286 | TAGT-1 | 6.34E−09 |
| | 5287 | TAGT-1 | 1.02E−08 |
| | 5290 | TAGT-1 | 6.73E−09 |
| | 5722 | TAGT-11 | 3.08E−08 |
| | 6030 | TAGT-2 | 8.27E−08 |
| | 7370 | TAGT-5 | 1.07E−08 |
| | 7385 | TAGT-5 | 3.26E−09 |
| HVR-H1_3 and HVR-H2_2 | 4036 | TAGT-8 | 3.13E−09 |
| | 4096 | TAGT-8 | 2.70E−09 |
| | 5323 | TAGT-6 | 1.04E−08 |
| | 5387 | TAGT-8 | 1.13E−09 |
| | 5756 | TAGT-11 | 3.00E−08 |
| | 5985 | TAGT-12 | 3.92E−08 |
| | 5986 | TAGT-12 | 4.65E−08 |
| | 7163 | TAGT-6 | 1.26E−08 |
| | 7375 | TAGT-5 | 6.03E−09 |
| | 7391 | TAGT-5 | 1.35E−08 |
| HVR-H1_3 and HVR-H2_3 | 4026 | TAGT-8 | 3.08E−09 |
| | 4858 | TAGT-12 | 5.86E−09 |
| | 6533 | TAGT-3 | 2.62E−08 |
| | 7159 | TAGT-6 | 3.79E−08 |
| | 7166 | TAGT-6 | 1.24E−08 |
| | 7239 | TAGT-12 | 2.40E−08 |
| | 7274 | TAGT-5 | 1.63E−08 |
| | 7433 | TAGT-9 | 1.67E−08 |

TABLE 4-continued

| Affinity data for confirmed hits | | | |
|---|---|---|---|
| HVR-H1 and H2 Usage | Hit ID | Target ID | Kd (M) |
| HVR-H1_3 and HVR-H2_6 | 4857 | TAGT-12 | 4.05E−09 |
| | 5227 | TAGT-1 | 1.04E−08 |
| | 7221 | TAGT-12 | 5.58E−09 |
| | 7229 | TAGT-12 | 8.91E−09 |
| HVR-H1_2 and HVR-H2_7 | 4220 | TAGT-6 | 5.72E−08 |
| | 4861 | TAGT-12 | 5.11E−09 |
| | 5284 | TAGT-1 | 1.84E−08 |
| HVR-H1_1 and HVR-H2_7 | 4079 | TAGT-6 | 3.15E−08 |
| | 7129 | TAGT-6 | 1.90E−08 |
| HVR-H1_3 and HVR-H2_5 | 4072 | TAGT-6 | 6.95E−09 |
| HVR-H1_3 and HVR-H2_7 | 5333 | TAGT-6 | 5.02E−09 |

Hits containing the same HVR-H1 and HVR-H2 sequences were discovered that could bind different target antigens when these HVR-H1 and 2 sequences were paired with different HVR-H3 and VL sequences. For example, Hit IDs 4029, 7097, and 5906 contained the same HVR-H1 and HVR-H2 combination (HVR-H1_2 and HVR-H2_4) but were paired with different HVR-H3 and VL sequences, and bound three different target antigens (TAGT-8, TAGT-6, and TAGT-12, respectively). Hits 7040 and 5924 contained the same HVR-H1 and HVR-H2 combination (HVR-H1_2 and HVR-H2_6) but were paired with different HVR-H3 and VL sequences, and bound two different target antigens (TAGT-8 and TAGT-12, respectively).

Table 5 below shows sequence usage and number of targets bound for the HVR-H1 and HVR-H2s identified during the library analyses. Without wishing to be bound by theory, it is thought that a high number of antigens bound by an antibody comprising a given hypervariable region may be indicative of a high degree of flexibility of that particular hypervariable region, while a high segment usage of a given hypervariable region may be indicative of robust folding of the hypervariable region (and surrounding polypeptide sequence).

TABLE 5

| target binding capability of HVR-H1 and HVR-H2 designed variants | | |
|---|---|---|
| Variant ID | Sequence Usage Percent | Number of Antigens hit out of 14 |
| HVR-H1_1 | 45.0% | 11 |
| HVR-H1_2 | 33.8% | 14 |
| HVR-H1_3 | 19.1% | 8 |
| HVR-H2_1 | 7.9% | 8 |
| HVR-H2_2 | 6.6% | 8 |
| HVR-H2_3 | 6.8% | 11 |
| HVR-H2_4 | 36.4% | 12 |
| HVR-H2_5 | 16.8% | 8 |
| HVR-H2_6 | 21.8% | 13 |
| HVR-H2_7 | 0.9% | 3 |

Table 6 below shows sequence usage and number of antigens bound for the HVR-H1 and HVR-H2 combinations identified during the library analyses.

TABLE 6

HVR-H1 and HVR-H2 designed variants combination usage

| Preference Ranking | HVR-H1 Variant ID | HVR-H2 Variant ID | Sequence Usage Percent | Number of Antigens hit out of 14 |
|---|---|---|---|---|
| Tier 1 | HVR-H1_2 | HVR-H2_6 | 7.6% | 11 |
| Tier 1 | HVR-H1_2 | HVR-H2_4 | 11.6% | 10 |
| Tier 1 | HVR-H1_1 | HVR-H2_4 | 11.2% | 9 |
| Tier 1 | HVR-H1_1 | HVR-H2_6 | 13.5% | 7 |
| Tier 1 | HVR-H1_2 | HVR-H2_1 | 3.6% | 7 |
| Tier 1 | HVR-H1_2 | HVR-H2_2 | 3.4% | 7 |
| Tier 1 | HVR-H1_2 | HVR-H2_3 | 3.4% | 7 |
| Tier 1 | HVR-H1_1 | HVR-H2_3 | 2.2% | 7 |
| Tier 1 | HVR-H1_3 | HVR-H2_3 | 1.1% | 6 |
| Tier 1 | HVR-H1_3 | HVR-H2_4 | 13.1% | 5 |
| Tier 1 | HVR-H1_2 | HVR-H2_5 | 2.4% | 5 |
| Tier 1 | HVR-H1_1 | HVR-H2_2 | 1.7% | 5 |
| Tier 1 | HVR-H1_3 | HVR-H2_2 | 1.4% | 5 |
| Tier 1 | HVR-H1_1 | HVR-H2_5 | 13.4% | 4 |
| Tier 2 | HVR-H1_1 | HVR-H2_1 | 2.6% | 4 |
| Tier 2 | HVR-H1_3 | HVR-H2_3 | 1.7% | 3 |
| Tier 2 | HVR-H1_2 | HVR-H2_7 | 0.4% | 3 |
| Tier 2 | HVR-H1_3 | HVR-H2_6 | 0.6% | 2 |
| Tier 3 | HVR-H1_1 | HVR-H2_7 | 0.3% | 1 |
| Tier 3 | HVR-H1_3 | HVR-H2_5 | 0.1% | 1 |
| Tier 3 | HVR-H1_3 | HVR-H2_7 | 0.1% | 1 |

74 HVR-H1 sequences (SEQ ID NOS: 1-52 and 137-158, Table 1) and 90 HVR-2 sequences (SEQ ID NOS: 53-136 and 159-164, Table 1) were identified that appeared in >1 of the unique antibody hits described above. When combined with various HVR-H3s and variable light chain domains, these HVRs were capable of forming antibodies that bound to multiple antigens. An additional 65 novel HVR-H1 and HVR-H2 sequence combinations were identified that appeared in >1 of the unique antibody hits described. Table 7 below shows HVR-H1 and HVR-H2 usage and number of antigens bound during the library analysis using these new HVR sequences.

TABLE 7

Usage of new HVR-H1 and HVR-H2 sequences

| SEQ ID NO: | Number of hits | Number of Antigens hit out of 14 |
|---|---|---|
| 1 | 12 | 8 |
| 5 | 10 | 7 |
| 16 | 9 | 6 |
| 8 | 37 | 5 |
| 22 | 12 | 5 |
| 21 | 7 | 5 |
| 31 | 14 | 4 |
| 12 | 12 | 4 |
| 4 | 11 | 4 |
| 7 | 11 | 4 |
| 26 | 7 | 4 |
| 19 | 6 | 4 |
| 23 | 6 | 4 |
| 47 | 6 | 4 |
| 18 | 5 | 4 |
| 24 | 5 | 4 |
| 28 | 5 | 4 |
| 9 | 5 | 4 |
| 38 | 4 | 4 |
| 49 | 4 | 4 |
| 25 | 16 | 3 |
| 50 | 13 | 3 |
| 51 | 8 | 3 |

TABLE 7-continued

Usage of new HVR-H1 and HVR-H2 sequences

| SEQ ID NO: | Number of hits | Number of Antigens hit out of 14 |
|---|---|---|
| 27 | 5 | 3 |
| 11 | 5 | 3 |
| 40 | 4 | 3 |
| 43 | 4 | 3 |
| 20 | 3 | 3 |
| 33 | 3 | 3 |
| 42 | 3 | 3 |
| 45 | 3 | 3 |
| 13 | 27 | 2 |
| 34 | 7 | 2 |
| 35 | 5 | 2 |
| 41 | 5 | 2 |
| 3 | 4 | 2 |
| 15 | 3 | 2 |
| 30 | 3 | 2 |
| 44 | 3 | 2 |
| 46 | 3 | 2 |
| 32 | 2 | 2 |
| 37 | 2 | 2 |
| 39 | 2 | 2 |
| 2 | 2 | 2 |
| 14 | 2 | 2 |
| 48 | 6 | 1 |
| 29 | 3 | 1 |
| 6 | 3 | 1 |
| 17 | 2 | 1 |
| 36 | 2 | 1 |
| 52 | 2 | 1 |
| 10 | 2 | 1 |
| 63 | 40 | 7 |
| 93 | 12 | 5 |
| 66 | 8 | 5 |
| 122 | 7 | 5 |
| 65 | 6 | 5 |
| 105 | 5 | 5 |
| 124 | 14 | 4 |
| 123 | 7 | 4 |
| 70 | 4 | 4 |
| 110 | 46 | 3 |
| 129 | 26 | 3 |
| 121 | 15 | 3 |
| 89 | 9 | 3 |
| 134 | 9 | 3 |
| 128 | 7 | 3 |
| 60 | 4 | 3 |
| 67 | 4 | 3 |
| 95 | 3 | 3 |
| 117 | 14 | 2 |
| 82 | 11 | 2 |
| 130 | 11 | 2 |
| 132 | 10 | 2 |
| 53 | 9 | 2 |
| 131 | 7 | 2 |
| 109 | 6 | 2 |
| 72 | 5 | 2 |
| 118 | 5 | 2 |
| 100 | 4 | 2 |
| 103 | 4 | 2 |
| 106 | 4 | 2 |
| 61 | 3 | 2 |
| 71 | 3 | 2 |
| 75 | 3 | 2 |
| 77 | 3 | 2 |
| 79 | 3 | 2 |
| 108 | 3 | 2 |
| 112 | 3 | 2 |
| 113 | 3 | 2 |
| 55 | 2 | 2 |
| 56 | 2 | 2 |
| 59 | 2 | 2 |
| 62 | 2 | 2 |
| 64 | 2 | 2 |
| 68 | 2 | 2 |
| 69 | 2 | 2 |
| 73 | 2 | 2 |

TABLE 7-continued

| Usage of new HVR-H1 and HVR-H2 sequences | | |
|---|---|---|
| SEQ ID NO: | Number of hits | Number of Antigens hit out of 14 |
| 74 | 2 | 2 |
| 76 | 2 | 2 |
| 78 | 2 | 2 |
| 81 | 2 | 2 |
| 83 | 2 | 2 |
| 86 | 2 | 2 |
| 90 | 2 | 2 |
| 91 | 2 | 2 |
| 99 | 2 | 2 |
| 107 | 2 | 2 |
| 135 | 2 | 2 |
| 136 | 2 | 2 |
| 126 | 29 | 1 |
| 116 | 10 | 1 |
| 87 | 5 | 1 |
| 84 | 4 | 1 |
| 85 | 4 | 1 |
| 92 | 4 | 1 |
| 104 | 4 | 1 |
| 57 | 3 | 1 |
| 80 | 3 | 1 |
| 94 | 3 | 1 |
| 96 | 3 | 1 |
| 101 | 3 | 1 |
| 111 | 3 | 1 |
| 114 | 3 | 1 |
| 120 | 3 | 1 |
| 133 | 3 | 1 |
| 54 | 2 | 1 |
| 58 | 2 | 1 |
| 88 | 2 | 1 |
| 97 | 2 | 1 |
| 98 | 2 | 1 |
| 102 | 2 | 1 |
| 115 | 2 | 1 |
| 119 | 2 | 1 |
| 125 | 2 | 1 |
| 127 | 2 | 1 |

Table 8 below shows usage and number of antigens bound for the combination of new HVR-H1 and HVR-H2 sequences.

TABLE 8

| new HVR-H1 and HVR-H2 combination usage | | | | |
|---|---|---|---|---|
| Preference Ranking | HVR-H1 SEQ ID NO: | HVR-H2 SEQ ID NO: | Number of hits | Number of Antigens hit out of 14 |
| Tier 1 | 157 | 63 | 4 | 3 |
| Tier 1 | 1 | 122 | 4 | 3 |
| Tier 1 | 138 | 63 | 3 | 3 |
| Tier 1 | 154 | 63 | 5 | 2 |
| Tier 1 | 158 | 161 | 5 | 2 |
| Tier 1 | 158 | 63 | 3 | 2 |
| Tier 1 | 145 | 128 | 3 | 2 |
| Tier 1 | 22 | 61 | 2 | 2 |
| Tier 1 | 31 | 63 | 2 | 2 |
| Tier 1 | 153 | 63 | 2 | 2 |
| Tier 1 | 155 | 67 | 2 | 2 |
| Tier 1 | 156 | 100 | 2 | 2 |
| Tier 1 | 51 | 162 | 2 | 2 |
| Tier 1 | 138 | 123 | 2 | 2 |
| Tier 1 | 139 | 110 | 38 | 1 |
| Tier 1 | 8 | 126 | 29 | 1 |
| Tier 1 | 13 | 129 | 21 | 1 |
| Tier 1 | 31 | 124 | 11 | 1 |
| Tier 1 | 25 | 130 | 10 | 1 |
| Tier 1 | 150 | 132 | 9 | 1 |
| Tier 1 | 158 | 162 | 8 | 1 |
| Tier 1 | 12 | 82 | 8 | 1 |
| Tier 1 | 149 | 117 | 7 | 1 |

TABLE 8-continued

| new HVR-H1 and HVR-H2 combination usage | | | | |
|---|---|---|---|---|
| Preference Ranking | HVR-H1 SEQ ID NO: | HVR-H2 SEQ ID NO: | Number of hits | Number of Antigens hit out of 14 |
| Tier 1 | 7 | 134 | 6 | 1 |
| Tier 2 | 26 | 53 | 4 | 1 |
| Tier 2 | 151 | 53 | 4 | 1 |
| Tier 2 | 34 | 63 | 3 | 1 |
| Tier 2 | 50 | 162 | 3 | 1 |
| Tier 2 | 158 | 104 | 3 | 1 |
| Tier 2 | 5 | 121 | 3 | 1 |
| Tier 2 | 6 | 116 | 3 | 1 |
| Tier 2 | 7 | 121 | 3 | 1 |
| Tier 2 | 17 | 63 | 2 | 1 |
| Tier 2 | 25 | 101 | 2 | 1 |
| Tier 2 | 25 | 114 | 2 | 1 |
| Tier 2 | 29 | 112 | 2 | 1 |
| Tier 2 | 152 | 63 | 2 | 1 |
| Tier 2 | 156 | 89 | 2 | 1 |
| Tier 2 | 157 | 94 | 2 | 1 |
| Tier 2 | 48 | 58 | 2 | 1 |
| Tier 2 | 50 | 89 | 2 | 1 |
| Tier 2 | 50 | 163 | 2 | 1 |
| Tier 2 | 158 | 160 | 2 | 1 |
| Tier 2 | 158 | 87 | 2 | 1 |
| Tier 2 | 158 | 92 | 2 | 1 |
| Tier 2 | 158 | 93 | 2 | 1 |
| Tier 2 | 158 | 97 | 2 | 1 |
| Tier 2 | 158 | 103 | 2 | 1 |
| Tier 2 | 158 | 164 | 2 | 1 |
| Tier 2 | 137 | 54 | 2 | 1 |
| Tier 2 | 3 | 127 | 2 | 1 |
| Tier 2 | 4 | 85 | 2 | 1 |
| Tier 2 | 4 | 110 | 2 | 1 |
| Tier 2 | 139 | 109 | 2 | 1 |
| Tier 2 | 139 | 121 | 2 | 1 |
| Tier 2 | 8 | 120 | 2 | 1 |
| Tier 2 | 140 | 131 | 2 | 1 |
| Tier 2 | 141 | 116 | 2 | 1 |
| Tier 2 | 142 | 159 | 2 | 1 |
| Tier 2 | 143 | 116 | 2 | 1 |
| Tier 2 | 144 | 121 | 2 | 1 |
| Tier 2 | 146 | 110 | 2 | 1 |
| Tier 2 | 147 | 133 | 2 | 1 |
| Tier 2 | 148 | 63 | 2 | 1 |
| Tier 2 | 13 | 118 | 2 | 1 |

Table 9 shows affinity data for unique hits using the indicated new HVR-H1 and HVR-H2 sequences.

TABLE 9

| Affinity data for confirmed hits using new HVR-H1 and HVR-H2 sequences | | | |
|---|---|---|---|
| HVR SEQ ID NO(S): | Hit ID | Antigen | Kd (M) |
| 8 | 4025 | TAGT-8 | 2.89E−09 |
| 8 | 4033 | TAGT-8 | 8.75E−10 |
| 8 | 4614 | TAGT-8 | 3.53E−10 |
| 8 | 4615 | TAGT-8 | 2.28E−10 |
| 8 | 4617 | TAGT-8 | 2.88E−10 |
| 8 | 4622 | TAGT-8 | 2.74E−10 |
| 8 | 4627 | TAGT-8 | 1.82E−10 |
| 8 | 4631 | TAGT-8 | 1.83E−10 |
| 8 | 4633 | TAGT-8 | 3.22E−10 |
| 8 | 4634 | TAGT-8 | 2.07E−10 |
| 8 | 4638 | TAGT-8 | 3.14E−10 |
| 8 | 4642 | TAGT-8 | 1.89E−10 |
| 8 | 4644 | TAGT-8 | 2.48E−10 |
| 8 | 4645 | TAGT-8 | 2.96E−10 |
| 8 | 4650 | TAGT-8 | 3.57E−10 |
| 8 | 4651 | TAGT-8 | 3.01E−10 |
| 8 | 4652 | TAGT-8 | 2.94E−10 |
| 8 | 4654 | TAGT-8 | 2.32E−10 |
| 8 | 4658 | TAGT-8 | 1.42E−10 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 8 | 4665 | TAGT-8 | 3.69E−10 |
| 8 | 4673 | TAGT-8 | 3.23E−10 |
| 8 | 4674 | TAGT-8 | 5.02E−10 |
| 8 | 4681 | TAGT-8 | 5.43E−10 |
| 8 | 4689 | TAGT-8 | 1.63E−10 |
| 8 | 4690 | TAGT-8 | 4.67E−10 |
| 8 | 5532 | TAGT-2 | 3.65E−09 |
| 8 | 5558 | TAGT-2 | 2.43E−09 |
| 8 | 5970 | TAGT-12 | 1.35E−08 |
| 8 | 6190 | TAGT-10 | 2.55E−09 |
| 8 | 6203 | TAGT-10 | 1.05E−08 |
| 8 | 7032 | TAGT-8 | 2.08E−08 |
| 8 | 7043 | TAGT-8 | 1.34E−08 |
| 8 | 7367 | TAGT-5 | 2.04E−08 |
| 8 | BH3002 | TAGT-8 | 2.51E−10 |
| 8 | BH3004 | TAGT-8 | 3.00E−10 |
| 8 | BH3005 | TAGT-8 | 3.46E−10 |
| 8 | BH3006 | TAGT-8 | 1.94E−10 |
| 13 | 4043 | TAGT-8 | 2.69E−09 |
| 13 | 4084 | TAGT-8 | 2.94E−09 |
| 13 | 4618 | TAGT-8 | 1.08E−09 |
| 13 | 4620 | TAGT-8 | 3.48E−10 |
| 13 | 4623 | TAGT-8 | 4.85E−10 |
| 13 | 4624 | TAGT-8 | 1.00E−12 |
| 13 | 4625 | TAGT-8 | 4.02E−10 |
| 13 | 4630 | TAGT-8 | 2.67E−10 |
| 13 | 4653 | TAGT-8 | 3.27E−10 |
| 13 | 4659 | TAGT-8 | 2.12E−10 |
| 13 | 4662 | TAGT-8 | 8.98E−10 |
| 13 | 4666 | TAGT-8 | 1.17E−09 |
| 13 | 4668 | TAGT-8 | 5.79E−10 |
| 13 | 4670 | TAGT-8 | 8.21E−10 |
| 13 | 4675 | TAGT-8 | 1.00E−12 |
| 13 | 4676 | TAGT-8 | 1.62E−10 |
| 13 | 4678 | TAGT-8 | 5.98E−10 |
| 13 | 4683 | TAGT-8 | 8.97E−10 |
| 13 | 4684 | TAGT-8 | 6.69E−10 |
| 13 | 4685 | TAGT-8 | 4.78E−10 |
| 13 | 4686 | TAGT-8 | 4.78E−10 |
| 13 | 4687 | TAGT-8 | 4.08E−10 |
| 13 | 5739 | TAGT-11 | 1.29E−08 |
| 13 | 7025 | TAGT-8 | 4.87E−08 |
| 13 | 7035 | TAGT-8 | 3.04E−09 |
| 13 | 7037 | TAGT-8 | 2.10E−08 |
| 13 | 7038 | TAGT-8 | 2.33E−08 |
| 25 | 4201 | TAGT-6 | 1.41E−08 |
| 25 | 4217 | TAGT-6 | 9.67E−08 |
| 25 | 4218 | TAGT-6 | 2.85E−08 |
| 25 | 4813 | TAGT-12 | 2.45E−10 |
| 25 | 5113 | TAGT-12 | 6.80E−09 |
| 25 | 5114 | TAGT-12 | 3.42E−08 |
| 25 | 5116 | TAGT-12 | 1.46E−08 |
| 25 | 5119 | TAGT-12 | 7.54E−09 |
| 25 | 5121 | TAGT-12 | 9.29E−09 |
| 25 | 5123 | TAGT-12 | 5.67E−09 |
| 25 | 5125 | TAGT-12 | 2.42E−08 |
| 25 | 5128 | TAGT-12 | 7.12E−09 |
| 25 | 5138 | TAGT-12 | 8.55E−09 |
| 25 | 5968 | TAGT-12 | 1.27E−08 |
| 25 | 5990 | TAGT-12 | 1.15E−08 |
| 25 | 7442 | TAGT-9 | 6.83E−09 |
| 31 | 4027 | TAGT-8 | 1.55E−09 |
| 31 | 4027 | TAGT-8M | 3.81E−09 |
| 31 | 5020 | TAGT-8 | 8.78E−10 |
| 31 | 5020 | TAGT-8M | 7.00E−09 |
| 31 | 5023 | TAGT-8 | 9.46E−10 |
| 31 | 5023 | TAGT-8M | 5.77E−09 |
| 31 | 5030 | TAGT-8 | 7.03E−10 |
| 31 | 5030 | TAGT-8M | 4.27E−09 |
| 31 | 5037 | TAGT-8 | 1.06E−09 |
| 31 | 5037 | TAGT-8M | 4.36E−09 |
| 31 | 5039 | TAGT-8 | 4.30E−10 |
| 31 | 5039 | TAGT-8M | 2.69E−09 |
| 31 | 5040 | TAGT-8 | 4.37E−10 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 31 | 5040 | TAGT-8M | 3.13E−09 |
| 31 | 5045 | TAGT-8 | 1.00E−09 |
| 31 | 5045 | TAGT-8M | 3.91E−09 |
| 31 | 5048 | TAGT-8 | 5.10E−10 |
| 31 | 5048 | TAGT-8M | 2.52E−09 |
| 31 | 5066 | TAGT-8 | 5.23E−09 |
| 31 | 5066 | TAGT-8M | 9.99E−09 |
| 31 | 5070 | TAGT-8 | 1.34E−09 |
| 31 | 5070 | TAGT-8M | 6.63E−09 |
| 31 | 5658 | TAGT-11 | 2.61E−10 |
| 31 | 5926 | TAGT-12 | 3.23E−08 |
| 31 | 7394 | TAGT-5 | 8.75E−09 |
| 50 | 5929 | TAGT-12 | 3.20E−08 |
| 50 | 5978 | TAGT-12 | 3.25E−08 |
| 50 | 5999 | TAGT-12 | 6.29E−08 |
| 50 | 7077 | TAGT-6 | 1.88E−08 |
| 50 | 7090 | TAGT-6 | 5.55E−08 |
| 50 | 7128 | TAGT-6 | 3.97E−08 |
| 50 | 7209 | TAGT-12 | 9.36E−09 |
| 50 | 7219 | TAGT-12 | 1.44E−08 |
| 50 | 7235 | TAGT-12 | 2.18E−08 |
| 50 | 7240 | TAGT-12 | 1.17E−08 |
| 50 | 7256 | TAGT-12 | 7.08E−09 |
| 50 | 7257 | TAGT-12 | 1.11E−08 |
| 50 | 7375 | TAGT-5 | 6.03E−09 |
| 22 | 4116 | TAGT-10 | <1.0E−12 |
| 22 | 4129 | TAGT-6 | <1.0E−12 |
| 22 | 4140 | TAGT-6 | <1.0E−12 |
| 22 | 4842 | TAGT-12 | 4.01E−10 |
| 22 | 5212 | TAGT-1 | 9.19E−09 |
| 22 | 5218 | TAGT-1 | 6.04E−09 |
| 22 | 5271 | TAGT-1 | 1.24E−08 |
| 22 | 5284 | TAGT-1 | 1.84E−08 |
| 22 | 5301 | TAGT-6 | 2.61E−07 |
| 22 | 5336 | TAGT-6 | 6.04E−07 |
| 22 | 5906 | TAGT-12 | 1.50E−08 |
| 22 | 7207 | TAGT-5 | 4.99E−10 |
| 1 | 3757 | TAGT-6 | 1.84E−08 |
| 1 | 3869 | TAGT-11 | 2.35E−08 |
| 1 | 5103 | TAGT-10 | 2.67E−09 |
| 1 | 5163 | TAGT-11 | 1.71E−08 |
| 1 | 5201 | TAGT-1 | 5.33E−09 |
| 1 | 5287 | TAGT-1 | 1.02E−08 |
| 1 | 5315 | TAGT-6 | 2.10E−06 |
| 1 | 5612 | TAGT-2 | 7.85E−09 |
| 1 | 7129 | TAGT-6 | 1.90E−08 |
| 1 | 7317 | TAGT-5 | 2.02E−08 |
| 1 | 7411 | TAGT-4 | 3.82E−08 |
| 1 | 7419 | TAGT-9 | 1.72E−08 |
| 12 | 4048 | TAGT-10 | 3.24E−09 |
| 12 | 4163 | TAGT-8 | 1.37E−08 |
| 12 | 4723 | TAGT-10 | 9.11E−10 |
| 12 | 4733 | TAGT-10 | 3.05E−10 |
| 12 | 4734 | TAGT-10 | 5.72E−10 |
| 12 | 4767 | TAGT-10 | 2.77E−10 |
| 12 | 4771 | TAGT-10 | 7.23E−10 |
| 12 | 4797 | TAGT-10 | 5.63E−10 |
| 12 | 4807 | TAGT-10 | 1.17E−09 |
| 12 | 5200 | TAGT-1 | 1.53E−08 |
| 12 | 7030 | TAGT-8 | 3.47E−08 |
| 12 | 7324 | TAGT-5 | 5.68E−09 |
| 4 | 4054 | TAGT-10 | 1.58E−08 |
| 4 | 5203 | TAGT-1 | 1.31E−08 |
| 4 | 5354 | TAGT-6 | 4.96E−09 |
| 4 | 6179 | TAGT-10 | 1.99E−09 |
| 4 | 6183 | TAGT-10 | 2.70E−09 |
| 4 | 6206 | TAGT-10 | 3.44E−09 |
| 4 | 6217 | TAGT-10 | 4.99E−09 |
| 4 | 7260 | TAGT-5 | 2.30E−09 |
| 4 | 7278 | TAGT-5 | 1.53E−08 |
| 4 | 7371 | TAGT-5 | 2.31E−08 |
| 4 | 7374 | TAGT-5 | 1.97E−08 |
| 7 | 3898 | TAGT-11 | 1.83E−08 |
| 7 | 4065 | TAGT-10 | 4.31E−08 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 7 | 4182 | TAGT-10 | 4.24E−09 |
| 7 | 4741 | TAGT-10 | 1.66E−09 |
| 7 | 5149 | TAGT-11 | 2.91E−09 |
| 7 | 5159 | TAGT-11 | 4.09E−09 |
| 7 | 5160 | TAGT-11 | 8.07E−09 |
| 7 | 5162 | TAGT-11 | 9.87E−09 |
| 7 | 5165 | TAGT-11 | 4.06E−09 |
| 7 | 5510 | TAGT-2 | 2.62E−09 |
| 7 | 7370 | TAGT-5 | 1.07E−08 |
| 5 | 4060 | TAGT-10 | 1.10E−08 |
| 5 | 4130 | TAGT-6 | 1.00E−09 |
| 5 | 4798 | TAGT-10 | 4.35E−09 |
| 5 | 5204 | TAGT-1 | 1.48E−08 |
| 5 | 5526 | TAGT-2 | 1.54E−09 |
| 5 | 5600 | TAGT-2 | 5.33E−09 |
| 5 | 5733 | TAGT-11 | 7.15E−09 |
| 5 | 6219 | TAGT-10 | 3.15E−09 |
| 5 | 6531 | TAGT-3 | 1.08E−08 |
| 5 | 6539 | TAGT-4 | 3.45E−09 |
| 16 | 4034 | TAGT-8 | 4.27E−09 |
| 16 | 4102 | TAGT-8 | 2.54E−09 |
| 16 | 4903 | TAGT-12 | 1.91E−09 |
| 16 | 5220 | TAGT-1 | 5.03E−09 |
| 16 | 5321 | TAGT-6 | 7.16E−07 |
| 16 | 5720 | TAGT-11 | 1.93E−08 |
| 16 | 6010 | TAGT-12 | 2.83E−08 |
| 16 | 7183 | TAGT-6 | 1.48E−08 |
| 51 | 4074 | TAGT-6 | 1.95E−08 |
| 51 | 5347 | TAGT-6 | 1.21E−08 |
| 51 | 7190 | TAGT-6 | 1.03E−08 |
| 51 | 7237 | TAGT-12 | 2.13E−08 |
| 51 | 7242 | TAGT-12 | 1.71E−08 |
| 51 | 7251 | TAGT-12 | 2.69E−08 |
| 51 | 7253 | TAGT-12 | 1.62E−08 |
| 51 | 7433 | TAGT-9 | 1.67E−08 |
| 21 | 4038 | TAGT-8 | 2.98E−09 |
| 21 | 4127 | TAGT-6 | <1.0E−12 |
| 21 | 4844 | TAGT-12 | 6.95E−10 |
| 21 | 5235 | TAGT-1 | 1.41E−08 |
| 21 | 5328 | TAGT-6 | 3.42E−07 |
| 21 | 5924 | TAGT-12 | 5.95E−08 |
| 21 | 7395 | TAGT-5 | 1.65E−08 |
| 26 | 4052 | TAGT-10 | 9.73E−09 |
| 26 | 5094 | TAGT-10 | 4.34E−08 |
| 26 | 5097 | TAGT-10 | 1.27E−08 |
| 26 | 5109 | TAGT-10 | 2.59E−08 |
| 26 | 5275 | TAGT-1 | 9.65E−09 |
| 26 | 5399 | TAGT-9 | 3.62E−08 |
| 26 | 7040 | TAGT-8 | 2.72E−08 |
| 34 | 4836 | TAGT-12 | 2.49E−09 |
| 34 | 4839 | TAGT-12 | 6.16E−09 |
| 34 | 4852 | TAGT-12 | 2.26E−09 |
| 34 | 4876 | TAGT-12 | 7.75E−09 |
| 34 | 5349 | TAGT-6 | 6.20E−09 |
| 34 | 5351 | TAGT-6 | 7.29E−09 |
| 34 | 5369 | TAGT-6 | 2.05E−08 |
| 19 | 5282 | TAGT-1 | 1.07E−08 |
| 19 | 5298 | TAGT-6 | 3.41E−07 |
| 19 | 5316 | TAGT-6 | 1.14E−08 |
| 19 | 5404 | TAGT-6 | 3.30E−09 |
| 19 | 7386 | TAGT-5 | 1.32E−08 |
| 19 | 7426 | TAGT-9 | 1.12E−08 |
| 23 | 5215 | TAGT-1 | 6.64E−09 |
| 23 | 5272 | TAGT-1 | 2.49E−08 |
| 23 | 5491 | TAGT-11 | 1.43E−08 |
| 23 | 5744 | TAGT-11 | 1.14E−08 |
| 23 | 5933 | TAGT-12 | 3.13E−08 |
| 47 | 4072 | TAGT-6 | 6.95E−09 |
| 47 | 4132 | TAGT-6 | <1.0E−12 |
| 47 | 4200 | TAGT-6 | 5.68E−08 |
| 47 | 7229 | TAGT-12 | 8.91E−09 |
| 47 | 7275 | TAGT-5 | 6.85E−09 |
| 48 | 5314 | TAGT-6 | 8.39E−09 |
| 48 | 5326 | TAGT-6 | 7.84E−07 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 48 | 5342 | TAGT-6 | 3.89E−08 |
| 48 | 5348 | TAGT-6 | 1.02E−08 |
| 48 | 5364 | TAGT-6 | 7.26E−09 |
| 48 | 5413 | TAGT-6 | 9.93E−10 |
| 18 | 4809 | TAGT-12 | 3.69E−10 |
| 18 | 4861 | TAGT-12 | 5.11E−09 |
| 18 | 5363 | TAGT-6 | 9.87E−09 |
| 18 | 6555 | TAGT-3 | 4.18E−08 |
| 18 | 7513 | TAGT-9 | 8.43E−09 |
| 24 | 7097 | TAGT-6 | 2.43E−08 |
| 24 | 7228 | TAGT-12 | 7.62E−09 |
| 24 | 7244 | TAGT-12 | 1.05E−08 |
| 24 | 7388 | TAGT-5 | 2.72E−09 |
| 24 | 7421 | TAGT-9 | 2.47E−08 |
| 27 | 3761 | TAGT-6 | 9.65E−08 |
| 27 | 4135 | TAGT-6 | <1.0E−12 |
| 27 | 4846 | TAGT-12 | 3.19E−09 |
| 27 | 4874 | TAGT-12 | 4.19E−09 |
| 27 | 5236 | TAGT-1 | 1.49E−08 |
| 28 | 4925 | TAGT-7 | 1.32E−08 |
| 28 | 5317 | TAGT-6 | 3.34E−07 |
| 28 | 5341 | TAGT-6 | 2.93E−08 |
| 28 | 5584 | TAGT-2 | 1.76E−09 |
| 28 | 7315 | TAGT-5 | 5.15E−09 |
| 35 | 4849 | TAGT-12 | 8.40E−10 |
| 35 | 4850 | TAGT-12 | 1.23E−09 |
| 35 | 4851 | TAGT-12 | 3.84E−10 |
| 35 | 5694 | TAGT-11 | 9.45E−09 |
| 35 | 5980 | TAGT-12 | 1.14E−08 |
| 41 | 5934 | TAGT-12 | 1.66E−08 |
| 41 | 5983 | TAGT-12 | 2.09E−08 |
| 41 | 5993 | TAGT-12 | 1.13E−08 |
| 41 | 5995 | TAGT-12 | 1.42E−08 |
| 41 | 6475 | TAGT-4 | 7.22E−09 |
| 9 | 5297 | TAGT-6 | 1.77E−06 |
| 9 | 5561 | TAGT-2 | 1.64E−08 |
| 9 | 5568 | TAGT-2 | 1.14E−09 |
| 9 | 7268 | TAGT-5 | 3.76E−09 |
| 9 | 7431 | TAGT-9 | 3.53E−08 |
| 11 | 4051 | TAGT-10 | 1.80E−08 |
| 11 | 4067 | TAGT-10 | 1.97E−08 |
| 11 | 4103 | TAGT-8 | 3.59E−10 |
| 11 | 5300 | TAGT-6 | 1.53E−08 |
| 11 | 7047 | TAGT-8 | 2.15E−08 |
| 38 | 4204 | TAGT-10 | 6.83E−09 |
| 38 | 4204 | TAGT-10M | 6.89E−09 |
| 38 | 4847 | TAGT-12 | 3.64E−10 |
| 38 | 5398 | TAGT-9 | 1.97E−08 |
| 40 | 4029 | TAGT-8 | 1.89E−09 |
| 40 | 4076 | TAGT-6 | 7.44E−09 |
| 40 | 4126 | TAGT-6 | 7.27E−09 |
| 40 | 7444 | TAGT-9 | 5.53E−09 |
| 43 | 5408 | TAGT-6 | 2.36E−08 |
| 43 | 5992 | TAGT-12 | 1.70E−08 |
| 43 | 7249 | TAGT-12 | 5.36E−09 |
| 43 | 7264 | TAGT-5 | 3.17E−09 |
| 49 | 5756 | TAGT-11 | 3.00E−08 |
| 49 | 6543 | TAGT-3 | 6.78E−08 |
| 49 | 7420 | TAGT-9 | 1.38E−08 |
| 3 | 5614 | TAGT-2 | 5.29E−09 |
| 3 | 5642 | TAGT-2 | 3.84E−09 |
| 3 | 7044 | TAGT-8 | 1.12E−09 |
| 3 | 7045 | TAGT-8 | 1.11E−09 |
| 15 | 4077 | TAGT-6 | <1.0E−12 |
| 15 | 5409 | TAGT-6 | 1.70E−08 |
| 15 | 7380 | TAGT-5 | 1.24E−08 |
| 20 | 4037 | TAGT-8 | 5.53E−09 |
| 20 | 5732 | TAGT-11 | 5.24E−09 |
| 20 | 7258 | TAGT-12 | 9.72E−09 |
| 29 | 5930 | TAGT-12 | 5.66E−09 |
| 29 | 5932 | TAGT-12 | 1.12E−08 |
| 29 | 7254 | TAGT-12 | 1.07E−08 |
| 30 | 5411 | TAGT-6 | 1.25E−08 |
| 30 | 5420 | TAGT-6 | 1.41E−08 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 30 | 7272 | TAGT-5 | 3.49E−09 |
| 33 | 4180 | TAGT-10 | 7.39E−08 |
| 33 | 5228 | TAGT-1 | 3.06E−08 |
| 42 | 4141 | TAGT-6 | <1.0E−12 |
| 42 | 4816 | TAGT-12 | 5.32E−09 |
| 42 | 5274 | TAGT-1 | 2.52E−08 |
| 44 | 4045 | TAGT-8 | 1.10E−09 |
| 44 | 4875 | TAGT-12 | 1.03E−09 |
| 44 | 5921 | TAGT-12 | 8.01E−09 |
| 45 | 5403 | TAGT-6 | 8.26E−09 |
| 45 | 6526 | TAGT-4 | 1.16E−08 |
| 45 | 7379 | TAGT-5 | 5.43E−09 |
| 46 | 4828 | TAGT-12 | 1.10E−09 |
| 46 | 4863 | TAGT-12 | 6.63E−10 |
| 46 | 7427 | TAGT-9 | 5.58E−09 |
| 6 | 4752 | TAGT-10 | 3.34E−09 |
| 6 | 6210 | TAGT-10 | 5.17E−10 |
| 6 | 6212 | TAGT-10 | 2.25E−09 |
| 17 | 4818 | TAGT-12 | 1.02E−09 |
| 17 | 4841 | TAGT-12 | 4.50E−10 |
| 32 | 7248 | TAGT-12 | 1.28E−08 |
| 32 | 7310 | TAGT-5 | 1.41E−08 |
| 36 | 4815 | TAGT-12 | 5.91E−09 |
| 36 | 4825 | TAGT-12 | 6.05E−09 |
| 37 | 5360 | TAGT-6 | 2.41E−08 |
| 39 | 7358 | TAGT-3 | 5.15E−08 |
| 39 | 7389 | TAGT-5 | 4.50E−09 |
| 52 | 5370 | TAGT-6 | 1.91E−09 |
| 52 | 7166 | TAGT-6 | 1.24E−08 |
| 2 | 5438 | TAGT-9 | 9.30E−09 |
| 2 | 7373 | TAGT-5 | 5.13E−09 |
| 10 | 7055 | TAGT-8 | 7.57E−10 |
| 10 | 7067 | TAGT-8 | 3.41E−08 |
| 14 | 4062 | TAGT-10 | 2.11E−08 |
| 14 | 5237 | TAGT-1 | 3.28E−09 |
| 110 | 4055 | TAGT-10 | 1.07E−08 |
| 110 | 4061 | TAGT-10 | 3.42E−08 |
| 110 | 4066 | TAGT-10 | 4.76E−08 |
| 110 | 4181 | TAGT-10 | 4.27E−08 |
| 110 | 4693 | TAGT-10 | 4.87E−10 |
| 110 | 4696 | TAGT-10 | 4.58E−10 |
| 110 | 4697 | TAGT-10 | 6.21E−10 |
| 110 | 4698 | TAGT-10 | 5.70E−10 |
| 110 | 4700 | TAGT-10 | 2.62E−10 |
| 110 | 4701 | TAGT-10 | 5.60E−10 |
| 110 | 4702 | TAGT-10 | 5.02E−10 |
| 110 | 4703 | TAGT-10 | 2.85E−10 |
| 110 | 4704 | TAGT-10 | 6.65E−10 |
| 110 | 4705 | TAGT-10 | 3.02E−10 |
| 110 | 4706 | TAGT-10 | 2.50E−10 |
| 110 | 4707 | TAGT-10 | 4.29E−10 |
| 110 | 4708 | TAGT-10 | 5.29E−10 |
| 110 | 4710 | TAGT-10 | 6.26E−10 |
| 110 | 4714 | TAGT-10 | 4.46E−10 |
| 110 | 4717 | TAGT-10 | 4.61E−10 |
| 110 | 4718 | TAGT-10 | 5.32E−10 |
| 110 | 4722 | TAGT-10 | 7.46E−10 |
| 110 | 4725 | TAGT-10 | 4.84E−10 |
| 110 | 4729 | TAGT-10 | 8.80E−10 |
| 110 | 4731 | TAGT-10 | 4.67E−10 |
| 110 | 4732 | TAGT-10 | 3.33E−10 |
| 110 | 4738 | TAGT-10 | 5.34E−10 |
| 110 | 4743 | TAGT-10 | 7.40E−09 |
| 110 | 4744 | TAGT-10 | 3.73E−10 |
| 110 | 4748 | TAGT-10 | 3.92E−10 |
| 110 | 4749 | TAGT-10 | 2.55E−10 |
| 110 | 4750 | TAGT-10 | 7.86E−10 |
| 110 | 4753 | TAGT-10 | 3.43E−10 |
| 110 | 4759 | TAGT-10 | 6.59E−10 |
| 110 | 4766 | TAGT-10 | 4.09E−10 |
| 110 | 4788 | TAGT-10 | 2.88E−10 |
| 110 | 4794 | TAGT-10 | 5.56E−10 |
| 110 | 4803 | TAGT-10 | 1.88E−10 |
| 110 | 4805 | TAGT-10 | 4.26E−10 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 110 | 4808 | TAGT-10 | 8.28E−10 |
| 110 | 4909 | TAGT-10 | 2.90E−10 |
| 110 | 6010 | TAGT-12 | 2.83E−08 |
| 110 | 6183 | TAGT-10 | 2.70E−09 |
| 110 | 6191 | TAGT-10 | 6.58E−11 |
| 110 | 6206 | TAGT-10 | 3.44E−09 |
| 110 | 7066 | TAGT-8 | 1.80E−08 |
| 63 | 4036 | TAGT-8 | 3.13E−09 |
| 63 | 4096 | TAGT-8 | 2.70E−09 |
| 63 | 4812 | TAGT-12 | 2.89E−09 |
| 63 | 4815 | TAGT-12 | 5.91E−09 |
| 63 | 4817 | TAGT-12 | 2.06E−09 |
| 63 | 4818 | TAGT-12 | 1.02E−09 |
| 63 | 4836 | TAGT-12 | 2.49E−09 |
| 63 | 4840 | TAGT-12 | 2.08E−09 |
| 63 | 4841 | TAGT-12 | 4.50E−10 |
| 63 | 4846 | TAGT-12 | 3.19E−09 |
| 63 | 4852 | TAGT-12 | 2.26E−09 |
| 63 | 4860 | TAGT-12 | 2.44E−09 |
| 63 | 4876 | TAGT-12 | 7.75E−09 |
| 63 | 4880 | TAGT-12 | 2.77E−09 |
| 63 | 4897 | TAGT-12 | 6.83E−10 |
| 63 | 4901 | TAGT-12 | 3.19E−09 |
| 63 | 4904 | TAGT-12 | 5.39E−09 |
| 63 | 5115 | TAGT-12 | 1.16E−08 |
| 63 | 5195 | TAGT-1 | 2.62E−08 |
| 63 | 5216 | TAGT-1 | 3.08E−09 |
| 63 | 5286 | TAGT-1 | 6.34E−09 |
| 63 | 5287 | TAGT-1 | 1.02E−08 |
| 63 | 5290 | TAGT-1 | 6.73E−09 |
| 63 | 5323 | TAGT-6 | 1.04E−08 |
| 63 | 5387 | TAGT-8 | 1.13E−09 |
| 63 | 5404 | TAGT-6 | 3.30E−09 |
| 63 | 5421 | TAGT-9 | 1.05E−08 |
| 63 | 5422 | TAGT-9 | 5.12E−09 |
| 63 | 5658 | TAGT-11 | 2.61E−10 |
| 63 | 5722 | TAGT-11 | 3.08E−08 |
| 63 | 5756 | TAGT-11 | 3.00E−08 |
| 63 | 5985 | TAGT-12 | 3.92E−08 |
| 63 | 5986 | TAGT-12 | 4.65E−08 |
| 63 | 7273 | TAGT-5 | 6.01E−09 |
| 63 | 7316 | TAGT-5 | 2.04E−08 |
| 63 | 7370 | TAGT-5 | 1.07E−08 |
| 63 | 7375 | TAGT-5 | 6.03E−09 |
| 63 | 7385 | TAGT-5 | 3.26E−09 |
| 63 | 7391 | TAGT-5 | 1.35E−08 |
| 63 | 7394 | TAGT-5 | 8.75E−09 |
| 126 | 4033 | TAGT-8 | 8.75E−10 |
| 126 | 4614 | TAGT-8 | 3.53E−10 |
| 126 | 4615 | TAGT-8 | 2.28E−10 |
| 126 | 4617 | TAGT-8 | 2.88E−10 |
| 126 | 4622 | TAGT-8 | 2.74E−10 |
| 126 | 4627 | TAGT-8 | 1.82E−10 |
| 126 | 4631 | TAGT-8 | 1.83E−10 |
| 126 | 4633 | TAGT-8 | 3.22E−10 |
| 126 | 4634 | TAGT-8 | 2.07E−10 |
| 126 | 4638 | TAGT-8 | 3.14E−10 |
| 126 | 4642 | TAGT-8 | 1.89E−10 |
| 126 | 4644 | TAGT-8 | 2.48E−10 |
| 126 | 4645 | TAGT-8 | 2.96E−10 |
| 126 | 4650 | TAGT-8 | 3.57E−10 |
| 126 | 4651 | TAGT-8 | 3.01E−10 |
| 126 | 4652 | TAGT-8 | 2.94E−10 |
| 126 | 4654 | TAGT-8 | 2.32E−10 |
| 126 | 4658 | TAGT-8 | 1.42E−10 |
| 126 | 4665 | TAGT-8 | 3.69E−10 |
| 126 | 4673 | TAGT-8 | 3.23E−10 |
| 126 | 4674 | TAGT-8 | 5.02E−10 |
| 126 | 4681 | TAGT-8 | 5.43E−10 |
| 126 | 4689 | TAGT-8 | 1.63E−10 |
| 126 | 4690 | TAGT-8 | 4.67E−10 |
| 126 | 7043 | TAGT-8 | 1.34E−08 |
| 126 | BH3002 | TAGT-8 | 2.51E−10 |
| 126 | BH3004 | TAGT-8 | 3.00E−10 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 126 | BH3005 | TAGT-8 | 3.46E−10 |
| 126 | BH3006 | TAGT-8 | 1.94E−10 |
| 129 | 4038 | TAGT-8 | 2.98E−09 |
| 129 | 4084 | TAGT-8 | 2.94E−09 |
| 129 | 4618 | TAGT-8 | 1.08E−09 |
| 129 | 4620 | TAGT-8 | 3.48E−10 |
| 129 | 4623 | TAGT-8 | 4.85E−10 |
| 129 | 4624 | TAGT-8 | 1.00E−12 |
| 129 | 4625 | TAGT-8 | 4.02E−10 |
| 129 | 4630 | TAGT-8 | 2.67E−10 |
| 129 | 4653 | TAGT-8 | 3.27E−10 |
| 129 | 4659 | TAGT-8 | 2.12E−10 |
| 129 | 4662 | TAGT-8 | 8.98E−10 |
| 129 | 4666 | TAGT-8 | 1.17E−09 |
| 129 | 4668 | TAGT-8 | 5.79E−10 |
| 129 | 4670 | TAGT-8 | 8.21E−10 |
| 129 | 4675 | TAGT-8 | 1.00E−12 |
| 129 | 4676 | TAGT-8 | 1.62E−10 |
| 129 | 4678 | TAGT-8 | 5.98E−10 |
| 129 | 4683 | TAGT-8 | 8.97E−10 |
| 129 | 4684 | TAGT-8 | 6.69E−10 |
| 129 | 4685 | TAGT-8 | 4.78E−10 |
| 129 | 4686 | TAGT-8 | 4.78E−10 |
| 129 | 4687 | TAGT-8 | 4.08E−10 |
| 129 | 5970 | TAGT-12 | 1.35E−08 |
| 129 | 7213 | TAGT-12 | 8.87E−09 |
| 129 | 7232 | TAGT-12 | 8.06E−09 |
| 129 | 7357 | TAGT-3 | 6.14E−08 |
| 121 | 4054 | TAGT-10 | 1.58E−08 |
| 121 | 4060 | TAGT-10 | 1.10E−08 |
| 121 | 4065 | TAGT-10 | 4.31E−08 |
| 121 | 4072 | TAGT-6 | 6.95E−09 |
| 121 | 4182 | TAGT-10 | 4.24E−09 |
| 121 | 4741 | TAGT-10 | 1.66E−09 |
| 121 | 4798 | TAGT-10 | 4.35E−09 |
| 121 | 5295 | TAGT-9 | 2.21E−09 |
| 121 | 6185 | TAGT-10 | 1.57E−09 |
| 121 | 6187 | TAGT-10 | 2.74E−08 |
| 121 | 6195 | TAGT-10 | 4.30E−09 |
| 121 | 6197 | TAGT-10 | 8.56E−09 |
| 121 | 6198 | TAGT-10 | 2.85E−09 |
| 121 | 6209 | TAGT-10 | 3.35E−09 |
| 121 | 6219 | TAGT-10 | 3.15E−09 |
| 117 | 4031 | TAGT-8 | 1.06E−09 |
| 117 | 5126 | TAGT-8 | 9.54E−09 |
| 117 | 5129 | TAGT-8 | 1.12E−09 |
| 117 | 5132 | TAGT-8 | 3.06E−09 |
| 117 | 5145 | TAGT-8 | 7.00E−09 |
| 117 | 7067 | TAGT-8 | 3.41E−08 |
| 117 | 7068 | TAGT-8 | 1.11E−08 |
| 117 | 7073 | TAGT-8 | 3.19E−09 |
| 124 | 4027 | TAGT-8 | 1.55E−09 |
| 124 | 4027 | TAGT-8M | 3.81E−09 |
| 124 | 4043 | TAGT-8 | 2.69E−09 |
| 124 | 5020 | TAGT-8 | 8.78E−10 |
| 124 | 5020 | TAGT-8M | 7.00E−09 |
| 124 | 5023 | TAGT-8 | 9.46E−10 |
| 124 | 5023 | TAGT-8M | 5.77E−09 |
| 124 | 5030 | TAGT-8 | 7.03E−10 |
| 124 | 5030 | TAGT-8M | 4.27E−09 |
| 124 | 5037 | TAGT-8 | 1.06E−09 |
| 124 | 5037 | TAGT-8M | 4.36E−09 |
| 124 | 5039 | TAGT-8 | 4.30E−10 |
| 124 | 5039 | TAGT-8M | 2.69E−09 |
| 124 | 5040 | TAGT-8 | 4.37E−10 |
| 124 | 5040 | TAGT-8M | 3.13E−09 |
| 124 | 5045 | TAGT-8 | 1.00E−09 |
| 124 | 5045 | TAGT-8M | 3.91E−09 |
| 124 | 5048 | TAGT-8 | 5.10E−10 |
| 124 | 5048 | TAGT-8M | 2.52E−09 |
| 124 | 5066 | TAGT-8 | 5.23E−09 |
| 124 | 5066 | TAGT-8M | 9.99E−09 |
| 124 | 5070 | TAGT-8 | 1.34E−09 |
| 124 | 5070 | TAGT-8M | 6.63E−09 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 124 | 5994 | TAGT-12 | 1.58E−08 |
| 124 | 7442 | TAGT-9 | 6.83E−09 |
| 93 | 4062 | TAGT-10 | 2.11E−08 |
| 93 | 4132 | TAGT-6 | <1.0E−12 |
| 93 | 4201 | TAGT-6 | 1.41E−08 |
| 93 | 5300 | TAGT-6 | 1.53E−08 |
| 93 | 5694 | TAGT-11 | 9.45E−09 |
| 93 | 5906 | TAGT-12 | 1.50E−08 |
| 93 | 5926 | TAGT-12 | 3.23E−08 |
| 93 | 7078 | TAGT-6 | 2.52E−08 |
| 93 | 7087 | TAGT-6 | 6.96E−08 |
| 93 | 7120 | TAGT-6 | 3.45E−08 |
| 93 | 7190 | TAGT-6 | 1.03E−08 |
| 93 | 7271 | TAGT-5 | 3.13E−08 |
| 82 | 4048 | TAGT-10 | 3.24E−09 |
| 82 | 4051 | TAGT-10 | 1.80E−08 |
| 82 | 4723 | TAGT-10 | 9.11E−10 |
| 82 | 4733 | TAGT-10 | 3.05E−10 |
| 82 | 4734 | TAGT-10 | 5.72E−10 |
| 82 | 4767 | TAGT-10 | 2.77E−10 |
| 82 | 4771 | TAGT-10 | 7.23E−10 |
| 82 | 4797 | TAGT-10 | 5.63E−10 |
| 82 | 4807 | TAGT-10 | 1.17E−09 |
| 82 | 5346 | TAGT-6 | 1.61E−08 |
| 82 | 6221 | TAGT-10 | 6.92E−10 |
| 130 | 4813 | TAGT-12 | 2.45E−10 |
| 130 | 5113 | TAGT-12 | 6.80E−09 |
| 130 | 5114 | TAGT-12 | 3.42E−08 |
| 130 | 5116 | TAGT-12 | 1.46E−08 |
| 130 | 5119 | TAGT-12 | 7.54E−09 |
| 130 | 5121 | TAGT-12 | 9.29E−09 |
| 130 | 5123 | TAGT-12 | 5.67E−09 |
| 130 | 5125 | TAGT-12 | 2.42E−08 |
| 130 | 5128 | TAGT-12 | 7.12E−09 |
| 130 | 5138 | TAGT-12 | 8.55E−09 |
| 116 | 4752 | TAGT-10 | 3.34E−09 |
| 116 | 6194 | TAGT-10 | 2.49E−10 |
| 116 | 6196 | TAGT-10 | <1.0E−12 |
| 116 | 6202 | TAGT-10 | 1.03E−09 |
| 116 | 6204 | TAGT-10 | 6.46E−09 |
| 116 | 6208 | TAGT-10 | 3.50E−09 |
| 116 | 6210 | TAGT-10 | 5.17E−10 |
| 116 | 6212 | TAGT-10 | 2.25E−09 |
| 116 | 6214 | TAGT-10 | 1.51E−09 |
| 116 | 6217 | TAGT-10 | 4.99E−09 |
| 132 | 4032 | TAGT-8 | 5.11E−09 |
| 132 | 4032 | TAGT-8M | 4.84E−09 |
| 132 | 4050 | TAGT-10 | 1.65E−08 |
| 132 | 5012 | TAGT-8 | 1.76E−09 |
| 132 | 5012 | TAGT-8M | 2.03E−09 |
| 132 | 5014 | TAGT-8 | 2.43E−09 |
| 132 | 5014 | TAGT-8M | 3.87E−09 |
| 132 | 5016 | TAGT-8 | 3.56E−09 |
| 132 | 5016 | TAGT-8M | 2.84E−09 |
| 132 | 5022 | TAGT-8 | 3.68E−09 |
| 132 | 5022 | TAGT-8M | 3.03E−09 |
| 132 | 5024 | TAGT-8 | 4.52E−09 |
| 132 | 5024 | TAGT-8M | 3.48E−09 |
| 132 | 5041 | TAGT-8 | 1.68E−09 |
| 132 | 5041 | TAGT-8M | 1.67E−09 |
| 132 | 5074 | TAGT-8 | 4.31E−09 |
| 132 | 5074 | TAGT-8M | 2.98E−09 |
| 132 | 5082 | TAGT-8 | 4.79E−09 |
| 132 | 5082 | TAGT-8M | 3.23E−09 |
| 53 | 4052 | TAGT-10 | 9.73E−09 |
| 53 | 4059 | TAGT-10 | 3.30E−07 |
| 53 | 5094 | TAGT-10 | 4.34E−08 |
| 53 | 5095 | TAGT-10 | 1.27E−08 |
| 53 | 5097 | TAGT-10 | 1.27E−08 |
| 53 | 5099 | TAGT-10 | 4.20E−08 |
| 53 | 5109 | TAGT-10 | 2.59E−08 |
| 53 | 5280 | TAGT-1 | 8.43E−09 |
| 53 | 5936 | TAGT-10 | 1.75E−08 |
| 89 | 4045 | TAGT-8 | 1.10E−09 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 89 | 4123 | TAGT-6 | 5.98E−09 |
| 89 | 4125 | TAGT-6 | <1.0E−12 |
| 89 | 5910 | TAGT-12 | 3.30E−08 |
| 89 | 5920 | TAGT-12 | 1.88E−08 |
| 89 | 5929 | TAGT-12 | 3.20E−08 |
| 89 | 7079 | TAGT-6 | 2.99E−08 |
| 89 | 7133 | TAGT-6 | 4.03E−08 |
| 89 | 7219 | TAGT-12 | 1.44E−08 |
| 134 | 3898 | TAGT-11 | 1.83E−08 |
| 134 | 4925 | TAGT-7 | 1.32E−08 |
| 134 | 5149 | TAGT-11 | 2.91E−09 |
| 134 | 5159 | TAGT-11 | 4.09E−09 |
| 134 | 5160 | TAGT-11 | 8.07E−09 |
| 134 | 5162 | TAGT-11 | 9.87E−09 |
| 134 | 5165 | TAGT-11 | 4.06E−09 |
| 134 | 5752 | TAGT-11 | 6.33E−09 |
| 134 | 7231 | TAGT-12 | 3.38E−09 |
| 66 | 4161 | TAGT-8 | 2.98E−08 |
| 66 | 4180 | TAGT-10 | 7.39E−08 |
| 66 | 4809 | TAGT-12 | 3.69E−10 |
| 66 | 4847 | TAGT-12 | 3.64E−10 |
| 66 | 4879 | TAGT-12 | 3.13E−09 |
| 66 | 6533 | TAGT-3 | 2.62E−08 |
| 66 | 7372 | TAGT-5 | 7.27E−10 |
| 66 | 7386 | TAGT-5 | 1.32E−08 |
| 122 | 3757 | TAGT-6 | 1.84E−08 |
| 122 | 3869 | TAGT-11 | 2.35E−08 |
| 122 | 4163 | TAGT-8 | 1.37E−08 |
| 122 | 4828 | TAGT-12 | 1.10E−09 |
| 122 | 5103 | TAGT-10 | 2.67E−09 |
| 122 | 5163 | TAGT-11 | 1.71E−08 |
| 122 | 5740 | TAGT-11 | 7.26E−09 |
| 123 | 3762 | TAGT-6 | 3.04E−08 |
| 123 | 3780 | TAGT-8 | 1.47E−09 |
| 123 | 3865 | TAGT-11 | 9.48E−09 |
| 123 | 7030 | TAGT-8 | 3.47E−08 |
| 123 | 7035 | TAGT-8 | 3.04E−09 |
| 123 | 7055 | TAGT-8 | 7.57E−10 |
| 123 | 7358 | TAGT-3 | 5.15E−08 |
| 128 | 4101 | TAGT-8 | 2.12E−09 |
| 128 | 4661 | TAGT-8 | 1.62E−09 |
| 128 | 4792 | TAGT-10 | 7.39E−09 |
| 128 | 5997 | TAGT-12 | 8.51E−09 |
| 128 | 7040 | TAGT-8 | 2.72E−08 |
| 128 | 7221 | TAGT-12 | 5.58E−09 |
| 128 | 7228 | TAGT-12 | 7.62E−09 |
| 131 | 4103 | TAGT-8 | 3.59E−10 |
| 131 | 7215 | TAGT-12 | 1.61E−08 |
| 131 | 7229 | TAGT-12 | 8.91E−09 |
| 131 | 7243 | TAGT-12 | 4.95E−09 |
| 131 | 7244 | TAGT-12 | 1.05E−08 |
| 131 | 7254 | TAGT-12 | 1.07E−08 |
| 131 | 7258 | TAGT-12 | 9.72E−09 |
| 65 | 4037 | TAGT-8 | 5.53E−09 |
| 65 | 4823 | TAGT-12 | 2.62E−09 |
| 65 | 5292 | TAGT-1 | 1.57E−08 |
| 65 | 5741 | TAGT-11 | 1.91E−08 |
| 65 | 7239 | TAGT-12 | 2.40E−08 |
| 65 | 7433 | TAGT-9 | 1.67E−08 |
| 109 | 6179 | TAGT-10 | 1.99E−09 |
| 109 | 6184 | TAGT-10 | <1.0E−12 |
| 109 | 6188 | TAGT-10 | 8.76E−09 |
| 109 | 6189 | TAGT-10 | 2.38E−10 |
| 109 | 6216 | TAGT-10 | 6.58E−10 |
| 109 | 6539 | TAGT-4 | 3.45E−09 |
| 72 | 5301 | TAGT-6 | 2.61E−07 |
| 72 | 5326 | TAGT-6 | 7.84E−07 |
| 72 | 5420 | TAGT-6 | 1.41E−08 |
| 72 | 5710 | TAGT-11 | 1.01E−08 |
| 72 | 5746 | TAGT-11 | 5.00E−09 |
| 87 | 4216 | TAGT-6 | 2.59E−08 |
| 87 | 5320 | TAGT-6 | 6.13E−07 |
| 87 | 5408 | TAGT-6 | 2.36E−08 |
| 87 | 7183 | TAGT-6 | 1.48E−08 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 87 | 7201 | TAGT-6 | 3.26E−08 |
| 105 | 5218 | TAGT-1 | 6.04E−09 |
| 105 | 5316 | TAGT-6 | 1.14E−08 |
| 105 | 5513 | TAGT-2 | 1.07E−09 |
| 105 | 6543 | TAGT-3 | 6.78E−08 |
| 105 | 7427 | TAGT-9 | 5.58E−09 |
| 118 | 4851 | TAGT-12 | 3.84E−10 |
| 118 | 7025 | TAGT-8 | 4.87E−08 |
| 118 | 7036 | TAGT-8 | 1.59E−08 |
| 118 | 7037 | TAGT-8 | 2.10E−08 |
| 118 | 7047 | TAGT-8 | 2.15E−08 |
| 60 | 5226 | TAGT-1 | 8.36E−09 |
| 60 | 5281 | TAGT-1 | 4.70E−09 |
| 60 | 5425 | TAGT-9 | 2.15E−08 |
| 60 | 5744 | TAGT-11 | 1.14E−08 |
| 67 | 4026 | TAGT-8 | 3.08E−09 |
| 67 | 4820 | TAGT-12 | 3.96E−09 |
| 67 | 4839 | TAGT-12 | 6.16E−09 |
| 67 | 7274 | TAGT-5 | 1.63E−08 |
| 70 | 4041 | TAGT-8 | 1.54E−09 |
| 70 | 4844 | TAGT-12 | 6.95E−10 |
| 70 | 7159 | TAGT-6 | 3.79E−08 |
| 70 | 7380 | TAGT-5 | 1.24E−08 |
| 84 | 7204 | TAGT-5 | 2.33E−09 |
| 84 | 7323 | TAGT-5 | 3.23E−09 |
| 84 | 7373 | TAGT-5 | 5.13E−09 |
| 84 | 7378 | TAGT-5 | 5.66E−09 |
| 85 | 7260 | TAGT-5 | 2.30E−09 |
| 85 | 7365 | TAGT-5 | 1.82E−09 |
| 85 | 7369 | TAGT-5 | 2.46E−09 |
| 85 | 7374 | TAGT-5 | 1.97E−08 |
| 92 | 4073 | TAGT-6 | <1.0E−12 |
| 92 | 5355 | TAGT-6 | 8.71E−10 |
| 92 | 7080 | TAGT-6 | 2.44E−08 |
| 92 | 7081 | TAGT-6 | 4.31E−08 |
| 100 | 5328 | TAGT-6 | 3.42E−07 |
| 100 | 5417 | TAGT-6 | 4.04E−08 |
| 100 | 5974 | TAGT-12 | 5.02E−08 |
| 100 | 5977 | TAGT-12 | 2.70E−08 |
| 103 | 4075 | TAGT-6 | <1.0E−12 |
| 103 | 5961 | TAGT-12 | 2.41E−08 |
| 103 | 5993 | TAGT-12 | 1.13E−08 |
| 103 | 7255 | TAGT-12 | 1.20E−08 |
| 104 | 5912 | TAGT-12 | 1.68E−08 |
| 104 | 5923 | TAGT-12 | 1.60E−08 |
| 104 | 5978 | TAGT-12 | 3.25E−08 |
| 104 | 7226 | TAGT-12 | 7.57E−09 |
| 106 | 4141 | TAGT-6 | <1.0E−12 |
| 106 | 4222 | TAGT-6 | 5.55E−08 |
| 106 | 5321 | TAGT-6 | 7.16E−07 |
| 106 | 7317 | TAGT-5 | 2.02E−08 |
| 57 | 5303 | TAGT-6 | 5.12E−09 |
| 57 | 5359 | TAGT-6 | 7.10E−10 |
| 57 | 5365 | TAGT-6 | 2.56E−09 |
| 61 | 5230 | TAGT-1 | 9.21E−09 |
| 61 | 5271 | TAGT-1 | 1.24E−08 |
| 61 | 7207 | TAGT-5 | 4.99E−10 |
| 71 | 5336 | TAGT-6 | 6.04E−07 |
| 71 | 5418 | TAGT-6 | 2.02E−08 |
| 71 | 5438 | TAGT-9 | 9.30E−09 |
| 75 | 5194 | TAGT-1 | 1.29E−08 |
| 75 | 5235 | TAGT-1 | 1.41E−08 |
| 75 | 5403 | TAGT-6 | 8.26E−09 |
| 77 | 4063 | TAGT-10 | 1.90E−08 |
| 77 | 4067 | TAGT-10 | 1.97E−08 |
| 77 | 7429 | TAGT-9 | 2.12E−08 |
| 79 | 5353 | TAGT-6 | 1.61E−08 |
| 79 | 7419 | TAGT-9 | 1.72E−08 |
| 79 | 7431 | TAGT-9 | 3.53E−08 |
| 80 | 7276 | TAGT-5 | 1.02E−08 |
| 80 | 7311 | TAGT-5 | 9.20E−09 |
| 80 | 7371 | TAGT-5 | 2.31E−08 |
| 94 | 5371 | TAGT-6 | 3.97E−09 |
| 94 | 7088 | TAGT-6 | 4.36E−08 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 94 | 7100 | TAGT-6 | 3.50E−08 |
| 95 | 5236 | TAGT-1 | 1.49E−08 |
| 95 | 5983 | TAGT-12 | 2.09E−08 |
| 95 | 7128 | TAGT-6 | 3.97E−08 |
| 96 | 7077 | TAGT-6 | 1.88E−08 |
| 96 | 7107 | TAGT-6 | 1.22E−07 |
| 96 | 7109 | TAGT-6 | 3.20E−08 |
| 10 | 3761 | TAGT-6 | 9.65E−08 |
| 10 | 4217 | TAGT-6 | 9.67E−08 |
| 10 | 4218 | TAGT-6 | 2.85E−08 |
| 108 | 4034 | TAGT-8 | 4.27E−09 |
| 108 | 5351 | TAGT-6 | 7.29E−09 |
| 108 | 5357 | TAGT-6 | 7.14E−09 |
| 111 | 4827 | TAGT-12 | 1.51E−09 |
| 111 | 4834 | TAGT-12 | 9.68E−10 |
| 111 | 4875 | TAGT-12 | 1.03E−09 |
| 112 | 4025 | TAGT-8 | 2.89E−09 |
| 112 | 5930 | TAGT-12 | 5.66E−09 |
| 112 | 5932 | TAGT-12 | 1.12E−08 |
| 113 | 4116 | TAGT-10 | <1.0E−12 |
| 113 | 4863 | TAGT-12 | 6.63E−10 |
| 113 | 5980 | TAGT-12 | 1.14E−08 |
| 114 | 5921 | TAGT-12 | 8.01E−09 |
| 114 | 5968 | TAGT-12 | 1.27E−08 |
| 114 | 5990 | TAGT-12 | 1.15E−08 |
| 120 | 6180 | TAGT-10 | 6.11E−09 |
| 120 | 6190 | TAGT-10 | 2.55E−09 |
| 120 | 6203 | TAGT-10 | 1.05E−08 |
| 133 | 5935 | TAGT-12 | 8.78E−09 |
| 133 | 6008 | TAGT-12 | 5.10E−08 |
| 133 | 7222 | TAGT-12 | 1.26E−09 |
| 54 | 7277 | TAGT-5 | 2.56E−09 |
| 54 | 7390 | TAGT-5 | 1.44E−09 |
| 55 | 5238 | TAGT-1 | 5.04E−08 |
| 55 | 5370 | TAGT-6 | 1.91E−09 |
| 56 | 5285 | TAGT-1 | 1.42E−08 |
| 56 | 5310 | TAGT-6 | 5.72E−09 |
| 58 | 5314 | TAGT-6 | 8.39E−09 |
| 58 | 5342 | TAGT-6 | 3.89E−08 |
| 59 | 5202 | TAGT-1 | 1.50E−08 |
| 59 | 7032 | TAGT-8 | 2.08E−08 |
| 62 | 5220 | TAGT-1 | 5.03E−09 |
| 62 | 7163 | TAGT-6 | 1.26E−08 |
| 64 | 5211 | TAGT-1 | 2.11E−09 |
| 64 | 5584 | TAGT-2 | 1.76E−09 |
| 68 | 4177 | TAGT-8 | 1.48E−08 |
| 68 | 5234 | TAGT-1 | 1.28E−08 |
| 69 | 4838 | TAGT-12 | 2.52E−09 |
| 69 | 7166 | TAGT-6 | 1.24E−08 |
| 73 | 4878 | TAGT-12 | 4.07E−09 |
| 73 | 5315 | TAGT-6 | 2.10E−06 |
| 74 | 3760 | TAGT-6 | 1.26E−08 |
| 76 | 5297 | TAGT-6 | 1.77E−06 |
| 76 | 5745 | TAGT-11 | 1.06E−08 |
| 78 | 4058 | TAGT-10 | 1.13E−08 |
| 78 | 5291 | TAGT-1 | 6.57E−09 |
| 81 | 5212 | TAGT-1 | 9.19E−09 |
| 81 | 5568 | TAGT-2 | 1.14E−09 |
| 83 | 5411 | TAGT-6 | 1.25E−08 |
| 83 | 5565 | TAGT-2 | 3.02E−09 |
| 86 | 4129 | TAGT-6 | <1.0E−12 |
| 86 | 6473 | TAGT-4 | 2.30E−08 |
| 88 | 5905 | TAGT-12 | 3.83E−08 |
| 88 | 5919 | TAGT-12 | 2.38E−08 |
| 90 | 4029 | TAGT-8 | 1.89E−09 |
| 90 | 7097 | TAGT-6 | 2.43E−08 |
| 91 | 5272 | TAGT-1 | 2.49E−08 |
| 91 | 7242 | TAGT-12 | 1.71E−08 |
| 97 | 5915 | TAGT-12 | 1.82E−08 |
| 97 | 5964 | TAGT-12 | 1.40E−08 |
| 98 | 4131 | TAGT-6 | <1.0E−12 |
| 98 | 5347 | TAGT-6 | 1.21E−08 |
| 99 | 7090 | TAGT-6 | 5.55E−08 |
| 102 | 6004 | TAGT-12 | 5.50E−08 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 102 | 7251 | TAGT-12 | 2.69E−08 |
| 107 | 4133 | TAGT-6 | 3.90E−10 |
| 107 | 7262 | TAGT-5 | 2.63E−09 |
| 115 | 7310 | TAGT-5 | 1.41E−08 |
| 115 | 7379 | TAGT-5 | 5.43E−09 |
| 119 | 6193 | TAGT-10 | 3.18E−09 |
| 119 | 6220 | TAGT-10 | 3.45E−09 |
| 125 | 4030 | TAGT-8 | 4.90E−09 |
| 125 | 7038 | TAGT-8 | 2.33E−08 |
| 127 | 7044 | TAGT-8 | 1.12E−09 |
| 127 | 7045 | TAGT-8 | 1.11E−09 |
| 135 | 4204 | TAGT-10 | 6.83E−09 |
| 135 | 4204 | TAGT-10M | 6.89E−09 |
| 135 | 5423 | TAGT-9 | 4.90E−09 |
| 136 | 4861 | TAGT-12 | 5.11E−09 |
| 136 | 7129 | TAGT-6 | 1.90E−08 |
| 139 and 110 | 4181 | TAGT-10 | 4.27E−08 |
| 139 and 110 | 4693 | TAGT-10 | 4.87E−10 |
| 139 and 110 | 4696 | TAGT-10 | 4.58E−10 |
| 139 and 110 | 4697 | TAGT-10 | 6.21E−10 |
| 139 and 110 | 4698 | TAGT-10 | 5.70E−10 |
| 139 and 110 | 4700 | TAGT-10 | 2.62E−10 |
| 139 and 110 | 4701 | TAGT-10 | 5.60E−10 |
| 139 and 110 | 4702 | TAGT-10 | 5.02E−10 |
| 139 and 110 | 4703 | TAGT-10 | 2.85E−10 |
| 139 and 110 | 4704 | TAGT-10 | 6.65E−10 |
| 139 and 110 | 4705 | TAGT-10 | 3.02E−10 |
| 139 and 110 | 4706 | TAGT-10 | 2.50E−10 |
| 139 and 110 | 4707 | TAGT-10 | 4.29E−10 |
| 139 and 110 | 4708 | TAGT-10 | 5.29E−10 |
| 139 and 110 | 4710 | TAGT-10 | 6.26E−10 |
| 139 and 110 | 4714 | TAGT-10 | 4.46E−10 |
| 139 and 110 | 4717 | TAGT-10 | 4.61E−10 |
| 139 and 110 | 4718 | TAGT-10 | 5.32E−10 |
| 139 and 110 | 4722 | TAGT-10 | 7.46E−10 |
| 139 and 110 | 4725 | TAGT-10 | 4.84E−10 |
| 139 and 110 | 4729 | TAGT-10 | 8.80E−10 |
| 139 and 110 | 4731 | TAGT-10 | 4.67E−10 |
| 139 and 110 | 4732 | TAGT-10 | 3.33E−10 |
| 139 and 110 | 4738 | TAGT-10 | 5.34E−10 |
| 139 and 110 | 4744 | TAGT-10 | 3.73E−10 |
| 139 and 110 | 4748 | TAGT-10 | 3.92E−10 |
| 139 and 110 | 4749 | TAGT-10 | 2.55E−10 |
| 139 and 110 | 4750 | TAGT-10 | 7.86E−10 |
| 139 and 110 | 4753 | TAGT-10 | 3.43E−10 |
| 139 and 110 | 4759 | TAGT-10 | 6.59E−10 |
| 139 and 110 | 4766 | TAGT-10 | 4.09E−10 |
| 139 and 110 | 4788 | TAGT-10 | 2.88E−10 |
| 139 and 110 | 4794 | TAGT-10 | 5.56E−10 |
| 139 and 110 | 4803 | TAGT-10 | 1.88E−10 |
| 139 and 110 | 4805 | TAGT-10 | 4.26E−10 |
| 139 and 110 | 4808 | TAGT-10 | 8.28E−10 |
| 139 and 110 | 4909 | TAGT-10 | 2.90E−10 |
| 139 and 110 | 6191 | TAGT-10 | 6.58E−11 |
| 8 and 126 | 4033 | TAGT-8 | 8.75E−10 |
| 8 and 126 | 4614 | TAGT-8 | 3.53E−10 |
| 8 and 126 | 4615 | TAGT-8 | 2.28E−10 |
| 8 and 126 | 4617 | TAGT-8 | 2.88E−10 |
| 8 and 126 | 4622 | TAGT-8 | 2.74E−10 |
| 8 and 126 | 4627 | TAGT-8 | 1.82E−10 |
| 8 and 126 | 4631 | TAGT-8 | 1.83E−10 |
| 8 and 126 | 4633 | TAGT-8 | 3.22E−10 |
| 8 and 126 | 4634 | TAGT-8 | 2.07E−10 |
| 8 and 126 | 4638 | TAGT-8 | 3.14E−10 |
| 8 and 126 | 4642 | TAGT-8 | 1.89E−10 |
| 8 and 126 | 4644 | TAGT-8 | 2.48E−10 |
| 8 and 126 | 4645 | TAGT-8 | 2.96E−10 |
| 8 and 126 | 4650 | TAGT-8 | 3.57E−10 |
| 8 and 126 | 4651 | TAGT-8 | 3.01E−10 |
| 8 and 126 | 4652 | TAGT-8 | 2.94E−10 |
| 8 and 126 | 4654 | TAGT-8 | 2.32E−10 |
| 8 and 126 | 4658 | TAGT-8 | 1.42E−10 |
| 8 and 126 | 4665 | TAGT-8 | 3.69E−10 |
| 8 and 126 | 4673 | TAGT-8 | 3.23E−10 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 8 and 126 | 4674 | TAGT-8 | 5.02E−10 |
| 8 and 126 | 4681 | TAGT-8 | 5.43E−10 |
| 8 and 126 | 4689 | TAGT-8 | 1.63E−10 |
| 8 and 126 | 4690 | TAGT-8 | 4.67E−10 |
| 8 and 126 | 7043 | TAGT-8 | 1.34E−08 |
| 8 and 126 | BH3002 | TAGT-8 | 2.51E−10 |
| 8 and 126 | BH3004 | TAGT-8 | 3.00E−10 |
| 8 and 126 | BH3005 | TAGT-8 | 3.46E−10 |
| 8 and 126 | BH3006 | TAGT-8 | 1.94E−10 |
| 13 and 129 | 4084 | TAGT-8 | 2.94E−09 |
| 13 and 129 | 4618 | TAGT-8 | 1.08E−09 |
| 13 and 129 | 4620 | TAGT-8 | 3.48E−10 |
| 13 and 129 | 4623 | TAGT-8 | 4.85E−10 |
| 13 and 129 | 4624 | TAGT-8 | 1.00E−12 |
| 13 and 129 | 4625 | TAGT-8 | 4.02E−10 |
| 13 and 129 | 4630 | TAGT-8 | 2.67E−10 |
| 13 and 129 | 4653 | TAGT-8 | 3.27E−10 |
| 13 and 129 | 4659 | TAGT-8 | 2.12E−10 |
| 13 and 129 | 4662 | TAGT-8 | 8.98E−10 |
| 13 and 129 | 4666 | TAGT-8 | 1.17E−09 |
| 13 and 129 | 4668 | TAGT-8 | 5.79E−10 |
| 13 and 129 | 4670 | TAGT-8 | 8.21E−10 |
| 13 and 129 | 4675 | TAGT-8 | 1.00E−12 |
| 13 and 129 | 4676 | TAGT-8 | 1.62E−10 |
| 13 and 129 | 4678 | TAGT-8 | 5.98E−10 |
| 13 and 129 | 4683 | TAGT-8 | 8.97E−10 |
| 13 and 129 | 4684 | TAGT-8 | 6.69E−10 |
| 13 and 129 | 4685 | TAGT-8 | 4.78E−10 |
| 13 and 129 | 4686 | TAGT-8 | 4.78E−10 |
| 13 and 129 | 4687 | TAGT-8 | 4.08E−10 |
| 31 and 124 | 4027 | TAGT-8 | 1.55E−09 |
| 31 and 124 | 4027 | TAGT-8M | 3.81E−09 |
| 31 and 124 | 5020 | TAGT-8 | 8.78E−10 |
| 31 and 124 | 5020 | TAGT-8M | 7.00E−09 |
| 31 and 124 | 5023 | TAGT-8 | 9.46E−10 |
| 31 and 124 | 5023 | TAGT-8M | 5.77E−09 |
| 31 and 124 | 5030 | TAGT-8 | 7.03E−10 |
| 31 and 124 | 5030 | TAGT-8M | 4.27E−09 |
| 31 and 124 | 5037 | TAGT-8 | 1.06E−09 |
| 31 and 124 | 5037 | TAGT-8M | 4.36E−09 |
| 31 and 124 | 5039 | TAGT-8 | 4.30E−10 |
| 31 and 124 | 5039 | TAGT-8M | 2.69E−09 |
| 31 and 124 | 5040 | TAGT-8 | 4.37E−10 |
| 31 and 124 | 5040 | TAGT-8M | 3.13E−09 |
| 31 and 124 | 5045 | TAGT-8 | 1.00E−09 |
| 31 and 124 | 5045 | TAGT-8M | 3.91E−09 |
| 31 and 124 | 5048 | TAGT-8 | 5.10E−10 |
| 31 and 124 | 5048 | TAGT-8M | 2.52E−09 |
| 31 and 124 | 5066 | TAGT-8 | 5.23E−09 |
| 31 and 124 | 5066 | TAGT-8M | 9.99E−09 |
| 31 and 124 | 5070 | TAGT-8 | 1.34E−09 |
| 31 and 124 | 5070 | TAGT-8M | 6.63E−09 |
| 25 and 130 | 4813 | TAGT-12 | 2.45E−10 |
| 25 and 130 | 5113 | TAGT-12 | 6.80E−09 |
| 25 and 130 | 5114 | TAGT-12 | 3.42E−08 |
| 25 and 130 | 5116 | TAGT-12 | 1.46E−08 |
| 25 and 130 | 5119 | TAGT-12 | 7.54E−09 |
| 25 and 130 | 5121 | TAGT-12 | 9.29E−09 |
| 25 and 130 | 5123 | TAGT-12 | 5.67E−09 |
| 25 and 130 | 5125 | TAGT-12 | 2.42E−08 |
| 25 and 130 | 5128 | TAGT-12 | 7.12E−09 |
| 25 and 130 | 5138 | TAGT-12 | 8.55E−09 |
| 150 and 132 | 4032 | TAGT-8 | 5.11E−09 |
| 150 and 132 | 4032 | TAGT-8M | 4.84E−09 |
| 150 and 132 | 5012 | TAGT-8 | 1.76E−09 |
| 150 and 132 | 5012 | TAGT-8M | 2.03E−09 |
| 150 and 132 | 5014 | TAGT-8 | 2.43E−09 |
| 150 and 132 | 5014 | TAGT-8M | 3.87E−09 |
| 150 and 132 | 5016 | TAGT-8 | 3.56E−09 |
| 150 and 132 | 5016 | TAGT-8M | 2.84E−09 |
| 150 and 132 | 5022 | TAGT-8 | 3.68E−09 |
| 150 and 132 | 5022 | TAGT-8M | 3.03E−09 |
| 150 and 132 | 5024 | TAGT-8 | 4.52E−09 |
| 150 and 132 | 5024 | TAGT-8M | 3.48E−09 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 150 and 132 | 5041 | TAGT-8 | 1.68E−09 |
| 150 and 132 | 5041 | TAGT-8M | 1.67E−09 |
| 150 and 132 | 5074 | TAGT-8 | 4.31E−09 |
| 150 and 132 | 5074 | TAGT-8M | 2.98E−09 |
| 150 and 132 | 5082 | TAGT-8 | 4.79E−09 |
| 150 and 132 | 5082 | TAGT-8M | 3.23E−09 |
| 158 and 162 | 5962 | TAGT-12 | 8.06E−08 |
| 158 and 162 | 5996 | TAGT-12 | 2.21E−08 |
| 158 and 162 | 6000 | TAGT-12 | 7.86E−08 |
| 158 and 162 | 7210 | TAGT-12 | 9.85E−09 |
| 158 and 162 | 7218 | TAGT-12 | 1.49E−08 |
| 158 and 162 | 7225 | TAGT-12 | 9.53E−09 |
| 158 and 162 | 7241 | TAGT-12 | 6.43E−09 |
| 158 and 162 | 7247 | TAGT-12 | 8.93E−09 |
| 12 and 82 | 4048 | TAGT-10 | 3.24E−09 |
| 12 and 82 | 4723 | TAGT-10 | 9.11E−10 |
| 12 and 82 | 4733 | TAGT-10 | 3.05E−10 |
| 12 and 82 | 4734 | TAGT-10 | 5.72E−10 |
| 12 and 82 | 4767 | TAGT-10 | 2.77E−10 |
| 12 and 82 | 4771 | TAGT-10 | 7.23E−10 |
| 12 and 82 | 4797 | TAGT-10 | 5.63E−10 |
| 12 and 82 | 4807 | TAGT-10 | 1.17E−09 |
| 149 and 117 | 4031 | TAGT-8 | 1.06E−09 |
| 149 and 117 | 5126 | TAGT-8 | 9.54E−09 |
| 149 and 117 | 5129 | TAGT-8 | 1.12E−09 |
| 149 and 117 | 5132 | TAGT-8 | 3.06E−09 |
| 149 and 117 | 5145 | TAGT-8 | 7.00E−09 |
| 149 and 117 | 7068 | TAGT-8 | 1.11E−08 |
| 149 and 117 | 7073 | TAGT-8 | 3.19E−09 |
| 7 and 134 | 3898 | TAGT-11 | 1.83E−08 |
| 7 and 134 | 5149 | TAGT-11 | 2.91E−09 |
| 7 and 134 | 5159 | TAGT-11 | 4.09E−09 |
| 7 and 134 | 5160 | TAGT-11 | 8.07E−09 |
| 7 and 134 | 5162 | TAGT-11 | 9.87E−09 |
| 7 and 134 | 5165 | TAGT-11 | 4.06E−09 |
| 154 and 63 | 4812 | TAGT-12 | 2.89E−09 |
| 154 and 63 | 4904 | TAGT-12 | 5.39E−09 |
| 154 and 63 | 5115 | TAGT-12 | 1.16E−08 |
| 154 and 63 | 5421 | TAGT-9 | 1.05E−08 |
| 154 and 63 | 5422 | TAGT-9 | 5.12E−09 |
| 158 and 161 | 5922 | TAGT-12 | 1.95E−08 |
| 158 and 161 | 7135 | TAGT-6 | 3.17E−08 |
| 158 and 161 | 7245 | TAGT-12 | 1.38E−08 |
| 158 and 161 | 7246 | TAGT-12 | 6.22E−09 |
| 158 and 161 | 7252 | TAGT-12 | 9.56E−09 |
| 26 and 53 | 4052 | TAGT-10 | 9.73E−09 |
| 26 and 53 | 5094 | TAGT-10 | 4.34E−08 |
| 26 and 53 | 5097 | TAGT-10 | 1.27E−08 |
| 26 and 53 | 5109 | TAGT-10 | 2.59E−08 |
| 151 and 53 | 4059 | TAGT-10 | 3.30E−07 |
| 151 and 53 | 5095 | TAGT-10 | 1.27E−08 |
| 151 and 53 | 5099 | TAGT-10 | 4.20E−08 |
| 151 and 53 | 5936 | TAGT-10 | 1.75E−08 |
| 157 and 63 | 4036 | TAGT-8 | 3.13E−09 |
| 157 and 63 | 4096 | TAGT-8 | 2.70E−09 |
| 157 and 63 | 5323 | TAGT-6 | 1.04E−08 |
| 157 and 63 | 7391 | TAGT-5 | 1.35E−08 |
| 1 and 122 | 3757 | TAGT-6 | 1.84E−08 |
| 1 and 122 | 3869 | TAGT-11 | 2.35E−08 |
| 1 and 122 | 5103 | TAGT-10 | 2.67E−09 |
| 1 and 122 | 5163 | TAGT-11 | 1.71E−08 |
| 34 and 63 | 4836 | TAGT-12 | 2.49E−09 |
| 34 and 63 | 4852 | TAGT-12 | 2.26E−09 |
| 34 and 63 | 4876 | TAGT-12 | 7.75E−09 |
| 50 and 162 | 7240 | TAGT-12 | 1.17E−08 |
| 50 and 162 | 7256 | TAGT-12 | 7.08E−09 |
| 50 and 162 | 7257 | TAGT-12 | 1.11E−08 |
| 158 and 63 | 5387 | TAGT-8 | 1.13E−09 |
| 158 and 63 | 5985 | TAGT-12 | 3.92E−08 |
| 158 and 63 | 5986 | TAGT-12 | 4.65E−08 |
| 158 and 104 | 5912 | TAGT-12 | 1.68E−08 |
| 158 and 104 | 5923 | TAGT-12 | 1.60E−08 |
| 158 and 104 | 7226 | TAGT-12 | 7.57E−09 |
| 5 and 121 | 4060 | TAGT-10 | 1.10E−08 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 5 and 121 | 4798 | TAGT-10 | 4.35E−09 |
| 5 and 121 | 6219 | TAGT-10 | 3.15E−09 |
| 6 and 116 | 4752 | TAGT-10 | 3.34E−09 |
| 6 and 116 | 6210 | TAGT-10 | 5.17E−10 |
| 6 and 116 | 6212 | TAGT-10 | 2.25E−09 |
| 138 and 63 | 4840 | TAGT-12 | 2.08E−09 |
| 138 and 63 | 5722 | TAGT-11 | 3.08E−08 |
| 138 and 63 | 7385 | TAGT-5 | 3.26E−09 |
| 7 and 121 | 4065 | TAGT-10 | 4.31E−08 |
| 7 and 121 | 4182 | TAGT-10 | 4.24E−09 |
| 7 and 121 | 4741 | TAGT-10 | 1.66E−09 |
| 145 and 128 | 4101 | TAGT-8 | 2.12E−09 |
| 145 and 128 | 4661 | TAGT-8 | 1.62E−09 |
| 145 and 128 | 4792 | TAGT-10 | 7.39E−09 |
| 17 and 63 | 4818 | TAGT-12 | 1.02E−09 |
| 17 and 63 | 4841 | TAGT-12 | 4.50E−10 |
| 22 and 61 | 5271 | TAGT-1 | 1.24E−08 |
| 22 and 61 | 7207 | TAGT-5 | 4.99E−10 |
| 25 and 101 | 4217 | TAGT-6 | 9.67E−08 |
| 25 and 101 | 4218 | TAGT-6 | 2.85E−08 |
| 25 and 114 | 5968 | TAGT-12 | 1.27E−08 |
| 25 and 114 | 5990 | TAGT-12 | 1.15E−08 |
| 29 and 112 | 5930 | TAGT-12 | 5.66E−09 |
| 29 and 112 | 5932 | TAGT-12 | 1.12E−08 |
| 31 and 63 | 5658 | TAGT-11 | 2.61E−10 |
| 31 and 63 | 7394 | TAGT-5 | 8.75E−09 |
| 152 and 63 | 4897 | TAGT-12 | 6.83E−10 |
| 152 and 63 | 4901 | TAGT-12 | 3.19E−09 |
| 153 and 63 | 4817 | TAGT-12 | 2.06E−09 |
| 153 and 63 | 7316 | TAGT-5 | 2.04E−08 |
| 155 and 67 | 4026 | TAGT-8 | 3.08E−09 |
| 155 and 67 | 7274 | TAGT-5 | 1.63E−08 |
| 156 and 89 | 7079 | TAGT-6 | 2.99E−08 |
| 156 and 89 | 7133 | TAGT-6 | 4.03E−08 |
| 156 and 100 | 5417 | TAGT-6 | 4.04E−08 |
| 156 and 100 | 5974 | TAGT-12 | 5.02E−08 |
| 157 and 94 | 7088 | TAGT-6 | 4.36E−08 |
| 157 and 94 | 7100 | TAGT-6 | 3.50E−08 |
| 48 and 58 | 5314 | TAGT-6 | 8.39E−09 |
| 48 and 58 | 5342 | TAGT-6 | 3.89E−08 |
| 50 and 89 | 5929 | TAGT-12 | 3.20E−08 |
| 50 and 89 | 7219 | TAGT-12 | 1.44E−08 |
| 50 and 163 | 5999 | TAGT-12 | 6.29E−08 |
| 50 and 163 | 7235 | TAGT-12 | 2.18E−08 |
| 158 and 160 | 5911 | TAGT-12 | 3.35E−08 |
| 158 and 160 | 7216 | TAGT-12 | 1.88E−08 |
| 158 and 87 | 4216 | TAGT-6 | 2.59E−08 |
| 158 and 87 | 7201 | TAGT-6 | 3.26E−08 |
| 158 and 92 | 7080 | TAGT-6 | 2.44E−08 |
| 158 and 92 | 7081 | TAGT-6 | 4.31E−08 |
| 158 and 93 | 7078 | TAGT-6 | 2.52E−08 |
| 158 and 93 | 7087 | TAGT-6 | 6.96E−08 |
| 158 and 97 | 5915 | TAGT-12 | 1.82E−08 |
| 158 and 97 | 5964 | TAGT-12 | 1.40E−08 |
| 158 and 103 | 5961 | TAGT-12 | 2.41E−08 |
| 158 and 103 | 7255 | TAGT-12 | 1.20E−08 |
| 158 and 164 | 7211 | TAGT-12 | 1.26E−08 |
| 158 and 164 | 7220 | TAGT-12 | 9.12E−09 |
| 51 and 162 | 4074 | TAGT-6 | 1.95E−08 |
| 51 and 162 | 7237 | TAGT-12 | 2.13E−08 |
| 137 and 54 | 7277 | TAGT-5 | 2.56E−09 |
| 137 and 54 | 7390 | TAGT-5 | 1.44E−09 |
| 3 and 127 | 7044 | TAGT-8 | 1.12E−09 |
| 3 and 127 | 7045 | TAGT-8 | 1.11E−09 |
| 4 and 85 | 7260 | TAGT-5 | 2.30E−09 |
| 4 and 85 | 7374 | TAGT-5 | 1.97E−08 |
| 4 and 110 | 6183 | TAGT-10 | 2.70E−09 |
| 4 and 110 | 6206 | TAGT-10 | 3.44E−09 |
| 138 and 123 | 3762 | TAGT-6 | 3.04E−08 |
| 138 and 123 | 3865 | TAGT-11 | 9.48E−09 |
| 139 and 109 | 6184 | TAGT-10 | <1.0E−12 |
| 139 and 109 | 6216 | TAGT-10 | 6.58E−10 |
| 139 and 121 | 6187 | TAGT-10 | 2.74E−08 |
| 139 and 121 | 6197 | TAGT-10 | 8.56E−09 |

TABLE 9-continued

Affinity data for confirmed hits using new HVR-H1 and HVR-H2 sequences

| HVR SEQ ID NO(S): | Hit ID | Antigen | Kd (M) |
|---|---|---|---|
| 8 and 120 | 6190 | TAGT-10 | 2.55E−09 |
| 8 and 120 | 6203 | TAGT-10 | 1.05E−08 |
| 140 and 131 | 7215 | TAGT-12 | 1.61E−08 |
| 140 and 131 | 7243 | TAGT-12 | 4.95E−09 |
| 141 and 116 | 6204 | TAGT-10 | 6.46E−09 |
| 141 and 116 | 6214 | TAGT-10 | 1.51E−09 |
| 142 and 159 | 5554 | TAGT-2 | 2.88E−09 |
| 142 and 159 | 5622 | TAGT-2 | 3.06E−09 |
| 143 and 116 | 6194 | TAGT-10 | 2.49E−10 |
| 143 and 116 | 6196 | TAGT-10 | <1.0E−12 |
| 144 and 121 | 6185 | TAGT-10 | 1.57E−09 |
| 144 and 121 | 6209 | TAGT-10 | 3.35E−09 |
| 146 and 110 | 4055 | TAGT-10 | 1.07E−08 |
| 146 and 110 | 4743 | TAGT-10 | 7.40E−09 |
| 147 and 133 | 5935 | TAGT-12 | 8.78E−09 |
| 147 and 133 | 6008 | TAGT-12 | 5.10E−08 |
| 148 and 63 | 5195 | TAGT-1 | 2.62E−08 |
| 148 and 63 | 5290 | TAGT-1 | 6.73E−09 |
| 13 and 118 | 7025 | TAGT-8 | 4.87E−08 |
| 13 and 118 | 7037 | TAGT-8 | 2.10E−08 |

An HVR-H1 comprising SEQ ID NO:16 was used in 8 unique hits. Using this same HVR-H1 sequence, but different sequences of the other HVRs, those 8 hits were capable of binding to 5 different target antigens. Exemplary hit IDs 4034, 6010, and 7183, which bound to TAGT-8, TAGT-12, and TAGT-6, respectively, contained an HVR-H1 comprising SEQ ID NO:16.

An HVR-H2 comprising SEQ ID NO:63 was used in 40 unique hits. Using this same HVR-H2 sequence, but different sequences of the other HVRs, those 40 hits were capable of binding to 7 different target antigens. Exemplary hit IDs 4036, 5115, and 5404, which bound to TAGT-8, TAGT-12, and TAGT-6, respectively, contained an HVR-H2 comprising SEQ ID NO:63.

Exemplary hit IDs 3757 and 5103 contained the same heavy chain variable region, including the same HVR-H1 and HVR-H2 sequences (SEQ ID NOS: 1 and 122), but when combined with different variable light chain domains, they bound to two different target antigens (TAGT-6 and TAGT-10, respectively). Two additional hits with these same HVR-H1 and HVR-H2 sequences could bind to another target antigen, TAGT-11.

Exemplary hit ID 4027, containing the HVR-H1 and HVR-H2 sequences of SEQ ID NOS:31 and 124, was capable of binding the same antigen from two different species (TAGT-8H and TAGT-8M). Several other hits with these same HVR-H1 and HVR-H2 sequences demonstrated species cross-reactivity.

The novel methodology employed to identify the dynamic motif of the redefined hyper-variable regions of antibodies based upon structural and sequence variability has led to the design of a limited number of $V_H$ components that can bind to the same or multiple different targets depending upon the $V_L$ segment with which the $V_H$ components are paired. The data and antibodies described herein reveals that the heavy chain library, either used as a whole set or a subset, is robust enough to serve as the $V_H$ component for antibody discovery.

SEQUENCES

All polypeptide sequences are presented N-terminal to C-terminal unless otherwise noted. All polynucleotide sequences are presented 5' to 3' unless otherwise noted.

Designed HVR-H1 sequence 1: (SEQ ID NO: 1)
FTFTDYGIHWV

Designed HVR-H1 sequence 2: (SEQ ID NO: 2)
FTFTGYAIHWV

Designed HVR-H1 sequence 3: (SEQ ID NO: 3)
FTFTNYGIHWV

Designed HVR-H1 sequence 4: (SEQ ID NO: 4)
YTFSDYAIHWV

Designed HVR-H1 sequence 5: (SEQ ID NO: 5)
YTFSDYGIHWV

Designed HVR-H1 sequence 6: (SEQ ID NO: 6)
YTFSGYAIHWV

Designed HVR-H1 sequence 7: (SEQ ID NO: 7)
YTFSGYGIHWV

Designed HVR-H1 sequence 8: (SEQ ID NO: 8)
YTFSNYGIHWV

Designed HVR-H1 sequence 9: (SEQ ID NO: 9)
YTFSSYGIHWV

Designed HVR-H1 sequence 10: (SEQ ID NO: 10)
YTFSGYWIHWV

Designed HVR-H1 sequence 11: (SEQ ID NO: 11)
YTFSNYWIHWV

Designed HVR-H1 sequence 12: (SEQ ID NO: 12)
FTFSGYWIHWV

Designed HVR-H1 sequence 13: (SEQ ID NO: 13)
FTFSNYWIHWV

Designed HVR-H1 sequence 14: (SEQ ID NO: 14)
YTFSDYWIHWV

Designed HVR-H1 sequence 15: (SEQ ID NO: 15)
YSISSGHHWAWI

Designed HVR-H1 sequence 16: (SEQ ID NO: 16)
YSISSGHYWNWI

Designed HVR-H1 sequence 17: (SEQ ID NO: 17)
YSISSGHYWSWI

Designed HVR-H1 sequence 18: (SEQ ID NO: 18)
YSISSGHYWTWI

-continued

Designed HVR-H1 sequence 19: (SEQ ID NO: 19)
YSISSGYHWAWI

Designed HVR-H1 sequence 20: (SEQ ID NO: 20)
YSISSGYHWDWI

Designed HVR-H1 sequence 21: (SEQ ID NO: 21)
YSISSGYHWGWI

Designed HVR-H1 sequence 22: (SEQ ID NO: 22)
YSISSGYHWNWI

Designed HVR-H1 sequence 23: (SEQ ID NO: 23)
YSISSGYHWSWI

Designed HVR-H1 sequence 24: (SEQ ID NO: 24)
YSISSGHHWDWI

Designed HVR-H1 sequence 25: (SEQ ID NO: 25)
YSISSGYYWDWI

Designed HVR-H1 sequence 26: (SEQ ID NO: 26)
YSISSGYYWNWI

Designed HVR-H1 sequence 27: (SEQ ID NO: 27)
YSISSGYYWTWI

Designed HVR-H1 sequence 28: (SEQ ID NO: 28)
YSITSGHHWAWI

Designed HVR-H1 sequence 29: (SEQ ID NO: 29)
YSITSGHHWDWI

Designed HVR-H1 sequence 30: (SEQ ID NO: 30)
YSITSGHHWGWI

Designed HVR-H1 sequence 31: (SEQ ID NO: 31)
YSITSGHHWNWI

Designed HVR-H1 sequence 32: (SEQ ID NO: 32)
YSITSGHHWSWI

Designed HVR-H1 sequence 33: (SEQ ID NO: 33)
YSISSGHHWGWI

Designed HVR-H1 sequence 34: (SEQ ID NO: 34)
YSITSGHYWAWI

Designed HVR-H1 sequence 35: (SEQ ID NO: 35)
YSITSGHYWDWI

Designed HVR-H1 sequence 36: (SEQ ID NO: 36)
YSITSGHYWGWI

Designed HVR-H1 sequence 37: (SEQ ID NO: 37)
YSITSGHYWNWI

Designed HVR-H1 sequence 38: (SEQ ID NO: 38)
YSITSGHYWSWI

-continued

Designed HVR-H1 sequence 39: (SEQ ID NO: 39)
YSITSGYHWAWI

Designed HVR-H1 sequence 40: (SEQ ID NO: 40)
YSITSGYHWGWI

Designed HVR-H1 sequence 41: (SEQ ID NO: 41)
YSISSGHHWNWI

Designed HVR-H1 sequence 42: (SEQ ID NO: 42)
YSITSGYHWNWI

Designed HVR-H1 sequence 43: (SEQ ID NO: 43)
YSITSGYHWSWI

Designed HVR-H1 sequence 44: (SEQ ID NO: 44)
YSITSGYYWDWI

Designed HVR-H1 sequence 45: (SEQ ID NO: 45)
YSISSGHHWTWI

Designed HVR-H1 sequence 46: (SEQ ID NO: 46)
YSISSGHYWDWI

Designed HVR-H1 sequence 47: (SEQ ID NO: 47)
FSLSTSGVAVSWI

Designed HVR-H1 sequence 48: (SEQ ID NO: 48)
FSLSTGGVAVGWI

Designed HVR-H1 sequence 49: (SEQ ID NO: 49)
FSLSTGGVAVSWI

Designed HVR-H1 sequence 50: (SEQ ID NO: 50)
FSLSTGGVGVAWI

Designed HVR-H1 sequence 51: (SEQ ID NO: 51)
FSLSTGGVGVSWI

Designed HVR-H1 sequence 52: (SEQ ID NO: 52)
FSLSTSGVAVAWI

Designed HVR-H1 sequence 53: (SEQ ID NO: 137)
FTFSDYAIHWV

Designed HVR-H1 sequence 54: (SEQ ID NO: 138)
FTFSDYGIHWV

Designed HVR-H1 sequence 55: (SEQ ID NO: 139)
YTFSNYAIHWV

Designed HVR-H1 sequence 56: (SEQ ID NO: 140)
YTFSSYAIHWV

Designed HVR-H1 sequence 57: (SEQ ID NO: 141)
YTFTDYAIHWV

Designed HVR-H1 sequence 58: (SEQ ID NO: 142)
YTFTDYGIHWV

-continued

Designed HVR-H1 sequence 59: (SEQ ID NO: 143)
YTFTNYAIHWV

Designed HVR-H1 sequence 60: (SEQ ID NO: 144)
YTFTNYGIHWV

Designed HVR-H1 sequence 61: (SEQ ID NO: 145)
FTFSGYGIHWV

Designed HVR-H1 sequence 62: (SEQ ID NO: 146)
FTFSNYAIHWV

Designed HVR-H1 sequence 63: (SEQ ID NO: 147)
FTFSSYGIHWV

Designed HVR-H1 sequence 64: (SEQ ID NO: 148)
FTFSDYWIHWV

Designed HVR-H1 sequence 65: (SEQ ID NO: 149)
FTFTSYWIHWV

Designed HVR-H1 sequence 66: (SEQ ID NO: 150)
YSISSGYYWGWI

Designed HVR-H1 sequence 67: (SEQ ID NO: 151)
YSITSGYYWNWI

Designed HVR-H1 sequence 68: (SEQ ID NO: 152)
YSITSGYYWSWI

Designed HVR-H1 sequence 69: (SEQ ID NO: 153)
YSISSGHYWAWI

Designed HVR-H1 sequence 70: (SEQ ID NO: 154)
YSISSGHYWGWI

Designed HVR-H1 sequence 71: (SEQ ID NO: 155)
FSLSTSGVAVGWI

Designed HVR-H1 sequence 72: (SEQ ID NO: 156)
FSLSTSGVGVAWI

Designed HVR-H1 sequence 73: (SEQ ID NO: 157)
FSLSTSGVGVGWI

Designed HVR-H1 sequence 74: (SEQ ID NO: 158)
FSLSTGGVGVGWI

Designed HVR-H2 sequence 1: (SEQ ID NO: 53)
LARIDWDDDKRYSPSLKSRL

Designed HVR-H2 sequence 2: (SEQ ID NO: 54)
LALIDWDDDKRYSPSLKSRL

Designed HVR-H2 sequence 3: (SEQ ID NO: 55)
LALIDWDDDKRYSTSLKSRL

Designed HVR-H2 sequence 4: (SEQ ID NO: 56)
LALIDWDDDKYYSPSLKSRL

Designed HVR-H2 sequence 5:
(SEQ ID NO: 57)
LALIDWADDKYYSPSLKSRL

Designed HVR-H2 sequence 6:
(SEQ ID NO: 58)
LALIDWAGDKSYSTSLKSRL

Designed HVR-H2 sequence 7:
(SEQ ID NO: 59)
LARIDWDDDKYYSPSLKSRL

Designed HVR-H2 sequence 8:
(SEQ ID NO: 60)
LARIDWDDDKYYSTSLKSRL

Designed HVR-H2 sequence 9:
(SEQ ID NO: 61)
LARIDWDGDKYYSTSLKSRL

Designed HVR-H2 sequence 10:
(SEQ ID NO: 62)
IGDIYHSGSTYYSPSLKSRV

Designed HVR-H2 sequence 11:
(SEQ ID NO: 63)
IGEIYHSGSTYYSPSLKSRV

Designed HVR-H2 sequence 12:
(SEQ ID NO: 64)
IGEIYYSGSTYYSPSLKSRV

Designed HVR-H2 sequence 13:
(SEQ ID NO: 65)
IGSIYHSGNTNYNPSLKSRV

Designed HVR-H2 sequence 14:
(SEQ ID NO: 66)
IGEIYHSGNTYYNPSLKSRV

Designed HVR-H2 sequence 15:
(SEQ ID NO: 67)
IGEIYHSGSTYYNPSLKSRV

Designed HVR-H2 sequence 16:
(SEQ ID NO: 68)
IGEIYYSGSTYYNPSLKSRV

Designed HVR-H2 sequence 17:
(SEQ ID NO: 69)
IGDIYHSGNTYYNPSLKSRV

Designed HVR-H2 sequence 18:
(SEQ ID NO: 70)
IGDIYHSGSTYYNPSLKSRV

Designed HVR-H2 sequence 19:
(SEQ ID NO: 71)
VSAISGYGDTTYYADSVKGRF

Designed HVR-H2 sequence 20:
(SEQ ID NO: 72)
VSAISGYGGSTYYADSVKGRF

Designed HVR-H2 sequence 21:
(SEQ ID NO: 73)
VSAISGYGGTTYYADSVKGRF

Designed HVR-H2 sequence 22:
(SEQ ID NO: 74)
VSGISGAGDTTYYADSVKGRF

Designed HVR-H2 sequence 23:
(SEQ ID NO: 75)
VSGISGDGDTTYYADSVKGRF

Designed HVR-H2 sequence 24:
(SEQ ID NO: 76)
VSGISGDGGSTYYADSVKGRF

Designed HVR-H2 sequence 25:
(SEQ ID NO: 77)
VSGISGYGDTTYYADSVKGRF

Designed HVR-H2 sequence 26:
(SEQ ID NO: 78)
VSGISGYGGTTYYADSVKGRF

Designed HVR-H2 sequence 27:
(SEQ ID NO: 79)
VSVISGDGDTTYYADSVKGRF

Designed HVR-H2 sequence 28:
(SEQ ID NO: 80)
VSVISGYGGSTYYADSVKGRF

Designed HVR-H2 sequence 29:
(SEQ ID NO: 81)
VSGISGDGSTTYYADSVKGRF

Designed HVR-H2 sequence 30:
(SEQ ID NO: 82)
VSGISGYGSTTYYADSVKGRF

Designed HVR-H2 sequence 31:
(SEQ ID NO: 83)
VSVISGSGSTTYYADSVKGRF

Designed HVR-H2 sequence 32:
(SEQ ID NO: 84)
VSVISGYGSSTYYADSVKGRF

Designed HVR-H2 sequence 33:
(SEQ ID NO: 85)
VSVISGYGSTTYYADSVKGRF

Designed HVR-H2 sequence 34:
(SEQ ID NO: 86)
VSAISGYGSTTYYADSVKGRF

Designed HVR-H2 sequence 35:
(SEQ ID NO: 87)
VSSISGYGDTTYYADSVKGRF

Designed HVR-H2 sequence 36:
(SEQ ID NO: 88)
VSSISGYGGSTYYADSVKGRF

Designed HVR-H2 sequence 37:
(SEQ ID NO: 89)
VSSISGYGGTTYYADSVKGRF

Designed HVR-H2 sequence 38:
(SEQ ID NO: 90)
VSYISGAGDTTYYADSVKGRF

Designed HVR-H2 sequence 39:
(SEQ ID NO: 91)
VSSISGAGDTTYYADSVKGRF

Designed HVR-H2 sequence 40:
(SEQ ID NO: 92)
VSYISGAGGTTYYADSVKGRF

Designed HVR-H2 sequence 41:
(SEQ ID NO: 93)
VSYISGDGDTTYYADSVKGRF

Designed HVR-H2 sequence 42:
(SEQ ID NO: 94)
VSYISGDGGSTYYADSVKGRF

Designed HVR-H2 sequence 43:
(SEQ ID NO: 95)
VSYISGDGGTTYYADSVKGRF

Designed HVR-H2 sequence 44:
(SEQ ID NO: 96)
VSYISGSGDTTYYADSVKGRF

-continued

Designed HVR-H2 sequence 45: (SEQ ID NO: 97)
VSSISGAGGSTYYADSVKGRF

Designed HVR-H2 sequence 46: (SEQ ID NO: 98)
VSYISGYGDTTYYADSVKGRF

Designed HVR-H2 sequence 47: (SEQ ID NO: 99)
VSYISGYGGTTYYADSVKGRF

Designed HVR-H2 sequence 48: (SEQ ID NO: 100)
VSSISGAGGTTYYADSVKGRF

Designed HVR-H2 sequence 49: (SEQ ID NO: 101)
VSSISGDGDTTYYADSVKGRF

Designed HVR-H2 sequence 50: (SEQ ID NO: 102)
VSSISGDGGTTYYADSVKGRF

Designed HVR-H2 sequence 51: (SEQ ID NO: 103)
VSSISGAGSSTYYADSVKGRF

Designed HVR-H2 sequence 52: (SEQ ID NO: 104)
VSSISGAGSTTYYADSVKGRF

Designed HVR-H2 sequence 53: (SEQ ID NO: 105)
VSSISGDGSSTYYADSVKGRF

Designed HVR-H2 sequence 54: (SEQ ID NO: 106)
VSSISGDGSTTYYADSVKGRF

Designed HVR-H2 sequence 55: (SEQ ID NO: 107)
VSSISGYGSSTYYADSVKGRF

Designed HVR-H2 sequence 56: (SEQ ID NO: 108)
VSSISGYGSTTYYADSVKGRF

Designed HVR-H2 sequence 57: (SEQ ID NO: 109)
IGWINPNRGDTKYAQKFQGRV

Designed HVR-H2 sequence 58: (SEQ ID NO: 110)
IGWINPNRGDTNYAQKFQGRV

Designed HVR-H2 sequence 59: (SEQ ID NO: 111)
IGWINPNRGGTKYAQKFQGRV

Designed HVR-H2 sequence 60: (SEQ ID NO: 112)
IGWINPNRGGTNYAQKFQGRV

Designed HVR-H2 sequence 61: (SEQ ID NO: 113)
IGWINPNRGSTKYAQKFQGRV

Designed HVR-H2 sequence 62: (SEQ ID NO: 114)
IGWINPNRGSTNYAQKFQGRV

Designed HVR-H2 sequence 63: (SEQ ID NO: 115)
IGRINPNFGDTNYAQKFQGRV

Designed HVR-H2 sequence 64: (SEQ ID NO: 116)
IGWINPNFGDTNYAQKFQGRV

-continued

Designed HVR-H2 sequence 65: (SEQ ID NO: 117)
IGWINPNFGSTKYAQKFQGRV

Designed HVR-H2 sequence 66: (SEQ ID NO: 118)
IGWINPNFGSTNYAQKFQGRV

Designed HVR-H2 sequence 67: (SEQ ID NO: 119)
IGIINPNRGDTKYAQKFQGRV

Designed HVR-H2 sequence 68: (SEQ ID NO: 120)
IGIINPNRGDTNYAQKFQGRV

Designed HVR-H2 sequence 69: (SEQ ID NO: 121)
IGIINPNFGDTNYAQKFQGRV

Designed HVR-H2 sequence 70: (SEQ ID NO: 122)
IGWISPSGGGTKYAQKFQGRV

Designed HVR-H2 sequence 71: (SEQ ID NO: 123)
IGWISPSGGGTNYAQKFQGRV

Designed HVR-H2 sequence 72: (SEQ ID NO: 124)
IGWISPSSGGTKYAQKFQGRV

Designed HVR-H2 sequence 73: (SEQ ID NO: 125)
IGWISPSSGGTNYAQKFQGRV

Designed HVR-H2 sequence 74: (SEQ ID NO: 126)
IGWIYPSGGGTKYAQKFQGRV

Designed HVR-H2 sequence 75: (SEQ ID NO: 127)
IGWIYPSGGGTNYAQKFQGRV

Designed HVR-H2 sequence 76: (SEQ ID NO: 128)
IGWISPSGGSTNYAQKFQGRV

Designed HVR-H2 sequence 77: (SEQ ID NO: 129)
IGWISPSSGSTKYAQKFQGRV

Designed HVR-H2 sequence 78: (SEQ ID NO: 130)
IGWISPSSGSTNYAQKFQGRV

Designed HVR-H2 sequence 79: (SEQ ID NO: 131)
IGWISPSGGSTKYAQKFQGRV

Designed HVR-H2 sequence 80: (SEQ ID NO: 132)
IGIIYPSGGGTNYAQKFQGRV

Designed HVR-H2 sequence 81: (SEQ ID NO: 133)
IGIISPSGGGTKYAQKFQGRV

Designed HVR-H2 sequence 82: (SEQ ID No: 134)
IGIISPSGGGTNYAQKFQGRV

Designed HVR-H2 sequence 83: (SEQ ID NO: 135)
IGIIYPSGGSTNYAQKFQGRV

Designed HVR-H2 sequence 84: (SEQ ID NO: 136)
VGRIKSKTDGYTTEYAAPVKGRF

-continued

Designed HVR-H2 sequence 85:
(SEQ ID NO: 159)
VSAISGSGSTTYYADSVKGRF

Designed HVR-H2 sequence 86:
(SEQ ID NO: 160)
VSSISGSGDTTYYADSVKGRF

Designed HVR-H2 sequence 87:
(SEQ ID NO: 161)
VSSISGSGGSTYYADSVKGRF

Designed HVR-H2 sequence 88:
(SEQ ID NO: 162)
VSSISGSGGTTYYADSVKGRF

Designed HVR-H2 sequence 89:
(SEQ ID NO: 163)
VSSISGDGGSTYYADSVKGRF

Designed HVR-H2 sequence 90:
(SEQ ID NO: 164)
VSSISGSGSTTYYADSVKGRF

Framework FW-H1 sequence:
(SEQ ID NO: 165)
EVQLVESGGGLVQPGGSLRLSCAASG

Framework FW-H2 sequence:
(SEQ ID NO: 166)
RQAPGKGLEW

Framework FW-H3 sequence:
(SEQ ID NO: 167)
TISSRDNSKNTLYLQLNSLRAEDTAVYYC

Framework FW-H4 sequence:
(SEQ ID NO: 168)
WGQGTLVTVSS

Hit ID 4029—VH
(SEQ ID NO: 169)
EVQLVESGGGLVQPGGSLRLSCAASGYSITSGYHWGWIRQAPGKGLEWVSY
ISGAGDTTYYADSVKGRFTISRDNSKNTLYLQLNSLRAEDTAVYYCARDYG
DYYGFDYWGQGTLVTVSS

HIT ID 4029—VL
(SEQ ID NO: 170)
DIQLTQSPSSLSASVGDRVTITCRASQSVDFYGISFLAWYQQKPGKAPKLL
IYDASNLETGVPSRFSGSGSGTDFTLTISSLQPEDFATYYCQQSYRTPFTF
GQGTKVEIKR

Hit ID 7097—VH
(SEQ ID NO: 171)
EVQLVESGGGLVQPGGSLRLCAASGYSISSGHHWDWIRQAPGKGLEWVSYI
SGAGDTTYYADSVKGRFTISRDNSKNTLYLQLNSLRAEDTAVYYCAREGSD
AVLGDWFAYWGQGTLVTVSS

HIT ID 7097—VL
(SEQ ID NO: 172)
DIQLTQSPSSLSASVGDRVTITCRASQGISSYLAWYQQKPGKAPKLLIYDA
SNLETGVPSRFSGSGSGTDFTLTISSLQPEDFATYYCQQYYSTPLTFGQGT
KVEIKR

Hit ID 5906—VH
(SEQ ID NO: 173)
EVQLVESGGGLVQPGGSLRLSCAASGYSISSGYHWNWIRQAPGKGLEWVSY
ISGDGDTTYYADSVKGRFTISRDNSKNTLYLQLNSLRAEDTAVYYCARDLG
GYYGWGRYFDYWGQGTLVTVSS

-continued

HIT ID 5906—VL
(SEQ ID NO: 174)
DIQLTQSPSSLSASVGDRVTITCRASQSVSSYLAWYQQKPGKAPKLLIYDA
SNLETGVPSRFSGSGSGTDFTLTISSLQPEDFATYYCQQSYSTPLTFGQGT
KVEIKR

Hit ID 7040—VH
(SEQ ID NO: 175)
EVQLVESGGGLVQPGGSLRLSCAASGYSISSGYYWNWIRQAPGKGLEWIGW
ISPSGGSTNYAQKFQGRVTISRDNSKNTLYLQLNSLRAEDTAVYYCARDLT
AGGFDYWGQGTLVTVSS

HIT ID 7040—VL
(SEQ ID NO: 176)
DIQLTQSPSSLSASVGDRVTITCRASQGISSYLAWYQQKPGKAPKLLIYDA
SNLETGVPSRFSGSGSGTDFTLTISSLQPEDFATYYCQQYYSTPLTFGQGT
KVEIKR

Hit ID 5924—VH
(SEQ ID NO: 177)
EVQLVESGGGLVQPGGSLRLSCAASGYSISSGYHWGWIRQAPGKGLEWIGI
ISPSSGSTKYAQKFQGRVTISRDNSKNTLYLQLNSLRAEDTAVYYCARGAG
VHYALDYWGQGTLVTVSS

HIT ID 5924—VL
(SEQ ID NO: 178)
DIQLTQSPSSLSASVGDRVTITCRASQSVSSYLAWYQQKPGKAPKLLIYDA
SNLETGVPSRFSGSGSGTDFTLTISSLQPEDFATYYCQQSYSTPLTFGQGT
KVEIKR

Hit ID 4034—VH
(SEQ ID NO: 179)
EVQLVESGGGLVQPGGSLRLSCAASGYSISSGHYWNVVIRQAPGKGLEWVS
SISGYGSTTYYADSVKGRFTISRDNSKNTLYLQLNSLRAEDTAVYYCARER
YYGSTDYAFDYWGQGTLVTVSS

HIT ID 4034—VL
(SEQ ID NO: 180)
DIQLTQSPSSLSASVGDRVTITCSASSRVSHVFWYQQKPGKAPKLLIYAAS
TLQSGVPSRFSGSGSGTDFTLTISSLQPEDFATYFCLQGTHFPWTFGQGTK
VEIKR

Hit ID 6010—VH
(SEQ ID NO: 181)
EVQLVESGGGLVQPGGSLRLSCAASGYSISSGHYWNVVIRQAPGKGLEWIG
WINPNRGDTNYAQKFQGRVTISRDNSKNTLYLQLNSLRAEDTAVYYCARDY
YGDFDYWGQGTLVTVSS

HIT ID 6010—VL
(SEQ ID NO: 182)
DIQLTQSPSSLSASVGDRVTITCRASQSISSYLNVVYQQKPGKAPKLLIYD
ASNLETGVPSRFSGSGSGTDFTLTISSLQPEDFATYYCQHHYGTPLTFGQG
TKVEIKR

Hit ID 7183—VH
(SEQ ID NO: 183)
EVQLVESGGGLVQPGGSLRLSCAASGYSISSGHYWNWIRQAPGKGLEWVSS
ISGYGDTTYYADSVKGRFTISRDNSKNTLYLQLNSLRAEDTAVYYCAREGS
DTVLGDWFAYWGQGTLVTVSS

-continued

HIT ID 7183—VL (SEQ ID NO: 184)

DIQLTQSPSSLSASVGDRVTITCRASQSISSYLNVVYQQKPGKAPKLLIYD

ASNRATGIPSRFSGSGSGTDFTLTISSLQPEDFATYYCQQSYSTPPTFGQG

TKVEIKR

Hit ID 4036—VH (SEQ ID NO: 185)

EVQLVESGGGLVQPGGSLRLSCAASGFSLSTSGVGVGWIRQAPGKGLEWIG

EIYHSGSTYYSPSLKSRVTISRDNSKNTLYLQLNSLRAEDTAVYYCARERY

GSYYFDYWGQGTLVTVSS

HIT ID 4036—VL (SEQ ID NO: 186)

DIQLTQSPSSLSASVGDRVTITCRASQSVDFYGKSFLDWYQQKPGKAPKLL

IYDASSLESGVPSRFSGSGSGTDFTLTISSLQPEDFATYYCQQYYRIPPTF

GQGTKVEIKR

Hit ID 5115—VH (SEQ ID NO: 187)

EVQLVESGGGLVQPGGSLRLSCAASGYSISSGHYWGWIRQAPGKGLEWIGE

IYHSGSTYYSPSLKSRVTISRDNSKNTLYLQLNSLRAEDTAVYYCARESYY

AFDYWGQGTLVTVSS

HIT ID 5115—VL (SEQ ID NO: 188)

DIQLTQSPSSLSASVGDRVTITCRASQSVSSYLAWYQQKPGKAPKLLIYAA

STLQSGVPSRFSGSGSGTDFTLTISSLQPEDFATYYCQQYYTTPLTFGQGT

KVEIKR

Hit ID 5404—VH (SEQ ID NO: 189)

EVQLVESGGGLVQPGGSLRLSCAASGYSISSGYHWAWIRQAPGKGLEWIGE

IYHSGSTYYSPSLKSRVTISRDNSKNTLYLQLNSLRAEDTAVYYCARSPYY

YGVFDYWGQGTLVTVSS

HIT ID 5404—VL (SEQ ID NO: 190)

DIQLTQSPSSLSASVGDRVTITCSASSRVGSVYWYQQKPGKAPKLLIYDAS

NLETGVPSRFSGSGSGTDFTLTISSLQPEDFATYYCQQYTHDPVTFGQGTK

VEIKR

Hit ID 3757—VH (SEQ ID NO: 191)

EVQLVESGGGLVQPGGSLRLSCAASGFTFTDYGIHWVRQAPGKGLEWIGWI

SPSGGGTKYAQKFQGRVTISRDNSKNTLYLQLNSLRAEDTAVYYCARHSYY

GVGDFDYWGQGTLVTVSS

HIT ID 3757—VL (SEQ ID NO: 192)

DIQLTQSPSSLSASVGDRVTITCRASQSVSSYLAWYQQKPGKAPKLLIYDA

SNLETGVPSRFSGSGSGTDFTLTISSLQPEDFATYYCQQSYSTPLTFGQGT

KVEIKR

Hit ID 5103—VH (SEQ ID NO: 193)

EVQLVESGGGLVQPGGSLRLSCAASGFTFTDYGIHWVRQAPGKGLEWIGWI

SPSGGGTKYAQKFQGRVTISRDNSKNTLYLQLNSLRAEDTAVYYCARHSYY

GVGDFDYWGQGTLVTVSS

-continued

HIT ID 5103—VL (SEQ ID NO: 194)

DIQLTQSPSSLSASVGDRVTITCRASQSVSSYLAWYQQKPGKAPKLLIYDA

SNLETGVPSRFSGSGSGTDFTLTISSLQPEDFATYYCQQSYSTPLTFGQGT

KVEIKR

Hit ID 4027—VH (SEQ ID NO: 195)

EVQLVESGGGLVQPGGSLRLSCAASGYSITSGHHWNVVIRQAPGKGLEWIG

WISPSSGGTKYAQKFQGRVTISRDNSKNTLYLQLNSLRAEDTAVYYCARGF

DGFHYWGQGTLVTVSS

HIT ID 4027—VL (SEQ ID NO: 196)

DIQLTQSPSSLSASVGDRVTITCRASESVDFYGISFLPWYQQKPGKAPKLL

IYDASNRATGIPSRFSGSGSGTDFTLTISSLQPEDFATYYCQQSYSWPWTF

GQGTKVEIKR

VH in FIG. 1B (SEQ ID NO: 197)

EVQLVESGGGLVQPGGSLRLSCAASGFTFTSYGIHWVRQAPGKGLEWVSGI

SGAGDTTYYADSVKGRFTISRDNSKNTLYLQLNSLRAEDTAVYYCARERDY

DFDYWGQGTLVTVSS

Formula (I)

(SEQ ID NO: 198)

$X_1TFX_2X_3YX_4IHWV$,
wherein $X_1$ is F or Y, $X_2$ is S or T, $X_3$ is D, G, N, or S, and $X_4$ is A, G, or W Formula (II)

(SEQ ID NO: 199)

$YSIX_1SGX_2X_3WX_4WI$,
wherein $X_1$ is S or T, $X_2$ is H or Y, $X_3$ is H or Y, and $X_4$ is A, D, G, N, S, or T Formula (III)

(SEQ ID NO: 200)

$FSLSTX_1GVX_2VX_3WI$,
wherein $X_1$ is G or S, $X_2$ is A or G, and $X_3$ is A, G, S, or T Formula (IV)

(SEQ ID NO: 201)

$LAX_1IX_2WX_3X_4DKX_5YSX_6SLKSRL$,
wherein $X_1$ is L or R, $X_2$ is D or Y, $X_3$ is A, D, S, or Y, $X_4$ is D or G, $X_5$ is R, S, or Y, and $X_6$ is P or T Formula (V)

(SEQ ID NO: 202)

$IGX_1IX_2X_3SGSTYYSPSLKSRV$,
wherein $X_1$ is A, D, E, S, or Y, $X_2$ is S or Y, and $X_3$ is H or Y Formula (VI)

(SEQ ID NO: 203)

$IGX_1IYX_2SGX_3TX_4YNPSLKSRV$,
wherein $X_1$ is D, E, R, S, or Y, $X_2$ is H or Y, $X_3$ is N or S, and $X_4$ is N or Y Formula (VII)

(SEQ ID NO: 204)

$VSX_1ISGX_2GX_3X_4TYYADSVKGRF$,
wherein $X_1$ is A, G, S, V. or Y, $X_2$ is A, D, S, or Y, $X_3$ is D, G, or S, and $X_4$ is S or T Formula (VIII)

(SEQ ID NO: 205)

$IGX_1INPNX_2GX_3TX_4YAQKFQGRV$,
wherein $X_1$ is I, R, or W, $X_2$ is F or R, $X_3$ is D, G, or S, and $X_4$ is K or N -continued Formula (IX)

(SEQ ID NO: 206)

$IGX_1IX_2PSX_3GX_4TX_5YAQKFQGRV$,
wherein $X_1$ is I, R, or W, $X_2$ is S or Y, $X_3$ is G or S, $X_4$ is D, G, or S, and $X_5$ is K or N Formula (X)

(SEQ ID NO: 207)

$VGRIX_1SKX_2X_3GX_4TTX_5YAAX_6VKGRF$,
wherein $X_1$ is K or R, $X_2$ is A or T, $X_3$ is D or Y, $X_4$ is G or Y, $X_5$ is D or E, and $X_6$ is P or S Formula (XI)

(SEQ ID NO: 208)

$IGX_1IX_2X_3SGSTYYSPSLKSRV$,
wherein $X_1$ is A, D, or E, $X_2$ is S or Y, and $X_3$ is H or Y Formula (XII)

(SEQ ID NO: 209)

$IGX_1IYX_2SGX_3TX_4YNPSLKSRV$,
wherein $X_1$ is D, E, or S, $X_2$ is H or Y, $X_3$ is N or S, and $X_4$ is N or Y Formula (XIII)

(SEQ ID NO: 210)

$VGRIX_1SKX_2X_3GX_4TTEYAAX_5VKGRF$,
wherein $X_1$ is K or R, $X_2$ is A or T, $X_3$ is D or Y, $X_4$ is G or Y, $X_5$ is P or S Primer F_1999

(SEQ ID NO: 211)

CGTTTGTCCTGTGCAGCTTCCGG

Primer R_1999

(SEQ ID NO: 212)

CGAGGCCCTTACCCGGGGCCTGACG

Primer F_2003

(SEQ ID NO: 213)

CCGGGTAAGGGCCTCGAGTGG

Primer R_2003

(SEQ ID NO: 214)

GAGCACGTCCGTTCGAATTGTCGCGACTTATAG

Primer S1089

(SEQ ID NO: 215)

ACAACTGAACAGCTTAAGAGCTGAGGACACTGCCGTCTATTATTG

Primer S1090

(SEQ ID NO: 216)

GAGGAGACGGTGACTAGTGTTCCTTGACCCCA

Primer F_2898

(SEQ ID NO: 217)

TACTTATGTAGGCGATCGGGTCACCATCACCTGC

Primer R_2898

(SEQ ID NO: 218)

CGGAGCTTTTCCTGGTTTCTGTTGATAC

Primer F_2013

(SEQ ID NO: 219)

GAAACCAGGAAAAGCTCCGAAG

Primer R_2013

(SEQ ID NO: 220)

CGTCCCGGAACCGGATCCAGAGAAGCGAG

Primer F2929

(SEQ ID NO: 221)

ACCATCAGCAGTCTGCAGCCGGAAGACTTCGCAAC

Primer R2929

(SEQ ID NO: 222)

GATCTCCACCTTGGTACCCTGTCCGAA

HVR-H3 sequence 1:

(SEQ ID NO: 223)

ARDLGGYYGWGRYFDY

-continued

HVR-H3 sequence 2:

(SEQ ID NO: 224)

ARDLTAGGFDY

HVR-H3 sequence 3:

(SEQ ID NO: 225)

ARDPGVGGFDV

HVR-H3 sequence 4:

(SEQ ID NO: 226)

ARDPGYTWYFDV

HVR-H3 sequence 5:

(SEQ ID NO: 227)

ARDYGDYYGFDY

HVR-H3 sequence 6:

(SEQ ID NO: 228)

ARDYGYTWYFDV

HVR-H3 sequence 7:

(SEQ ID NO: 229)

ARDYYGDFDY

HVR-H3 sequence 8:

(SEQ ID NO: 230)

AREGSDAVLGDWFAY

HVR-H3 sequence 9:

(SEQ ID NO: 231)

AREGSDTVLGDWFAY

HVR-H3 sequence 10:

(SEQ ID NO: 232)

ARERYGSYYFDY

HVR-H3 sequence 11:

(SEQ ID NO: 233)

ARERYYGSTDYAFDY

HVR-H3 sequence 12:

(SEQ ID NO: 234)

ARESYYAFDY

HVR-H3 sequence 13:

(SEQ ID NO: 235)

ARGAGVHYALDY

HVR-H3 sequence 14:

(SEQ ID NO: 236)

ARGFDGFHY

HVR-H3 sequence 15:

(SEQ ID NO: 237)

ARGFYGGALDV

HVR-H3 sequence 16:

(SEQ ID NO: 238)

ARGGGGYYFDV

HVR-H3 sequence 17:

(SEQ ID NO: 239)

ARGGGLGFDY

HVR-H3 sequence 18:

(SEQ ID NO: 240)

ARGGLGPFDI

HVR-H3 sequence 19:

(SEQ ID NO: 241)

ARGGSDTVIGDWFAY

HVR-H3 sequence 20:

(SEQ ID NO: 242)

ARGGVGPFDI

HVR-H3 sequence 21:

(SEQ ID NO: 243)

ARGGYGGYLDV

HVR-H3 sequence 22: (SEQ ID NO: 244)
ARGLSSGYFDY

HVR-H3 sequence 23: (SEQ ID NO: 245)
ARGSWYFDV

HVR-H3 sequence 24: (SEQ ID NO: 246)
ARGTRGLDY

HVR-H3 sequence 25: (SEQ ID NO: 247)
ARGYSDYFDY

HVR-H3 sequence 26: (SEQ ID NO: 248)
ARGYYYGRAFDY

HVR-H3 sequence 27: (SEQ ID NO: 249)
ARHSYYGVGDFDY

HVR-H3 sequence 28: (SEQ ID NO: 250)
ARLFEGFPY

HVR-H3 sequence 29: (SEQ ID NO: 251)
ARLYDYFAY

HVR-H3 sequence 30: (SEQ ID NO: 252)
ARSGYYALDY

HVR-H3 sequence 31: (SEQ ID NO: 253)
ARSPYYYGVFDY

HVR-H3 sequence 32: (SEQ ID NO: 254)
ARSYVYFDY

HVR-H3 sequence 33: (SEQ ID NO: 255)
ARDGLGLRGVYYYYYGLDV

HVR-H3 sequence 34: (SEQ ID NO: 256)
ARVGESGGIESPYYYYGLDV

HVR-L1 sequence 1: (SEQ ID NO: 257)
RASESVDFYGISFLP

HVR-L1 sequence 2: (SEQ ID NO: 258)
RASQSVDFYGISFLA

HVR-L1 sequence 3: (SEQ ID NO: 259)
RASQSVDFYGKSFLD

HVR-L1 sequence 4: (SEQ ID NO: 260)
SASSRVGSVY

HVR-L1 sequence 5: (SEQ ID NO: 261)
SASSRVSHVF

HVR-L1 sequence 6: (SEQ ID NO: 262)
RASQGISSYLA

HVR-L1 sequence 7: (SEQ ID NO: 263)
RASQSVSSYLA

HVR-L1 sequence 8: (SEQ ID NO: 264)
RASQSISSYLN

HVR-L3 sequence 1: (SEQ ID NO: 265)
FCLQGTHFPWT

HVR-L3 sequence 2: (SEQ ID NO: 266)
YCQQSYRTPFT

HVR-L3 sequence 3: (SEQ ID NO: 267)
YCQQSYSWPWT

HVR-L3 sequence 4: (SEQ ID NO: 268)
YCQQYTHDPVT

HVR-L3 sequence 5: (SEQ ID NO: 269)
YCQQYYRIPPT

HVR-L3 sequence 6: (SEQ ID NO: 270)
YCQHHYGTPLT

HVR-L3 sequence 7: (SEQ ID NO: 271)
YCQQSYSTPLT

HVR-L3 sequence 8: (SEQ ID NO: 272)
YCQQSYSTPPT

HVR-L3 sequence 9: (SEQ ID NO: 273)
YCQQYYSTPLT

HVR-L3 sequence 10: (SEQ ID NO: 274)
YCQQYYTTPLT

What is claimed is:

1. A library comprising polynucleotides that encode antibody heavy chain variable domains ($V_H$s), wherein each of the $V_H$s comprises a HVR-H1, a HVR-H2 and a HVR-H3, and wherein at least one $V_H$ comprises an HVR-H1 that comprises an amino acid sequence according to a formula selected from the group consisting of:

(Formula I) $X_1$TF$X_2X_3$Y$X_4$IHWV (SEQ ID NO:198), wherein $X_1$ is F or Y, $X_2$ is S or T, $X_3$ is D, G, N, or S, and $X_4$ is A, G, or W;

(Formula II) YSI$X_1$SG$X_2X_3$W$X_4$WI (SEQ ID NO:199), wherein $X_1$ is S or T, $X_2$ is H or Y, $X_3$ is H or Y, and $X_4$ is A, D, G, N, S, or T; and (Formula III) FSLST$X_1$GV$X_2$V$X_3$WI (SEQ ID NO:200), wherein $X_1$ is G or S, $X_2$ is A or G, and $X_3$ is A, G, S, or T; and an HVR-H2 that comprises an amino acid sequence according to a formula selected from the group consisting of:

(Formula IV) LA$X_1$I$X_2$W$X_3X_4$DK$X_5$YS$X_6$SLKSRL (SEQ ID NO:201), wherein $X_1$ is L or R, $X_2$ is D or Y, $X_3$ is A, D, S, or Y, $X_4$ is D or G, $X_5$ is R, S, or Y, and $X_6$ is P or T;

(Formula V) IG$X_1$I$X_2X_3$SGSTYYSPSLKSRV (SEQ ID NO:202), wherein $X_1$ is A, D, E, S, or Y, $X_2$ is S or Y, and $X_3$ is H or Y;

(Formula VI) IG$X_1$IY$X_2$SG$X_3$T$X_4$YNPSLKSRV (SEQ ID NO:203), wherein $X_1$ is D, E, R, S, or Y, $X_2$ is H or Y, $X_3$ is N or S, and $X_4$ is N or Y;

(Formula VII) VS$X_1$ISG$X_2$G$X_3X_4$TYYADSVKGRF (SEQ ID NO:204), wherein $X_1$ is A, G, S, V, or Y, $X_2$ is A, D, S, or Y, $X_3$ is D, G, or S, and $X_4$ is S or T;

(Formula VIII) IG$X_1$INPN$X_2$G$X_3$T$X_4$YAQKFQGRV (SEQ ID NO:205), wherein $X_1$ is I, R, or W, $X_2$ is F or R, $X_3$ is D, G, or S, and $X_4$ is K or N;

(Formula IX) IG$X_1$I$X_2$PS$X_3$G$X_4$TX5YAQKFQGRV (SEQ ID NO:206), wherein $X_1$ is I, R, or W, $X_2$ is S or Y, $X_3$ is G or S, $X_4$ is D, G, or S, and $X_5$ is K or N; and (Formula X) VGRI$X_1$SK$X_2X_3$G$X_4$TT$X_5$ YAA$X_6$VKGRF (SEQ ID NO:207), wherein $X_1$ is K or R, $X_2$ is A or T, $X_3$ is D or Y, $X_4$ is G or Y, $X_5$ is D or E, and $X_6$ is P or S.

2. The library of claim 1, wherein at least two, at least three, at least four, at least five or at least ten of the $V_H$s comprise, an HVR-H1 that comprises an amino acid sequence according to a formula selected from the group consisting of:

(Formula I) $X_1$TF$X_2X_3$Y$X_4$IHWV (SEQ ID NO:198), wherein $X_1$ is F or Y, $X_2$ is S or T, $X_3$ is D, G, N, or S, and $X_4$ is A, G, or W;

(Formula II) YSI$X_1$SG$X_2X_3$W$X_4$WI (SEQ ID NO:199), wherein $X_1$ is S or T, $X_2$ is H or Y, $X_3$ is H or Y, and $X_4$ is A, D, G, N, S, or T; and (Formula III) FSLST$X_1$GV$X_2$V$X_3$WI (SEQ ID NO:200), wherein $X_1$ is G or S, $X_2$ is A or G, and $X_3$ is A, G, S, or T; and an HVR-H1 that comprises an amino acid sequence according to a formula selected from the group consisting of:

(Formula IV) LA$X_1$I$X_2$W$X_3X_4$DK$X_5$YS$X_6$SLKSRL (SEQ ID NO:201), wherein $X_1$ is L or R, $X_2$ is D or Y, $X_3$ is A, D, S, or Y, $X_4$ is D or G, $X_5$ is R, S, or Y, and $X_6$ is P or T;

(Formula V) IG$X_1$I$X_2X_3$SGSTYYSPSLKSRV (SEQ ID NO:202), wherein $X_1$ is A, D, E, S, or Y, $X_2$ is S or Y, and $X_3$ is H or Y;

(Formula VI) IG$X_1$IY$X_2$SG$X_3$T$X_4$YNPSLKSRV (SEQ ID NO:203), wherein $X_1$ is D, E, R, S, or Y, $X_2$ is H or Y, $X_3$ is N or S, and $X_4$ is N or Y;

(Formula VII) VS$X_1$ISG$X_2$G$X_3X_4$TYYADSVKGRF (SEQ ID NO:204), wherein $X_1$ is A, G, S, V, or Y, $X_2$ is A, D, S, or Y, $X_3$ is D, G, or S, and $X_4$ is S or T;

(Formula VIII) IG$X_1$INPN$X_2$G$X_3$T$X_4$YAQKFQGRV (SEQ ID NO:205), wherein $X_1$ is I, R, or W, $X_2$ is F or R, $X_3$ is D, G, or S, and $X_4$ is K or N;

(Formula IX) IG$X_1$I$X_2$PS$X_3$G$X_4$T$X_5$YAQKFQGRV (SEQ ID NO:206), wherein $X_1$ is I, R, or W, $X_2$ is S or Y, $X_3$ is G or S, $X_4$ is D, G, or S, and $X_5$ is K or N; and (Formula X) VGRI$X_1$SK$X_2X_3$G$X_4$TT$X_5$ YAA$X_6$VKGRF (SEQ ID NO:207), wherein $X_1$ is K or R, $X_2$ is A or T, $X_3$ is D or Y, $X_4$ is G or Y, $X_5$ is D or E, and $X_6$ is P or S.

3. The library of claim 1, wherein the HVR-H2 comprises an amino acid sequence according to a formula selected from the group consisting of:

(Formula XI) $IGX_1IX_2X_3SGSTYYSPSLKSRV$ (SEQ ID NO:208), wherein $X_1$ is A, D, or E, $X_2$ is S or Y, and $X_3$ is H or Y;

(Formula XII) $IGX_1IYX_2SGX_3TX_4YNPSLKSRV$ (SEQ ID NO:209), wherein $X_1$ is D, E, or S, $X_2$ is H or Y, $X_3$ is N or S, and $X_4$ is N or Y; and (Formula XIII) $VGRIX_1SKX_2X_3GX_4TTEYAAX_5VKGRF$ (SEQ ID NO:210), wherein $X_1$ is K or R, $X_2$ is A or T, $X_3$ is D or Y, $X_4$ is G or Y, $X_5$ is P or S.

4. The library of claim 1, wherein each of the $V_H$s comprises an HVR-H1 that comprises an amino acid sequence selected from the group consisting of SEQ ID NOS:1-52 and 137-158.

5. The library of claim 1, wherein at least one of the $V_H$s comprises an HVR-H1 that comprises an amino acid sequence selected from the group consisting of SEQ ID NOS:1-52.

6. The library of claim 1, wherein each of the $V_H$s comprises an HVR-H2 that comprises an amino acid sequence selected from the group consisting of SEQ ID NOS:53-136 and 159-164.

7. The library of claim 1, wherein at least one of the $V_H$s comprises an HVR-H2 that comprises an amino acid sequence selected from the group consisting of SEQ ID NOS:53-136.

8. The library of claim 1, wherein the $V_H$s contain fewer than about $6.5*10^4$ unique combinations of HVR-H1 and HVR-H2 sequences.

9. The library of claim 8, wherein the $V_H$s contain fewer than about 6700 unique combinations of HVR-H1 and HVR-H2 sequences.

10. The library of claim 9, wherein the $V_H$s contain about 6660 or contain fewer unique combinations of HVR-H1 and HVR-H2 sequences.

11. The library of claim 1, wherein each of the $V_H$s comprises a HVR-H1 comprising an amino acid sequence selected from the group consisting of SEQ ID NOS:1-52 and 137-158, and a HVR-H2 of the antibody comprises an amino acid sequence selected from the group consisting of SEQ ID NOS:53-136 and 159-164.

12. The library of claim 1, wherein at least one of the $V_H$s comprises a HVR-H1 comprising an amino acid sequence selected from the group consisting of SEQ ID NOS:1-52, and a HVR-H2 of the antibody comprises an amino acid sequence selected from the group consisting of SEQ ID NOS:53-136.

13. The library of claim 1, wherein the HVR-H1 and HVR-H2 of the at least one $V_H$ are selected from the group consisting of:

a HVR-H1 comprising the amino acid sequence of Formula (II) and a HVR-H2 comprising the amino acid sequence of Formula (IX);

a HVR-H1 comprising the amino acid sequence of Formula (II) and a HVR-H2 comprising the amino acid sequence of Formula (VII);

a HVR-H1 comprising the amino acid sequence of Formula (I) and a HVR-H2 comprising the amino acid sequence of Formula (VII);

a HVR-H1 comprising the amino acid sequence of Formula (I) and a HVR-H2 comprising the amino acid sequence of Formula (IX);

a HVR-H1 comprising the amino acid sequence of Formula (II) and a HVR-H2 comprising the amino acid sequence of Formula (IV);

a HVR-H1 comprising the amino acid sequence of Formula (II) and a HVR-H2 comprising the amino acid sequence of Formula (V);

a HVR-H1 comprising the amino acid sequence of Formula (II) and a HVR-H2 comprising the amino acid sequence of Formula (VI);

a HVR-H1 comprising the amino acid sequence of Formula (I) and a HVR-H2 comprising the amino acid sequence of Formula (VI);

a HVR-H1 comprising the amino acid sequence of Formula (III) and a HVR-H2 comprising the amino acid sequence of Formula (VI);

a HVR-H1 comprising the amino acid sequence of Formula (III) and a HVR-H2 comprising the amino acid sequence of Formula (VII);

a HVR-H1 comprising the amino acid sequence of Formula (II) and a HVR-H2 comprising the amino acid sequence of Formula (VIII);

a HVR-H1 comprising the amino acid sequence of Formula (I) and a HVR-H2 comprising the amino acid sequence of Formula (V);

a HVR-H1 comprising the amino acid sequence of Formula (III) and a HVR-H2 comprising the amino acid sequence of Formula (V); and a HVR-H1 comprising the amino acid sequence of Formula (I) and a HVR-H2 comprising the amino acid sequence of Formula (VIII).

14. The library of claim 1, wherein the HVR-H1 and HVR-H2 of the at least one $V_H$ are selected from the group consisting of: a HVR-H1 comprising the amino acid sequence of SEQ ID NO:157, and a HVR-H2 comprising the amino acid sequence of SEQ ID NO:63; a HVR-H1 comprising the amino acid sequence of SEQ ID NO:1, and a HVR-H2 comprising the amino acid sequence of SEQ ID NO:122; a HVR-H1 comprising the amino acid sequence of SEQ ID NO:138, and a HVR-H2 comprising the amino acid sequence of SEQ ID NO:63; a HVR-H1 comprising the amino acid sequence of SEQ ID NO:154, and a HVR-H2 comprising the amino acid sequence of SEQ ID NO:63; a HVR-H1 comprising the amino acid sequence of SEQ ID NO:158, and a HVR-H2 comprising the amino acid sequence of SEQ ID NO:161; a HVR-H1 comprising the amino acid sequence of SEQ ID NO:158, and a HVR-H2 comprising the amino acid sequence of SEQ ID NO:63; a HVR-H1 comprising the amino acid sequence of SEQ ID NO:145, and a HVR-H2 comprising the amino acid sequence of SEQ ID NO:128; a HVR-H1 comprising the amino acid sequence of SEQ ID NO:22, and a HVR-H2 comprising the amino acid sequence of SEQ ID NO:61; a HVR-H1 comprising the amino acid sequence of SEQ ID NO:31, and a HVR-H2 comprising the amino acid sequence of SEQ ID NO:63; a HVR-H1 comprising the amino acid sequence of SEQ ID NO:153, and a HVR-H2 comprising the amino acid sequence of SEQ ID NO:63; a HVR-H1 comprising the amino acid sequence of SEQ ID NO:155, and a HVR-H2 comprising the amino acid sequence of SEQ ID NO:67; a HVR-H1 comprising the amino acid sequence of SEQ ID NO:156, and a HVR-H2 comprising the amino acid sequence of SEQ ID NO:100; a HVR-H1 comprising the amino acid sequence of SEQ ID NO:51, and a HVR-H2 comprising the amino acid sequence of SEQ ID NO:162; a HVR-H1 comprising the amino acid sequence of SEQ ID NO:138, and a HVR-H2 comprising the amino acid sequence of SEQ ID NO:123; a HVR-H1 comprising the amino acid sequence of SEQ ID NO:139, and a HVR-H2 comprising the amino acid sequence of SEQ ID NO:110; a HVR-H1 comprising the amino acid sequence of SEQ ID NO:8, and a HVR-H2 comprising the amino acid sequence of SEQ ID NO:126; a HVR-H1 comprising the amino acid sequence of SEQ ID NO:13, and a HVR-H2 comprising the amino acid sequence of SEQ ID NO:129; a HVR-H1 comprising the amino acid sequence of SEQ ID NO:31, and a HVR-H2 comprising the amino acid sequence of SEQ ID NO:124; a HVR-H1 comprising the amino acid sequence of SEQ ID NO:25, and a HVR-H2 comprising the amino acid sequence of SEQ ID NO:130; a HVR-H1 comprising the amino acid sequence of SEQ ID NO:150, and a HVR-H2 comprising the amino acid sequence of SEQ ID NO:132; a HVR-H1 comprising the amino acid sequence of SEQ ID NO:158, and a HVR-H2 comprising the amino acid sequence of SEQ ID NO:162; a HVR-H1 comprising the amino acid sequence of SEQ ID NO:12, and a HVR-H2 comprising the amino acid sequence of SEQ ID NO:82; a HVR-H1 comprising the amino acid sequence of SEQ ID NO:149, and a HVR-H2 comprising the amino acid sequence of SEQ ID NO:117; and a HVR-H1 comprising the amino acid sequence of SEQ ID NO:7, and a HVR-H2 comprising the amino acid sequence of SEQ ID NO:134.

15. The library of claim 1, wherein the at least one $V_H$ comprises a HVR-H3 comprising an amino acid sequence selected from the group consisting of SEQ ID NOs: 223-256.

16. The library of claim 1, wherein the at least one $V_H$ comprises a FW-H1 comprising the amino acid sequence of SEQ ID NO:165, a FW-H2 comprising the amino acid sequence of SEQ ID NO:166, a FW-H3 comprising the amino acid sequence of SEQ ID NO:167, and/or a FW-H4 comprising the amino acid sequence of SEQ ID NO:168.

17. The library of claim 1, wherein the at least one $V_H$ comprises a sequence selected from the group consisting of SEQ ID NOs: 169, 171, 173, 175, 177, 179, 181, 183, 185, 187, 189, 191, 193, and 195.

18. The library of claim 1, wherein the polynucleotides that encode $V_H$s encode full-length antibody heavy chains.

19. The library of claim 1, further comprising polynucleotides that encode antibody light chain variable regions.

20. The library of claim 19, wherein the at least one $V_L$ comprises a HVR-L1, a HVR-L2 and a HVR-L3, wherein the HVR-L1 comprises an amino acid sequence selected from the group consisting of SEQ ID NOs: 257-264 and/or the HVR-L3 comprises an amino acid sequence selected from the group consisting of SEQ ID NOs: 265-274.

21. The library of claim 19, wherein the at least one of the polynucleotides that encodes the $V_L$ includes at least one unique $V_L$ sequence.

22. The library of claim 19, wherein the at least one of the polynucleotides that encodes the $V_L$ includes at least about 280 unique$_V$ sequences.

23. The library of claim 19, wherein the at least one of the polynucleotides that encodes the $V_L$ includes at least about $10^5$ unique $V_L$ sequences.

24. The library of claim 19, wherein the polynucleotides that encode $V_H$s and the polynucleotides that encode the at least one $V_L$ together encode a plurality of unique antibodies, wherein the $V_H$s of each antibody of the plurality comprise an identical sequence.

25. The library of claim 1, wherein at least one of the HVR-H1 and HVR-H2 of the at least one $V_H$ adopts multiple conformations, as assayed by structural determination and/or computational modeling.

26. The library of claim 1, wherein at least one of the polynucleotides encoding the $V_H$s is in a vector.

27. The library of claim 26, wherein the vector is an expression vector.

28. The library of claim 26, wherein the vector is a display vector.

29. The library of claim 1, wherein at least one of the polynucleotides encoding the $V_H$s is in a cell.

30. The library of claim 29, wherein the cell is a bacterial, yeast, or mammalian cell.

31. A method of preparing a library comprising providing and assembling the polynucleotide sequences of the library of claim 1.

32. A kit comprising the library of polynucleotides of claim 1.

33. The library of claim 16, wherein all of the VHs comprise a FW-H1 comprising the amino acid sequence of SEQ ID NO:165, a FW-H2 comprising the amino acid sequence of SEQ ID NO:166, a FW-H3 comprising the amino acid sequence of SEQ ID NO:167, and/or a FW-H4 comprising the amino acid sequence of SEQ ID NO:168.

34. The library of claim 26, wherein each of the polynucleotides encoding the $V_H$s is in a vector.

* * * * *

SEQUENCE LISTING

```
<160> NUMBER OF SEQ ID NOS: 274

<210> SEQ ID NO 1
<211> LENGTH: 11
<212> TYPE: PRT
<213> ORGANISM: artificial sequence
<220> FEATURE:
<223> OTHER INFORMATION: Designed HVR-H1 sequence 1

<400> SEQUENCE: 1
```

Phe Thr Phe Thr Asp Tyr Gly Ile His Trp Val
1 5 10

<210> SEQ ID NO 2
<211> LENGTH: 11
<212> TYPE: PRT
<213> ORGANISM: artificial sequence
<220> FEATURE:
<223> OTHER INFORMATION: Designed HVR-H1 sequence 2

<400> SEQUENCE: 2

Phe Thr Phe Thr Gly Tyr Ala Ile His Trp Val
1 5 10

<210> SEQ ID NO 3
<211> LENGTH: 11
<212> TYPE: PRT
<213> ORGANISM: artificial sequence
<220> FEATURE:
<223> OTHER INFORMATION: Designed HVR-H1 sequence 3

<400> SEQUENCE: 3

Phe Thr Phe Thr Asn Tyr Gly Ile His Trp Val
1 5 10

<210> SEQ ID NO 4
<211> LENGTH: 11
<212> TYPE: PRT
<213> ORGANISM: artificial sequence
<220> FEATURE:
<223> OTHER INFORMATION: Designed HVR-H1 sequence 4

<400> SEQUENCE: 4

Tyr Thr Phe Ser Asp Tyr Ala Ile His Trp Val
1 5 10

<210> SEQ ID NO 5
<211> LENGTH: 11
<212> TYPE: PRT
<213> ORGANISM: artificial sequence
<220> FEATURE:
<223> OTHER INFORMATION: Designed HVR-H1 sequence 5

<400> SEQUENCE: 5

Tyr Thr Phe Ser Asp Tyr Gly Ile His Trp Val
1 5 10

<210> SEQ ID NO 6
<211> LENGTH: 11
<212> TYPE: PRT
<213> ORGANISM: artificial sequence
<220> FEATURE:
<223> OTHER INFORMATION: Designed HVR-H1 sequence 6

<400> SEQUENCE: 6

Tyr Thr Phe Ser Gly Tyr Ala Ile His Trp Val
1 5 10

<210> SEQ ID NO 7
<211> LENGTH: 11
<212> TYPE: PRT
<213> ORGANISM: artificial sequence
<220> FEATURE:
<223> OTHER INFORMATION: Designed HVR-H1 sequence 7

<400> SEQUENCE: 7

-continued

Tyr Thr Phe Ser Gly Tyr Gly Ile His Trp Val
1 5 10

<210> SEQ ID NO 8
<211> LENGTH: 11
<212> TYPE: PRT
<213> ORGANISM: artificial sequence
<220> FEATURE:
<223> OTHER INFORMATION: Designed HVR-H1 sequence 8

<400> SEQUENCE: 8

Tyr Thr Phe Ser Asn Tyr Gly Ile His Trp Val
1 5 10

<210> SEQ ID NO 9
<211> LENGTH: 11
<212> TYPE: PRT
<213> ORGANISM: artificial sequence
<220> FEATURE:
<223> OTHER INFORMATION: Designed HVR-H1 sequence 9

<400> SEQUENCE: 9

Tyr Thr Phe Ser Ser Tyr Gly Ile His Trp Val
1 5 10

<210> SEQ ID NO 10
<211> LENGTH: 11
<212> TYPE: PRT
<213> ORGANISM: artificial sequence
<220> FEATURE:
<223> OTHER INFORMATION: Designed HVR-H1 sequence 10

<400> SEQUENCE: 10

Tyr Thr Phe Ser Gly Tyr Trp Ile His Trp Val
1 5 10

<210> SEQ ID NO 11
<211> LENGTH: 11
<212> TYPE: PRT
<213> ORGANISM: artificial sequence
<220> FEATURE:
<223> OTHER INFORMATION: Designed HVR-H1 sequence 11

<400> SEQUENCE: 11

Tyr Thr Phe Ser Asn Tyr Trp Ile His Trp Val
1 5 10

<210> SEQ ID NO 12
<211> LENGTH: 11
<212> TYPE: PRT
<213> ORGANISM: artificial sequence
<220> FEATURE:
<223> OTHER INFORMATION: Designed HVR-H1 sequence 12

<400> SEQUENCE: 12

Phe Thr Phe Ser Gly Tyr Trp Ile His Trp Val
1 5 10

<210> SEQ ID NO 13
<211> LENGTH: 11
<212> TYPE: PRT
<213> ORGANISM: artificial sequence
<220> FEATURE:
<223> OTHER INFORMATION: Designed HVR-H1 sequence 13

<400> SEQUENCE: 13

Phe Thr Phe Ser Asn Tyr Trp Ile His Trp Val

-continued 1 5 10

<210> SEQ ID NO 14
<211> LENGTH: 11
<212> TYPE: PRT
<213> ORGANISM: artificial sequence
<220> FEATURE:
<223> OTHER INFORMATION: Designed HVR-H1 sequence 14

<400> SEQUENCE: 14

Tyr Thr Phe Ser Asp Tyr Trp Ile His Trp Val
1 5 10

<210> SEQ ID NO 15
<211> LENGTH: 12
<212> TYPE: PRT
<213> ORGANISM: artificial sequence
<220> FEATURE:
<223> OTHER INFORMATION: Designed HVR-H1 sequence 15

<400> SEQUENCE: 15

Tyr Ser Ile Ser Ser Gly His His Trp Ala Trp Ile
1 5 10

<210> SEQ ID NO 16
<211> LENGTH: 12
<212> TYPE: PRT
<213> ORGANISM: artificial sequence
<220> FEATURE:
<223> OTHER INFORMATION: Designed HVR-H1 sequence 16

<400> SEQUENCE: 16

Tyr Ser Ile Ser Ser Gly His Tyr Trp Asn Trp Ile
1 5 10

<210> SEQ ID NO 17
<211> LENGTH: 12
<212> TYPE: PRT
<213> ORGANISM: artificial sequence
<220> FEATURE:
<223> OTHER INFORMATION: Designed HVR-H1 sequence 17

<400> SEQUENCE: 17

Tyr Ser Ile Ser Ser Gly His Tyr Trp Ser Trp Ile
1 5 10

<210> SEQ ID NO 18
<211> LENGTH: 12
<212> TYPE: PRT
<213> ORGANISM: artificial sequence
<220> FEATURE:
<223> OTHER INFORMATION: Designed HVR-H1 sequence 18

<400> SEQUENCE: 18

Tyr Ser Ile Ser Ser Gly His Tyr Trp Thr Trp Ile
1 5 10

<210> SEQ ID NO 19
<211> LENGTH: 12
<212> TYPE: PRT
<213> ORGANISM: artificial sequence
<220> FEATURE:
<223> OTHER INFORMATION: Designed HVR-H1 sequence 19

<400> SEQUENCE: 19

Tyr Ser Ile Ser Ser Gly Tyr His Trp Ala Trp Ile
1 5 10

<210> SEQ ID NO 20
<211> LENGTH: 12
<212> TYPE: PRT
<213> ORGANISM: artificial sequence
<220> FEATURE:
<223> OTHER INFORMATION: Designed HVR-H1 sequence 20

<400> SEQUENCE: 20

Tyr Ser Ile Ser Ser Gly Tyr His Trp Asp Trp Ile
1 5 10

<210> SEQ ID NO 21
<211> LENGTH: 12
<212> TYPE: PRT
<213> ORGANISM: artificial sequence
<220> FEATURE:
<223> OTHER INFORMATION: Designed HVR-H1 sequence 21

<400> SEQUENCE: 21

Tyr Ser Ile Ser Ser Gly Tyr His Trp Gly Trp Ile
1 5 10

<210> SEQ ID NO 22
<211> LENGTH: 12
<212> TYPE: PRT
<213> ORGANISM: artificial sequence
<220> FEATURE:
<223> OTHER INFORMATION: Designed HVR-H1 sequence 22

<400> SEQUENCE: 22

Tyr Ser Ile Ser Ser Gly Tyr His Trp Asn Trp Ile
1 5 10

<210> SEQ ID NO 23
<211> LENGTH: 12
<212> TYPE: PRT
<213> ORGANISM: artificial sequence
<220> FEATURE:
<223> OTHER INFORMATION: Designed HVR-H1 sequence 23

<400> SEQUENCE: 23

Tyr Ser Ile Ser Ser Gly Tyr His Trp Ser Trp Ile
1 5 10

<210> SEQ ID NO 24
<211> LENGTH: 12
<212> TYPE: PRT
<213> ORGANISM: artificial sequence
<220> FEATURE:
<223> OTHER INFORMATION: Designed HVR-H1 sequence 24

<400> SEQUENCE: 24

Tyr Ser Ile Ser Ser Gly His His Trp Asp Trp Ile
1 5 10

<210> SEQ ID NO 25
<211> LENGTH: 12
<212> TYPE: PRT
<213> ORGANISM: artificial sequence
<220> FEATURE:
<223> OTHER INFORMATION: Designed HVR-H1 sequence

<400> SEQUENCE: 25

Tyr Ser Ile Ser Ser Gly Tyr Tyr Trp Asp Trp Ile
1 5 10

<210> SEQ ID NO 26
<211> LENGTH: 12
<212> TYPE: PRT
<213> ORGANISM: artificial sequence
<220> FEATURE:
<223> OTHER INFORMATION: Designed HVR-H1 sequence 26

<400> SEQUENCE: 26

Tyr Ser Ile Ser Ser Gly Tyr Tyr Trp Asn Trp Ile
1 5 10

<210> SEQ ID NO 27
<211> LENGTH: 12
<212> TYPE: PRT
<213> ORGANISM: artificial sequence
<220> FEATURE:
<223> OTHER INFORMATION: Designed HVR-H1 sequence 27

<400> SEQUENCE: 27

Tyr Ser Ile Ser Ser Gly Tyr Tyr Trp Thr Trp Ile
1 5 10

<210> SEQ ID NO 28
<211> LENGTH: 12
<212> TYPE: PRT
<213> ORGANISM: artificial sequence
<220> FEATURE:
<223> OTHER INFORMATION: Designed HVR-H1 sequence 28

<400> SEQUENCE: 28

Tyr Ser Ile Thr Ser Gly His His Trp Ala Trp Ile
1 5 10

<210> SEQ ID NO 29
<211> LENGTH: 12
<212> TYPE: PRT
<213> ORGANISM: artificial sequence
<220> FEATURE:
<223> OTHER INFORMATION: Designed HVR-H1 sequence 29

<400> SEQUENCE: 29

Tyr Ser Ile Thr Ser Gly His His Trp Asp Trp Ile
1 5 10

<210> SEQ ID NO 30
<211> LENGTH: 12
<212> TYPE: PRT
<213> ORGANISM: artificial sequence
<220> FEATURE:
<223> OTHER INFORMATION: Designed HVR-H1 sequence 30

<400> SEQUENCE: 30

Tyr Ser Ile Thr Ser Gly His His Trp Gly Trp Ile
1 5 10

<210> SEQ ID NO 31
<211> LENGTH: 12
<212> TYPE: PRT
<213> ORGANISM: artificial sequence
<220> FEATURE:
<223> OTHER INFORMATION: Designed HVR-H1 sequence 31

<400> SEQUENCE: 31

Tyr Ser Ile Thr Ser Gly His His Trp Asn Trp Ile
1 5 10

<210> SEQ ID NO 32
<211> LENGTH: 12
<212> TYPE: PRT
<213> ORGANISM: artificial sequence
<220> FEATURE:
<223> OTHER INFORMATION: Designed HVR-H1 sequence 32

<400> SEQUENCE: 32

Tyr Ser Ile Thr Ser Gly His His Trp Ser Trp Ile
1               5                   10

<210> SEQ ID NO 33
<211> LENGTH: 12
<212> TYPE: PRT
<213> ORGANISM: artificial sequence
<220> FEATURE:
<223> OTHER INFORMATION: Designed HVR-H1 sequence 33

<400> SEQUENCE: 33

Tyr Ser Ile Ser Ser Gly His His Trp Gly Trp Ile
1               5                   10

<210> SEQ ID NO 34
<211> LENGTH: 12
<212> TYPE: PRT
<213> ORGANISM: artificial sequence
<220> FEATURE:
<223> OTHER INFORMATION: Designed HVR-H1 sequence 34

<400> SEQUENCE: 34

Tyr Ser Ile Thr Ser Gly His Tyr Trp Ala Trp Ile
1               5                   10

<210> SEQ ID NO 35
<211> LENGTH: 12
<212> TYPE: PRT
<213> ORGANISM: artificial sequence
<220> FEATURE:
<223> OTHER INFORMATION: Designed HVR-H1 sequence 35

<400> SEQUENCE: 35

Tyr Ser Ile Thr Ser Gly His Tyr Trp Asp Trp Ile
1               5                   10

<210> SEQ ID NO 36
<211> LENGTH: 12
<212> TYPE: PRT
<213> ORGANISM: artificial sequence
<220> FEATURE:
<223> OTHER INFORMATION: Designed HVR-H1 sequence 36

<400> SEQUENCE: 36

Tyr Ser Ile Thr Ser Gly His Tyr Trp Gly Trp Ile
1               5                   10

<210> SEQ ID NO 37
<211> LENGTH: 12
<212> TYPE: PRT
<213> ORGANISM: artificial sequence
<220> FEATURE:
<223> OTHER INFORMATION: Designed HVR-H1 sequence 37

<400> SEQUENCE: 37

Tyr Ser Ile Thr Ser Gly His Tyr Trp Asn Trp Ile
1               5                   10

<210> SEQ ID NO 38

<211> LENGTH: 12
<212> TYPE: PRT
<213> ORGANISM: artificial sequence
<220> FEATURE:
<223> OTHER INFORMATION: Designed HVR-H1 sequence 38

<400> SEQUENCE: 38

Tyr Ser Ile Thr Ser Gly His Tyr Trp Ser Trp Ile
1 5 10

<210> SEQ ID NO 39
<211> LENGTH: 12
<212> TYPE: PRT
<213> ORGANISM: artificial sequence
<220> FEATURE:
<223> OTHER INFORMATION: Designed HVR-H1 sequence 39

<400> SEQUENCE: 39

Tyr Ser Ile Thr Ser Gly Tyr His Trp Ala Trp Ile
1 5 10

<210> SEQ ID NO 40
<211> LENGTH: 12
<212> TYPE: PRT
<213> ORGANISM: artificial sequence
<220> FEATURE:
<223> OTHER INFORMATION: Designed HVR-H1 sequence 40

<400> SEQUENCE: 40

Tyr Ser Ile Thr Ser Gly Tyr His Trp Gly Trp Ile
1 5 10

<210> SEQ ID NO 41
<211> LENGTH: 12
<212> TYPE: PRT
<213> ORGANISM: artificial sequence
<220> FEATURE:
<223> OTHER INFORMATION: Designed HVR-H1 sequence 41

<400> SEQUENCE: 41

Tyr Ser Ile Ser Ser Gly His His Trp Asn Trp Ile
1 5 10

<210> SEQ ID NO 42
<211> LENGTH: 12
<212> TYPE: PRT
<213> ORGANISM: artificial sequence
<220> FEATURE:
<223> OTHER INFORMATION: Designed HVR-H1 sequence 42

<400> SEQUENCE: 42

Tyr Ser Ile Thr Ser Gly Tyr His Trp Asn Trp Ile
1 5 10

<210> SEQ ID NO 43
<211> LENGTH: 12
<212> TYPE: PRT
<213> ORGANISM: artificial sequence
<220> FEATURE:
<223> OTHER INFORMATION: Designed HVR-H1 sequence 43

<400> SEQUENCE: 43

Tyr Ser Ile Thr Ser Gly Tyr His Trp Ser Trp Ile
1 5 10

<210> SEQ ID NO 44
<211> LENGTH: 12

<212> TYPE: PRT
<213> ORGANISM: artificial sequence
<220> FEATURE:
<223> OTHER INFORMATION: Designed HVR-H1 sequence 44

<400> SEQUENCE: 44

Tyr Ser Ile Thr Ser Gly Tyr Tyr Trp Asp Trp Ile
1 5 10

<210> SEQ ID NO 45
<211> LENGTH: 12
<212> TYPE: PRT
<213> ORGANISM: artificial sequence
<220> FEATURE:
<223> OTHER INFORMATION: Designed HVR-H1 sequence 45

<400> SEQUENCE: 45

Tyr Ser Ile Ser Ser Gly His His Trp Thr Trp Ile
1 5 10

<210> SEQ ID NO 46
<211> LENGTH: 12
<212> TYPE: PRT
<213> ORGANISM: artificial sequence
<220> FEATURE:
<223> OTHER INFORMATION: Designed HVR-H1 sequence 46

<400> SEQUENCE: 46

Tyr Ser Ile Ser Ser Gly His Tyr Trp Asp Trp Ile
1 5 10

<210> SEQ ID NO 47
<211> LENGTH: 13
<212> TYPE: PRT
<213> ORGANISM: artificial sequence
<220> FEATURE:
<223> OTHER INFORMATION: Designed HVR-H1 sequence 47

<400> SEQUENCE: 47

Phe Ser Leu Ser Thr Ser Gly Val Ala Val Ser Trp Ile
1 5 10

<210> SEQ ID NO 48
<211> LENGTH: 13
<212> TYPE: PRT
<213> ORGANISM: artificial sequence
<220> FEATURE:
<223> OTHER INFORMATION: Designed HVR-H1 sequence 48

<400> SEQUENCE: 48

Phe Ser Leu Ser Thr Gly Gly Val Ala Val Gly Trp Ile
1 5 10

<210> SEQ ID NO 49
<211> LENGTH: 13
<212> TYPE: PRT
<213> ORGANISM: artificial sequence
<220> FEATURE:
<223> OTHER INFORMATION: Designed HVR-H1 sequence 49

<400> SEQUENCE: 49

Phe Ser Leu Ser Thr Gly Gly Val Ala Val Ser Trp Ile
1 5 10

<210> SEQ ID NO 50
<211> LENGTH: 13
<212> TYPE: PRT

<213> ORGANISM: artificial sequence
<220> FEATURE:
<223> OTHER INFORMATION: Designed HVR-H1 sequence 50

<400> SEQUENCE: 50

Phe Ser Leu Ser Thr Gly Gly Val Gly Val Ala Trp Ile
1 5 10

<210> SEQ ID NO 51
<211> LENGTH: 13
<212> TYPE: PRT
<213> ORGANISM: artificial sequence
<220> FEATURE:
<223> OTHER INFORMATION: Designed HVR-H1 sequence 51

<400> SEQUENCE: 51

Phe Ser Leu Ser Thr Gly Gly Val Gly Val Ser Trp Ile
1 5 10

<210> SEQ ID NO 52
<211> LENGTH: 13
<212> TYPE: PRT
<213> ORGANISM: artificial sequence
<220> FEATURE:
<223> OTHER INFORMATION: Designed HVR-H1 sequence 52

<400> SEQUENCE: 52

Phe Ser Leu Ser Thr Ser Gly Val Ala Val Ala Trp Ile
1 5 10

<210> SEQ ID NO 53
<211> LENGTH: 20
<212> TYPE: PRT
<213> ORGANISM: artificial sequence
<220> FEATURE:
<223> OTHER INFORMATION: Designed HVR-H2 sequence 1

<400> SEQUENCE: 53

Leu Ala Arg Ile Asp Trp Asp Asp Asp Lys Arg Tyr Ser Pro Ser Leu
1 5 10 15

Lys Ser Arg Leu
20

<210> SEQ ID NO 54
<211> LENGTH: 20
<212> TYPE: PRT
<213> ORGANISM: artificial sequence
<220> FEATURE:
<223> OTHER INFORMATION: Designed HVR-H2 sequence 2

<400> SEQUENCE: 54

Leu Ala Leu Ile Asp Trp Asp Asp Asp Lys Arg Tyr Ser Pro Ser Leu
1 5 10 15

Lys Ser Arg Leu
20

<210> SEQ ID NO 55
<211> LENGTH: 20
<212> TYPE: PRT
<213> ORGANISM: artificial sequence
<220> FEATURE:
<223> OTHER INFORMATION: Designed HVR-H2 sequence 3

<400> SEQUENCE: 55

Leu Ala Leu Ile Asp Trp Asp Asp Asp Lys Arg Tyr Ser Thr Ser Leu
1 5 10 15

Lys Ser Arg Leu
20

<210> SEQ ID NO 56
<211> LENGTH: 20
<212> TYPE: PRT
<213> ORGANISM: artificial sequence
<220> FEATURE:
<223> OTHER INFORMATION: Designed HVR-H2 sequence 4

<400> SEQUENCE: 56

Leu Ala Leu Ile Asp Trp Asp Asp Asp Lys Tyr Tyr Ser Pro Ser Leu
1 5 10 15

Lys Ser Arg Leu
20

<210> SEQ ID NO 57
<211> LENGTH: 20
<212> TYPE: PRT
<213> ORGANISM: artificial sequence
<220> FEATURE:
<223> OTHER INFORMATION: Designed HVR-H2 sequence 5

<400> SEQUENCE: 57

Leu Ala Leu Ile Asp Trp Ala Asp Asp Lys Tyr Tyr Ser Pro Ser Leu
1 5 10 15

Lys Ser Arg Leu
20

<210> SEQ ID NO 58
<211> LENGTH: 20
<212> TYPE: PRT
<213> ORGANISM: artificial sequence
<220> FEATURE:
<223> OTHER INFORMATION: Designed HVR-H2 sequence 6

<400> SEQUENCE: 58

Leu Ala Leu Ile Asp Trp Ala Gly Asp Lys Ser Tyr Ser Thr Ser Leu
1 5 10 15

Lys Ser Arg Leu
20

<210> SEQ ID NO 59
<211> LENGTH: 20
<212> TYPE: PRT
<213> ORGANISM: artificial sequence
<220> FEATURE:
<223> OTHER INFORMATION: Designed HVR-H2 sequence 7

<400> SEQUENCE: 59

Leu Ala Arg Ile Asp Trp Asp Asp Asp Lys Tyr Tyr Ser Pro Ser Leu
1 5 10 15

Lys Ser Arg Leu
20

<210> SEQ ID NO 60
<211> LENGTH: 20
<212> TYPE: PRT
<213> ORGANISM: artificial sequence
<220> FEATURE:
<223> OTHER INFORMATION: Designed HVR-H2 sequence 8

<400> SEQUENCE: 60

Leu Ala Arg Ile Asp Trp Asp Asp Asp Lys Tyr Tyr Ser Thr Ser Leu

```
1               5                   10                  15

Lys Ser Arg Leu
            20


<210> SEQ ID NO 61
<211> LENGTH: 20
<212> TYPE: PRT
<213> ORGANISM: artificial sequence
<220> FEATURE:
<223> OTHER INFORMATION: Designed HVR-H2 sequence 9

<400> SEQUENCE: 61

Leu Ala Arg Ile Asp Trp Asp Gly Asp Lys Tyr Tyr Ser Thr Ser Leu
1               5                   10                  15

Lys Ser Arg Leu
            20


<210> SEQ ID NO 62
<211> LENGTH: 20
<212> TYPE: PRT
<213> ORGANISM: artificial sequence
<220> FEATURE:
<223> OTHER INFORMATION: Designed HVR-H2 sequence 10

<400> SEQUENCE: 62

Ile Gly Asp Ile Tyr His Ser Gly Ser Thr Tyr Tyr Ser Pro Ser Leu
1               5                   10                  15

Lys Ser Arg Val
            20


<210> SEQ ID NO 63
<211> LENGTH: 20
<212> TYPE: PRT
<213> ORGANISM: artificial sequence
<220> FEATURE:
<223> OTHER INFORMATION: Designed HVR-H2 sequence 11

<400> SEQUENCE: 63

Ile Gly Glu Ile Tyr His Ser Gly Ser Thr Tyr Tyr Ser Pro Ser Leu
1               5                   10                  15

Lys Ser Arg Val
            20


<210> SEQ ID NO 64
<211> LENGTH: 20
<212> TYPE: PRT
<213> ORGANISM: artificial sequence
<220> FEATURE:
<223> OTHER INFORMATION: Designed HVR-H2 sequence 12

<400> SEQUENCE: 64

Ile Gly Glu Ile Tyr Tyr Ser Gly Ser Thr Tyr Tyr Ser Pro Ser Leu
1               5                   10                  15

Lys Ser Arg Val
            20


<210> SEQ ID NO 65
<211> LENGTH: 20
<212> TYPE: PRT
<213> ORGANISM: artificial sequence
<220> FEATURE:
<223> OTHER INFORMATION: Designed HVR-H2 sequence 13

<400> SEQUENCE: 65
```

```
Ile Gly Ser Ile Tyr His Ser Gly Asn Thr Asn Tyr Asn Pro Ser Leu
1               5                   10                  15

Lys Ser Arg Val
            20


<210> SEQ ID NO 66
<211> LENGTH: 20
<212> TYPE: PRT
<213> ORGANISM: artificial sequence
<220> FEATURE:
<223> OTHER INFORMATION: Designed HVR-H2 sequence 14

<400> SEQUENCE: 66

Ile Gly Glu Ile Tyr His Ser Gly Asn Thr Tyr Tyr Asn Pro Ser Leu
1               5                   10                  15

Lys Ser Arg Val
            20


<210> SEQ ID NO 67
<211> LENGTH: 20
<212> TYPE: PRT
<213> ORGANISM: artificial sequence
<220> FEATURE:
<223> OTHER INFORMATION: Designed HVR-H2 sequence 15

<400> SEQUENCE: 67

Ile Gly Glu Ile Tyr His Ser Gly Ser Thr Tyr Tyr Asn Pro Ser Leu
1               5                   10                  15

Lys Ser Arg Val
            20


<210> SEQ ID NO 68
<211> LENGTH: 20
<212> TYPE: PRT
<213> ORGANISM: artificial sequence
<220> FEATURE:
<223> OTHER INFORMATION: Designed HVR-H2 sequence 16

<400> SEQUENCE: 68

Ile Gly Glu Ile Tyr Tyr Ser Gly Ser Thr Tyr Tyr Asn Pro Ser Leu
1               5                   10                  15

Lys Ser Arg Val
            20


<210> SEQ ID NO 69
<211> LENGTH: 20
<212> TYPE: PRT
<213> ORGANISM: artificial sequence
<220> FEATURE:
<223> OTHER INFORMATION: Designed HVR-H2 sequence 17

<400> SEQUENCE: 69

Ile Gly Asp Ile Tyr His Ser Gly Asn Thr Tyr Tyr Asn Pro Ser Leu
1               5                   10                  15

Lys Ser Arg Val
            20


<210> SEQ ID NO 70
<211> LENGTH: 20
<212> TYPE: PRT
<213> ORGANISM: artificial sequence
<220> FEATURE:
<223> OTHER INFORMATION: Designed HVR-H2 sequence 18

<400> SEQUENCE: 70
```

Ile Gly Asp Ile Tyr His Ser Gly Ser Thr Tyr Tyr Asn Pro Ser Leu
1 5 10 15

Lys Ser Arg Val
20

<210> SEQ ID NO 71
<211> LENGTH: 21
<212> TYPE: PRT
<213> ORGANISM: artificial sequence
<220> FEATURE:
<223> OTHER INFORMATION: Designed HVR-H2 sequence 19

<400> SEQUENCE: 71

Val Ser Ala Ile Ser Gly Tyr Gly Asp Thr Thr Tyr Tyr Ala Asp Ser
1 5 10 15

Val Lys Gly Arg Phe
20

<210> SEQ ID NO 72
<211> LENGTH: 21
<212> TYPE: PRT
<213> ORGANISM: artificial sequence
<220> FEATURE:
<223> OTHER INFORMATION: Designed HVR-H2 sequence 20

<400> SEQUENCE: 72

Val Ser Ala Ile Ser Gly Tyr Gly Gly Ser Thr Tyr Tyr Ala Asp Ser
1 5 10 15

Val Lys Gly Arg Phe
20

<210> SEQ ID NO 73
<211> LENGTH: 21
<212> TYPE: PRT
<213> ORGANISM: artificial sequence
<220> FEATURE:
<223> OTHER INFORMATION: Designed HVR-H2 sequence 21

<400> SEQUENCE: 73

Val Ser Ala Ile Ser Gly Tyr Gly Gly Thr Thr Tyr Tyr Ala Asp Ser
1 5 10 15

Val Lys Gly Arg Phe
20

<210> SEQ ID NO 74
<211> LENGTH: 21
<212> TYPE: PRT
<213> ORGANISM: artificial sequence
<220> FEATURE:
<223> OTHER INFORMATION: Designed HVR-H2 sequence 22

<400> SEQUENCE: 74

Val Ser Gly Ile Ser Gly Ala Gly Asp Thr Thr Tyr Tyr Ala Asp Ser
1 5 10 15

Val Lys Gly Arg Phe
20

<210> SEQ ID NO 75
<211> LENGTH: 21
<212> TYPE: PRT
<213> ORGANISM: artificial sequence
<220> FEATURE:
<223> OTHER INFORMATION: Designed HVR-H2 sequence 23

<400> SEQUENCE: 75

Val Ser Gly Ile Ser Gly Asp Gly Asp Thr Thr Tyr Tyr Ala Asp Ser
1 5 10 15

Val Lys Gly Arg Phe
20

<210> SEQ ID NO 76
<211> LENGTH: 21
<212> TYPE: PRT
<213> ORGANISM: artificial sequence
<220> FEATURE:
<223> OTHER INFORMATION: Designed HVR-H2 sequence 24

<400> SEQUENCE: 76

Val Ser Gly Ile Ser Gly Asp Gly Gly Ser Thr Tyr Tyr Ala Asp Ser
1 5 10 15

Val Lys Gly Arg Phe
20

<210> SEQ ID NO 77
<211> LENGTH: 21
<212> TYPE: PRT
<213> ORGANISM: artificial sequence
<220> FEATURE:
<223> OTHER INFORMATION: Designed HVR-H2 sequence 25

<400> SEQUENCE: 77

Val Ser Gly Ile Ser Gly Tyr Gly Asp Thr Thr Tyr Tyr Ala Asp Ser
1 5 10 15

Val Lys Gly Arg Phe
20

<210> SEQ ID NO 78
<211> LENGTH: 21
<212> TYPE: PRT
<213> ORGANISM: artificial sequence
<220> FEATURE:
<223> OTHER INFORMATION: Designed HVR-H2 sequence 26

<400> SEQUENCE: 78

Val Ser Gly Ile Ser Gly Tyr Gly Gly Thr Thr Tyr Tyr Ala Asp Ser
1 5 10 15

Val Lys Gly Arg Phe
20

<210> SEQ ID NO 79
<211> LENGTH: 21
<212> TYPE: PRT
<213> ORGANISM: artificial sequence
<220> FEATURE:
<223> OTHER INFORMATION: Designed HVR-H2 sequence 27

<400> SEQUENCE: 79

Val Ser Val Ile Ser Gly Asp Gly Asp Thr Thr Tyr Tyr Ala Asp Ser
1 5 10 15

Val Lys Gly Arg Phe
20

<210> SEQ ID NO 80
<211> LENGTH: 21
<212> TYPE: PRT
<213> ORGANISM: artificial sequence
<220> FEATURE:
<223> OTHER INFORMATION: Designed HVR-H2 sequence 28

<400> SEQUENCE: 80

Val Ser Val Ile Ser Gly Tyr Gly Gly Ser Thr Tyr Tyr Ala Asp Ser
1 5 10 15

Val Lys Gly Arg Phe
20

<210> SEQ ID NO 81
<211> LENGTH: 21
<212> TYPE: PRT
<213> ORGANISM: artificial sequence
<220> FEATURE:
<223> OTHER INFORMATION: Designed HVR-H2 sequence 29

<400> SEQUENCE: 81

Val Ser Gly Ile Ser Gly Asp Gly Ser Thr Thr Tyr Tyr Ala Asp Ser
1 5 10 15

Val Lys Gly Arg Phe
20

<210> SEQ ID NO 82
<211> LENGTH: 21
<212> TYPE: PRT
<213> ORGANISM: artificial sequence
<220> FEATURE:
<223> OTHER INFORMATION: Designed HVR-H2 sequence 30

<400> SEQUENCE: 82

Val Ser Gly Ile Ser Gly Tyr Gly Ser Thr Thr Tyr Tyr Ala Asp Ser
1 5 10 15

Val Lys Gly Arg Phe
20

<210> SEQ ID NO 83
<211> LENGTH: 21
<212> TYPE: PRT
<213> ORGANISM: artificial sequence
<220> FEATURE:
<223> OTHER INFORMATION: Designed HVR-H2 sequence 31

<400> SEQUENCE: 83

Val Ser Val Ile Ser Gly Ser Gly Ser Thr Thr Tyr Tyr Ala Asp Ser
1 5 10 15

Val Lys Gly Arg Phe
20

<210> SEQ ID NO 84
<211> LENGTH: 21
<212> TYPE: PRT
<213> ORGANISM: artificial sequence
<220> FEATURE:
<223> OTHER INFORMATION: Designed HVR-H2 sequence 32

<400> SEQUENCE: 84

Val Ser Val Ile Ser Gly Tyr Gly Ser Ser Thr Tyr Tyr Ala Asp Ser
1 5 10 15

Val Lys Gly Arg Phe
20

<210> SEQ ID NO 85
<211> LENGTH: 21
<212> TYPE: PRT
<213> ORGANISM: artificial sequence
<220> FEATURE:

<223> OTHER INFORMATION: Designed HVR-H2 sequence 33

<400> SEQUENCE: 85

Val Ser Val Ile Ser Gly Tyr Gly Ser Thr Thr Tyr Tyr Ala Asp Ser
1               5                   10                  15

Val Lys Gly Arg Phe
            20

<210> SEQ ID NO 86
<211> LENGTH: 21
<212> TYPE: PRT
<213> ORGANISM: artificial sequence
<220> FEATURE:
<223> OTHER INFORMATION: Designed HVR-H2 sequence 34

<400> SEQUENCE: 86

Val Ser Ala Ile Ser Gly Tyr Gly Ser Thr Thr Tyr Tyr Ala Asp Ser
1               5                   10                  15

Val Lys Gly Arg Phe
            20

<210> SEQ ID NO 87
<211> LENGTH: 21
<212> TYPE: PRT
<213> ORGANISM: artificial sequence
<220> FEATURE:
<223> OTHER INFORMATION: Designed HVR-H2 sequence 35

<400> SEQUENCE: 87

Val Ser Ser Ile Ser Gly Tyr Gly Asp Thr Thr Tyr Tyr Ala Asp Ser
1               5                   10                  15

Val Lys Gly Arg Phe
            20

<210> SEQ ID NO 88
<211> LENGTH: 21
<212> TYPE: PRT
<213> ORGANISM: artificial sequence
<220> FEATURE:
<223> OTHER INFORMATION: Designed HVR-H2 sequence 36

<400> SEQUENCE: 88

Val Ser Ser Ile Ser Gly Tyr Gly Gly Ser Thr Tyr Tyr Ala Asp Ser
1               5                   10                  15

Val Lys Gly Arg Phe
            20

<210> SEQ ID NO 89
<211> LENGTH: 21
<212> TYPE: PRT
<213> ORGANISM: artificial sequence
<220> FEATURE:
<223> OTHER INFORMATION: Designed HVR-H2 sequence 37

<400> SEQUENCE: 89

Val Ser Ser Ile Ser Gly Tyr Gly Gly Thr Thr Tyr Tyr Ala Asp Ser
1               5                   10                  15

Val Lys Gly Arg Phe
            20

<210> SEQ ID NO 90
<211> LENGTH: 21
<212> TYPE: PRT
<213> ORGANISM: artificial sequence
<220> FEATURE:
<223> OTHER INFORMATION: Designed HVR-H2 sequence 38

<400> SEQUENCE: 90

Val Ser Tyr Ile Ser Gly Ala Gly Asp Thr Thr Tyr Tyr Ala Asp Ser
1 5 10 15

Val Lys Gly Arg Phe
20

<210> SEQ ID NO 91
<211> LENGTH: 21
<212> TYPE: PRT
<213> ORGANISM: artificial sequence
<220> FEATURE:
<223> OTHER INFORMATION: Designed HVR-H2 sequence 39

<400> SEQUENCE: 91

Val Ser Ser Ile Ser Gly Ala Gly Asp Thr Thr Tyr Tyr Ala Asp Ser
1 5 10 15

Val Lys Gly Arg Phe
20

<210> SEQ ID NO 92
<211> LENGTH: 21
<212> TYPE: PRT
<213> ORGANISM: artificial sequence
<220> FEATURE:
<223> OTHER INFORMATION: Designed HVR-H2 sequence 40

<400> SEQUENCE: 92

Val Ser Tyr Ile Ser Gly Ala Gly Gly Thr Thr Tyr Tyr Ala Asp Ser
1 5 10 15

Val Lys Gly Arg Phe
20

<210> SEQ ID NO 93
<211> LENGTH: 21
<212> TYPE: PRT
<213> ORGANISM: artificial sequence
<220> FEATURE:
<223> OTHER INFORMATION: Designed HVR-H2 sequence 41

<400> SEQUENCE: 93

Val Ser Tyr Ile Ser Gly Asp Gly Asp Thr Thr Tyr Tyr Ala Asp Ser
1 5 10 15

Val Lys Gly Arg Phe
20

<210> SEQ ID NO 94
<211> LENGTH: 21
<212> TYPE: PRT
<213> ORGANISM: artificial sequence
<220> FEATURE:
<223> OTHER INFORMATION: Designed HVR-H2 sequence 42

<400> SEQUENCE: 94

Val Ser Tyr Ile Ser Gly Asp Gly Gly Ser Thr Tyr Tyr Ala Asp Ser
1 5 10 15

Val Lys Gly Arg Phe
20

<210> SEQ ID NO 95
<211> LENGTH: 21
<212> TYPE: PRT

-continued

<213> ORGANISM: artificial sequence
<220> FEATURE:
<223> OTHER INFORMATION: Designed HVR-H2 sequence 43

<400> SEQUENCE: 95

Val Ser Tyr Ile Ser Gly Asp Gly Gly Thr Thr Tyr Tyr Ala Asp Ser
1 5 10 15

Val Lys Gly Arg Phe
20

<210> SEQ ID NO 96
<211> LENGTH: 21
<212> TYPE: PRT
<213> ORGANISM: artificial sequence
<220> FEATURE:
<223> OTHER INFORMATION: Designed HVR-H2 sequence 44

<400> SEQUENCE: 96

Val Ser Tyr Ile Ser Gly Ser Gly Asp Thr Thr Tyr Tyr Ala Asp Ser
1 5 10 15

Val Lys Gly Arg Phe
20

<210> SEQ ID NO 97
<211> LENGTH: 21
<212> TYPE: PRT
<213> ORGANISM: artificial sequence
<220> FEATURE:
<223> OTHER INFORMATION: Designed HVR-H2 sequence 45

<400> SEQUENCE: 97

Val Ser Ser Ile Ser Gly Ala Gly Gly Ser Thr Tyr Tyr Ala Asp Ser
1 5 10 15

Val Lys Gly Arg Phe
20

<210> SEQ ID NO 98
<211> LENGTH: 21
<212> TYPE: PRT
<213> ORGANISM: artificial sequence
<220> FEATURE:
<223> OTHER INFORMATION: Designed HVR-H2 sequence 46

<400> SEQUENCE: 98

Val Ser Tyr Ile Ser Gly Tyr Gly Asp Thr Thr Tyr Tyr Ala Asp Ser
1 5 10 15

Val Lys Gly Arg Phe
20

<210> SEQ ID NO 99
<211> LENGTH: 21
<212> TYPE: PRT
<213> ORGANISM: artificial sequence
<220> FEATURE:
<223> OTHER INFORMATION: Designed HVR-H2 sequence 47

<400> SEQUENCE: 99

Val Ser Tyr Ile Ser Gly Tyr Gly Gly Thr Thr Tyr Tyr Ala Asp Ser
1 5 10 15

Val Lys Gly Arg Phe
20

<210> SEQ ID NO 100
<211> LENGTH: 21

<212> TYPE: PRT
<213> ORGANISM: artificial sequence
<220> FEATURE:
<223> OTHER INFORMATION: Designed HVR-H2 sequence 48

<400> SEQUENCE: 100

Val Ser Ser Ile Ser Gly Ala Gly Gly Thr Thr Tyr Tyr Ala Asp Ser
1 5 10 15

Val Lys Gly Arg Phe
20

<210> SEQ ID NO 101
<211> LENGTH: 21
<212> TYPE: PRT
<213> ORGANISM: artificial sequence
<220> FEATURE:
<223> OTHER INFORMATION: Designed HVR-H2 sequence 49

<400> SEQUENCE: 101

Val Ser Ser Ile Ser Gly Asp Gly Asp Thr Thr Tyr Tyr Ala Asp Ser
1 5 10 15

Val Lys Gly Arg Phe
20

<210> SEQ ID NO 102
<211> LENGTH: 21
<212> TYPE: PRT
<213> ORGANISM: artificial sequence
<220> FEATURE:
<223> OTHER INFORMATION: Designed HVR-H2 sequence 50

<400> SEQUENCE: 102

Val Ser Ser Ile Ser Gly Asp Gly Gly Thr Thr Tyr Tyr Ala Asp Ser
1 5 10 15

Val Lys Gly Arg Phe
20

<210> SEQ ID NO 103
<211> LENGTH: 21
<212> TYPE: PRT
<213> ORGANISM: artificial sequence
<220> FEATURE:
<223> OTHER INFORMATION: Designed HVR-H2 sequence 51

<400> SEQUENCE: 103

Val Ser Ser Ile Ser Gly Ala Gly Ser Ser Thr Tyr Tyr Ala Asp Ser
1 5 10 15

Val Lys Gly Arg Phe
20

<210> SEQ ID NO 104
<211> LENGTH: 21
<212> TYPE: PRT
<213> ORGANISM: artificial sequence
<220> FEATURE:
<223> OTHER INFORMATION: Designed HVR-H2 sequence 52

<400> SEQUENCE: 104

Val Ser Ser Ile Ser Gly Ala Gly Ser Thr Thr Tyr Tyr Ala Asp Ser
1 5 10 15

Val Lys Gly Arg Phe
20

<210> SEQ ID NO 105

<211> LENGTH: 21
<212> TYPE: PRT
<213> ORGANISM: artificial sequence
<220> FEATURE:
<223> OTHER INFORMATION: Designed HVR-H2 sequence 53

<400> SEQUENCE: 105

Val Ser Ser Ile Ser Gly Asp Gly Ser Ser Thr Tyr Tyr Ala Asp Ser
1 5 10 15

Val Lys Gly Arg Phe
20

<210> SEQ ID NO 106
<211> LENGTH: 21
<212> TYPE: PRT
<213> ORGANISM: artificial sequence
<220> FEATURE:
<223> OTHER INFORMATION: Designed HVR-H2 sequence 54

<400> SEQUENCE: 106

Val Ser Ser Ile Ser Gly Asp Gly Ser Thr Thr Tyr Tyr Ala Asp Ser
1 5 10 15

Val Lys Gly Arg Phe
20

<210> SEQ ID NO 107
<211> LENGTH: 21
<212> TYPE: PRT
<213> ORGANISM: artificial sequence
<220> FEATURE:
<223> OTHER INFORMATION: Designed HVR-H2 sequence 55

<400> SEQUENCE: 107

Val Ser Ser Ile Ser Gly Tyr Gly Ser Ser Thr Tyr Tyr Ala Asp Ser
1 5 10 15

Val Lys Gly Arg Phe
20

<210> SEQ ID NO 108
<211> LENGTH: 21
<212> TYPE: PRT
<213> ORGANISM: artificial sequence
<220> FEATURE:
<223> OTHER INFORMATION: Designed HVR-H2 sequence 56

<400> SEQUENCE: 108

Val Ser Ser Ile Ser Gly Tyr Gly Ser Thr Thr Tyr Tyr Ala Asp Ser
1 5 10 15

Val Lys Gly Arg Phe
20

<210> SEQ ID NO 109
<211> LENGTH: 21
<212> TYPE: PRT
<213> ORGANISM: artificial sequence
<220> FEATURE:
<223> OTHER INFORMATION: Designed HVR-H2 sequence 57

<400> SEQUENCE: 109

Ile Gly Trp Ile Asn Pro Asn Arg Gly Asp Thr Lys Tyr Ala Gln Lys
1 5 10 15

Phe Gln Gly Arg Val
20

<210> SEQ ID NO 110
<211> LENGTH: 21
<212> TYPE: PRT
<213> ORGANISM: artificial sequence
<220> FEATURE:
<223> OTHER INFORMATION: Designed HVR-H2 sequence 58

<400> SEQUENCE: 110

```
Ile Gly Trp Ile Asn Pro Asn Arg Gly Asp Thr Asn Tyr Ala Gln Lys
1               5                   10                  15

Phe Gln Gly Arg Val
            20
```

<210> SEQ ID NO 111
<211> LENGTH: 21
<212> TYPE: PRT
<213> ORGANISM: artificial sequence
<220> FEATURE:
<223> OTHER INFORMATION: Designed HVR-H2 sequence 59

<400> SEQUENCE: 111

```
Ile Gly Trp Ile Asn Pro Asn Arg Gly Gly Thr Lys Tyr Ala Gln Lys
1               5                   10                  15

Phe Gln Gly Arg Val
            20
```

<210> SEQ ID NO 112
<211> LENGTH: 21
<212> TYPE: PRT
<213> ORGANISM: artificial sequence
<220> FEATURE:
<223> OTHER INFORMATION: Designed HVR-H2 sequence 60

<400> SEQUENCE: 112

```
Ile Gly Trp Ile Asn Pro Asn Arg Gly Gly Thr Asn Tyr Ala Gln Lys
1               5                   10                  15

Phe Gln Gly Arg Val
            20
```

<210> SEQ ID NO 113
<211> LENGTH: 21
<212> TYPE: PRT
<213> ORGANISM: artificial sequence
<220> FEATURE:
<223> OTHER INFORMATION: Designed HVR-H2 sequence 61

<400> SEQUENCE: 113

```
Ile Gly Trp Ile Asn Pro Asn Arg Gly Ser Thr Lys Tyr Ala Gln Lys
1               5                   10                  15

Phe Gln Gly Arg Val
            20
```

<210> SEQ ID NO 114
<211> LENGTH: 21
<212> TYPE: PRT
<213> ORGANISM: artificial sequence
<220> FEATURE:
<223> OTHER INFORMATION: Designed HVR-H2 sequence 62

<400> SEQUENCE: 114

```
Ile Gly Trp Ile Asn Pro Asn Arg Gly Ser Thr Asn Tyr Ala Gln Lys
1               5                   10                  15

Phe Gln Gly Arg Val
            20
```

<210> SEQ ID NO 115
<211> LENGTH: 21
<212> TYPE: PRT
<213> ORGANISM: artificial sequence
<220> FEATURE:
<223> OTHER INFORMATION: Designed HVR-H2 sequence 63

<400> SEQUENCE: 115

Ile Gly Arg Ile Asn Pro Asn Phe Gly Asp Thr Asn Tyr Ala Gln Lys
1               5                   10                  15

Phe Gln Gly Arg Val
            20

<210> SEQ ID NO 116
<211> LENGTH: 21
<212> TYPE: PRT
<213> ORGANISM: artificial sequence
<220> FEATURE:
<223> OTHER INFORMATION: Designed HVR-H2 sequence 64

<400> SEQUENCE: 116

Ile Gly Trp Ile Asn Pro Asn Phe Gly Asp Thr Asn Tyr Ala Gln Lys
1               5                   10                  15

Phe Gln Gly Arg Val
            20

<210> SEQ ID NO 117
<211> LENGTH: 21
<212> TYPE: PRT
<213> ORGANISM: artificial sequence
<220> FEATURE:
<223> OTHER INFORMATION: Designed HVR-H2 sequence 65

<400> SEQUENCE: 117

Ile Gly Trp Ile Asn Pro Asn Phe Gly Ser Thr Lys Tyr Ala Gln Lys
1               5                   10                  15

Phe Gln Gly Arg Val
            20

<210> SEQ ID NO 118
<211> LENGTH: 21
<212> TYPE: PRT
<213> ORGANISM: artificial sequence
<220> FEATURE:
<223> OTHER INFORMATION: Designed HVR-H2 sequence 66

<400> SEQUENCE: 118

Ile Gly Trp Ile Asn Pro Asn Phe Gly Ser Thr Asn Tyr Ala Gln Lys
1               5                   10                  15

Phe Gln Gly Arg Val
            20

<210> SEQ ID NO 119
<211> LENGTH: 21
<212> TYPE: PRT
<213> ORGANISM: artificial sequence
<220> FEATURE:
<223> OTHER INFORMATION: Designed HVR-H2 sequence 67

<400> SEQUENCE: 119

Ile Gly Ile Ile Asn Pro Asn Arg Gly Asp Thr Lys Tyr Ala Gln Lys
1               5                   10                  15

Phe Gln Gly Arg Val
            20

<210> SEQ ID NO 120
<211> LENGTH: 21
<212> TYPE: PRT
<213> ORGANISM: artificial sequence
<220> FEATURE:
<223> OTHER INFORMATION: Designed HVR-H2 sequence 68

<400> SEQUENCE: 120

Ile Gly Ile Ile Asn Pro Asn Arg Gly Asp Thr Asn Tyr Ala Gln Lys
1 5 10 15

Phe Gln Gly Arg Val
20

<210> SEQ ID NO 121
<211> LENGTH: 21
<212> TYPE: PRT
<213> ORGANISM: artificial sequence
<220> FEATURE:
<223> OTHER INFORMATION: Designed HVR-H2 sequence 69

<400> SEQUENCE: 121

Ile Gly Ile Ile Asn Pro Asn Phe Gly Asp Thr Asn Tyr Ala Gln Lys
1 5 10 15

Phe Gln Gly Arg Val
20

<210> SEQ ID NO 122
<211> LENGTH: 21
<212> TYPE: PRT
<213> ORGANISM: artificial sequence
<220> FEATURE:
<223> OTHER INFORMATION: Designed HVR-H2 sequence 70

<400> SEQUENCE: 122

Ile Gly Trp Ile Ser Pro Ser Gly Gly Gly Thr Lys Tyr Ala Gln Lys
1 5 10 15

Phe Gln Gly Arg Val
20

<210> SEQ ID NO 123
<211> LENGTH: 21
<212> TYPE: PRT
<213> ORGANISM: artificial sequence
<220> FEATURE:
<223> OTHER INFORMATION: Designed HVR-H2 sequence 71

<400> SEQUENCE: 123

Ile Gly Trp Ile Ser Pro Ser Gly Gly Gly Thr Asn Tyr Ala Gln Lys
1 5 10 15

Phe Gln Gly Arg Val
20

<210> SEQ ID NO 124
<211> LENGTH: 21
<212> TYPE: PRT
<213> ORGANISM: artificial sequence
<220> FEATURE:
<223> OTHER INFORMATION: Designed HVR-H2 sequence 72

<400> SEQUENCE: 124

Ile Gly Trp Ile Ser Pro Ser Ser Gly Gly Thr Lys Tyr Ala Gln Lys
1 5 10 15

Phe Gln Gly Arg Val

20

<210> SEQ ID NO 125
<211> LENGTH: 21
<212> TYPE: PRT
<213> ORGANISM: artificial sequence
<220> FEATURE:
<223> OTHER INFORMATION: Designed HVR-H2 sequence 73

<400> SEQUENCE: 125

Ile Gly Trp Ile Ser Pro Ser Ser Gly Gly Thr Asn Tyr Ala Gln Lys
1 5 10 15

Phe Gln Gly Arg Val
20

<210> SEQ ID NO 126
<211> LENGTH: 21
<212> TYPE: PRT
<213> ORGANISM: artificial sequence
<220> FEATURE:
<223> OTHER INFORMATION: Designed HVR-H2 sequence 74

<400> SEQUENCE: 126

Ile Gly Trp Ile Tyr Pro Ser Gly Gly Gly Thr Lys Tyr Ala Gln Lys
1 5 10 15

Phe Gln Gly Arg Val
20

<210> SEQ ID NO 127
<211> LENGTH: 21
<212> TYPE: PRT
<213> ORGANISM: artificial sequence
<220> FEATURE:
<223> OTHER INFORMATION: Designed HVR-H2 sequence 75

<400> SEQUENCE: 127

Ile Gly Trp Ile Tyr Pro Ser Gly Gly Gly Thr Asn Tyr Ala Gln Lys
1 5 10 15

Phe Gln Gly Arg Val
20

<210> SEQ ID NO 128
<211> LENGTH: 21
<212> TYPE: PRT
<213> ORGANISM: artificial sequence
<220> FEATURE:
<223> OTHER INFORMATION: Designed HVR-H2 sequence 76

<400> SEQUENCE: 128

Ile Gly Trp Ile Ser Pro Ser Gly Gly Ser Thr Asn Tyr Ala Gln Lys
1 5 10 15

Phe Gln Gly Arg Val
20

<210> SEQ ID NO 129
<211> LENGTH: 21
<212> TYPE: PRT
<213> ORGANISM: artificial sequence
<220> FEATURE:
<223> OTHER INFORMATION: Designed HVR-H2 sequence 77

<400> SEQUENCE: 129

Ile Gly Trp Ile Ser Pro Ser Ser Gly Ser Thr Lys Tyr Ala Gln Lys
1 5 10 15

Phe Gln Gly Arg Val
20

<210> SEQ ID NO 130
<211> LENGTH: 21
<212> TYPE: PRT
<213> ORGANISM: artificial sequence
<220> FEATURE:
<223> OTHER INFORMATION: Designed HVR-H2 sequence 78

<400> SEQUENCE: 130

Ile Gly Trp Ile Ser Pro Ser Ser Gly Ser Thr Asn Tyr Ala Gln Lys
1 5 10 15

Phe Gln Gly Arg Val
20

<210> SEQ ID NO 131
<211> LENGTH: 21
<212> TYPE: PRT
<213> ORGANISM: artificial sequence
<220> FEATURE:
<223> OTHER INFORMATION: Designed HVR-H2 sequence 79

<400> SEQUENCE: 131

Ile Gly Trp Ile Ser Pro Ser Gly Gly Ser Thr Lys Tyr Ala Gln Lys
1 5 10 15

Phe Gln Gly Arg Val
20

<210> SEQ ID NO 132
<211> LENGTH: 21
<212> TYPE: PRT
<213> ORGANISM: artificial sequence
<220> FEATURE:
<223> OTHER INFORMATION: Designed HVR-H2 sequence 80

<400> SEQUENCE: 132

Ile Gly Ile Ile Tyr Pro Ser Gly Gly Gly Thr Asn Tyr Ala Gln Lys
1 5 10 15

Phe Gln Gly Arg Val
20

<210> SEQ ID NO 133
<211> LENGTH: 21
<212> TYPE: PRT
<213> ORGANISM: artificial sequence
<220> FEATURE:
<223> OTHER INFORMATION: Designed HVR-H2 sequence 81

<400> SEQUENCE: 133

Ile Gly Ile Ile Ser Pro Ser Gly Gly Gly Thr Lys Tyr Ala Gln Lys
1 5 10 15

Phe Gln Gly Arg Val
20

<210> SEQ ID NO 134
<211> LENGTH: 21
<212> TYPE: PRT
<213> ORGANISM: artificial sequence
<220> FEATURE:
<223> OTHER INFORMATION: Designed HVR-H2 sequence 82

<400> SEQUENCE: 134

Ile Gly Ile Ile Ser Pro Ser Gly Gly Gly Thr Asn Tyr Ala Gln Lys
1 5 10 15

```
Phe Gln Gly Arg Val
            20


<210> SEQ ID NO 135
<211> LENGTH: 21
<212> TYPE: PRT
<213> ORGANISM: artificial sequence
<220> FEATURE:
<223> OTHER INFORMATION: Designed HVR-H2 sequence 83

<400> SEQUENCE: 135

Ile Gly Ile Ile Tyr Pro Ser Gly Gly Ser Thr Asn Tyr Ala Gln Lys
1               5                   10                  15

Phe Gln Gly Arg Val
            20


<210> SEQ ID NO 136
<211> LENGTH: 23
<212> TYPE: PRT
<213> ORGANISM: artificial sequence
<220> FEATURE:
<223> OTHER INFORMATION: Designed HVR-H2 sequence 84

<400> SEQUENCE: 136

Val Gly Arg Ile Lys Ser Lys Thr Asp Gly Tyr Thr Thr Glu Tyr Ala
1               5                   10                  15

Ala Pro Val Lys Gly Arg Phe
            20


<210> SEQ ID NO 137
<211> LENGTH: 11
<212> TYPE: PRT
<213> ORGANISM: artificial sequence
<220> FEATURE:
<223> OTHER INFORMATION: Designed HVR-H1 sequence 53

<400> SEQUENCE: 137

Phe Thr Phe Ser Asp Tyr Ala Ile His Trp Val
1               5                   10


<210> SEQ ID NO 138
<211> LENGTH: 11
<212> TYPE: PRT
<213> ORGANISM: artificial sequence
<220> FEATURE:
<223> OTHER INFORMATION: Designed HVR-H1 sequence 54

<400> SEQUENCE: 138

Phe Thr Phe Ser Asp Tyr Gly Ile His Trp Val
1               5                   10


<210> SEQ ID NO 139
<211> LENGTH: 11
<212> TYPE: PRT
<213> ORGANISM: artificial sequence
<220> FEATURE:
<223> OTHER INFORMATION: Designed HVR-H1 sequence 55

<400> SEQUENCE: 139

Tyr Thr Phe Ser Asn Tyr Ala Ile His Trp Val
1               5                   10


<210> SEQ ID NO 140
<211> LENGTH: 11
<212> TYPE: PRT
```

<213> ORGANISM: artificial sequence
<220> FEATURE:
<223> OTHER INFORMATION: Designed HVR-H1 sequence 56

<400> SEQUENCE: 140

Tyr Thr Phe Ser Ser Tyr Ala Ile His Trp Val
1 5 10

<210> SEQ ID NO 141
<211> LENGTH: 11
<212> TYPE: PRT
<213> ORGANISM: artificial sequence
<220> FEATURE:
<223> OTHER INFORMATION: Designed HVR-H1 sequence 57

<400> SEQUENCE: 141

Tyr Thr Phe Thr Asp Tyr Ala Ile His Trp Val
1 5 10

<210> SEQ ID NO 142
<211> LENGTH: 11
<212> TYPE: PRT
<213> ORGANISM: artificial sequence
<220> FEATURE:
<223> OTHER INFORMATION: Designed HVR-H1 sequence 58

<400> SEQUENCE: 142

Tyr Thr Phe Thr Asp Tyr Gly Ile His Trp Val
1 5 10

<210> SEQ ID NO 143
<211> LENGTH: 11
<212> TYPE: PRT
<213> ORGANISM: artificial sequence
<220> FEATURE:
<223> OTHER INFORMATION: Designed HVR-H1 sequence 60

<400> SEQUENCE: 143

Tyr Thr Phe Thr Asn Tyr Gly Ile His Trp Val
1 5 10

<210> SEQ ID NO 144
<211> LENGTH: 11
<212> TYPE: PRT
<213> ORGANISM: artificial sequence
<220> FEATURE:
<223> OTHER INFORMATION: Designed HVR-H1 sequence 61

<400> SEQUENCE: 144

Phe Thr Phe Ser Gly Tyr Gly Ile His Trp Val
1 5 10

<210> SEQ ID NO 145
<211> LENGTH: 11
<212> TYPE: PRT
<213> ORGANISM: artificial sequence
<220> FEATURE:
<223> OTHER INFORMATION: Designed HVR-H1 sequence 62

<400> SEQUENCE: 145

Phe Thr Phe Ser Asn Tyr Ala Ile His Trp Val
1 5 10

<210> SEQ ID NO 146
<211> LENGTH: 11
<212> TYPE: PRT
<213> ORGANISM: artificial sequence
<220> FEATURE:
<223> OTHER INFORMATION: Designed HVR-H1 sequence 63

<400> SEQUENCE: 146

Phe Thr Phe Ser Ser Tyr Gly Ile His Trp Val
1 5 10

<210> SEQ ID NO 147
<211> LENGTH: 11
<212> TYPE: PRT
<213> ORGANISM: artificial sequence
<220> FEATURE:
<223> OTHER INFORMATION: Designed HVR-H1 sequence 64

<400> SEQUENCE: 147

Phe Thr Phe Ser Asp Tyr Trp Ile His Trp Val
1 5 10

<210> SEQ ID NO 148
<211> LENGTH: 11
<212> TYPE: PRT
<213> ORGANISM: artificial sequence
<220> FEATURE:
<223> OTHER INFORMATION: Designed HVR-H1 sequence 65

<400> SEQUENCE: 148

Phe Thr Phe Thr Ser Tyr Trp Ile His Trp Val
1 5 10

<210> SEQ ID NO 149
<211> LENGTH: 12
<212> TYPE: PRT
<213> ORGANISM: artificial sequence
<220> FEATURE:
<223> OTHER INFORMATION: Designed HVR-H1 sequence 66

<400> SEQUENCE: 149

Tyr Ser Ile Ser Ser Gly Tyr Tyr Trp Gly Trp Ile
1 5 10

<210> SEQ ID NO 150
<211> LENGTH: 12
<212> TYPE: PRT
<213> ORGANISM: artificial sequence
<220> FEATURE:
<223> OTHER INFORMATION: Designed HVR-H1 sequence 67

<400> SEQUENCE: 150

Tyr Ser Ile Thr Ser Gly Tyr Tyr Trp Asn Trp Ile
1 5 10

<210> SEQ ID NO 151
<211> LENGTH: 12
<212> TYPE: PRT
<213> ORGANISM: artificial sequence
<220> FEATURE:
<223> OTHER INFORMATION: Designed HVR-H1 sequence 68

<400> SEQUENCE: 151

Tyr Ser Ile Thr Ser Gly Tyr Tyr Trp Ser Trp Ile
1 5 10

<210> SEQ ID NO 152
<211> LENGTH: 12
<212> TYPE: PRT
<213> ORGANISM: artificial sequence
<220> FEATURE:

<223> OTHER INFORMATION: Designed HVR-H1 sequence 69

<400> SEQUENCE: 152

Tyr Ser Ile Ser Ser Gly His Tyr Trp Ala Trp Ile
1 5 10

<210> SEQ ID NO 153
<211> LENGTH: 12
<212> TYPE: PRT
<213> ORGANISM: artificial sequence
<220> FEATURE:
<223> OTHER INFORMATION: Designed HVR-H1 sequence 70

<400> SEQUENCE: 153

Tyr Ser Ile Ser Ser Gly His Tyr Trp Gly Trp Ile
1 5 10

<210> SEQ ID NO 154
<211> LENGTH: 13
<212> TYPE: PRT
<213> ORGANISM: artificial sequence
<220> FEATURE:
<223> OTHER INFORMATION: Designed HVR-H1 sequence 71

<400> SEQUENCE: 154

Phe Ser Leu Ser Thr Ser Gly Val Ala Val Gly Trp Ile
1 5 10

<210> SEQ ID NO 155
<211> LENGTH: 13
<212> TYPE: PRT
<213> ORGANISM: artificial sequence
<220> FEATURE:
<223> OTHER INFORMATION: Designed HVR-H1 sequence 72

<400> SEQUENCE: 155

Phe Ser Leu Ser Thr Ser Gly Val Gly Val Ala Trp Ile
1 5 10

<210> SEQ ID NO 156
<211> LENGTH: 13
<212> TYPE: PRT
<213> ORGANISM: artificial sequence
<220> FEATURE:
<223> OTHER INFORMATION: Designed HVR-H1 sequence 73

<400> SEQUENCE: 156

Phe Ser Leu Ser Thr Ser Gly Val Gly Val Gly Trp Ile
1 5 10

<210> SEQ ID NO 157
<211> LENGTH: 13
<212> TYPE: PRT
<213> ORGANISM: artificial sequence
<220> FEATURE:
<223> OTHER INFORMATION: Designed HVR-H1 sequence 74

<400> SEQUENCE: 157

Phe Ser Leu Ser Thr Gly Gly Val Gly Val Gly Trp Ile
1 5 10

<210> SEQ ID NO 158
<211> LENGTH: 21
<212> TYPE: PRT
<213> ORGANISM: artificial sequence
<220> FEATURE:
<223> OTHER INFORMATION: Designed HVR-H2 sequence 85

-continued

<400> SEQUENCE: 158

Val Ser Ala Ile Ser Gly Ser Gly Ser Thr Thr Tyr Tyr Ala Asp Ser
1 5 10 15

Val Lys Gly Arg Phe
20

<210> SEQ ID NO 159
<211> LENGTH: 21
<212> TYPE: PRT
<213> ORGANISM: artificial sequence
<220> FEATURE:
<223> OTHER INFORMATION: Designed HVR-H2 sequence 86

<400> SEQUENCE: 159

Val Ser Ser Ile Ser Gly Ser Gly Asp Thr Thr Tyr Tyr Ala Asp Ser
1 5 10 15

Val Lys Gly Arg Phe
20

<210> SEQ ID NO 160
<211> LENGTH: 21
<212> TYPE: PRT
<213> ORGANISM: artificial sequence
<220> FEATURE:
<223> OTHER INFORMATION: Designed HVR-H2 sequence 87

<400> SEQUENCE: 160

Val Ser Ser Ile Ser Gly Ser Gly Gly Ser Thr Tyr Tyr Ala Asp Ser
1 5 10 15

Val Lys Gly Arg Phe
20

<210> SEQ ID NO 161
<211> LENGTH: 21
<212> TYPE: PRT
<213> ORGANISM: artificial sequence
<220> FEATURE:
<223> OTHER INFORMATION: Designed HVR-H2 sequence 88

<400> SEQUENCE: 161

Val Ser Ser Ile Ser Gly Ser Gly Gly Thr Thr Tyr Tyr Ala Asp Ser
1 5 10 15

Val Lys Gly Arg Phe
20

<210> SEQ ID NO 162
<211> LENGTH: 21
<212> TYPE: PRT
<213> ORGANISM: artificial sequence
<220> FEATURE:
<223> OTHER INFORMATION: Designed HVR-H2 sequence 89

<400> SEQUENCE: 162

Val Ser Ser Ile Ser Gly Asp Gly Gly Ser Thr Tyr Tyr Ala Asp Ser
1 5 10 15

Val Lys Gly Arg Phe
20

<210> SEQ ID NO 163
<211> LENGTH: 21
<212> TYPE: PRT
<213> ORGANISM: artificial sequence
<220> FEATURE:

<223> OTHER INFORMATION: Designed HVR-H2 sequence 90

<400> SEQUENCE: 163

Val Ser Ser Ile Ser Gly Ser Gly Ser Thr Thr Tyr Tyr Ala Asp Ser
1 5 10 15

Val Lys Gly Arg Phe
20

<210> SEQ ID NO 164
<211> LENGTH: 26
<212> TYPE: PRT
<213> ORGANISM: artificial sequence
<220> FEATURE:
<223> OTHER INFORMATION: Framework FW-H1 sequence

<400> SEQUENCE: 164

Glu Val Gln Leu Val Glu Ser Gly Gly Gly Leu Val Gln Pro Gly Gly
1 5 10 15

Ser Leu Arg Leu Ser Cys Ala Ala Ser Gly
20 25

<210> SEQ ID NO 165
<211> LENGTH: 10
<212> TYPE: PRT
<213> ORGANISM: artificial sequence
<220> FEATURE:
<223> OTHER INFORMATION: Framework FW-H2 sequence

<400> SEQUENCE: 165

Arg Gln Ala Pro Gly Lys Gly Leu Glu Trp
1 5 10

<210> SEQ ID NO 166
<211> LENGTH: 29
<212> TYPE: PRT
<213> ORGANISM: artificial sequence
<220> FEATURE:
<223> OTHER INFORMATION: Framework FW-H3 sequence

<400> SEQUENCE: 166

Thr Ile Ser Ser Arg Asp Asn Ser Lys Asn Thr Leu Tyr Leu Gln Leu
1 5 10 15

Asn Ser Leu Arg Ala Glu Asp Thr Ala Val Tyr Tyr Cys
20 25

<210> SEQ ID NO 167
<211> LENGTH: 11
<212> TYPE: PRT
<213> ORGANISM: artificial sequence
<220> FEATURE:
<223> OTHER INFORMATION: Framework FW-H4 sequence

<400> SEQUENCE: 167

Trp Gly Gln Gly Thr Leu Val Thr Val Ser Ser
1 5 10

<210> SEQ ID NO 168
<211> LENGTH: 120
<212> TYPE: PRT
<213> ORGANISM: artificial sequence
<220> FEATURE:
<223> OTHER INFORMATION: Hit ID 4029 - VH

<400> SEQUENCE: 168

Glu Val Gln Leu Val Glu Ser Gly Gly Gly Leu Val Gln Pro Gly Gly

-continued

```
1               5                   10                  15

Ser Leu Arg Leu Ser Cys Ala Ala Ser Gly Tyr Ser Ile Thr Ser Gly
            20                  25                  30

Tyr His Trp Gly Trp Ile Arg Gln Ala Pro Gly Lys Gly Leu Glu Trp
        35                  40                  45

Val Ser Tyr Ile Ser Gly Ala Gly Asp Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Asp Tyr Gly Asp Tyr Tyr Gly Phe Asp Tyr Trp Gly Gln
            100                 105                 110

Gly Thr Leu Val Thr Val Ser Ser
        115                 120


<210> SEQ ID NO 169
<211> LENGTH: 112
<212> TYPE: PRT
<213> ORGANISM: artificial sequence
<220> FEATURE:
<223> OTHER INFORMATION: HIT ID 4029 - VL

<400> SEQUENCE: 169

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Ile Ser Phe Leu Ala Trp Tyr Gln Gln Lys Pro Gly Lys Ala Pro
        35                  40                  45

Lys Leu Leu Ile Tyr Asp Ala Ser Asn Leu Glu Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Tyr
                85                  90                  95

Arg Thr Pro Phe Thr Phe Gly Gln Gly Thr Lys Val Glu Ile Lys Arg
            100                 105                 110


<210> SEQ ID NO 170
<211> LENGTH: 11
<212> TYPE: PRT
<213> ORGANISM: artificial sequence
<220> FEATURE:
<223> OTHER INFORMATION: Designed HVR-H1 sequence 59

<400> SEQUENCE: 170

Tyr Thr Phe Thr Asn Tyr Ala Ile His Trp Val
1               5                   10


<210> SEQ ID NO 171
<211> LENGTH: 123
<212> TYPE: PRT
<213> ORGANISM: artificial sequence
<220> FEATURE:
<223> OTHER INFORMATION: Hit ID 7097 - VH

<400> SEQUENCE: 171

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Ser Ile Ser Ser Gly
            20                  25                  30

His His Trp Asp Trp Ile Arg Gln Ala Pro Gly Lys Gly Leu Glu Trp
        35                  40                  45

Val Ser Tyr Ile Ser Gly Ala Gly Asp Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Asp Ala Val Leu Gly Asp Trp Phe Ala Tyr
            100                 105                 110

Trp Gly Gln Gly Thr Leu Val Thr Val Ser Ser
        115                 120


<210> SEQ ID NO 172
<211> LENGTH: 108
<212> TYPE: PRT
<213> ORGANISM: artificial sequence
<220> FEATURE:
<223> OTHER INFORMATION: HIT ID 7097 - VL

<400> SEQUENCE: 172

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105


<210> SEQ ID NO 173
<211> LENGTH: 124
<212> TYPE: PRT
<213> ORGANISM: artificial sequence
<220> FEATURE:
<223> OTHER INFORMATION: Hit ID 5906 - VH

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Asn Trp Ile Arg Gln Ala Pro Gly Lys Gly Leu Glu Trp
        35                  40                  45

Val Ser Tyr Ile Ser Gly Asp Gly Asp Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
```

```
                85                  90                  95

Cys Ala Arg Asp Leu Gly Gly Tyr Tyr Gly Trp Gly Arg Tyr Phe Asp
            100                 105                 110

Tyr Trp Gly Gln Gly Thr Leu Val Thr Val Ser Ser
        115                 120


<210> SEQ ID NO 174
<211> LENGTH: 108
<212> TYPE: PRT
<213> ORGANISM: artificial sequence
<220> FEATURE:
<223> OTHER INFORMATION: HIT ID 5906 - VL

<400> SEQUENCE: 174

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg
            100                 105


<210> SEQ ID NO 175
<211> LENGTH: 119
<212> TYPE: PRT
<213> ORGANISM: artificial sequence
<220> FEATURE:
<223> OTHER INFORMATION: Hit ID 7040 - VH

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr Tyr Trp Asn Trp Ile Arg Gln Ala Pro Gly Lys Gly Leu Glu Trp
        35                  40                  45

Ile Gly Trp Ile Ser Pro Ser Gly Gly Ser Thr Asn Tyr Ala Gln Lys
    50                  55                  60

Phe Gln Gly Arg Val Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Asp Leu Thr Ala Gly Gly Phe Asp Tyr Trp Gly Gln Gly
            100                 105                 110

Thr Leu Val Thr Val Ser Ser
        115


<210> SEQ ID NO 176
<211> LENGTH: 108
<212> TYPE: PRT
<213> ORGANISM: artificial sequence
<220> FEATURE:
```

<223> OTHER INFORMATION: HIT ID 7040 - VL

<400> SEQUENCE: 176

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105
```

<210> SEQ ID NO 177
<211> LENGTH: 120
<212> TYPE: PRT
<213> ORGANISM: artificial sequence
<220> FEATURE:
<223> OTHER INFORMATION: Hit ID 5924 - VH

<400> SEQUENCE: 177

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Gly Trp Ile Arg Gln Ala Pro Gly Lys Gly Leu Glu Trp
        35                  40                  45

Ile Gly Ile Ile Ser Pro Ser Ser Gly Ser Thr Lys Tyr Ala Gln Lys
    50                  55                  60

Phe Gln Gly Arg Val Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Ala Gly Val His Tyr Ala Leu Asp Tyr Trp Gly Gln
            100                 105                 110

Gly Thr Leu Val Thr Val Ser Ser
        115                 120
```

<210> SEQ ID NO 178
<211> LENGTH: 108
<212> TYPE: PRT
<213> ORGANISM: artificial sequence
<220> FEATURE:
<223> OTHER INFORMATION: HIT ID 5924 - VL

<400> SEQUENCE: 178

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg
            100                 105


<210> SEQ ID NO 179
<211> LENGTH: 123
<212> TYPE: PRT
<213> ORGANISM: artificial sequence
<220> FEATURE:
<223> OTHER INFORMATION: Hit ID 4034 - VH

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

His Tyr Trp Asn Trp Ile Arg Gln Ala Pro Gly Lys Gly Leu Glu Trp
        35                  40                  45

Val Ser Ser Ile Ser Gly Tyr Gly Ser Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Arg Tyr Tyr Gly Ser Thr Asp Tyr Ala Phe Asp Tyr
            100                 105                 110

Trp Gly Gln Gly Thr Leu Val Thr Val Ser Ser
        115                 120


<210> SEQ ID NO 180
<211> LENGTH: 107
<212> TYPE: PRT
<213> ORGANISM: artificial sequence
<220> FEATURE:
<223> OTHER INFORMATION: HIT ID 4034 - VL

<400> SEQUENCE: 180

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Arg Val Ser His Val
            20                  25                  30

Phe Trp Tyr Gln Gln Lys Pro Gly Lys Ala Pro Lys Leu Leu Ile Tyr
        35                  40                  45

Ala Ala Ser Thr Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Phe Cys Leu Gln Gly Thr His Phe Pro Trp Thr
                85                  90                  95

Phe Gly Gln Gly Thr Lys Val Glu Ile Lys Arg
            100                 105


<210> SEQ ID NO 181
<211> LENGTH: 118
```

<212> TYPE: PRT
<213> ORGANISM: artificial sequence
<220> FEATURE:
<223> OTHER INFORMATION: Hit ID 6010 - VH

<400> SEQUENCE: 181

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

His Tyr Trp Asn Trp Ile Arg Gln Ala Pro Gly Lys Gly Leu Glu Trp
        35                  40                  45

Ile Gly Trp Ile Asn Pro Asn Arg Gly Asp Thr Asn Tyr Ala Gln Lys
    50                  55                  60

Phe Gln Gly Arg Val Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Asp Tyr Tyr Gly Asp Phe Asp Tyr Trp Gly Gln Gly Thr
            100                 105                 110

Leu Val Thr Val Ser Ser
        115
```

<210> SEQ ID NO 182
<211> LENGTH: 108
<212> TYPE: PRT
<213> ORGANISM: artificial sequence
<220> FEATURE:
<223> OTHER INFORMATION: HIT ID 6010 - VL

<400> SEQUENCE: 182

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gln Gly Thr Lys Val Glu Ile Lys Arg
            100                 105
```

<210> SEQ ID NO 183
<211> LENGTH: 123
<212> TYPE: PRT
<213> ORGANISM: artificial sequence
<220> FEATURE:
<223> OTHER INFORMATION: Hit ID 7183 - VH

<400> SEQUENCE: 183

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

His Tyr Trp Asn Trp Ile Arg Gln Ala Pro Gly Lys Gly Leu Glu Trp
```

```
        35                  40                  45

Val Ser Ser Ile Ser Gly Tyr Gly Asp Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Asp Thr Val Leu Gly Asp Trp Phe Ala Tyr
            100                 105                 110

Trp Gly Gln Gly Thr Leu Val Thr Val Ser Ser
        115                 120


<210> SEQ ID NO 184
<211> LENGTH: 108
<212> TYPE: PRT
<213> ORGANISM: artificial sequence
<220> FEATURE:
<223> OTHER INFORMATION: HIT ID 7183 - VL

<400> SEQUENCE: 184

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg
            100                 105


<210> SEQ ID NO 185
<211> LENGTH: 120
<212> TYPE: PRT
<213> ORGANISM: artificial sequence
<220> FEATURE:
<223> OTHER INFORMATION: Hit ID 4036 - VH

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Ile Gly Glu Ile Tyr His Ser Gly Ser Thr Tyr Tyr Ser Pro Ser
    50                  55                  60

Leu Lys Ser Arg Val Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Arg Tyr Gly Ser Tyr Tyr Phe Asp Tyr Trp Gly Gln
            100                 105                 110
```

Gly Thr Leu Val Thr Val Ser Ser
115 120

<210> SEQ ID NO 186
<211> LENGTH: 112
<212> TYPE: PRT
<213> ORGANISM: artificial sequence
<220> FEATURE:
<223> OTHER INFORMATION: HIT ID 4036 - VL

<400> SEQUENCE: 186

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Val Asp Phe Tyr
20 25 30

Gly Lys Ser Phe Leu Asp Trp Tyr Gln Gln Lys Pro Gly Lys Ala Pro
35 40 45

Lys Leu Leu Ile Tyr Asp Ala Ser Ser Leu Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Gln Gln Tyr Tyr
85 90 95

Arg Ile Pro Pro Thr Phe Gly Gln Gly Thr Lys Val Glu Ile Lys Arg
100 105 110

<210> SEQ ID NO 187
<211> LENGTH: 117
<212> TYPE: PRT
<213> ORGANISM: artificial sequence
<220> FEATURE:
<223> OTHER INFORMATION: Hit ID 5115 - VH

<400> SEQUENCE: 187

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Ser Ser Gly
20 25 30

His Tyr Trp Gly Trp Ile Arg Gln Ala Pro Gly Lys Gly Leu Glu Trp
35 40 45

Ile Gly Glu Ile Tyr His Ser Gly Ser Thr Tyr Tyr Ser Pro Ser Leu
50 55 60

Lys Ser Arg Val Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Glu Ser Tyr Tyr Ala Phe Asp Tyr Trp Gly Gln Gly Thr Leu
100 105 110

Val Thr Val Ser Ser
115

<210> SEQ ID NO 188
<211> LENGTH: 108
<212> TYPE: PRT
<213> ORGANISM: artificial sequence
<220> FEATURE:
<223> OTHER INFORMATION: HIT ID 5115 - VL

<400> SEQUENCE: 188

Asp Ile Gln Leu Thr Gln Ser Pro Ser Ser Leu Ser Ala Ser Val Gly

```
1               5                   10                  15

Asp Arg Val Thr Ile Thr Cys Arg Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Pro Leu
                85                  90                  95

Thr Phe Gly Gln Gly Thr Lys Val Glu Ile Lys Arg
            100                 105


<210> SEQ ID NO 189
<211> LENGTH: 119
<212> TYPE: PRT
<213> ORGANISM: artificial sequence
<220> FEATURE:
<223> OTHER INFORMATION: Hit ID 5404 - VH

<400> SEQUENCE: 189

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Ala Trp Ile Arg Gln Ala Pro Gly Lys Gly Leu Glu Trp
        35                  40                  45

Ile Gly Glu Ile Tyr His Ser Gly Ser Thr Tyr Tyr Ser Pro Ser Leu
    50                  55                  60

Lys Ser Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Pro Tyr Tyr Tyr Gly Val Phe Asp Tyr Trp Gly Gln Gly
            100                 105                 110

Thr Leu Val Thr Val Ser Ser
        115


<210> SEQ ID NO 190
<211> LENGTH: 107
<212> TYPE: PRT
<213> ORGANISM: artificial sequence
<220> FEATURE:
<223> OTHER INFORMATION: HIT ID 5404 - VL

<400> SEQUENCE: 190

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Arg Val Gly Ser Val
            20                  25                  30

Tyr Trp Tyr Gln Gln Lys Pro Gly Lys Ala Pro Lys Leu Leu Ile Tyr
        35                  40                  45

Asp Ala Ser Asn Leu Glu Thr Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80
```

```
Asp Phe Ala Thr Tyr Tyr Cys Gln Gln Tyr Thr His Asp Pro Val Thr
            85                  90                  95

Phe Gly Gln Gly Thr Lys Val Glu Ile Lys Arg
            100                 105


<210> SEQ ID NO 191
<211> LENGTH: 120
<212> TYPE: PRT
<213> ORGANISM: artificial sequence
<220> FEATURE:
<223> OTHER INFORMATION: Hit ID 3757 - VH

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Gly Ile His Trp Val Arg Gln Ala Pro Gly Lys Gly Leu Glu Trp Ile
        35                  40                  45

Gly Trp Ile Ser Pro Ser Gly Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg His Ser Tyr Tyr Gly Val Gly Asp Phe Asp Tyr Trp Gly Gln
            100                 105                 110

Gly Thr Leu Val Thr Val Ser Ser
        115                 120


<210> SEQ ID NO 192
<211> LENGTH: 108
<212> TYPE: PRT
<213> ORGANISM: artificial sequence
<220> FEATURE:
<223> OTHER INFORMATION: HIT ID 3757 - VL

<400> SEQUENCE: 192

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg
            100                 105


<210> SEQ ID NO 193
<211> LENGTH: 120
<212> TYPE: PRT
<213> ORGANISM: artificial sequence
<220> FEATURE:
<223> OTHER INFORMATION: Hit ID 5103 - VH
```

<400> SEQUENCE: 193

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Gly Ile His Trp Val Arg Gln Ala Pro Gly Lys Gly Leu Glu Trp Ile
        35                  40                  45

Gly Trp Ile Ser Pro Ser Gly Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg His Ser Tyr Tyr Gly Val Gly Asp Phe Asp Tyr Trp Gly Gln
            100                 105                 110

Gly Thr Leu Val Thr Val Ser Ser
        115                 120
```

<210> SEQ ID NO 194
<211> LENGTH: 108
<212> TYPE: PRT
<213> ORGANISM: artificial sequence
<220> FEATURE:
<223> OTHER INFORMATION: HIT ID 5103 - VL

<400> SEQUENCE: 194

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg
            100                 105
```

<210> SEQ ID NO 195
<211> LENGTH: 117
<212> TYPE: PRT
<213> ORGANISM: artificial sequence
<220> FEATURE:
<223> OTHER INFORMATION: Hit ID 4027 - VH

<400> SEQUENCE: 195

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

His His Trp Asn Trp Ile Arg Gln Ala Pro Gly Lys Gly Leu Glu Trp
        35                  40                  45

Ile Gly Trp Ile Ser Pro Ser Ser Gly Gly Thr Lys Tyr Ala Gln Lys
    50                  55                  60
```

```
Phe Gln Gly Arg Val Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Phe Asp Gly Phe His Tyr Trp Gly Gln Gly Thr Leu
            100                 105                 110

Val Thr Val Ser Ser
        115


<210> SEQ ID NO 196
<211> LENGTH: 112
<212> TYPE: PRT
<213> ORGANISM: artificial sequence
<220> FEATURE:
<223> OTHER INFORMATION: HIT ID 4027 - VL

<400> SEQUENCE: 196

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Tyr
            20                  25                  30

Gly Ile Ser Phe Leu Pro Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Tyr
                85                  90                  95

Ser Trp Pro Trp Thr Phe Gly Gln Gly Thr Lys Val Glu Ile Lys Arg
            100                 105                 110


<210> SEQ ID NO 197
<211> LENGTH: 117
<212> TYPE: PRT
<213> ORGANISM: artificial sequence
<220> FEATURE:
<223> OTHER INFORMATION: VH in FIG. 1B

<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Gly Ile His Trp Val Arg Gln Ala Pro Gly Lys Gly Leu Glu Trp Val
        35                  40                  45

Ser Gly Ile Ser Gly Ala Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Glu Arg Asp Tyr Asp Phe Asp Tyr Trp Gly Gln Gly Thr Leu
            100                 105                 110

Val Thr Val Ser Ser
        115


<210> SEQ ID NO 198
```

<211> LENGTH: 11
<212> TYPE: PRT
<213> ORGANISM: artificial sequence
<220> FEATURE:
<223> OTHER INFORMATION: Formula (I)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 198

```
Xaa Thr Phe Xaa Xaa Tyr Xaa Ile His Trp Val
1               5                   10
```

<210> SEQ ID NO 199
<211> LENGTH: 12
<212> TYPE: PRT
<213> ORGANISM: artificial sequence
<220> FEATURE:
<223> OTHER INFORMATION: Formula (II)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 199

```
Tyr Ser Ile Xaa Ser Gly Xaa Xaa Trp Xaa Trp Ile
1               5                   10
```

<210> SEQ ID NO 200
<211> LENGTH: 13
<212> TYPE: PRT
<213> ORGANISM: artificial sequence
<220> FEATURE:
<223> OTHER INFORMATION: Formula (III)
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 200

```
Phe Ser Leu Ser Thr Xaa Gly Val Xaa Val Xaa Trp Ile
1               5                   10
```

<210> SEQ ID NO 201
<211> LENGTH: 20
<212> TYPE: PRT
<213> ORGANISM: artificial sequence
<220> FEATURE:

<223> OTHER INFORMATION: Formula (IV)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 201

```
Leu Ala Xaa Ile Xaa Trp Xaa Xaa Asp Lys Xaa Tyr Ser Xaa Ser Leu
1               5                   10                  15

Lys Ser Arg Leu
            20
```

<210> SEQ ID NO 202
<211> LENGTH: 20
<212> TYPE: PRT
<213> ORGANISM: artificial sequence
<220> FEATURE:
<223> OTHER INFORMATION: Formula (V)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 202

```
Ile Gly Xaa Ile Xaa Xaa Ser Gly Ser Thr Tyr Tyr Ser Pro Ser Leu
1               5                   10                  15

Lys Ser Arg Val
            20
```

<210> SEQ ID NO 203
<211> LENGTH: 20
<212> TYPE: PRT
<213> ORGANISM: artificial sequence
<220> FEATURE:
<223> OTHER INFORMATION: Formula (VI)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 203

```
Ile Gly Xaa Ile Tyr Xaa Ser Gly Xaa Thr Xaa Tyr Asn Pro Ser Leu
1               5                   10                  15

Lys Ser Arg Val
            20


<210> SEQ ID NO 204
<211> LENGTH: 21
<212> TYPE: PRT
<213> ORGANISM: artificial sequence
<220> FEATURE:
<223> OTHER INFORMATION: Formula (VII)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 204

Val Ser Xaa Ile Ser Gly Xaa Gly Xaa Xaa Thr Tyr Tyr Ala Asp Ser
1               5                   10                  15

Val Lys Gly Arg Phe
            20


<210> SEQ ID NO 205
<211> LENGTH: 21
<212> TYPE: PRT
<213> ORGANISM: artificial sequence
<220> FEATURE:
<223> OTHER INFORMATION: Formula (VIII)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 205

Ile Gly Xaa Ile Asn Pro Asn Xaa Gly Xaa Thr Xaa Tyr Ala Gln Lys
1               5                   10                  15

Phe Gln Gly Arg Val
            20


<210> SEQ ID NO 206
<211> LENGTH: 21
<212> TYPE: PRT
<213> ORGANISM: artificial sequence
<220> FEATURE:
<223> OTHER INFORMATION: Formula (IX)
<220> FEATURE:
<221> NAME/KEY: misc_feature
<222> LOCATION: (3)..(3)
<223> OTHER INFORMATION: Xaa can be any naturally occurring amino acid
<220> FEATURE:
```

<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 206

```
Ile Gly Xaa Ile Xaa Pro Ser Xaa Gly Xaa Thr Xaa Tyr Ala Gln Lys
1               5                   10                  15

Phe Gln Gly Arg Val
            20
```

<210> SEQ ID NO 207
<211> LENGTH: 23
<212> TYPE: PRT
<213> ORGANISM: artificial sequence
<220> FEATURE:
<223> OTHER INFORMATION: Formula (X)
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 207

```
Val Gly Arg Ile Xaa Ser Lys Xaa Xaa Gly Xaa Thr Thr Xaa Tyr Ala
1               5                   10                  15

Ala Xaa Val Lys Gly Arg Phe
            20
```

<210> SEQ ID NO 208
<211> LENGTH: 20
<212> TYPE: PRT
<213> ORGANISM: artificial sequence
<220> FEATURE:
<223> OTHER INFORMATION: Formula (XI)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 208

```
Ile Gly Xaa Ile Xaa Xaa Ser Gly Ser Thr Tyr Tyr Ser Pro Ser Leu
```

1 5 10 15

Lys Ser Arg Val
20

<210> SEQ ID NO 209
<211> LENGTH: 20
<212> TYPE: PRT
<213> ORGANISM: artificial sequence
<220> FEATURE:
<223> OTHER INFORMATION: Formula (XII)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 209

Ile Gly Xaa Ile Tyr Xaa Ser Gly Xaa Thr Xaa Tyr Asn Pro Ser Leu
1 5 10 15

Lys Ser Arg Val
20

<210> SEQ ID NO 210
<211> LENGTH: 23
<212> TYPE: PRT
<213> ORGANISM: artificial sequence
<220> FEATURE:
<223> OTHER INFORMATION: Formula (XIII)
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 210

Val Gly Arg Ile Xaa Ser Lys Xaa Xaa Gly Xaa Thr Thr Glu Tyr Ala
1 5 10 15

Ala Xaa Val Lys Gly Arg Phe
20

<210> SEQ ID NO 211
<211> LENGTH: 23
<212> TYPE: DNA
<213> ORGANISM: artificial sequence
<220> FEATURE:
<223> OTHER INFORMATION: Primer F_1999

<400> SEQUENCE: 211
cgtttgtcct gtgcagcttc cgg 23

<210> SEQ ID NO 212
<211> LENGTH: 25
<212> TYPE: DNA
<213> ORGANISM: artificial sequence
<220> FEATURE:
<223> OTHER INFORMATION: Primer R_1999

<400> SEQUENCE: 212
cgaggccctt acccggggcc tgacg 25

<210> SEQ ID NO 213
<211> LENGTH: 21
<212> TYPE: DNA
<213> ORGANISM: artificial sequence
<220> FEATURE:
<223> OTHER INFORMATION: Primer F_2003

<400> SEQUENCE: 213
ccgggtaagg gcctcgagtg g 21

<210> SEQ ID NO 214
<211> LENGTH: 33
<212> TYPE: DNA
<213> ORGANISM: artificial sequence
<220> FEATURE:
<223> OTHER INFORMATION: Primer R_2003

<400> SEQUENCE: 214
gagcacgtcc gttcgaattg tcgcgactta tag 33

<210> SEQ ID NO 215
<211> LENGTH: 45
<212> TYPE: DNA
<213> ORGANISM: artificial sequence
<220> FEATURE:
<223> OTHER INFORMATION: Primer S1089

<400> SEQUENCE: 215
acaactgaac agcttaagag ctgaggacac tgccgtctat tattg 45

<210> SEQ ID NO 216
<211> LENGTH: 32
<212> TYPE: DNA
<213> ORGANISM: artificial sequence
<220> FEATURE:
<223> OTHER INFORMATION: Primer S1090

<400> SEQUENCE: 216
gaggagacgg tgactagtgt tccttgaccc ca 32

<210> SEQ ID NO 217
<211> LENGTH: 34
<212> TYPE: DNA
<213> ORGANISM: artificial sequence
<220> FEATURE:
<223> OTHER INFORMATION: Primer F_2898

<400> SEQUENCE: 217
tacttatgta ggcgatcggg tcaccatcac ctgc 34

<210> SEQ ID NO 218
<211> LENGTH: 28
<212> TYPE: DNA
<213> ORGANISM: artificial sequence
<220> FEATURE:
<223> OTHER INFORMATION: Primer R_2898

<400> SEQUENCE: 218
cggagctttt cctggtttct gttgatac 28

<210> SEQ ID NO 219
<211> LENGTH: 22
<212> TYPE: DNA
<213> ORGANISM: artificial sequence
<220> FEATURE:
<223> OTHER INFORMATION: Primer F_2013

<400> SEQUENCE: 219
gaaaccagga aaagctccga ag 22

<210> SEQ ID NO 220
<211> LENGTH: 29
<212> TYPE: DNA
<213> ORGANISM: artificial sequence
<220> FEATURE:
<223> OTHER INFORMATION: Primer R_2013

<400> SEQUENCE: 220
cgtcccggaa ccggatccag agaagcgag 29

<210> SEQ ID NO 221
<211> LENGTH: 35
<212> TYPE: DNA
<213> ORGANISM: artificial sequence
<220> FEATURE:
<223> OTHER INFORMATION: Primer F2929

<400> SEQUENCE: 221
accatcagca gtctgcagcc ggaagacttc gcaac 35

<210> SEQ ID NO 222
<211> LENGTH: 27
<212> TYPE: DNA
<213> ORGANISM: artificial sequence
<220> FEATURE:
<223> OTHER INFORMATION: Primer R2929

<400> SEQUENCE: 222
gatctccacc ttggtaccct gtccgaa 27

<210> SEQ ID NO 223
<211> LENGTH: 16
<212> TYPE: PRT
<213> ORGANISM: artificial sequence
<220> FEATURE:
<223> OTHER INFORMATION: HVR-H3 sequence 1

<400> SEQUENCE: 223

Ala Arg Asp Leu Gly Gly Tyr Tyr Gly Trp Gly Arg Tyr Phe Asp Tyr
1 5 10 15

<210> SEQ ID NO 224
<211> LENGTH: 11
<212> TYPE: PRT
<213> ORGANISM: artificial sequence
<220> FEATURE:
<223> OTHER INFORMATION: HVR-H3 sequence 2

<400> SEQUENCE: 224

Ala Arg Asp Leu Thr Ala Gly Gly Phe Asp Tyr 1 5 10

<210> SEQ ID NO 225
<211> LENGTH: 11
<212> TYPE: PRT
<213> ORGANISM: artificial sequence
<220> FEATURE:
<223> OTHER INFORMATION: HVR-H3 sequence 3

<400> SEQUENCE: 225

Ala Arg Asp Pro Gly Val Gly Gly Phe Asp Val
1 5 10

<210> SEQ ID NO 226
<211> LENGTH: 12
<212> TYPE: PRT
<213> ORGANISM: artificial sequence
<220> FEATURE:
<223> OTHER INFORMATION: HVR-H3 sequence 4

<400> SEQUENCE: 226

Ala Arg Asp Pro Gly Tyr Thr Trp Tyr Phe Asp Val
1 5 10

<210> SEQ ID NO 227
<211> LENGTH: 12
<212> TYPE: PRT
<213> ORGANISM: artificial sequence
<220> FEATURE:
<223> OTHER INFORMATION: HVR-H3 sequence 5

<400> SEQUENCE: 227

Ala Arg Asp Tyr Gly Asp Tyr Tyr Gly Phe Asp Tyr
1 5 10

<210> SEQ ID NO 228
<211> LENGTH: 12
<212> TYPE: PRT
<213> ORGANISM: artificial sequence
<220> FEATURE:
<223> OTHER INFORMATION: HVR-H3 sequence 6

<400> SEQUENCE: 228

Ala Arg Asp Tyr Gly Tyr Thr Trp Tyr Phe Asp Val
1 5 10

<210> SEQ ID NO 229
<211> LENGTH: 10
<212> TYPE: PRT
<213> ORGANISM: artificial sequence
<220> FEATURE:
<223> OTHER INFORMATION: HVR-H3 sequence 7

<400> SEQUENCE: 229

Ala Arg Asp Tyr Tyr Gly Asp Phe Asp Tyr
1 5 10

<210> SEQ ID NO 230
<211> LENGTH: 15
<212> TYPE: PRT
<213> ORGANISM: artificial sequence
<220> FEATURE:
<223> OTHER INFORMATION: HVR-H3 sequence 8

<400> SEQUENCE: 230

Ala Arg Glu Gly Ser Asp Ala Val Leu Gly Asp Trp Phe Ala Tyr
1 5 10 15

<210> SEQ ID NO 231
<211> LENGTH: 15
<212> TYPE: PRT
<213> ORGANISM: artificial sequence
<220> FEATURE:
<223> OTHER INFORMATION: HVR-H3 sequence 9

<400> SEQUENCE: 231

Ala Arg Glu Gly Ser Asp Thr Val Leu Gly Asp Trp Phe Ala Tyr
1               5                   10                  15

<210> SEQ ID NO 232
<211> LENGTH: 12
<212> TYPE: PRT
<213> ORGANISM: artificial sequence
<220> FEATURE:
<223> OTHER INFORMATION: HVR-H3 sequence 10

<400> SEQUENCE: 232

Ala Arg Glu Arg Tyr Gly Ser Tyr Tyr Phe Asp Tyr
1               5                   10

<210> SEQ ID NO 233
<211> LENGTH: 15
<212> TYPE: PRT
<213> ORGANISM: artificial sequence
<220> FEATURE:
<223> OTHER INFORMATION: HVR-H3 sequence 11

<400> SEQUENCE: 233

Ala Arg Glu Arg Tyr Tyr Gly Ser Thr Asp Tyr Ala Phe Asp Tyr
1               5                   10                  15

<210> SEQ ID NO 234
<211> LENGTH: 10
<212> TYPE: PRT
<213> ORGANISM: artificial sequence
<220> FEATURE:
<223> OTHER INFORMATION: HVR-H3 sequence 12

<400> SEQUENCE: 234

Ala Arg Glu Ser Tyr Tyr Ala Phe Asp Tyr
1               5                   10

<210> SEQ ID NO 235
<211> LENGTH: 12
<212> TYPE: PRT
<213> ORGANISM: artificial sequence
<220> FEATURE:
<223> OTHER INFORMATION: HVR-H3 sequence 13

<400> SEQUENCE: 235

Ala Arg Gly Ala Gly Val His Tyr Ala Leu Asp Tyr
1               5                   10

<210> SEQ ID NO 236
<211> LENGTH: 9
<212> TYPE: PRT
<213> ORGANISM: artificial sequence
<220> FEATURE:
<223> OTHER INFORMATION: HVR-H3 sequence 14

<400> SEQUENCE: 236

Ala Arg Gly Phe Asp Gly Phe His Tyr
1               5

<210> SEQ ID NO 237
<211> LENGTH: 11
<212> TYPE: PRT
<213> ORGANISM: artificial sequence
<220> FEATURE:
<223> OTHER INFORMATION: HVR-H3 sequence 15

<400> SEQUENCE: 237

Ala Arg Gly Phe Tyr Gly Gly Ala Leu Asp Val
1 5 10

<210> SEQ ID NO 238
<211> LENGTH: 11
<212> TYPE: PRT
<213> ORGANISM: artificial sequence
<220> FEATURE:
<223> OTHER INFORMATION: HVR-H3 sequence 16

<400> SEQUENCE: 238

Ala Arg Gly Gly Gly Gly Tyr Tyr Phe Asp Val
1 5 10

<210> SEQ ID NO 239
<211> LENGTH: 10
<212> TYPE: PRT
<213> ORGANISM: artificial sequence
<220> FEATURE:
<223> OTHER INFORMATION: HVR-H3 sequence 17

<400> SEQUENCE: 239

Ala Arg Gly Gly Gly Leu Gly Phe Asp Tyr
1 5 10

<210> SEQ ID NO 240
<211> LENGTH: 10
<212> TYPE: PRT
<213> ORGANISM: artificial sequence
<220> FEATURE:
<223> OTHER INFORMATION: HVR-H3 sequence 18

<400> SEQUENCE: 240

Ala Arg Gly Gly Leu Gly Pro Phe Asp Ile
1 5 10

<210> SEQ ID NO 241
<211> LENGTH: 15
<212> TYPE: PRT
<213> ORGANISM: artificial sequence
<220> FEATURE:
<223> OTHER INFORMATION: HVR-H3 sequence 19

<400> SEQUENCE: 241

Ala Arg Gly Gly Ser Asp Thr Val Ile Gly Asp Trp Phe Ala Tyr
1 5 10 15

<210> SEQ ID NO 242
<211> LENGTH: 10
<212> TYPE: PRT
<213> ORGANISM: artificial sequence
<220> FEATURE:
<223> OTHER INFORMATION: HVR-H3 sequence 20

<400> SEQUENCE: 242

Ala Arg Gly Gly Val Gly Pro Phe Asp Ile
1 5 10

<210> SEQ ID NO 243
<211> LENGTH: 11
<212> TYPE: PRT
<213> ORGANISM: artificial sequence
<220> FEATURE:
<223> OTHER INFORMATION: HVR-H3 sequence 21

<400> SEQUENCE: 243

Ala Arg Gly Gly Tyr Gly Gly Tyr Leu Asp Val
1 5 10

<210> SEQ ID NO 244
<211> LENGTH: 11
<212> TYPE: PRT
<213> ORGANISM: artificial sequence
<220> FEATURE:
<223> OTHER INFORMATION: HVR-H3 sequence 22

<400> SEQUENCE: 244

Ala Arg Gly Leu Ser Ser Gly Tyr Phe Asp Tyr
1 5 10

<210> SEQ ID NO 245
<211> LENGTH: 9
<212> TYPE: PRT
<213> ORGANISM: artificial sequence
<220> FEATURE:
<223> OTHER INFORMATION: HVR-H3 sequence 23

<400> SEQUENCE: 245

Ala Arg Gly Ser Trp Tyr Phe Asp Val
1 5

<210> SEQ ID NO 246
<211> LENGTH: 9
<212> TYPE: PRT
<213> ORGANISM: artificial sequence
<220> FEATURE:
<223> OTHER INFORMATION: HVR-H3 sequence 24

<400> SEQUENCE: 246

Ala Arg Gly Thr Arg Gly Leu Asp Tyr
1 5

<210> SEQ ID NO 247
<211> LENGTH: 10
<212> TYPE: PRT
<213> ORGANISM: artificial sequence
<220> FEATURE:
<223> OTHER INFORMATION: HVR-H3 sequence 25

<400> SEQUENCE: 247

Ala Arg Gly Tyr Ser Asp Tyr Phe Asp Tyr
1 5 10

<210> SEQ ID NO 248
<211> LENGTH: 12
<212> TYPE: PRT
<213> ORGANISM: artificial sequence
<220> FEATURE:
<223> OTHER INFORMATION: HVR-H3 sequence 26

<400> SEQUENCE: 248

Ala Arg Gly Tyr Tyr Tyr Gly Arg Ala Phe Asp Tyr
1 5 10

<210> SEQ ID NO 249

<211> LENGTH: 13
<212> TYPE: PRT
<213> ORGANISM: artificial sequence
<220> FEATURE:
<223> OTHER INFORMATION: HVR-H3 sequence 27

<400> SEQUENCE: 249

Ala Arg His Ser Tyr Tyr Gly Val Gly Asp Phe Asp Tyr
1 5 10

<210> SEQ ID NO 250
<211> LENGTH: 9
<212> TYPE: PRT
<213> ORGANISM: artificial sequence
<220> FEATURE:
<223> OTHER INFORMATION: HVR-H3 sequence 28

<400> SEQUENCE: 250

Ala Arg Leu Phe Glu Gly Phe Pro Tyr
1 5

<210> SEQ ID NO 251
<211> LENGTH: 9
<212> TYPE: PRT
<213> ORGANISM: artificial sequence
<220> FEATURE:
<223> OTHER INFORMATION: HVR-H3 sequence 29

<400> SEQUENCE: 251

Ala Arg Leu Tyr Asp Tyr Phe Ala Tyr
1 5

<210> SEQ ID NO 252
<211> LENGTH: 10
<212> TYPE: PRT
<213> ORGANISM: artificial sequence
<220> FEATURE:
<223> OTHER INFORMATION: HVR-H3 sequence 30

<400> SEQUENCE: 252

Ala Arg Ser Gly Tyr Tyr Ala Leu Asp Tyr
1 5 10

<210> SEQ ID NO 253
<211> LENGTH: 12
<212> TYPE: PRT
<213> ORGANISM: artificial sequence
<220> FEATURE:
<223> OTHER INFORMATION: HVR-H3 sequence 31

<400> SEQUENCE: 253

Ala Arg Ser Pro Tyr Tyr Tyr Gly Val Phe Asp Tyr
1 5 10

<210> SEQ ID NO 254
<211> LENGTH: 9
<212> TYPE: PRT
<213> ORGANISM: artificial sequence
<220> FEATURE:
<223> OTHER INFORMATION: HVR-H3 sequence 32

<400> SEQUENCE: 254

Ala Arg Ser Tyr Val Tyr Phe Asp Tyr
1 5

<210> SEQ ID NO 255
<211> LENGTH: 19

```
<212> TYPE: PRT
<213> ORGANISM: artificial sequence
<220> FEATURE:
<223> OTHER INFORMATION: HVR-H3 sequence 33

<400> SEQUENCE: 255

Ala Arg Asp Gly Leu Gly Leu Arg Gly Val Tyr Tyr Tyr Tyr Tyr Gly
1               5                   10                  15

Leu Asp Val


<210> SEQ ID NO 256
<211> LENGTH: 20
<212> TYPE: PRT
<213> ORGANISM: artificial sequence
<220> FEATURE:
<223> OTHER INFORMATION: HVR-H3 sequence 34

<400> SEQUENCE: 256

Ala Arg Val Gly Glu Ser Gly Gly Ile Glu Ser Pro Tyr Tyr Tyr Tyr
1               5                   10                  15

Gly Leu Asp Val
            20


<210> SEQ ID NO 257
<211> LENGTH: 15
<212> TYPE: PRT
<213> ORGANISM: artificial sequence
<220> FEATURE:
<223> OTHER INFORMATION: HVR-L1 sequence 1

<400> SEQUENCE: 257

Arg Ala Ser Glu Ser Val Asp Phe Tyr Gly Ile Ser Phe Leu Pro
1               5                   10                  15


<210> SEQ ID NO 258
<211> LENGTH: 15
<212> TYPE: PRT
<213> ORGANISM: artificial sequence
<220> FEATURE:
<223> OTHER INFORMATION: HVR-L1 sequence 2

<400> SEQUENCE: 258

Arg Ala Ser Gln Ser Val Asp Phe Tyr Gly Ile Ser Phe Leu Ala
1               5                   10                  15


<210> SEQ ID NO 259
<211> LENGTH: 15
<212> TYPE: PRT
<213> ORGANISM: artificial sequence
<220> FEATURE:
<223> OTHER INFORMATION: HVR-L1 sequence 3

<400> SEQUENCE: 259

Arg Ala Ser Gln Ser Val Asp Phe Tyr Gly Lys Ser Phe Leu Asp
1               5                   10                  15


<210> SEQ ID NO 260
<211> LENGTH: 10
<212> TYPE: PRT
<213> ORGANISM: artificial sequence
<220> FEATURE:
<223> OTHER INFORMATION: HVR-L1 sequence 4

<400> SEQUENCE: 260

Ser Ala Ser Ser Arg Val Gly Ser Val Tyr
1               5                   10
```

<210> SEQ ID NO 261
<211> LENGTH: 10
<212> TYPE: PRT
<213> ORGANISM: artificial sequence
<220> FEATURE:
<223> OTHER INFORMATION: HVR-L1 sequence 5

<400> SEQUENCE: 261

Ser Ala Ser Ser Arg Val Ser His Val Phe
1 5 10

<210> SEQ ID NO 262
<211> LENGTH: 11
<212> TYPE: PRT
<213> ORGANISM: artificial sequence
<220> FEATURE:
<223> OTHER INFORMATION: HVR-L1 sequence 6

<400> SEQUENCE: 262

Arg Ala Ser Gln Gly Ile Ser Ser Tyr Leu Ala
1 5 10

<210> SEQ ID NO 263
<211> LENGTH: 11
<212> TYPE: PRT
<213> ORGANISM: artificial sequence
<220> FEATURE:
<223> OTHER INFORMATION: HVR-L1 sequence 7

<400> SEQUENCE: 263

Arg Ala Ser Gln Ser Val Ser Ser Tyr Leu Ala
1 5 10

<210> SEQ ID NO 264
<211> LENGTH: 11
<212> TYPE: PRT
<213> ORGANISM: artificial sequence
<220> FEATURE:
<223> OTHER INFORMATION: HVR-L1 sequence 8

<400> SEQUENCE: 264

Arg Ala Ser Gln Ser Ile Ser Ser Tyr Leu Asn
1 5 10

<210> SEQ ID NO 265
<211> LENGTH: 11
<212> TYPE: PRT
<213> ORGANISM: artificial sequence
<220> FEATURE:
<223> OTHER INFORMATION: HVR-L3 sequence 1

<400> SEQUENCE: 265

Phe Cys Leu Gln Gly Thr His Phe Pro Trp Thr
1 5 10

<210> SEQ ID NO 266
<211> LENGTH: 11
<212> TYPE: PRT
<213> ORGANISM: artificial sequence
<220> FEATURE:
<223> OTHER INFORMATION: HVR-L3 sequence 2

<400> SEQUENCE: 266

Tyr Cys Gln Gln Ser Tyr Arg Thr Pro Phe Thr
1 5 10

```
<210> SEQ ID NO 267
<211> LENGTH: 11
<212> TYPE: PRT
<213> ORGANISM: artificial sequence
<220> FEATURE:
<223> OTHER INFORMATION: HVR-L3 sequence 3

<400> SEQUENCE: 267

Tyr Cys Gln Gln Ser Tyr Ser Trp Pro Trp Thr
1               5                   10


<210> SEQ ID NO 268
<211> LENGTH: 11
<212> TYPE: PRT
<213> ORGANISM: artificial sequence
<220> FEATURE:
<223> OTHER INFORMATION: HVR-L3 sequence 4

<400> SEQUENCE: 268

Tyr Cys Gln Gln Tyr Thr His Asp Pro Val Thr
1               5                   10


<210> SEQ ID NO 269
<211> LENGTH: 11
<212> TYPE: PRT
<213> ORGANISM: artificial sequence
<220> FEATURE:
<223> OTHER INFORMATION: HVR-L3 sequence 5

<400> SEQUENCE: 269

Tyr Cys Gln Gln Tyr Tyr Arg Ile Pro Pro Thr
1               5                   10


<210> SEQ ID NO 270
<211> LENGTH: 11
<212> TYPE: PRT
<213> ORGANISM: artificial sequence
<220> FEATURE:
<223> OTHER INFORMATION: HVR-L3 sequence 6

<400> SEQUENCE: 270

Tyr Cys Gln His His Tyr Gly Thr Pro Leu Thr
1               5                   10


<210> SEQ ID NO 271
<211> LENGTH: 11
<212> TYPE: PRT
<213> ORGANISM: artificial sequence
<220> FEATURE:
<223> OTHER INFORMATION: HVR-L3 sequence 7

<400> SEQUENCE: 271

Tyr Cys Gln Gln Ser Tyr Ser Thr Pro Leu Thr
1               5                   10


<210> SEQ ID NO 272
<211> LENGTH: 11
<212> TYPE: PRT
<213> ORGANISM: artificial sequence
<220> FEATURE:
<223> OTHER INFORMATION: HVR-L3 sequence 8

<400> SEQUENCE: 272

Tyr Cys Gln Gln Ser Tyr Ser Thr Pro Pro Thr
1               5                   10
```

-continued

<210> SEQ ID NO 273
<211> LENGTH: 11
<212> TYPE: PRT
<213> ORGANISM: artificial sequence
<220> FEATURE:
<223> OTHER INFORMATION: HVR-L3 sequence 9

<400> SEQUENCE: 273

Tyr Cys Gln Gln Tyr Tyr Ser Thr Pro Leu Thr
1 5 10

<210> SEQ ID NO 274
<211> LENGTH: 11
<212> TYPE: PRT
<213> ORGANISM: artificial sequence
<220> FEATURE:
<223> OTHER INFORMATION: HVR-L3 sequence 10

<400> SEQUENCE: 274

Tyr Cys Gln Gln Tyr Tyr Thr Thr Pro Leu Thr
1 5 10

UNITED STATES PATENT AND TRADEMARK OFFICE
CERTIFICATE OF CORRECTION

PATENT NO. : 11,578,426 B2  Page 1 of 1
APPLICATION NO. : 16/640679
DATED : February 14, 2023
INVENTOR(S) : Peter Peizhi Luo et al.

It is certified that error appears in the above-identified patent and that said Letters Patent is hereby corrected as shown below:

In the Claims

In Claim 2, Column 242, Line number 41, please delete "HVR-H1" and insert --HVR-H2--

Signed and Sealed this
Twenty-fourth Day of June, 2025

Coke Morgan Stewart
*Acting Director of the United States Patent and Trademark Office*